(12) United States Patent
Crosignani et al.

(10) Patent No.: US 10,995,101 B2
(45) Date of Patent: May 4, 2021

(54) 2-OXO-THIAZOLE DERIVATIVES AS A2A INHIBITORS AND COMPOUNDS FOR USE IN THE TREATMENT OF CANCERS

(71) Applicant: iTeos Therapeutics SA, Gosselies (BE)

(72) Inventors: Stefano Crosignani, Gosselies (BE); Bruno Gomes, Huningue (FR); Erica Houthuys, Petit-Enghien (BE)

(73) Assignee: iTeos Therapeutics SA, Gosselies (BE)

( * ) Notice: Subject to any disclaimer, the term of this patent is extended or adjusted under 35 U.S.C. 154(b) by 0 days.

(21) Appl. No.: 16/354,022

(22) Filed: Mar. 14, 2019

(65) Prior Publication Data

US 2019/0276473 A1    Sep. 12, 2019

Related U.S. Application Data

(63) Continuation of application No. PCT/EP2018/058301, filed on Mar. 30, 2018.

(60) Provisional application No. 62/565,281, filed on Sep. 29, 2017.

(30) Foreign Application Priority Data

| Mar. 30, 2017 | (EP) | ................................ 17163781 |
| Sep. 29, 2017 | (EP) | ................................ 17194084 |
| Mar. 28, 2018 | (AR) | .......................... P2018010778 |

(51) Int. Cl.
| C07D 513/14 | (2006.01) |
| C07D 497/14 | (2006.01) |
| A61P 35/00 | (2006.01) |

(52) U.S. Cl.
CPC ............ *C07D 513/14* (2013.01); *A61P 35/00* (2018.01); *C07D 497/14* (2013.01)

(58) Field of Classification Search
CPC ...... A61P 35/00; C07D 497/14; C07D 513/14
See application file for complete search history.

(56) References Cited

U.S. PATENT DOCUMENTS

| 2005/0239795 A1 | 10/2005 | Neustadt et al. |
| 2020/0102319 A1 | 4/2020 | Crosignani |

FOREIGN PATENT DOCUMENTS

| IN | 274489 B | 1/2011 |
| WO | 2000/015231 A1 | 3/2000 |
| WO | 2003/095457 A1 | 11/2003 |
| WO | WO-2004/092171 A2 | 10/2004 |
| WO | 2007140181 A2 | 12/2007 |
| WO | 2009011897 A1 | 1/2009 |
| WO | 2011/112687 A2 | 9/2011 |
| WO | 2012038980 A2 | 3/2012 |
| WO | 2012055015 A1 | 5/2012 |
| WO | WO-2012/135084 A1 | 10/2012 |
| WO | 2018136700 A1 | 7/2018 |
| WO | 2018178338 A1 | 10/2018 |
| WO | 2019/123482 A1 | 6/2019 |
| WO | 2020053263 A1 | 3/2020 |
| WO | 2020065036 A1 | 4/2020 |

OTHER PUBLICATIONS

West, Anthony R., Solid State Chemistry and Its Applications, Wiley, New York, 1988, 358. (Year: 1988).*
Allard, B., et al., "Immunosuppressive activities of adenosine in cancer.", Curr. Opin. Pharmacol., Aug. 2016, vol. 29: pp. 7-16.
Hauser, R.A., et al., "Preladenant as an Adjunctive Therapy With Levodopa in Parkinson Disease: Two Randomized Clinical Trials and Lessons Learned", JAMA Neurol., Dec. 2015, vol. 72, Issue 12: pp. 1491-500.
Hodgson, R. A., et al., "Characterization of the Potent and Highly Selective A2A Receptor Antagonists Preladenant and SCH 412348 [7-[2-[4-2,4-Difluorophenyl]-1-piperazinyl]ethyl]-2-(2-furanyl)-7H-pyrazolo[4,3-e][1,2,4]triazolo[1,5-c]pyrimidin-5-amine] in Rodent Models of Movement Disorders and Depression", The Journal of Pharmacology and Experimental Therapeutics, Jul. 2009, vol. 330, Issue 1: pp. 294-303.
Ohta, A., "A Metabolic Immune Checkpoint: Adenosine in Tumor Microenvironment", Frontiers in Immunology, Mar. 29, 2016, vol. 7, Article 109: pp. 1-11.
PCT International Search Report and Written Opinion, PCT Application No. PCT/EP2018/058301, dated Apr. 10, 2018, 10 pages.
Pinna A., "Adenosine A2A Receptor Antagonists in Parkinson's Disease: Progress in Clinical Trials from the Newly Approved Istradefylline to Drugs in Early Development and Those Already Discontinued", CNS Drugs, May 2014, vol. 28, Issue 5: pp. 455-474.
Andre B. Da Fonseca Antunes, et al., "Gelucire 44/14 based immediate release formulations for poorly water-soluble drugs", Drug Development and Industrial Pharmacy,vol. 39, No. 5, May 1, 2013, pp. 791-798.

(Continued)

*Primary Examiner* — Erich A Leeser
(74) *Attorney, Agent, or Firm* — Goodwin Procter LLP

(57) ABSTRACT

The present invention relates to compounds of Formula I

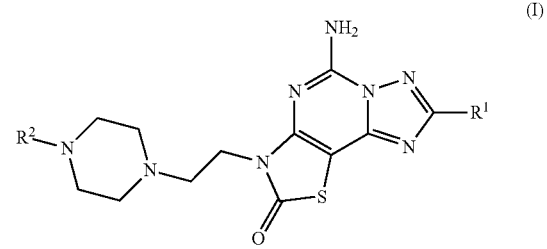

or pharmaceutically acceptable salts or solvates thereof. The invention further relates to the use of the compounds of Formula I as A2A inhibitors. The invention also relates to the use of the compounds of Formula I for the treatment and/or prevention of cancer. The invention also relates to a process for manufacturing compounds of Formula I.

22 Claims, 2 Drawing Sheets

(56) References Cited

OTHER PUBLICATIONS

Barbara Cacciari, et al., "A2A Adenosine Receptor Antagonists as Therapeutic Candidates: Are They Still an Interesting Challenge?", Mini Reviews in Medicinal Chemistry, vol. 18, No. 14, Jul. 9, 2018, pp. 1168-1174.

Conglian Yang, et al., "Recent Advances in the Application of Vitamin E TPGS for Drug Delivery", Theranostics, vol. 8, No. 2, Jan. 1, 2018, pp. 464-485.

Gengyang Yuan, et al., "Fluorinated Adenosine A 2A Receptor Antagonists Inspired by Preladenant as Potential cancer Immunotherapeutics", International Journal of Medicinal Chemistry, vol. 2017, Jan. 1, 2017, pp. 1-8.

Hatfield Stephen M, et al., "A2A adenosine receptor antagonists to weaken the hypoxia-HIF-1'alpha' driven mmunosuppression and improve immunotherapies of cancer", Current Opinion in Pharmacology, Elsevier Science Publishers, NL, vol. 29, Jul. 17, 2016, pp. 90-96.

Houthuys Erica, et al., "Abstract LB-291: EOS100850, an insurmountable and non-brain penetrant A2A receptor antagonist, inhibits adenosine-mediated T cell suppression, demonstrates anti-tumor activity and exhibits best-in class characteristics I Cancer Research", Cancer Research Apr. 1, 2018, Retrieved from the Internet: URL:https://cancerres.aacrjournals.org/content/78/13_Supplement/LB-291.

International Search Report and Written Opinion for PCT/EP2019/074208 dated Jan. 17, 2020.

International Search Report and Written Opinion for PCT/EP2019/076244 dated Jan. 8, 2020.

Nakagawa H, et al., "Basis for dosing time-dependent change in the anti-tumor effect of imatinib in mice", Nov. 15, 2006, vol. 72, No. 10, pp. 1237-1245.

Stephen B. Willingham, et al., "Azar Antagonism with CPI-444 Induces Antitumor Responses and Augments Efficacy to Anti-PD-(L)1 and Anti-CTLA-4 in Preclinical Models", Cancer Immunology Research, vol. 6, No. 10, 21 Aug. 2018, pp. 1136-1149.

STN Chemical Structure Search Results dated May 12, 2020 (31 pages).

STN Chemical Structure Search Results dated May 12, 2020 (41 pages).

\* cited by examiner

2-OXO-THIAZOLE DERIVATIVES AS A2A INHIBITORS AND COMPOUNDS FOR USE IN THE TREATMENT OF CANCERS

CROSS-REFERENCE TO RELATED APPLICATIONS

This application is a continuation of International Patent Application No. PCT/EP2018/058301, filed Mar. 30, 2018, which claims priority to European Patent Application No. 17163781.2, filed Mar. 30, 2017, European Patent Application No. 17194084.4, filed Sep. 29, 2017, U.S. Provisional Application No. 62/565,281, filed Sep. 29, 2017, and Argentinian Patent Application No. P 20180100778, filed Mar. 28, 2018, the entire disclosure of each of which is incorporated by reference herein for all purposes.

FIELD OF INVENTION

The present invention relates to novel thiocarbamate derivatives, including pharmaceutically acceptable salts and solvates thereof. Compounds of the invention are inhibitors of adenosine A2A receptor and are useful as therapeutic compounds, particularly in the treatment and/or prevention of cancers.

BACKGROUND OF INVENTION

Many of the immunosuppressive mechanisms in tumors are common to physiological immunoregulation in normal tissues. Such immunoregulation is very important in keeping the immune system under control in order to block a self-reactive immune response and to prevent an ongoing immune response from causing critical tissue damage. The lack of physiological immunoregulation often results in overwhelming immune activation that accompanies autoimmunity. For example, CTLA-4 is a physiological mechanism that negatively regulates T cell activity by blocking a costimulatory signal through CD28-B7 interaction. The lack of CTLA4 causes non-specific T cell activation, and CTLA-4-deficient mice die in several weeks with massive lymphocytic tissue infiltration. PD-1 also provides a T cell inhibitory signal upon interaction with its ligands, PD-L1 and PD-L2. Deficiency of PD-1 in mice is known to cause various types of autoimmune disorders depending on the genetic strains. Besides cell surface transducers of immunosuppressive signal, e.g., CTLA-4 and PD-1, immunosuppression in the tumor microenvironment involves anti-inflammatory cytokines (IL-10, TGF-β), enzymes (indoleamine-2,3-dioxygenase), and professional immunoregulatory cells (regulatory T cells, myeloid-derived suppressor cells MDSCs). These immunosuppressive mechanisms play an important role in controlling immune response in normal tissues. Since tumors take advantage of such physiological immunoregulatory mechanisms to protect their tissue from immune attack, these mechanisms intended to prevent inflammatory complication, now turn out to be major obstacles hampering spontaneous cancer regression and immunological cancer treatment. The identification of immunosuppressive mechanisms in tumors pointed out molecular targets to restore the antitumor immune response. Thus, these negative immunoregulatory mechanisms, so-called immune checkpoints, became a focus in drug discovery. Antibodies agains PD1, PDL1 or CTLA4 have been approved as anticancer therapies on a large number of indications, such as Metastatic Melanoma, Non-Small Cell Lung Cancer, Renal Cell Carcinoma, Hodgkin's Lymphoma, Head and Neck Cancer, Urothelial Carcinoma, Hepatocellular Carcinoma, as well as treatment of for patients with solid tumors that have one of two specific genetic features known as mismatch repair deficiency and high microsatellite instability (irrespective of cancer type).

Extracellular adenosine has been known as an inhibitor of immune functions. While intracellular adenosine is involved in energy metabolism, nucleic acid metabolism, and the methionine cycle, extracellular adenosine plays an important role in intercellular signaling. Its signal is transmitted by G protein-coupled adenosine receptors on the cell surface, and it affects diverse physiological functions including neurological, cardiovascular, and immunological systems.

Tumors contain high levels of extracellular adenosine, suggesting that tumor cells may benefit from its immunosuppressive effect and catabolic energy production (Allard et al., Curr. Opin. Pharmacol., 2016, 29, 7-16; Otta A., Frontiers in Immunology, 2016, 7: 109). This high level of extracellular adenosine is probably due to overexpression of the enzyme CD73, which is responsible for production of extracellular adenosine. CD73 is overexpressed by a large number of tumors, with all the following tumors expresign medium or high levels of CD73 in >50% of tumor surface by immunohistochemistry (www.proteinatlas.org): Breast, Carcinoid, Cervical, Colorectal, Endometrial, Glioma, Head and Neck, Liver, Lung, Melanoma, Ovarian, Pancreatic, Prostate, Renal, Gastric, Thyroid, Urothelial.

Of the four known types of adenosine receptors, A2A adenosine receptor (A2AR) is the predominantly expressed subtype in most immune cells. Stimulation of A2AR generally provides an immunosuppressive signal that inhibits activities of T cells (proliferation, cytokine production, cytotoxicity), NK cells (cytotoxicity), NKT cells (cytokine production, CD40L upregulation), macrophages/dendritic cells (antigen presentation, cytokine production), and neutrophils (oxidative burst). The presence of high levels of extracellular adenosine in tumors was found to play a significant role in the evasion of antitumor immune response. Especially, it was shown that A2AR-deficient mice could spontaneously regress the inoculated tumor, whereas no wild-type mice showed similar tumor regression. A2AR antagonists were also beneficial in tumor-bearing wild-type animals. Importantly, depletion of T cells and NK cells impaired the retardation of tumor growth by A2AR antagonists, suggesting improvement of antitumor cellular immune response. Effector functions of T cells and NK cells are susceptible to A2AR stimulation. In addition, when activated in the presence of A2AR agonist, the effector function of T cells is persistently impaired even after removal of A2AR agonist. This result suggests that the adenosine-rich environment in tumors may induce T cells that are anergic to the tumor cells.

Therefore, given that A2A receptor is expressed in most immune cells and particularly effector immune cells such as T cells and NK cells and given that A2A receptor is engaged in tissues where adenosine is produced, it is thought that A2A inhibitors can be helpful in all the cancer indications.

Consequently, there is a need for A2A inhibitors able to restore immune functions in tumors environment.

Adenosine is known to be an endogenous modulator of a number of other physiological functions. For example, at the central nervous system (CNS) level, adenosine in known to induce sedative, anxiolotic and antiepileptic effects level.

Thus, A2A inhibitors were previously developed for the treatment of depression and neurodegenerative diseases such as Parkinson's disease or Alzheimer's disease (Pinna A., CNS Drugs, 2014, 28, 455). One of the most advanced A2A inhibitors developed for the treatment of CNS diseases is Preladenant (Hodgson R A et al., J. Pharmacol. Exp. Ther., 2009, 330(1), 294-303; Hauser R A et al., JAMA Neurol., 2015, 72(12), 1491-500).

However, such previously developed A2A inhibitors were designed to cross the blood brain barrier, in order to target A2A receptor in the CNS.

Given the higher level of adenosine in tumors when compared to the brain, much higher amounts of compounds will be needed to achieve the desired effect on immune functions restoration for treating cancers. Thus, in order to avoid deleterious side effects, one should provide A2A inhibitors which have a limited, if any, CNS penetrance, contrary to all previously developed A2A inhibitors.

As evidenced in the experimental part below, the Applicant hereby provides new A2A inhibitors which do not have any significant CNS penetrance, and which may thus be useful in the treatment of cancers.

SUMMARY

This invention thus relates to a compound of Formula (I)

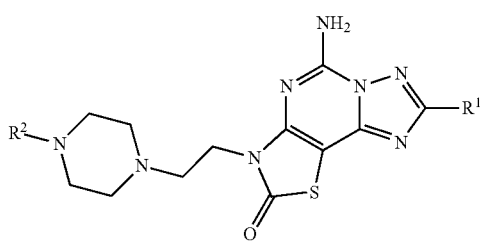

(I)

or a pharmaceutically acceptable salt or solvate thereof, wherein $R^1$ and $R^2$ are as defined below.

According to one embodiment, compounds of Formula (I) are of Formula (Ia)

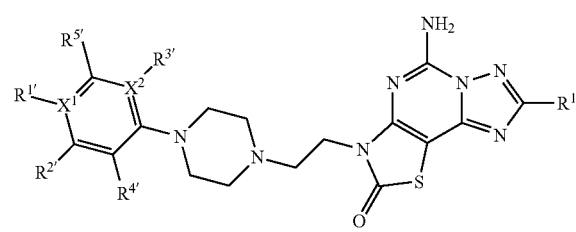

(Ia)

or a pharmaceutically acceptable salt or solvate thereof, wherein $R^1$, $R^{1'}$, $R^{2'}$, $R^{3'}$, $R^{4'}$ and $R^{5'}$ are as defined below.

According to one embodiment, compounds of Formula (Ia) are of Formula (Ia-1)

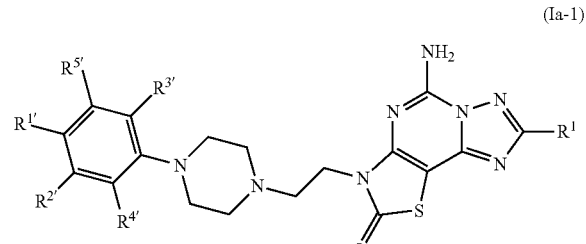

(Ia-1)

or a pharmaceutically acceptable salt or solvate thereof, wherein $R^1$, $R^{1'}$, $R^{2'}$, $R^{3'}$, $R^{4'}$ and $R^{5'}$ are as defined in Formula (Ia).

According to one embodiment, compounds of Formula (Ia) are of Formulae (Ia-2) or (Ia-3)

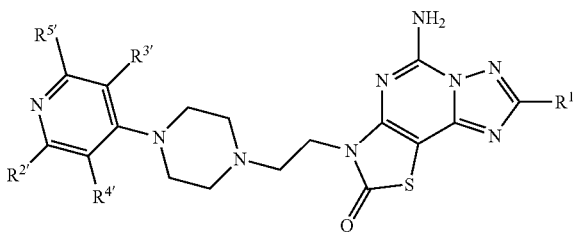

(Ia-2)

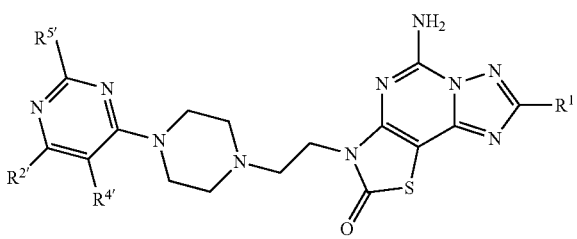

(Ia-3)

or a pharmaceutically acceptable salt or solvate thereof, wherein $R^1$, $R^{2'}$, $R^{3'}$, $R^{4'}$ and $R^{5'}$ are as defined in Formula (Ia).

The invention also relates to a pharmaceutical composition comprising a compound according to the invention, or a pharmaceutically acceptable salt or solvate thereof, and at least one pharmaceutically acceptable carrier.

The invention further relates to a medicament comprising a compound according to the invention, or a pharmaceutically acceptable salt or solvate thereof.

The invention also provides a compound according to the invention or a pharmaceutically acceptable salt or solvate thereof for use in the treatment and/or prevention of cancer.

The invention further relates to a compound according to the invention or a pharmaceutically acceptable salt or solvate thereof for use as A2A inhibitor.

It is also provided a process for manufacturing a compound of Formula (Ia) according to the invention or a pharmaceutically acceptable salt or solvate thereof, characterized in that it comprises the coupling between amine intermediate of Formula (A)

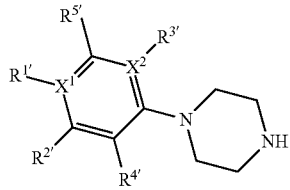

(A)

wherein $X^1$, $R^2$, $R^{1'}$, $R^{2'}$, $R^{3'}$, $R^{4'}$ and $R^{5'}$ are as defined in below; and intermediate of Formula (B)

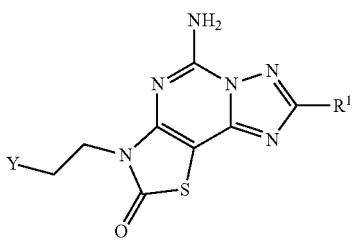

wherein R¹ is as defined below and Y represents halo, alkylsulfonyloxy having 1 to 6 carbon atoms or arylsulfonyloxy having 6 to 10 carbon atoms.

The invention also relates to intermediates of synthesis of Formula (A).

Definitions

In the present invention, the following terms have the following meanings: The term "aldehyde" refers to a group —CHO.

The term "aldehydealkyl" refers to a group -alkyl-CHO wherein alkyl is as herein defined.

The term "alkenyl" refers to unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkenylcarbonyl" refers to a group —(C=O)-alkenyl wherein alkenyl is as herein defined.

The term "alkenylcarbonylalkyl" refers to a group -alkyl-(C=O)-alkenyl wherein alkyl and alkenyl are as herein defined.

The term "alkenylcarbonylamino" refers to a group —NH—(C=O)-alkenyl wherein alkenyl is as herein defined.

The term "alkenylcarbonylaminoalkyl" refers to a group -alkyl-NH—(C=O)-alkenyl wherein alkyl and alkenyl are as herein defined.

The term "alkoxy" refers to a group —O-alkyl wherein alkyl is as herein defined.

The term "alkyl" refers to a hydrocarbyl radical of formula $C_nH_{2n+1}$ wherein n is a number greater than or equal to 1. Generally, alkyl groups of this invention comprise from 1 to 8 carbon atoms, more preferably, alkyl groups of this invention comprise from 1 to 6 carbon atoms. Alkyl groups may be linear or branched. Suitable alkyl groups include methyl, ethyl, propyl, butyl, pentyl, hexyl, heptyl and octyl.

The term "alkylaminoalkyl" refers to a group -alkyl-NH-alkyl wherein alkyl is as herein defined.

The term "alkylaminoalkylaminocarbonyl" refers to a group —(C=O)—NH-alkyl-NH-alkyl wherein alkyl is as herein defined.

The term "(alkylaminoalkyl)(alkyl)aminocarbonyl" refers to a group —(C=O)—NR¹R² wherein R¹ is an alkyl group and R² is a -alkyl-NH-alkyl group, wherein alkyl is as herein defined.

The term "alkylaminoalkylcarbonyl" refers to a group —(C=O)-alkyl-NH-alkyl wherein alkyl is as herein defined.

The term "alkylcarbonyl" refers to a group —(C=O)-alkyl wherein alkyl is as herein defined.

The term "alkylheteroaryl" refers to any heteroaryl substituted by an alkyl group wherein alkyl is as herein defined.

The term "alkyloxycarbonyl" refers to a group —(C=O)—O-alkyl wherein alkyl is as herein defined.

The term "alkylsulfonyl" refers to a group —SO₂-alkyl wherein alkyl is as herein defined.

The term "alkylsulfonealkyl" refers to a group -alkyl-SO₂-alkyl wherein alkyl is as herein defined.

The term "alkylsulfonimidoyl" refers to a group —S(=O)(=NH)-alkyl wherein alkyl is as herein defined.

The term "alkylsulfoxide" refers to a group —(S=O)-alkyl wherein alkyl is as herein defined.

The term "alkylsulfoxidealkyl" refers to a group -alkyl-SO-alkyl wherein alkyl is as herein defined.

The term "alkyne" refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkyl groups. Non-limiting examples of alkynyl groups are ethynyl, 2-propynyl, 2-butynyl, 3-butynyl, 2-pentynyl and its isomers, 2-hexynyl and its isomers- and the like.

The term "alkynealkyl" refers to a group -alkyl-alkyne wherein alkyl and alkyne are as herein defined.

The term "alkynecarbonylalkyl" refers to a group -alkyl-(C=O)-alkyne wherein alkyl and alkyne are as herein defined.

The term "amino" refers to a group —NH₂.

The term "aminoalkyl" refers to a group -alkyl-NH₂ wherein alkyl is as herein defined.

The term "aminoalkylaminocarbonyl" refers to a group —(C=O)—NH-alkyl-NH₂ wherein alkyl is as herein defined.

The term "aminoalkylcarbonylamino" refers to a group —NH—(C=O)-alkyl-NH₂ wherein alkyl is as herein defined.

The term "aminocarbonyl" refers to a group —(C=O)—NH₂.

The term "(aminocarbonylalkyl)(alkyl)amino" refers to a group —NR¹R² wherein R¹ is an alkyl group and R² is a -alkyl-(C=O)—NH₂ group, wherein alkyl is as herein defined.

The term "aminocarbonylalkylamino" refers to a group —NH-alkyl-(C=O)—NH₂ wherein alkyl is as herein defined.

The term "aminosulfonyl" refers to a group —SO₂—NH₂.

The term "aryl" refers to a polyunsaturated, aromatic hydrocarbyl group having a single ring (i.e. phenyl) or multiple aromatic rings fused together (e.g. naphtyl), typically containing 5 to 12 atoms; preferably 5 to 10; more preferably the aryl is a 5- or 6-membered aryl. Non-limiting examples of aryl comprise phenyl, naphthalenyl.

The term "carbonyl" refers to a group —(C=O)—.

The term "carbonylamino" refers to a group —NH—(C=O)—.

The term "cycloalkyl" refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms; still more preferably more preferably the cycloalkyl is a 5- or 6-membered cycloalkyl. Examples of cycloalkyl groups include but are not limited to cyclopropyl, cyclobutyl, cyclopentyl, cyclohexyl.

The term "cycloalkyloxy" refers to a group —O-cycloalkyl wherein cycloalkyl is as herein defined.

The term "dialkylamino" refers to a group —NR$^1$R$^2$ wherein R$^1$ and R$^2$ are both independently alkyl group as herein defined.

The term "dialkylaminoalkyl" refers to a group -alkyl-NR$^1$R$^2$ wherein R$^1$ and R$^2$ are both independently alkyl group, as herein defined.

The term "dialkylaminoalkylaminocarbonyl" refers to a group —(C═O)—NH-alkyl-NR$^1$R$^2$ wherein R$^1$ and R$^2$ are both alkyl group, as herein defined.

The term "dialkylaminoalkylcarbonyl" refers to a group —(C═O)-alkyl-NR$^1$R$^2$ wherein R$^1$ and R$^2$ are both alkyl group, as herein defined.

The term "dihydroxyalkyl" refers to a group alkyl is as herein defined substituted by two hydroxyl (—OH) groups.

The term "halo" or "halogen" refers to fluoro, chloro, bromo, or iodo.

The term "heteroaryl" refers to an aryl group as herein defined wherein at least one carbon atom is replaced with a heteroatom. In other words, it refers to 5 to 12 carbon-atom aromatic single rings or ring systems containing 2 rings which are fused together, typically containing 5 to 6 atoms; in which one or more carbon atoms is replaced by oxygen, nitrogen and/or sulfur atoms where the nitrogen and sulfur heteroatoms may optionally be oxidized and the nitrogen heteroatoms may optionally be quaternized. Non-limiting examples of such heteroaryl, include: oxazolyl, thiazolyl, imidazolyl, furanyl and pyrrolyl. Preferably the heteroaryl is a 5- or 6-membered heteroaryl, more preferably the 5- or 6-membered heteroaryl is a furyl.

The term "heterocyclyl" refers to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Preferably the heretocyclyl is a 5- or 6-membered heretocyclyl. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include aziridinyl, oxiranyl, thiiranyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, succinimidyl, 3H-indolyl, indolinyl, isoindolinyl, 2H-pyrrolyl, 1-pyrrolinyl, 2-pyrrolinyl, 3-pyrrolinyl, pyrrolidinyl, 4H-quinolizinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydropyranyl, tetrahydrofuranyl, tetrahydrothiophenyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, 1-oxido-1-thiomorpholin-4-yl, 1-dioxido-1-thiomorpholin-4-yl, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, and morpholin-4-yl.

The term "heterocyclylalkylaminocarbonyl" refers to a group —(C═O)—NH-alkyl-heterocyclyl, wherein alkyl and heterocyclyl are as herein defined.

The term "(heterocyclyl)(alkyl)aminoalkyl" refers to a group -alkyl-NR$^1$R$^2$ wherein R$^1$ is an alkyl group and R$^2$ is an heterocyclyl group, wherein alkyl and heterocyclyl are as herein defined.

The term "heterocyclylcarbonyl" refers to a group —(C═O)-heterocyclyl wherein heterocyclyl is as herein defined.

The term "heterocyclylalkyl" refers to a group -alkyl-heterocyclyl wherein alkyl and heterocyclyl are as herein defined.

The term "heterocyclyloxy" to a group —O-heterocyclyl wherein heterocyclyl is as herein defined.

The term "heterocyclylsulfonyl" refers to a group —SO$_2$-heterocyclyl wherein heterocyclyl is as herein defined.

The term "hydroxyalkyl" refers to a group -alkyl-OH wherein alkyl is as herein defined.

The term "hydroxyalkylaminoalkyl" refers to a group -alkyl-NH-alkyl-OH wherein alkyl is as herein defined.

The term "hydroxycarbonyl" refers to a group —C(═O)—OH wherein carbonyl is as herein defined. In other words, "hydroxycarbonyl" corresponds to a carboxylic acid group.

The term "oxo" refers to a ═O substituent.

The term "sulfonylamino" refers to a group —NH—SO$_2$.

The term "about", preceding a figure, means plus or less 10% of the value of said figure.

The term "administration", or a variant thereof (e.g. "administering"), means providing the active agent or active ingredient (e.g. a A2A inhibitor), alone or as part of a pharmaceutically acceptable composition, to the patient in whom/which the condition, symptom, or disease is to be treated or prevented.

The terms "IC$_{50}$" or "half maximal inhibitory concentration" represent the concentration of an inhibitor that is required for 50% inhibition in vitro.

The term "inhibitor" refers to a natural or synthetic compound that has a biological effect to inhibit or significantly reduce or down-regulate the expression of a gene and/or a protein or that has a biological effect to inhibit or significantly reduce the biological activity of a protein. Consequently, an "A2A inhibitor" refers to a compound that has a biological effect to inhibit or significantly reduce or down-regulate the biological activity of A2A receptor.

The term "human" refers to a subject of both genders and at any stage of development (i.e. neonate, infant, juvenile, adolescent, adult).

The term "patient" refers to a warm-blooded animal, more preferably a human, who/which is awaiting the receipt of, or is receiving medical care or is/will be the object of a medical procedure.

The expression "pharmaceutically acceptable" refers to the ingredients of a pharmaceutical composition are compatible with each other and not deleterious to the subject to which it is administered.

The expression "pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, e.g., FDA Office or EMA.

The term "predrug", as used herein, means any compound that will be modified to form a drug species, wherein the modification may take place either inside or outside of the body, and either before or after the predrug reaches the area of the body where administration of the drug is indicated.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "prodrug" as used herein means the pharmacologically acceptable derivatives of compounds of Formula I, such as for example esters or amides, whose in vivo biotransformation product generates the biologically active drug. Prodrugs are generally characterized by increased bio-availability and are readily metabolized into biologically active compounds in vivo.

The terms "treating" or "treatment" refer to both therapeutic treatment and prophylactic or preventative measures; wherein the object is to prevent or slow down the targeted pathologic condition or disease. Those in need of treatment include those already with the disease as well as those prone to have the disease or those in whom the disease is to be prevented. A subject or mammal is successfully "treated" for a disease or affection or condition if, after receiving the treatment according to the present invention, the subject or mammal shows observable and/or measurable reduction in or absence of one or more of the following: reduction of tumors; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "volunteer" or "subject" refers to an animal, including a human. In the sense of the present invention, a subject may be a patient, i.e., a person receiving medical attention, undergoing or having underwent a medical treatment, or monitored for the development of a disease. In one embodiment, the subject is a male. In another embodiment, the subject is a female.

DETAILED DESCRIPTION

Compounds
This invention relates to compounds of Formula I

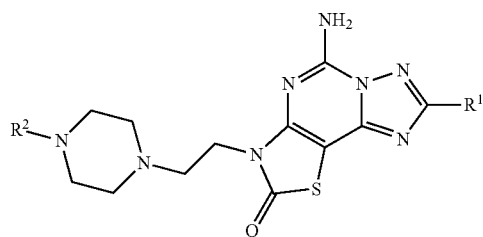

(I)

or a pharmaceutically acceptable salt or solvate thereof, wherein:
represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably represents furyl;

$R^2$ represents 6-membered aryl or 6-membered heteroaryl,
wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino and alkylsulfonealkyl;
said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl alkylsulfonyl and alkylsulfonealkyl;
or the heteroaryl or aryl groups are optionally substituted with two substituents that form together with the atoms to which they are attached a 5- or 6-membered aryl ring, a 5- or 6-membered heretoaryl ring, a 5- or 6-membered cycloalkyl ring or a 5- or 6-membered heretocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

According to one embodiment, in Formula I:
$R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

R² represents 6-membered aryl or 6-membered heteroaryl, wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, carbonylamino, sulfonylamino and alkylsulfonealkyl;

said substituents being optionally substituted by one or more substituent selected from hydroxy, cyano, alkyl, alkenyl, aldehyde, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl alkylsulfonyl and alkylsulfonealkyl.

According to one embodiment, in Formula I:

R¹ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably R¹ represents 5-membered heteroaryl; more preferably R¹ represents furyl;

R² represents 6-membered aryl or 6-membered heteroaryl, wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, carbonylamino and sulfonylamino;

said substituents being optionally substituted by one or more substituent selected from hydroxy, cyano, alkyl, alkenyl, aldehyde, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl.

According to a preferred embodiment, this invention relates to compounds of Formula (Ia):

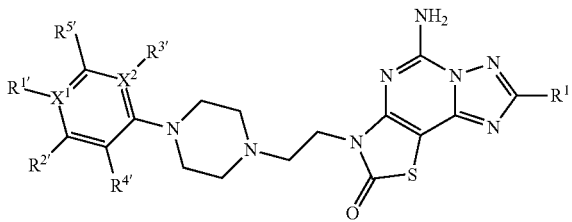

or a pharmaceutically acceptable salt or solvate thereof, wherein:

R¹ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably R¹ represents 5-membered heteroaryl; more preferably R¹ represents furyl;

X¹ and X² represent each independently C or N;

R¹' is absent when X¹ is N; or when X¹ is C, R¹' represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

R²' represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)

amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

or $R^{1'}$ and $R^{2'}$ form together with the atoms to which they are attached a 5- or 6-membered aryl ring, a 5- or 6-membered heretoaryl ring, a 5- or 6-membered cycloalkyl ring or a 5- or 6-membered heretocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{3'}$ is absent when $X^2$ is N; or when $X^2$ is C, $R^{3'}$ represents H or halo, preferably H or F;

$R^{4'}$ represents H or halo, preferably H or F; and $R^{5'}$ represents H or halo, preferably H or F.

According to one embodiment, in Formula (Ia):

$R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

$X^1$ and $X^2$ represent each independently C or N;

$R^{1'}$ is absent when $X^1$ is N; or when $X^1$ is C, $R^{1'}$ represents H, halo, alkyl, alkoxy, heterocyclyloxy, alkylcarbonyl, carbonyl, aminocarbonyl, hydroxycarbonyl, heterocyclyl, heterocyclylcarbonyl, alkylsulfoxide, alkylsulfonyl, aminosulfonyl or heterocyclylsulfonyl;

said substituents being optionally substituted by one or more substituent selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide, alkylsulfoxidealkyl, alkylsulfonealkyl;

$R^{2'}$ represents H, alkoxy, cycloalkyloxy, heterocyclyloxy, alkylsulfoxide, carbonyl, carbonylamino, aminocarbonyl or sulfonylamino;

wherein alkoxy, cycloalkyloxy, heterocyclyloxy, alkylsulfoxide, carbonyl, carbonylamino, aminocarbonyl or sulfonylamino are optionally substituted by one or more substituent selected from hydroxy, cyano, alkyl, alkenyl, aldehyde, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonealkyl;

or $R^{1'}$ and $R^{2'}$ form together with the atoms to which they are attached a 5- or 6-membered aryl ring, a 5- or 6-membered heretoaryl ring, a 5- or 6-membered cycloalkyl ring, a 5- or 6-membered heretocyclyl ring; optionally substituted by one or more substituent selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide, alkylsulfonealkyl;

$R^{3'}$ is absent when $X^2$ is N; or when $X^2$ is C, $R^{3'}$ represents H or halo, preferably H or F;

$R^{4'}$ represents H or halo, preferably H or F; and $R^{5'}$ represents H or halo, preferably H or F.

According to one embodiment, in Formula (Ia):

$R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

$X^1$ and $X^2$ represent each independently C or N;

$R^{1'}$ is absent when $X^1$ is N; or when $X^1$ is C, $R^{1'}$ represents H, halo, alkyl, alkoxy, heterocyclyloxy, alkylcarbonyl, carbonyl, aminocarbonyl, hydroxycarbonyl, heterocyclyl, heterocyclylcarbonyl, alkylsulfoxide, alkylsulfonyl, aminosulfonyl or heterocyclylsulfonyl;

said substituents being optionally substituted by one or more substituent selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl) amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide, alkylsulfoxidealkyl;

$R^{2'}$ represents H, alkoxy, cycloalkyloxy, heterocyclyloxy, alkylsulfoxide, carbonyl, carbonylamino, aminocarbonyl or sulfonylamino;

wherein alkoxy, cycloalkyloxy, heterocyclyloxy, alkylsulfoxide, carbonyl, carbonylamino, aminocarbonyl or sulfonylamino are optionally substituted by one or more substituent selected from hydroxy, cyano, alkyl, alkenyl, aldehyde, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl;

or $R^{1'}$ and $R^{2'}$ form together with the atoms to which they are attached a 5- or 6-membered aryl ring, a 5- or 6-membered heteroaryl ring, a 5- or 6-membered cycloalkyl ring, a 5- or 6-membered heterocyclyl ring; optionally substituted by one or more substituent selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide;

$R^{3'}$ is absent when $X^2$ is N; or when $X^2$ is C, $R^{3'}$ represents H or halo, preferably H or F;

$R^{4'}$ represents H or halo, preferably H or F; and $R^{5'}$ represents H or halo, preferably H or F.

In one specific embodiment of the invention, $R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro).

In a preferred embodiment, $R^1$ represents 5-membered heteroaryl; more preferably, $R^1$ represents furyl.

In one specific embodiment of the invention, $X^1$ and $X^2$ represent each independently C or N. In another specific embodiment, $X^1$ and $X^2$ both represent C.

In one specific embodiment of the invention, $R^{1'}$ is absent when $X^1$ is N.

In another specific embodiment, when $X^1$ is C, $R^{1'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, when $X^1$ is C, $R^{1'}$ represents H, halo, alkyl, alkoxy, heterocyclyloxy, alkylcarbonyl, carbonyl, aminocarbonyl, hydroxycarbonyl, heterocyclyl heterocyclylcarbonyl, alkylsulfoxide, alkylsulfonyl, aminosulfonyl or heterocyclylsulfonyl; said substituents being optionally substituted by one or more substituent selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide, alkylsulfoxidealkyl.

In a preferred embodiment, $R^{1'}$ substituents are optionally substituted by one or more substituent selected from halo, hydroxy, alkyl, heterocyclylalkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkoxy, amino, dialkylamino, aminoalkylcarbonylamino, aminocarbonylalkylamino, heterocyclylalkylaminocarbonyl, (aminocarbonylalkyl)(alkyl)amino, hydroxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, heterocyclylcarbonyl, alkylsulfoxide and alkylsulfonealkyl.

In a preferred embodiment, $R^{1'}$ substituents are optionally substituted by one or more substituent selected from hydroxy, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkoxy, amino, dialkylamino, aminoalkylcarbonylamino, aminocarbonylalkylamino, (aminocarbonylalkyl)(alkyl)amino, hydroxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, heterocyclylcarbonyl, alkylsulfoxide, alkylsulfonealkyl.

In one specific embodiment of the invention, $R^{2'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, $R^{2'}$ represents H, alkoxy, cycloalkyloxy, heterocyclyloxy, alkylsulfoxide, carbonyl, carbonylamino, aminocarbonyl or sulfonylamino; wherein alkoxy, cycloalkyloxy, heterocyclyloxy, alkylsulfoxide, carbonyl, carbonylamino, aminocarbonyl or sulfonylamino are optionally substituted by one or more substituent selected from hydroxy, cyano, alkyl, alkenyl, aldehyde, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl.

In a preferred embodiment, $R^{2'}$ substituents are optionally substituted by one or more substituent selected from oxo, halo, hydroxy, cyano, alkyl, heterocyclylalkyl, dihydroxyalkyl, dialkylaminoalkyl, heteroaryl, alkylheteroaryl, hydroxycarbonyl, alkyloxycarbonyl, aminocarbonyl, heterocyclylalkylaminocarbonyl, alkylaminoalkylcarbonyl, dialkylaminoalkylcarbonyl, alkylsulfoxide, alkylsulfonealkyl.

In a preferred embodiment, $R^{2'}$ substituents are optionally substituted by one or more substituent selected from hydroxy, cyano, alkyl, dialkylaminoalkyl, heteroaryl, alkylheteroaryl, hydroxycarbonyl, alkyloxycarbonyl, aminocarbonyl, alkylaminoalkylcarbonyl, dialkylaminoalkylcarbonyl, alkylsulfoxide, alkylsulfonealkyl.

In another specific embodiment of the invention, $R^{1'}$ and $R^{2'}$ form together with the atoms to which they are attached a 5- or 6-membered aryl ring, a 5- or 6-membered heteroaryl ring, a 5- or 6-membered cycloalkyl ring or a 5- or 6-membered heretocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, $R^{1'}$ and $R^{2'}$ form together with the atoms to which they are attached a 5- or 6-membered aryl ring, a 5- or 6-membered heretoaryl ring, a 5- or 6-membered cycloalkyl ring, a 5- or 6-membered heretocyclyl ring; optionally substituted by one or more substituent selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide, alkylsulfonealkyl.

In one specific embodiment of the invention, $R^{3'}$ is absent when $X^2$ is N. In another specific embodiment of the invention, when $X^2$ is C, $R^{3'}$ represents H or halo. In a preferred embodiment, when $X^2$ is C, $R^{3'}$ represents H or F.

In one specific embodiment of the invention, $R^{4'}$ represents H or halo. In a preferred embodiment, $R^{4'}$ represents H or F.

In one specific embodiment of the invention, $R^{5'}$ represents H or halo. In a preferred embodiment, $R^{5'}$ represents H or F.

In one embodiment, preferred compounds of Formula (Ia) are those of Formula (Ia-1):

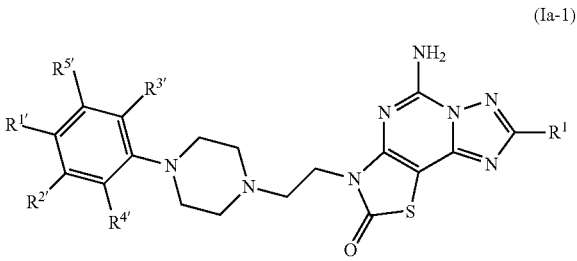

(Ia-1)

or a pharmaceutically acceptable salt or solvate thereof, wherein $R^1$, $R^{1'}$, $R^{2'}$, $R^{3'}$, $R^{4'}$ and $R^{5'}$ are as defined in Formula (Ia).

In one embodiment, preferred compounds of Formula (Ia-1) are those of Formula (Ia-1a):

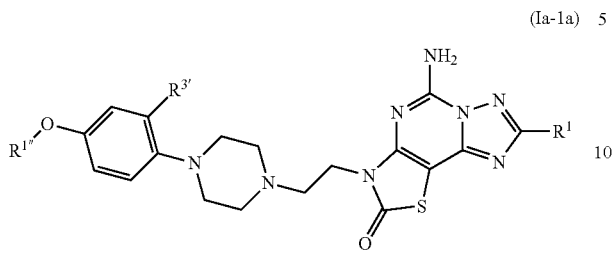

(Ia-1a)

or a pharmaceutically acceptable salt or solvate thereof, wherein:
$R^1$ and $R^{3'}$ are as defined in Formula (Ia); and
$R^{1''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

According to one embodiment, in Formula (Ia-la):
$R^1$ and $R^{3'}$ are as defined in Formula (Ia); and
$R^{1''}$ represents an alkyl or heterocyclyl group substituted by one or more group selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide, alkylsulfonealkyl.

According to one embodiment, in Formula (Ia-la):
$R^1$ and $R^{3'}$ are as defined in Formula (Ia); and
$R^{1''}$ represents an alkyl or heterocyclyl group substituted by one or more group selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide.

In one specific embodiment of the invention, $R^{1''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, represents an alkyl or heterocyclyl group substituted by one or more group selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide.

In a preferred embodiment, $R^{1''}$ represents an alkyl or heterocyclyl group substituted by one or more group selected from hydroxy, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, heterocyclylcarbonyl, alkylsulfoxide, alkylsulfonealkyl.

In one embodiment, preferred compounds of Formula (Ia-1) are those of Formula (Ia-1b):

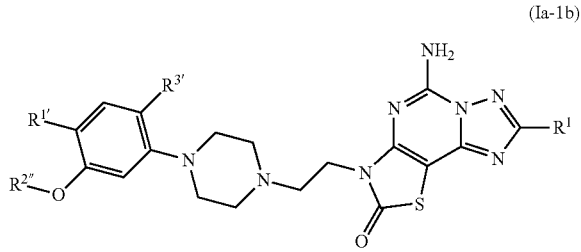

(Ia-1b)

or a pharmaceutically acceptable salt or solvate thereof, wherein:
$R^1$ and $R^{3'}$ are as defined in Formula (Ia);
$R^{1'}$ represents H or halo, preferably H or F; and
$R^{2''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

According to one embodiment, in Formula (Ia-1b):
$R^1$ and $R^{3'}$ are as defined in Formula (Ia);
$R^{1'}$ represents H or halo, preferably H or F; and
$R^{2''}$ represents an alkyl or heterocyclyl group substituted by one or more group selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl) aminocarbonyl, alkylaminoalkylcarbonyl, dialkylaminoalkylcarbonyl, heterocyclylcarbonyl, alkylsulfoxide, alkylsulfonealkyl.

According to one embodiment, in Formula (Ia-1b):
$R^1$ and $R^{3'}$ are as defined in Formula (Ia);
$R^{1'}$ represents H or halo, preferably H or F; and
$R^{2''}$ represents an alkyl or heterocyclyl group substituted by one or more group selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl) aminocarbonyl, alkylaminoalkylcarbonyl, dialkylaminoalkylcarbonyl, heterocyclylcarbonyl, alkylsulfoxide.

In one specific embodiment of the invention, $R^{1'}$ represents H or halo. In a preferred embodiment, $R^{1'}$ represents H or F.

In one specific embodiment of the invention, $R^{2''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In a preferred embodiment, $R^{2''}$ represents an alkyl or heterocyclyl group substituted by one or more group selected from hydroxy, cyano, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxide.

In a preferred embodiment, $R^{2''}$ represents an alkyl or heterocyclyl group substituted by one or more group selected from hydroxy, cyano, heteroaryl, alkylheteroaryl, alkyne, hydroxycarbonyl, alkyloxycarbonyl, aminocarbonyl, alkylaminoalkylcarbonyl, dialkylaminoalkylcarbonyl, alkylsulfoxide, alkylsulfonealkyl.

In one embodiment, preferred compounds of Formula (Ia-1) are those of Formula (Ia-1c) or (Ia-1d):

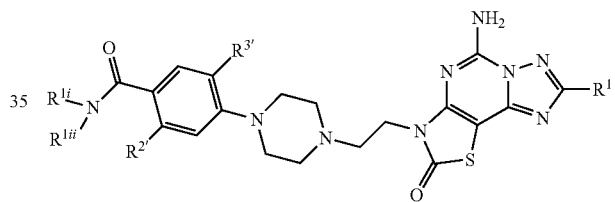

(Ia-1c)

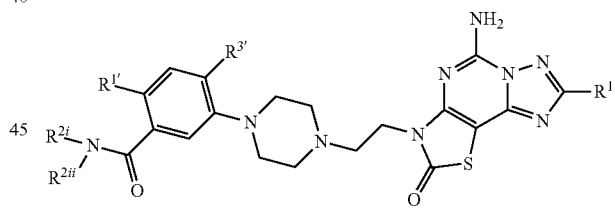

(Ia-1d)

or a pharmaceutically acceptable salt or solvate thereof, wherein:
$R^1$ and $R^{3'}$ are as defined in Formula (Ia);
$R^{1'}$ represents H or halo, preferably H or F;
$R^{2'}$ represents H or halo, preferably H or F;
$R^{1i}$ and $R^{1ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl; and $R^{2i}$ and $R^{2ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

According to one embodiment, in Formula (Ia-1c) or (Ia-1d):

$R^1$ and $R^{3'}$ are as defined in Formula (Ia);
$R^{1'}$ represents H or halo, preferably H or F;
$R^{2'}$ represents H or halo, preferably H or F;
$R^{1i}$ and $R^{1ii}$ represent each independently hydrogen, hydroxy, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxidealkyl, alkylsulfonealkyl; and $R^{2i}$ and $R^{2ii}$ represent each independently hydrogen, hydroxy, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxidealkyl, alkylsulfonealkyl.

According to one embodiment, in Formula (Ia-1c) or (Ia-1d):

$R^1$ and $R^{3'}$ are as defined in Formula (Ia);
$R^{1'}$ represents H or halo, preferably H or F;
$R^{2'}$ represents H or halo, preferably H or F;
$R^{1i}$ and $R^{1ii}$ represent each independently hydrogen, hydroxy, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxidealkyl, alkylsulfonealkyl; and $R^{2i}$ and $R^{2ii}$ represent each independently hydrogen, hydroxy, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxidealkyl, alkylsulfonealkyl.

In one specific embodiment of the invention, $R^{1'}$ represents H or halo. In a preferred embodiment, $R^{1'}$ represents H or F.

In one specific embodiment of the invention, $R^{2'}$ represents H or halo. In a preferred embodiment, $R^{2'}$ represents H or F.

In one specific embodiment of the invention, $R^{1i}$ and $R^{1ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

In a preferred embodiment, $R^{1i}$ and $R^{1ii}$ represent each independently hydrogen, hydroxy, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxidealkyl, alkylsulfonealkyl.

In a preferred embodiment, $R^{1i}$ and $R^{1ii}$ represent each independently hydrogen, alkyl, heterocyclylalkyl, hydroxyalkyl, hydroxyalkylaminoalkyl, aminoalkyl, alkylaminoalkyl, dialkylaminoalkyl, (heterocyclyl)(alkyl)aminoalkyl or heterocyclylalkylaminocarbonyl.

In a preferred embodiment, $R^{1i}$ and $R^{1ii}$ represent each independently hydrogen, alkyl, hydroxyalkyl, hydroxyalkylaminoalkyl, aminoalkyl, alkylaminoalkyl, dialkylaminoalkyl or (heterocyclyl)(alkyl)aminoalkyl.

In one specific embodiment of the invention, $R^{2i}$ and $R^{2ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

In a preferred embodiment, $R^{2i}$ and $R^{2ii}$ represent each independently hydrogen, hydroxy, alkyl, hydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, hydroxycarbonyl, alkyloxycarbonyl, aminocarbonyl, aminoalkylaminocarbonyl, alkylaminoalkylaminocarbonyl, dialkylaminoalkylaminocarbonyl, (alkylaminoalkyl)(alkyl)aminocarbonyl, alkylaminoalkylcarbonyl, dialkylaminoalkylcarbonyl, heterocyclylcarbonyl, alkylsulfoxidealkyl.

In a preferred embodiment, $R^{2i}$ and $R^{2ii}$ represent each independently hydrogen, alkyl, heterocyclylalkyl, dihydroxyalkyl, dialkylaminoalkyl or heterocyclylalkylaminocarbonyl. In a preferred embodiment, $R^{2i}$ and $R^{1ii}$ represent each independently hydrogen, alkyl or dialkylaminoalkyl.

In one embodiment, preferred compounds of Formula (Ia) are those of Formulae (Ia-2) or (Ia-3):

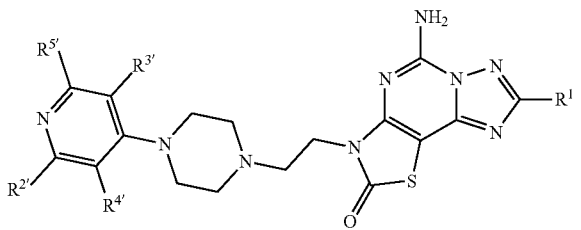

(Ia-2)

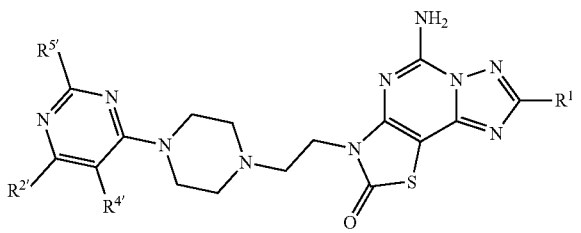

(Ia-3)

or a pharmaceutically acceptable salt or solvate thereof, wherein $R^1$, $R^{2'}$, $R^{3'}$, $R^{4'}$ and $R^{5'}$ are as defined in Formula (Ia).

Particularly preferred compounds of Formula I of the invention are those listed in Table 1 hereafter.

TABLE 1

| Cpd no | Structure | Chemical name | MW |
|---|---|---|---|
| 1 | 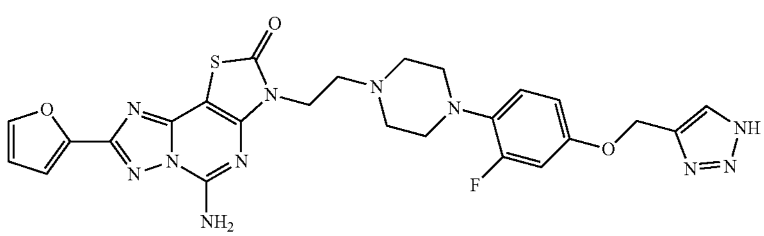 [SMILES: Nc1nc2c(sc(=O)n2CCN2CCN(c3ccc(OCc4c[nH]nn4)cc3F)CC2)c2nc(-c3ccco3)nn12] | 3-(2-(4-(4-((1H-1,2,3-triazolo-4yl)methoxy-2fluorophenyl)piperazine-1-yl)ethyl)-5-amino-(8-(furan-2-yl)thiazolo[5,4-e][1,2,4]triazolo[1,5-c]pyrimidine-2(3H)-one | 577.60 |
| 2 | 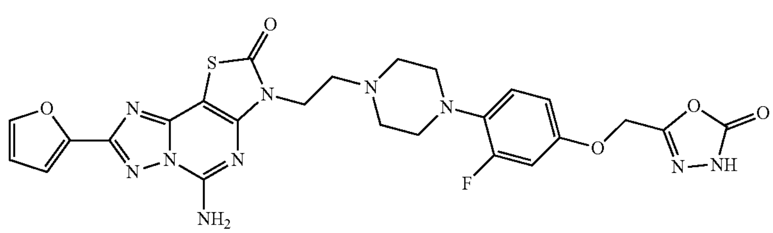 [SMILES: Nc1nc2c(sc(=O)n2CCN2CCN(c3ccc(OCc4n[nH]c(=O)o4)cc3F)CC2)c2nc(-c3ccco3)nn12] | 5-((4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)methyl)-1,3,4-oxadiazol-2(3H)-one | 594.58 |
| 3 | 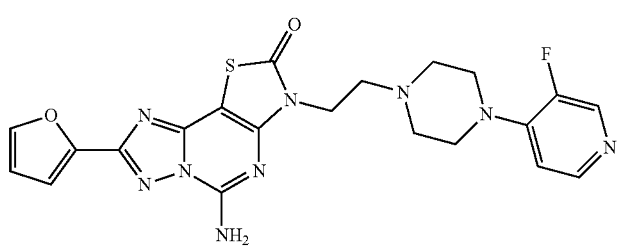 [SMILES: Nc1nc2c(sc(=O)n2CCN2CCN(c3ccncc3F)CC2)c2nc(-c3ccco3)nn12] | 5-amino-3-(2-(4-(3-fluoropyridin-4-yl)piperazin-1-yl)ethyl)-8-(furan-2-yl)thiazolo[5,4-e][1,2,4]triazolo[1,5-c]pyrimidin-2(3H)-one | 481.51 |

TABLE 1-continued

| Cpd no | Structure | Chemical name | MW |
|---|---|---|---|
| 4 | 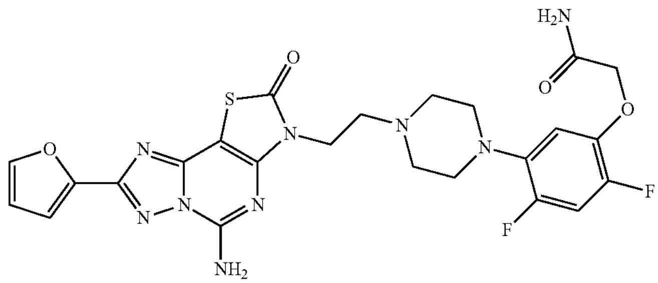 [SMILES: NC(=O)COc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)acetamide | 571.56 |
| 5 | 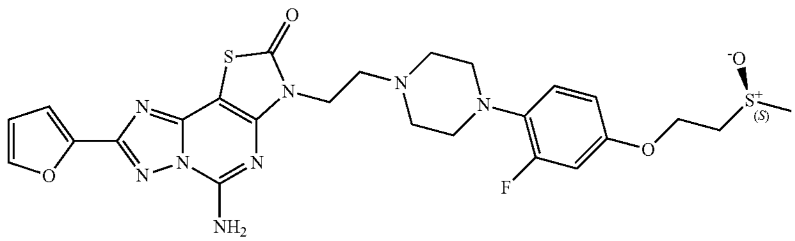 | (S)-5-amino-3-(2-(4-(2-fluoro-4-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 586.66 |
| 6 | 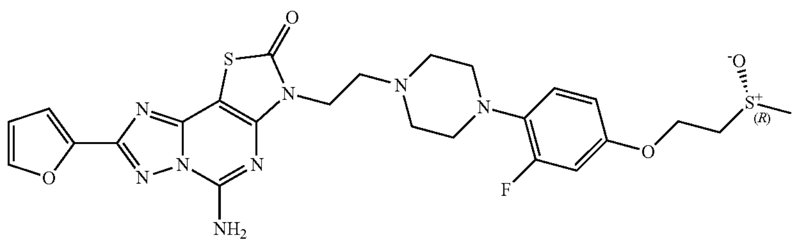 | (R)-5-amino-3-(2-(4-(2-fluoro-4-(2-(methylsulfinyl)ethoxy)phenyl)-piperazin-1-yl)ethyl)-8-(furan-2-yl)thiazolo[5,4-e][1,2,4]triazolo[1,5-c]pyrimidin-2(3H)-one | 586.66 |
| 7 | 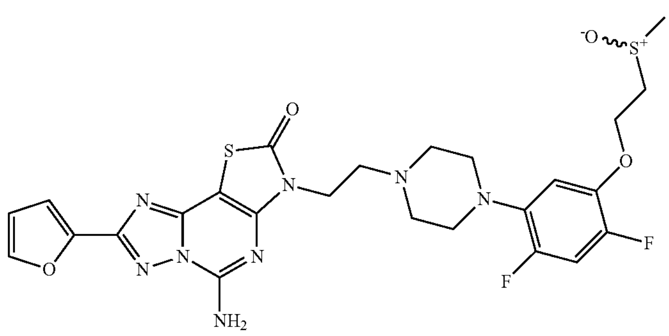 | (R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 604.65 |
| 8a | 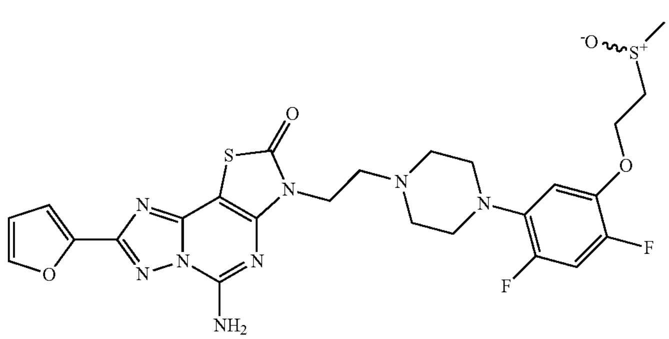 | (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 604.65 |

TABLE 1-continued

| Cpd no | Structure | Chemical name | MW |
|---|---|---|---|
| 8b | 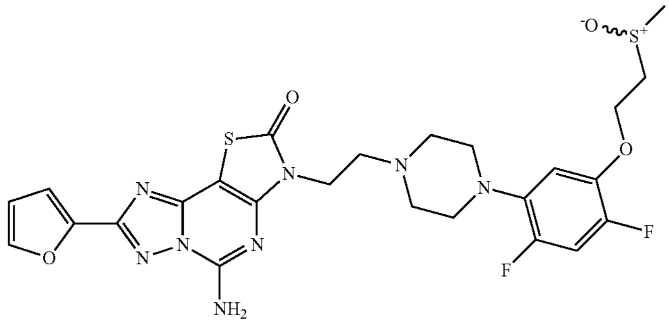 | (−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one | 604.65 |
| 9 | 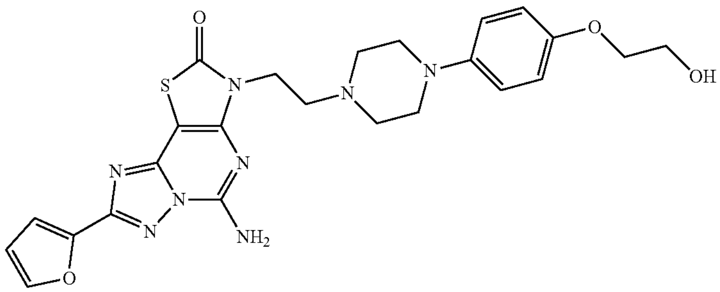 [SMILES: Nc1nc2c(sc(=O)n2CCN2CCN(c3ccc(OCCO)cc3)CC2)c2nc(-c3ccco3)nn12] | 5-amino-8-(furan-2-yl)-3-(2-(4-(4-(2-hydroxyethoxy)phenyl)piperazin-1-yl)ethyl)thiazolo[5,4-e][1,2,4]triazolo[1,5-c]pyrimidin-2(3H)-one | 522.58 |
| 10 | 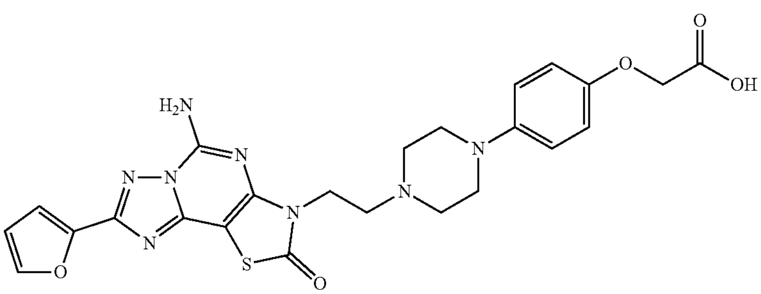 [SMILES: Nc1nc2c(sc(=O)n2CCN2CCN(c3ccc(OCC(=O)O)cc3)CC2)c2nc(-c3ccco3)nn12] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)phenoxy)acetic acid | 536.56 |
| 11 | 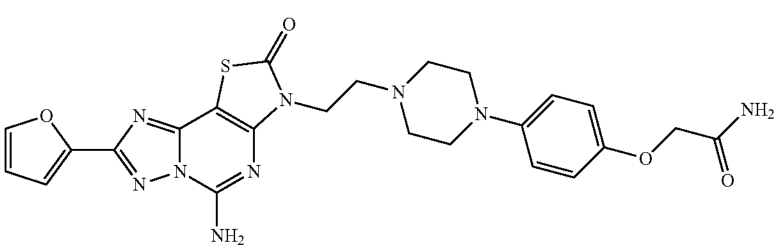 [SMILES: NC(=O)COc1ccc(N2CCN(CCn3c(=O)sc4c3nc(N)n3nc(-c5ccco5)nc43)CC2)cc1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)phenoxy)acetamide | 535.58 |
| 12 | 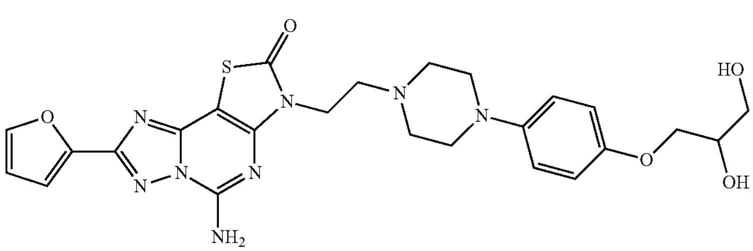 [SMILES: Nc1nc2c(sc(=O)n2CCN2CCN(c3ccc(OCC(O)CO)cc3)CC2)c2nc(-c3ccco3)nn12] | 5-amino-3-(2-(4-(4-(2,3-dihydroxypropoxy)phenyl)piperazin-1-yl)ethyl)-8-(furan-2-yl)thiazolo[5,4-e][1,2,4]triazolo[1,5-c]pyrimidin-2(3H)-one | 552.61 |

TABLE 1-continued

| Cpd no | Structure | Chemical name | MW |
|---|---|---|---|
| 13 | 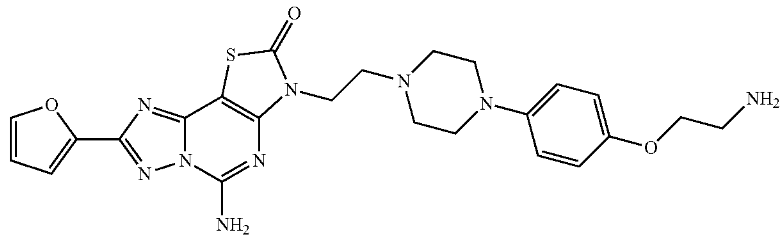 [SMILES: NCCOc1ccc(N2CCN(CCn3c(=O)sc4c3nc(N)n3nc(-c5ccco5)nc43)CC2)cc1] | 5-amino-3-(2-(4-(4-(2-aminoethoxy)phenyl)piperazin-1-yl)ethyl)-8-(furan-2-yl)thiazolo[5,4-e][1,2,4]triazolo[1,5-c]pyrimidin-2(3H)-one | 521.60 |
| 14 | 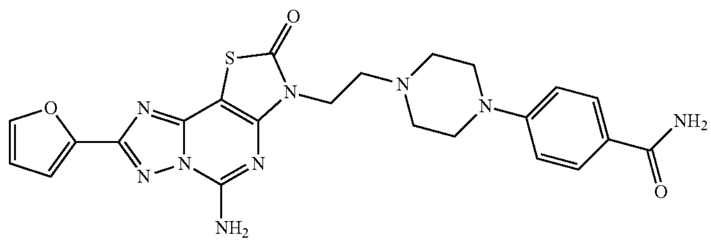 [SMILES: NC(=O)c1ccc(N2CCN(CCn3c(=O)sc4c3nc(N)n3nc(-c5ccco5)nc43)CC2)cc1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzamide | 505.55 |
| 15 | 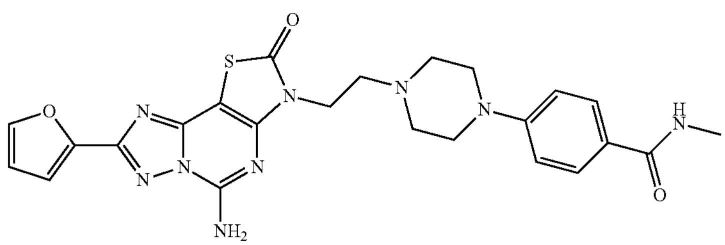 [SMILES: CNC(=O)c1ccc(N2CCN(CCn3c(=O)sc4c3nc(N)n3nc(-c5ccco5)nc43)CC2)cc1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-methylbenzamide | 519.58 |
| 16 | 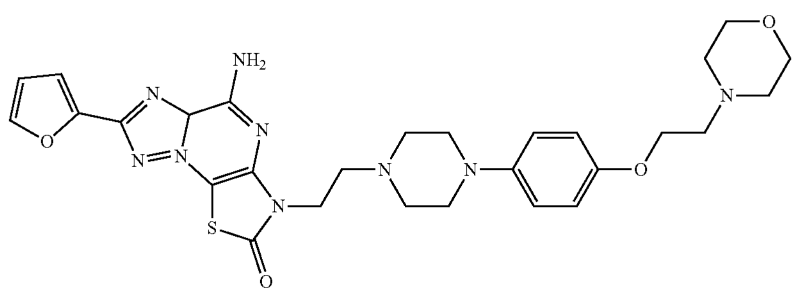 | 5-amino-8-(furan-2-yl)-3-(2-(4-(4-(2-morpholinoethoxy)phenyl)piperazin-1-yl)ethyl)thiazolo[5,4-e][1,2,4]triazolo[1,5-c]pyrimidin-2(3H)-one | 591.68 |
| 17 | 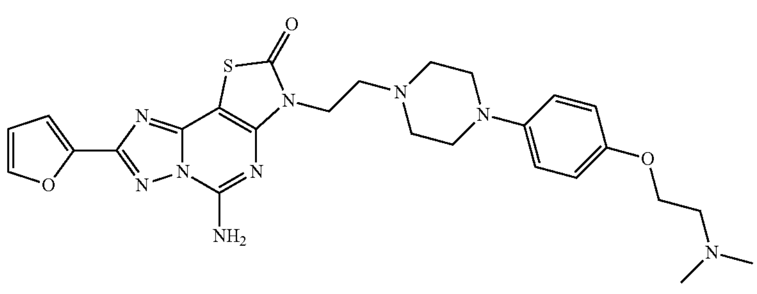 [SMILES: CN(C)CCOc1ccc(N2CCN(CCn3c(=O)sc4c3nc(N)n3nc(-c5ccco5)nc43)CC2)cc1] | 5-amino-3-(2-(4-(4-(2-(dimethylamino)ethoxy)phenyl)piperazin-1-yl)ethyl)-8-(furan-2-yl)thiazolo[5,4-e][1,2,4]triazolo[1,5-c]pyrimidin-2(3H)-one | 549.65 |
| 18 | 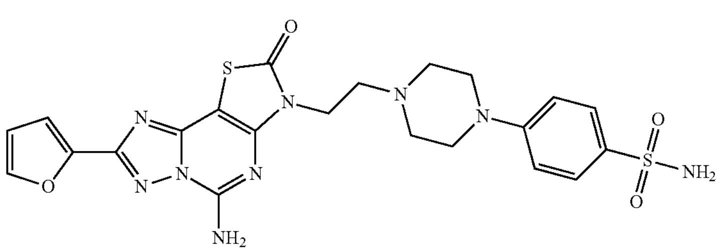 [SMILES: Nc1nc2c(sc(=O)n2CCN2CCN(c3ccc(S(N)(=O)=O)cc3)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzenesulfonamide | 541.61 |

TABLE 1-continued

| Cpd no | Structure | Chemical name | MW |
|---|---|---|---|
| 19 | 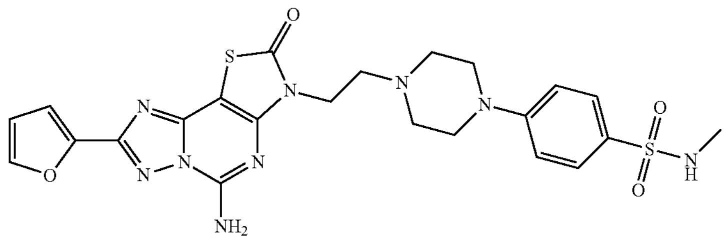 [SMILES: CNS(=O)(=O)c1ccc(N2CCN(CCn3c(=O)sc4c3nc(N)n3nc(-c5ccco5)nc43)CC2)cc1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-methylbenzenesulfonamide | 555.63 |
| 20 | 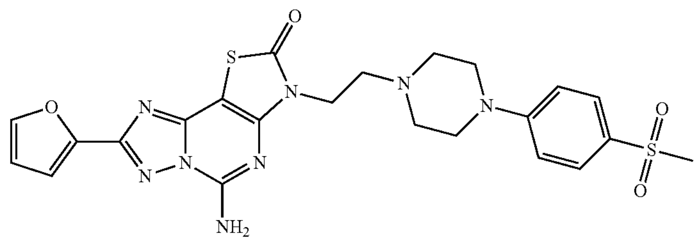 [SMILES: CS(=O)(=O)c1ccc(N2CCN(CCn3c(=O)sc4c3nc(N)n3nc(-c5ccco5)nc43)CC2)cc1] | 5-amino-8-(furan-2-yl)-3-(2-(4-(4-(methylsulfonyl)phenyl)piperazin-1-yl)ethyl)thiazolo[5,4-e][1,2,4]triazolo[1,5-c]pyrimidin-2(3H)-one | 540.62 |
| 21 | 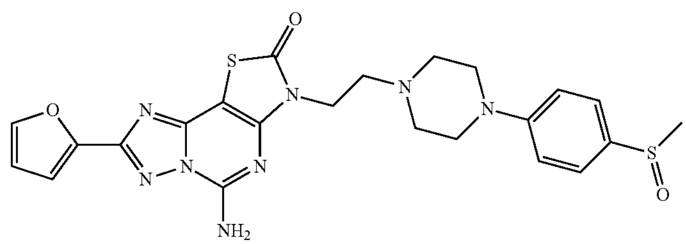 [SMILES: CS(=O)c1ccc(N2CCN(CCn3c(=O)sc4c3nc(N)n3nc(-c5ccco5)nc43)CC2)cc1] | 5-amino-8-(furan-2-yl)-3-(2-(4-(4-(methylsulfinyl)phenyl)piperazin-1-yl)ethyl)thiazolo[5,4-e][1,2,4]triazolo[1,5-c]pyrimidin-2(3H)-one | 524.62 |
| 22 | 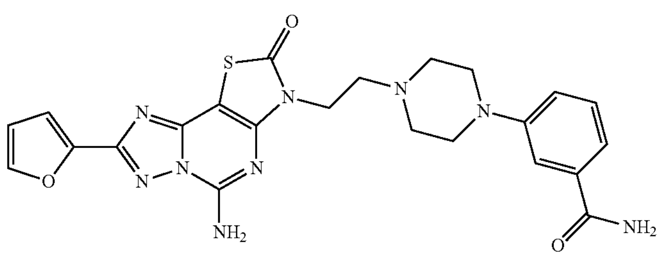 [SMILES: NC(=O)c1cccc(N2CCN(CCn3c(=O)sc4c3nc(N)n3nc(-c5ccco5)nc43)CC2)c1] | 3-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzamide | 505.55 |
| 23 | 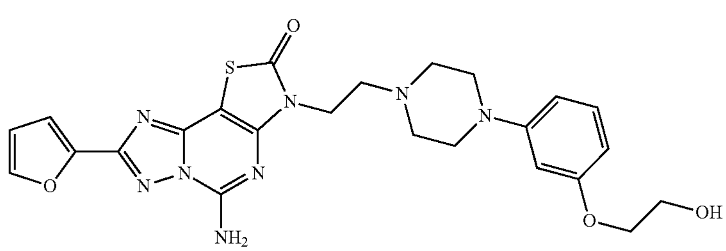 [SMILES: Nc1nc2c(sc(=O)n2CCN2CCN(c3cccc(OCCO)c3)CC2)c2nc(-c3ccco3)nn12] | 5-amino-8-(furan-2-yl)-3-(2-(4-(3-(2-hydroxyethoxy)phenyl)piperazin-1-yl)ethyl)thiazolo[5,4-e][1,2,4]triazolo[1,5-c]pyrimidin-2(3H)-one | 522.58 |
| 24 | 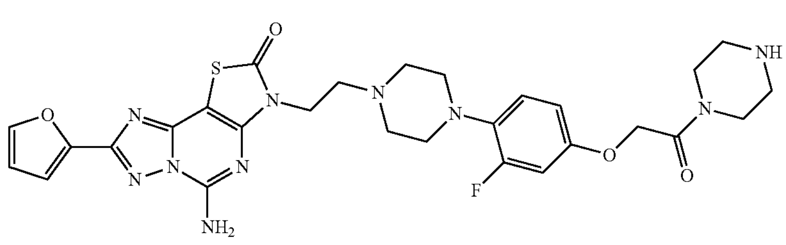 [SMILES: Nc1nc2c(sc(=O)n2CCN2CCN(c3ccc(OCC(=O)N4CCNCC4)cc3F)CC2)c2nc(-c3ccco3)nn12] | 5-amino-3-(2-(4-(2-fluoro-4-(2-oxo-2-(piperazin-1-yl)ethoxy)phenyl)piperazin-1-yl)ethyl)-8-(furan-2-yl)thiazolo[5,4-e][1,2,4]triazolo[1,5-c]pyrimidin-2(3H)-one | 622.67 |

TABLE 1-continued

| Cpd no | Structure | Chemical name | MW |
|---|---|---|---|
| 25 | 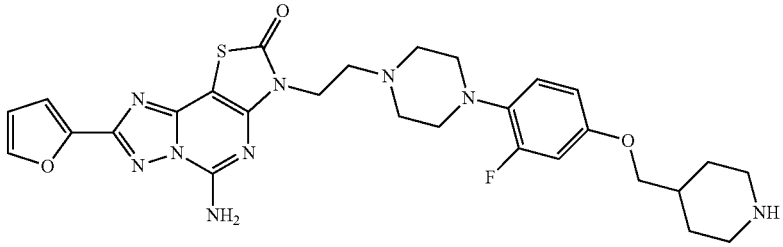 [SMILES: Nc1nc2c(sc(=O)n2CCN2CCN(c3ccc(OCC4CCNCC4)cc3F)CC2)c2nc(-c3ccco3)nn12] | 5-amino-3-(2-(4-(2-fluoro-4-(piperidin-4-ylmethoxy)phenyl)piperazin-1-yl)ethyl)-8-(furan-2-yl)thiazolo[5,4-e][1,2,4]triazolo[1,5-c]pyrimidin-2(3H)-one | 593.68 |
| 26 | 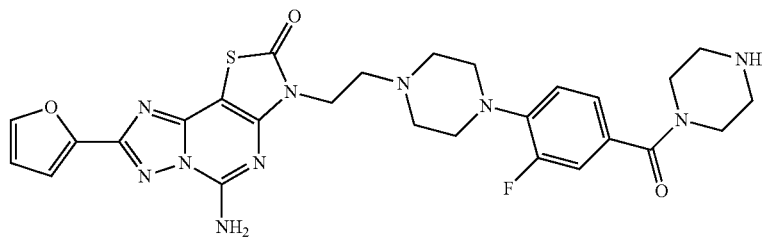 [SMILES: Nc1nc2c(sc(=O)n2CCN2CCN(c3ccc(C(=O)N4CCNCC4)cc3F)CC2)c2nc(-c3ccco3)nn12] | 5-amino-3-(2-(4-(2-fluoro-4-(piperazine-1-carbonyl)phenyl)piperazin-1-yl)ethyl)-8-(furan-2-yl)thiazolo[5,4-e][1,2,4]triazolo[1,5-c]pyrimidin-2(3H)-one | 592.65 |
| 27 | 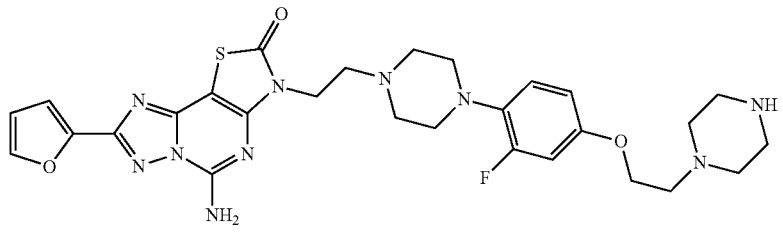 [SMILES: Nc1nc2c(sc(=O)n2CCN2CCN(c3ccc(OCCN4CCNCC4)cc3F)CC2)c2nc(-c3ccco3)nn12] | 5-amino-3-(2-(4-(2-fluoro-4-(2-(piperazin-1-yl)ethoxy)phenyl)piperazin-1-yl)ethyl)-8-(furan-2-yl)thiazolo[5,4-e][1,2,4]triazolo[1,5-c]pyrimidin-2(3H)-one | 608.69 |
| 28 | 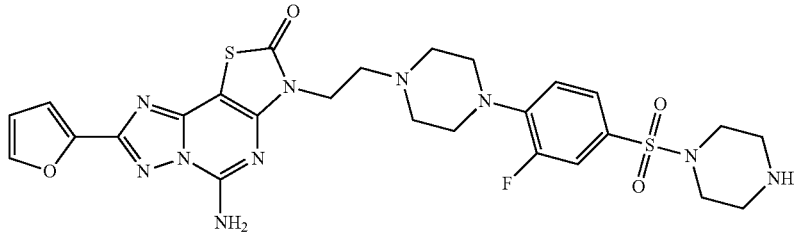 [SMILES: Nc1nc2c(sc(=O)n2CCN2CCN(c3ccc(S(=O)(=O)N4CCNCC4)cc3F)CC2)c2nc(-c3ccco3)nn12] | 5-amino-3-(2-(4-(2-fluoro-4-(piperazin-1-ylsulfonyl)phenyl)piperazin-1-yl)ethyl)-8-(furan-2-yl)thiazolo[5,4-e][1,2,4]triazolo[1,5-c]pyrimidin-2(3H)-one | 628.70 |
| 29 | 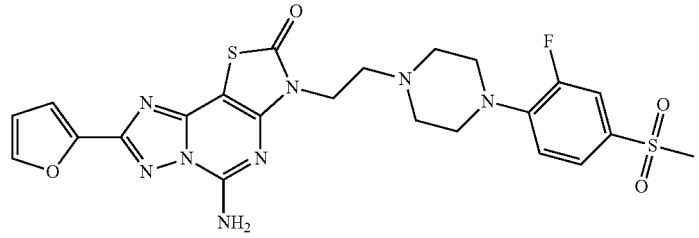 | 5-amino-3-(2-(4-(2-fluoro-4-(methylsulfonyl)phenyl)piperazin-1-yl)ethyl)-8-(furan-2-yl)thiazolo[5,4-e][1,2,4]triazolo[1,5-c]pyrimidin-2(3H)-one | 558.61 |
| 30 | 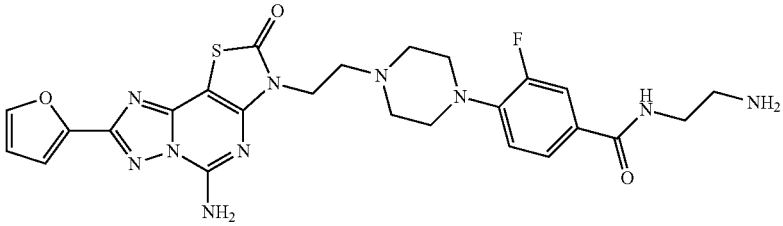 [SMILES: NCCNC(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-aminoethyl)-3-fluorobenzamide | 566.61 |

TABLE 1-continued

| Cpd no | Structure | Chemical name | MW |
|---|---|---|---|
| 31 | 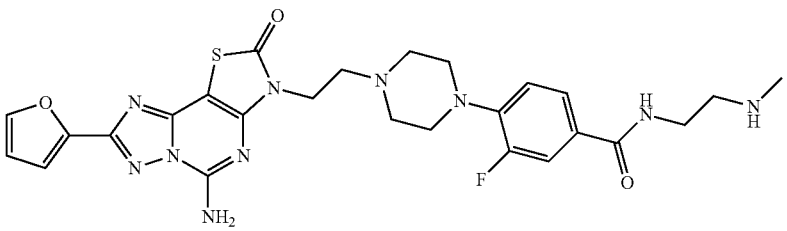 [SMILES: CNCCNC(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylamino)ethyl)benzamide | 580.64 |
| 32 | 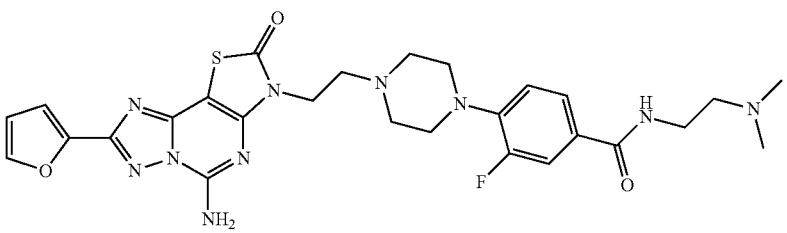 [SMILES: CN(C)CCNC(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-3-fluorobenzamide | 594.66 |
| 33 | 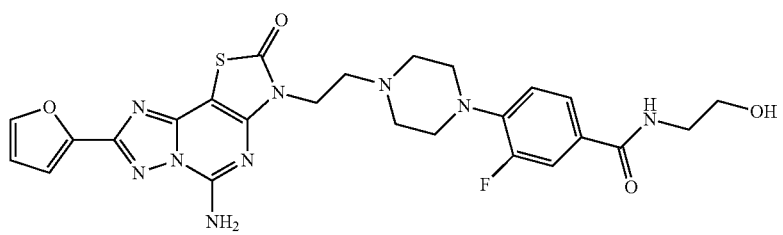 [SMILES: Nc1nc2c(sc(=O)n2CCN2CCN(c3ccc(C(=O)NCCO)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-hydroxyethyl)benzamide | 567.60 |
| 34 | 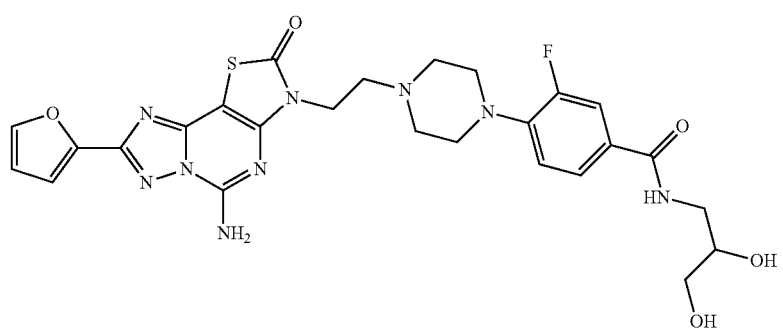 [SMILES: Nc1nc2c(sc(=O)n2CCN2CCN(c3ccc(C(=O)NCC(O)CO)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-3-fluorobenzamide | 597.62 |
| 35 | 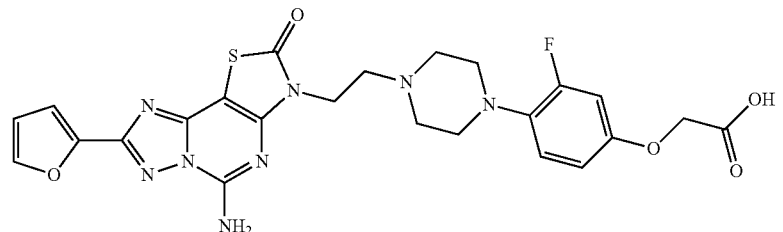 | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)acetic acid | 554.55 |
| 36 | 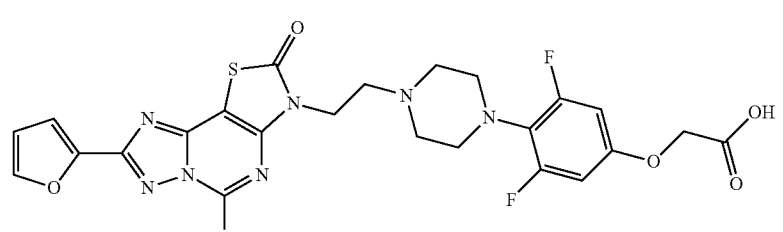 | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3,5-difluorophenoxy)acetic acid | 572.54 |

TABLE 1-continued

| Cpd no | Structure | Chemical name | MW |
|---|---|---|---|
| 37 | 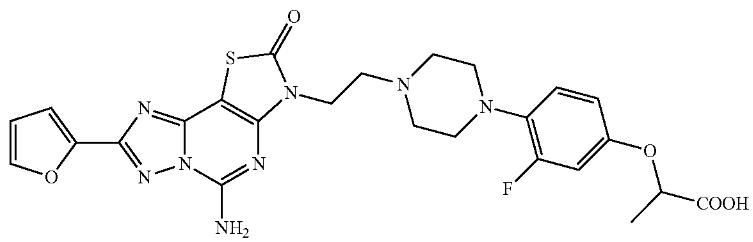 | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid | 568.58 |
| 38 | 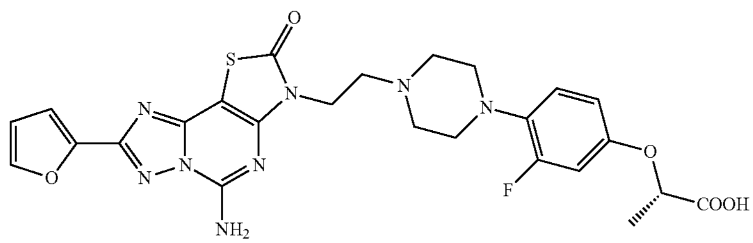 [SMILES: CC(Oc1ccc(N2CCN(CCn3c(=O)sc4c3nc(N)n3nc(-c5ccco5)nc43)CC2)c(F)c1)C(=O)O] | (S)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid | 568.58 |
| 39 | 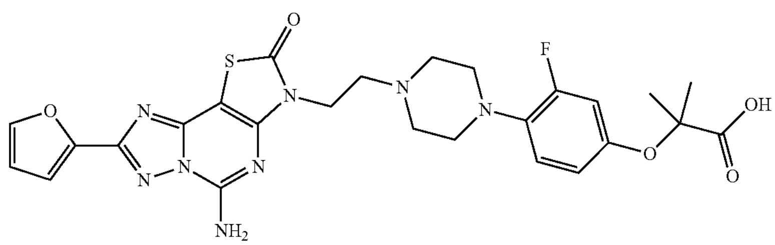 [SMILES: CC(C)(Oc1ccc(N2CCN(CCn3c(=O)sc4c3nc(N)n3nc(-c5ccco5)nc43)CC2)c(F)c1)C(=O)O] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-2-methylpropanoic acid | 582.61 |
| 40 | 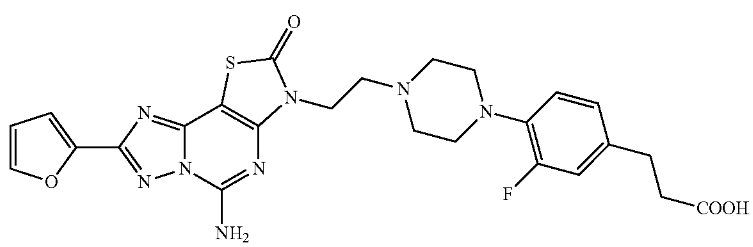 [SMILES: Nc1nc2c(sc(=O)n2CCN2CCN(c3ccc(CCC(=O)O)cc3F)CC2)c2nc(-c3ccco3)nn12] | 3-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenyl)propanoic acid | 552.58 |
| 41 | 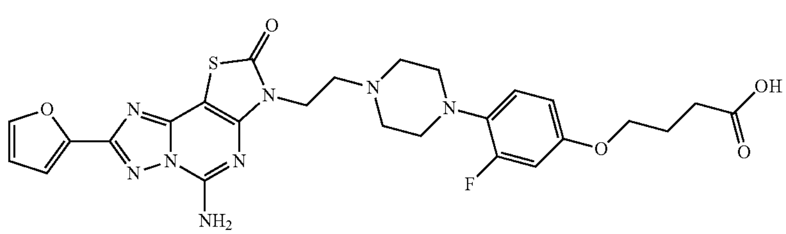 [SMILES: Nc1nc2c(sc(=O)n2CCN2CCN(c3ccc(OCCCC(=O)O)cc3F)CC2)c2nc(-c3ccco3)nn12] | 4-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)butanoic acid | 582.61 |
| 42 | 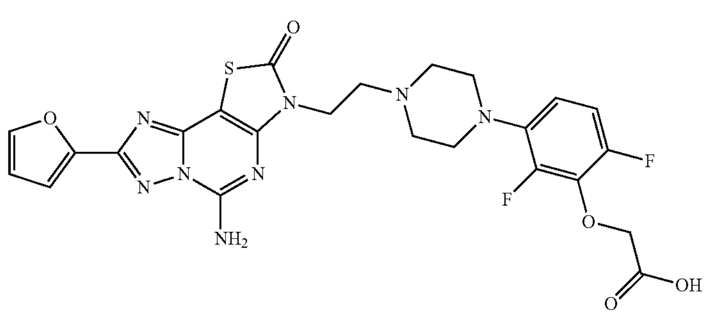 [SMILES: Nc1nc2c(sc(=O)n2CCN2CCN(c3ccc(F)c(OCC(=O)O)c3F)CC2)c2nc(-c3ccco3)nn12] | 2-(3-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,6-difluorophenoxy) acetic acid | 572.54 |

TABLE 1-continued

| Cpd no | Structure | Chemical name | MW |
|---|---|---|---|
| 43 | 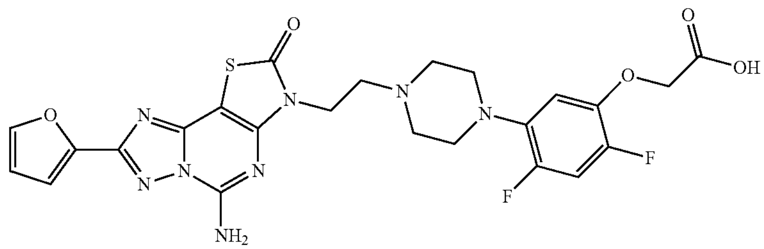 [SMILES: Nc1nc2c(sc(=O)n2CCN2CCN(c3cc(OCC(=O)O)c(F)cc3F)CC2)c2nc(-c3ccco3)nn12] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) acetic acid | 572.54 |
| 44 | 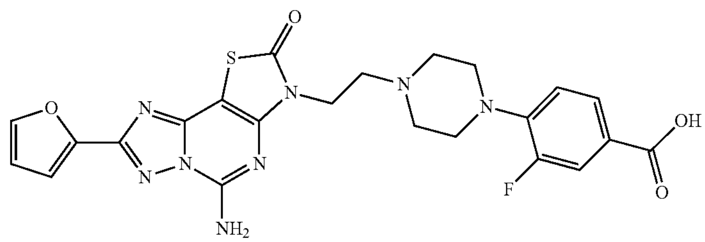 [SMILES: Nc1nc2c(sc(=O)n2CCN2CCN(c3ccc(C(=O)O)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorobenzoic acid | 524.53 |
| 45 | 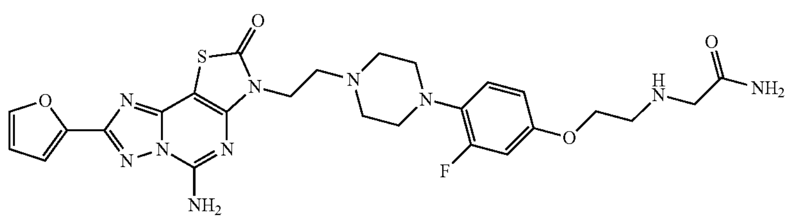 [SMILES: NC(=O)CNCCOc1ccc(N2CCN(CCn3c(=O)sc4c3nc(N)n3nc(-c5ccco5)nc43)CC2)c(F)c1] | 2-((2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)amino)acetamide | 596.64 |
| 46 | 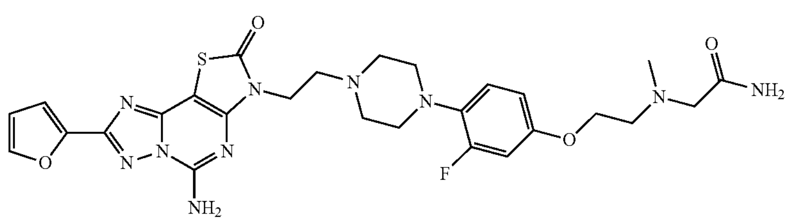 [SMILES: CN(CCOc1ccc(N2CCN(CCn3c(=O)sc4c3nc(N)n3nc(-c5ccco5)nc43)CC2)c(F)c1)CC(N)=O] | 2-((2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)(methyl)amino)acetamide | 610.66 |
| 47 | 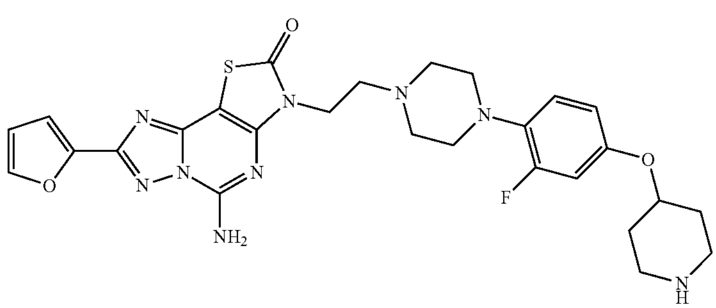 [SMILES: Nc1nc2c(sc(=O)n2CCN2CCN(c3ccc(OC4CCNCC4)cc3F)CC2)c2nc(-c3ccco3)nn12] | 5-amino-3-(2-(4-(2-fluoro-4-(piperidin-4-yloxy)phenyl)piperazin-1-yl)ethyl)-8-(furan-2-yl)thiazolo[5,4-e][1,2,4]triazolo[1,5-c]pyrimidin-2(3H)-one | 579.65 |
| 48 | 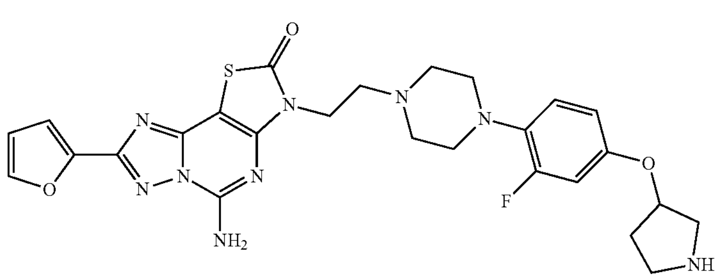 [SMILES: Nc1nc2c(sc(=O)n2CCN2CCN(c3ccc(OC4CCNC4)cc3F)CC2)c2nc(-c3ccco3)nn12] | 5-amino-3-(2-(4-(2-fluoro-4-(pyrrolidin-3-yloxy)phenyl)piperazin-1-yl)ethyl)-8-(furan-2-yl)thiazolo[5,4-e][1,2,4]triazolo[1,5-c]pyrimidin-2(3H)-one | 565.62 |

TABLE 1-continued

| Cpd no | Structure | Chemical name | MW |
|---|---|---|---|
| 49 | 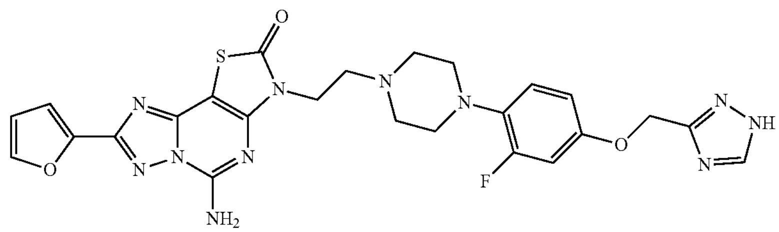 [SMILES: Nc1nc2c(sc(=O)n2CCN2CCN(c3ccc(OCc4nc[nH]n4)cc3F)CC2)c2nc(-c3ccco3)nn12] | 3-(2-(4-(4-((1H-1,2,4-triazol-3-yl)methoxy)-2-fluorophenyl)piperazin-1-yl)ethyl)-5-amino-8-(furan-2-yl)thiazolo[5,4-e][1,2,4]triazolo[1,5-c]pyrimidin-2(3H)-one | 577.59 |
| 50 | 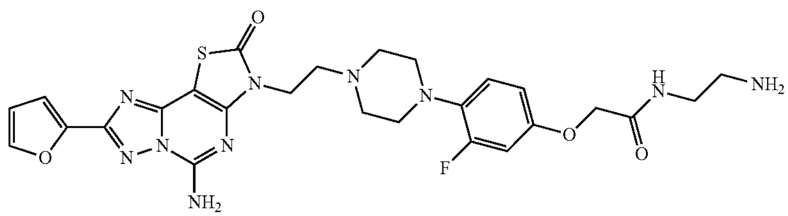 [SMILES: NCCNC(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-(methylamino)ethyl)acetamide | 610.66 |
| 51 | 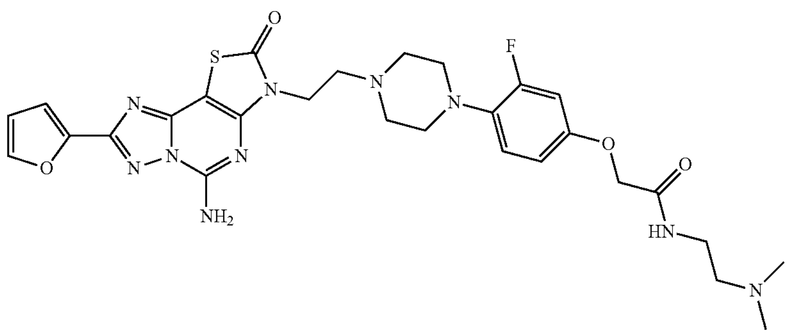 [SMILES: CN(C)CCNC(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-(dimethylamino)ethyl)acetamide | 624.69 |
| 52 | 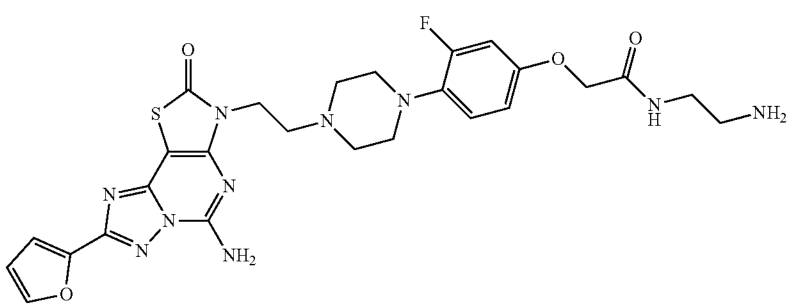 [SMILES: NCCNC(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-aminoethyl)acetamide | 596.64 |
| 53 | 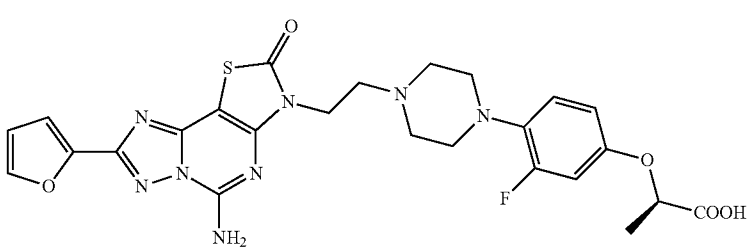 [SMILES: C[C@@H](Oc1ccc(N2CCN(CCn3c(=O)sc4c3nc(N)n3nc(-c5ccco5)nc43)CC2)c(F)c1)C(=O)O] | (R)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid | 568.58 |
| 54 | 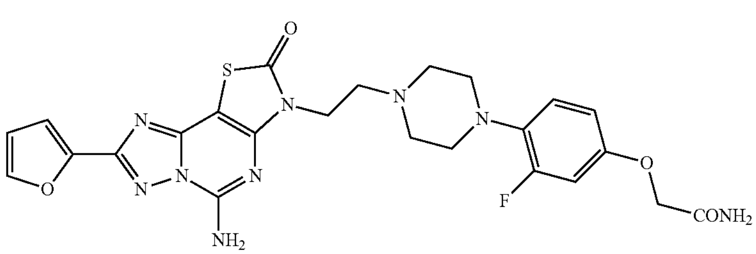 [SMILES: NC(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)acetamide | 553.57 |

TABLE 1-continued

| Cpd no | Structure | Chemical name | MW |
|---|---|---|---|
| 55 | 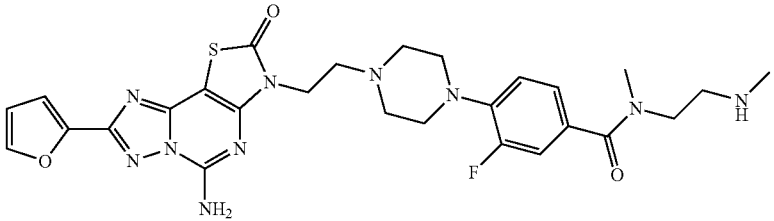 | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-methyl-N-(2-(methylamino)ethyl) benzamide | 594.66 |
| 56 | 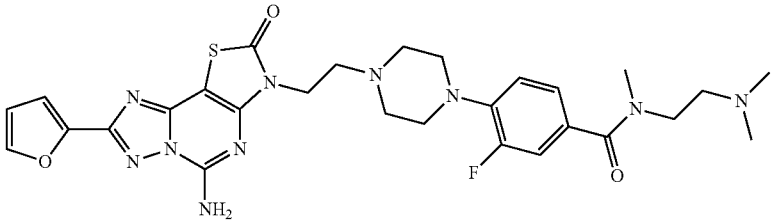 [SMILES: CN(C)CCN(C)C(=O)c1ccc(N2CCN(CCn3c(=O)sc4c3nc(N)n3nc(-c5ccco5)nc43)CC2)c(F)c1] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-3-fluoro-N-methylbenzamide | 608.69 |
| 57 | 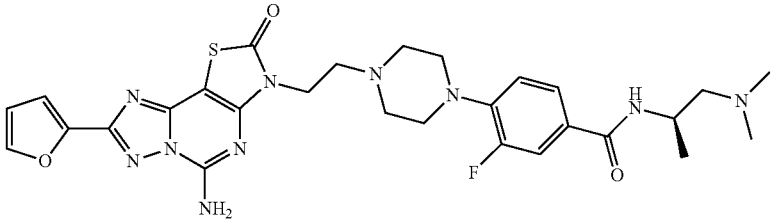 [SMILES: C[C@H](CN(C)C)NC(=O)c1ccc(N2CCN(CCn3c(=O)sc4c3nc(N)n3nc(-c5ccco5)nc43)CC2)c(F)c1] | (R)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(1-(dimethylamino) propan-2-yl)-3-fluorobenzamide | 608.69 |
| 58 | 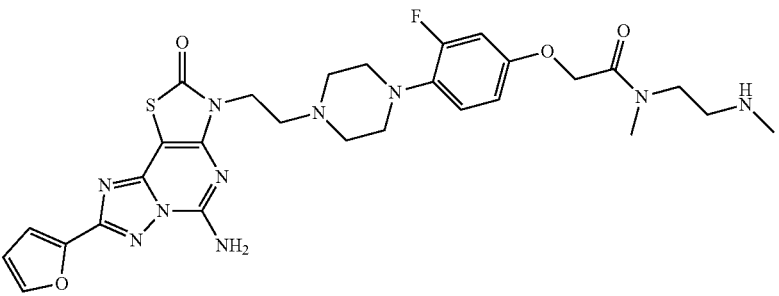 [SMILES: CNCCN(C)C(=O)COc1ccc(N2CCN(CCn3c(=O)sc4c3nc(N)n3nc(-c5ccco5)nc43)CC2)c(F)c1] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-methyl-N-(2-(methylamino)ethyl) acetamide | 624.69 |
| 59 | 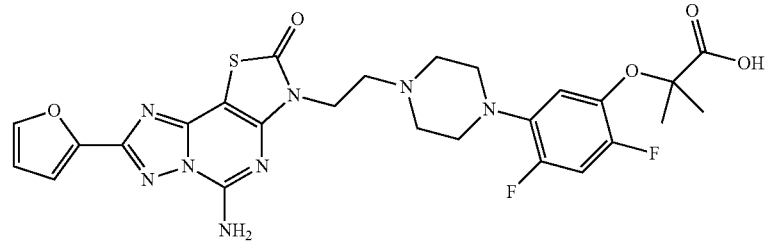 [SMILES: CC(C)(Oc1cc(N2CCN(CCn3c(=O)sc4c3nc(N)n3nc(-c5ccco5)nc43)CC2)c(F)cc1F)C(=O)O] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-2-methylpropanoic acid | 600.60 |
| 60 | 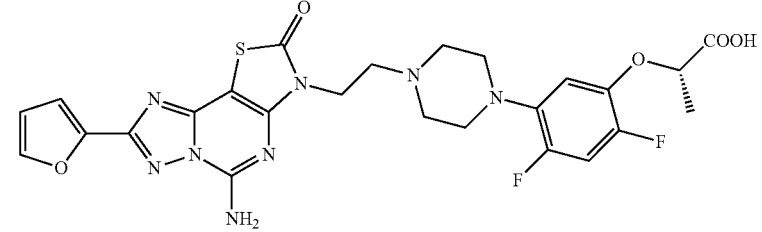 [SMILES: C[C@H](Oc1cc(N2CCN(CCn3c(=O)sc4c3nc(N)n3nc(-c5ccco5)nc43)CC2)c(F)cc1F)C(=O)O] | (S)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) propanoic acid | 586.57 |

TABLE 1-continued

| Cpd no | Structure | Chemical name | MW |
|---|---|---|---|
| 61 | 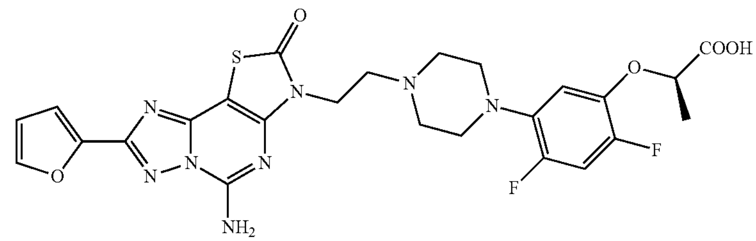 | (R)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) propanoic acid | 586.57 |
| 62 | 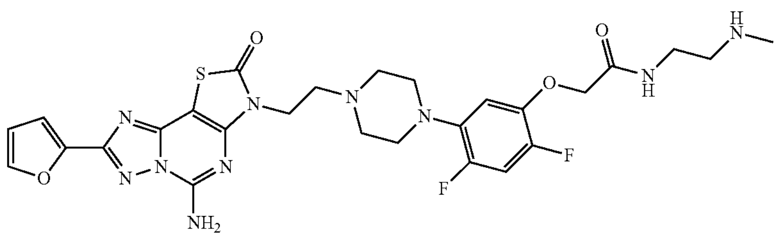 [SMILES: CNCCNC(=O)COc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-(methylamino)ethyl) acetamide | 628.65 |
| 63 | 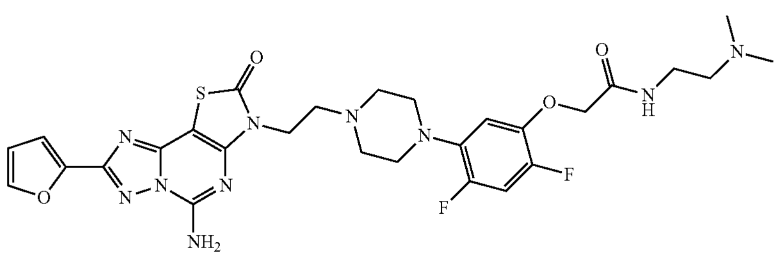 [SMILES: CN(C)CCNC(=O)COc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-(dimethylamino)ethyl) acetamide | 642.68 |
| 64 | 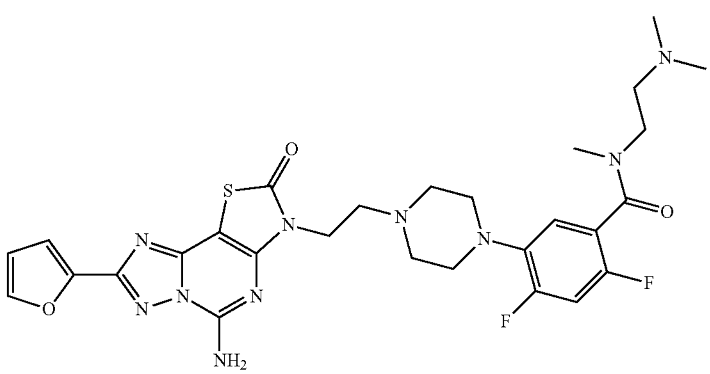 [SMILES: CN(C)CCN(C)C(=O)c1cc(N2CCN(CCn3c(=O)sc4c3nc(N)n3nc(-c5ccco5)nc43)CC2)c(F)cc1F] | 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-2,4-difluoro-N-methylbenzamide | 626.69 |
| 65 | 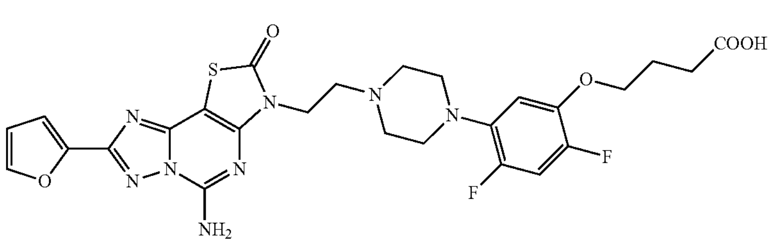 [SMILES: Nc1nc2c(sc(=O)n2CCN2CCN(c3cc(OCCCC(=O)O)c(F)cc3F)CC2)c2nc(-c3ccco3)nn12] | 4-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) butanoic acid | 600.60 |

TABLE 1-continued

| Cpd no | Structure | Chemical name | MW |
|---|---|---|---|
| 66 | 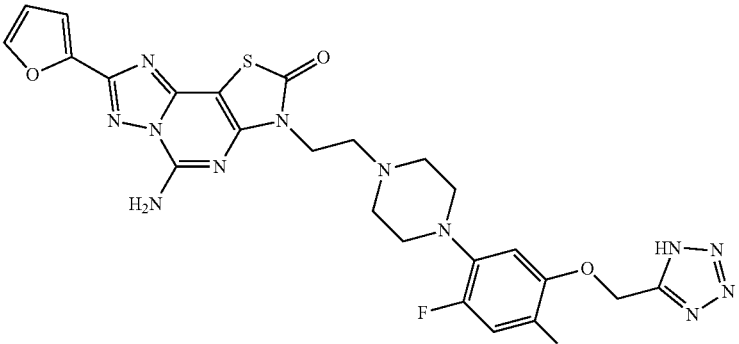 | 3-(2-(4-(5-((1H-tetrazol-5-yl)methoxy)-2,4-difluorophenyl)piperazin-1-yl)ethyl)-5-amino-8-(furan-2-yl)thiazolo[5,4-e][1,2,4]triazolo[1,5-c]pyrimidin-2(3H)-one | 596.58 |
| 67 | 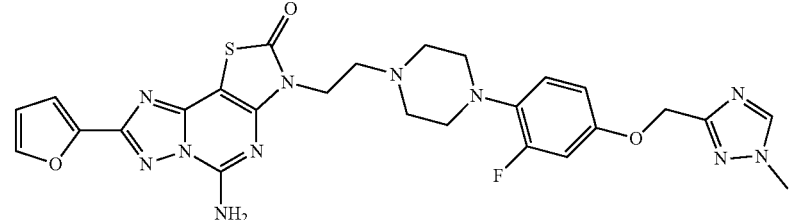 | 5-amino-3-(2-(4-(2-fluoro-4-((1-methyl-1H-1,2,4-triazol-3-yl)methoxy)phenyl)piperazin-1-yl)ethyl)-8-(furan-2-yl)thiazolo[5,4-e][1,2,4]triazolo[1,5-c]pyrimidin-2(3H)-one | 591.62 |
| 68 | 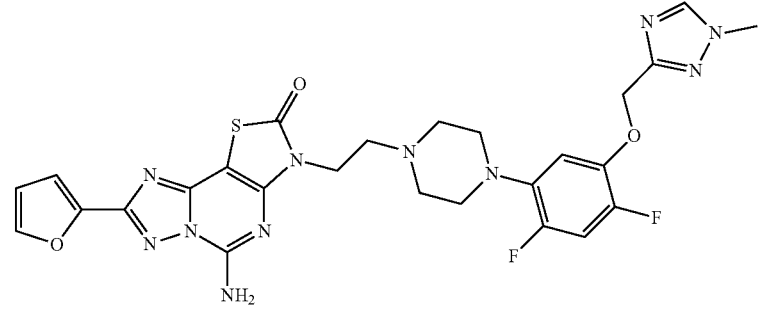 [SMILES: Cn1cnc(COc2cc(N3CCN(CCn4c(=O)sc5c4nc(N)n4nc(-c6ccco6)nc54)CC3)c(F)cc2F)n1] | 5-amino-3-(2-(4-(2,4-difluoro-5-((1-methyl-1H-1,2,4-triazol-3-yl)methoxy)phenyl)piperazin-1-yl)ethyl)-8-(furan-2-yl)thiazolo[5,4-e][1,2,4]triazolo[1,5-c]pyrimidin-2(3H)-one | 609.62 |
| 69 | 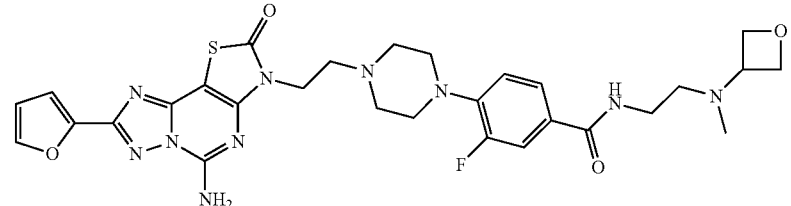 | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methyl(oxetan-3-yl)amino)ethyl)benzamide | 636.70 |
| 70 | 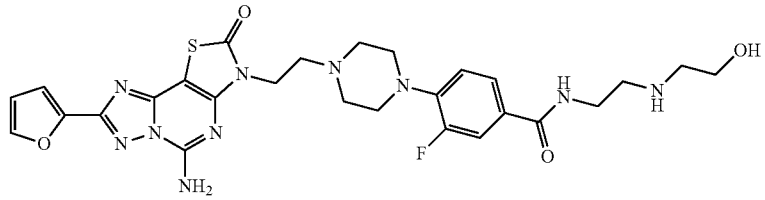 [SMILES: Nc1nc2c(sc(=O)n2CCN2CCN(c3ccc(C(=O)NCCNCCO)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-((2-hydroxyethyl)amino)ethyl)benzamide | 610.67 |
| 71 | 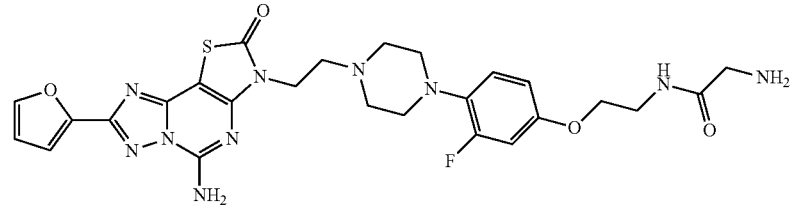 [SMILES: NCC(=O)NCCOc1ccc(N2CCN(CCn3c(=O)sc4c3nc(N)n3nc(-c5ccco5)nc43)CC2)c(F)c1] | 2-amino-N-(2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)acetamide | 596.64 |

TABLE 1-continued

| Cpd no | Structure | Chemical name | MW |
|---|---|---|---|
| 72 | 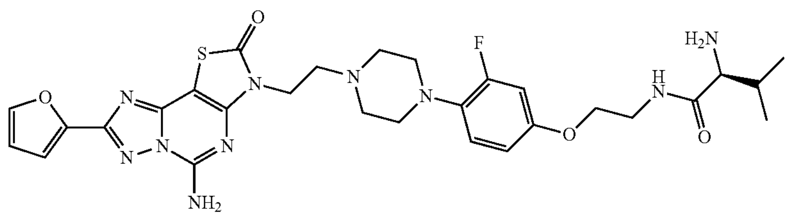 [SMILES: CC(C)[C@H](N)C(=O)NCCOc1ccc(N2CCN(CCn3c(=O)sc4c3nc(N)n3nc(-c5ccco5)nc43)CC2)c(F)c1] | (S)-2-amino-N-(2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)-3-methylbutanamide | 638.72 |
| 73 | 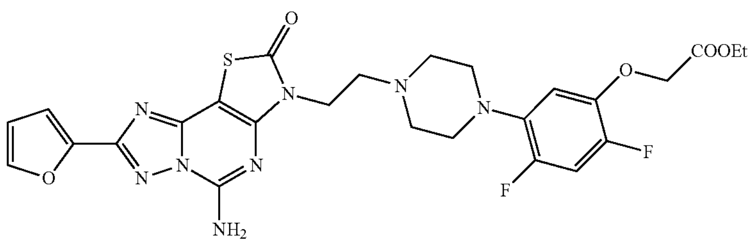 [SMILES: CCOC(=O)COc1cc(N2CCN(CCn3c(=O)sc4c3nc(N)n3nc(-c5ccco5)nc43)CC2)c(F)cc1F] | ethyl 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) acetate | 600.60 |
| 74 | 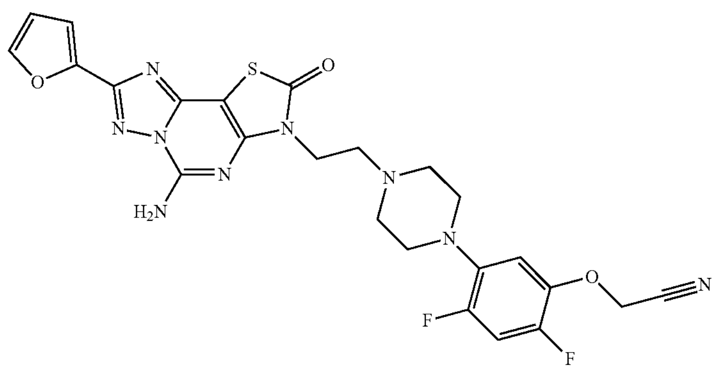 [SMILES: N#CCOc1cc(N2CCN(CCn3c(=O)sc4c3nc(N)n3nc(-c5ccco5)nc43)CC2)c(F)cc1F] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy) acetonitrile | 553.54 |
| 75 | 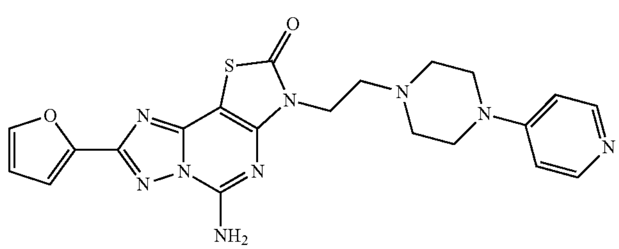 | 5-amino-8-(furan-2-yl)-3-(2-(4-(pyridin-4-yl)piperazin-1-yl)ethyl)thiazolo[5,4-e][1,2,4]triazolo[1,5-c]pyrimidin-2(3H)-one | 463.52 |
| 76 | 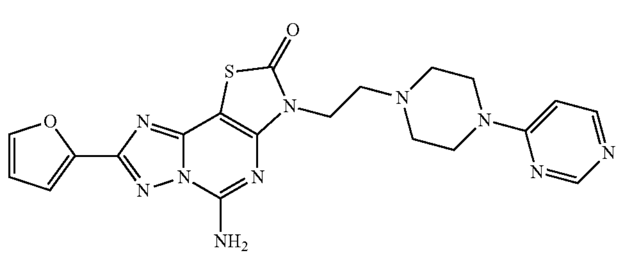 [SMILES: Nc1nc2c(sc(=O)n2CCN2CCN(c3ccncn3)CC2)c2nc(-c3ccco3)nn12] | 5-amino-8-(furan-2-yl)-3-(2-(4-(pyrimidin-4-yl)piperazin-1-yl)ethyl)thiazolo[5,4-e][1,2,4]triazolo[1,5-c]pyrimidin-2(3H)-one | 464.50 |

TABLE 1-continued

| Cpd no | Structure | Chemical name | MW |
|---|---|---|---|
| 77 | 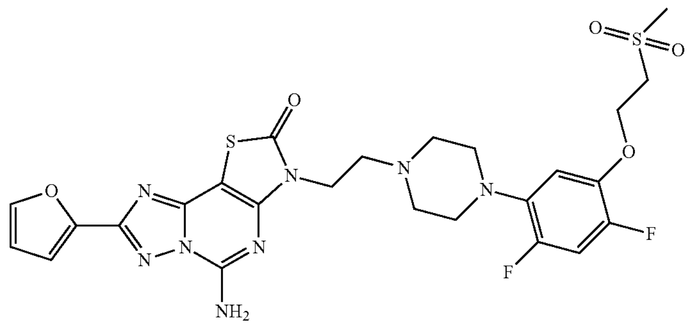 [SMILES: CS(=O)(=O)CCOc1cc(N2CCN(CCn3c(=O)sc4c3nc(N)n3nc(-c5ccco5)nc43)CC2)c(F)cc1F] | 5-amino-3-(2-(4-(2,4-difluoro-5-(2-(methylsulfonyl)ethoxy)phenyl)piperazin-1-yl)ethyl)-8-(furan-2-yl)thiazolo[5,4-e][1,2,4]triazolo[1,5-c]pyrimidin-2(3H)-one | 620.65 |
| 78 | 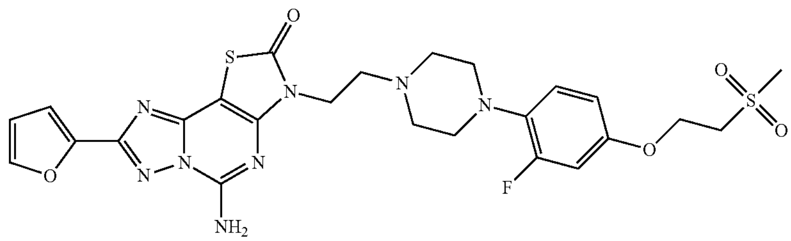 [SMILES: CS(=O)(=O)CCOc1ccc(N2CCN(CCn3c(=O)sc4c3nc(N)n3nc(-c5ccco5)nc43)CC2)c(F)c1] | 5-amino-3-(2-(4-(2-fluoro-4-(2-(methylsulfonyl)ethoxy)phenyl)piperazin-1-yl)ethyl)-8-(furan-2-yl)thiazolo[5,4-e][1,2,4]triazolo[1,5-c]pyrimidin-2(3H)-one | 602.66 |
| 79 | 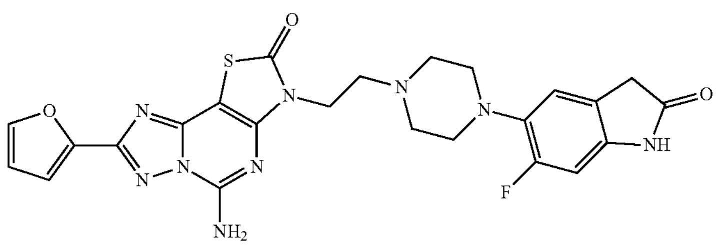 [SMILES: Nc1nc2c(sc(=O)n2CCN2CCN(c3cc4c(cc3F)NC(=O)C4)CC2)c2nc(-c3ccco3)nn12] | 5-amino-3-(2-(4-(6-fluoro-2-oxoindolin-5-yl)piperazin-1-yl)ethyl)-8-(furan-2-yl)thiazolo[5,4-e][1,2,4]triazolo[1,5-c]pyrimidin-2(3H)-one | 535.55 |
| 80 | 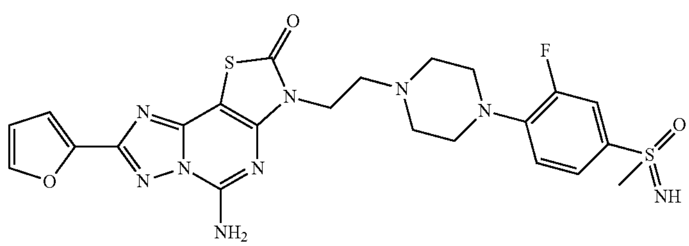 [SMILES: CS(=N)(=O)c1ccc(N2CCN(CCn3c(=O)sc4c3nc(N)n3nc(-c5ccco5)nc43)CC2)c(F)c1] | 5-amino-3-(2-(4-(2-fluoro-4-(S-methylsulfonimidoyl)phenyl)piperazin-1-yl)ethyl)-8-(furan-2-yl)thiazolo[5,4-e][1,2,4]triazolo[1,5-c]pyrimidin-2(3H)-one | 557.62 |
| 81 | 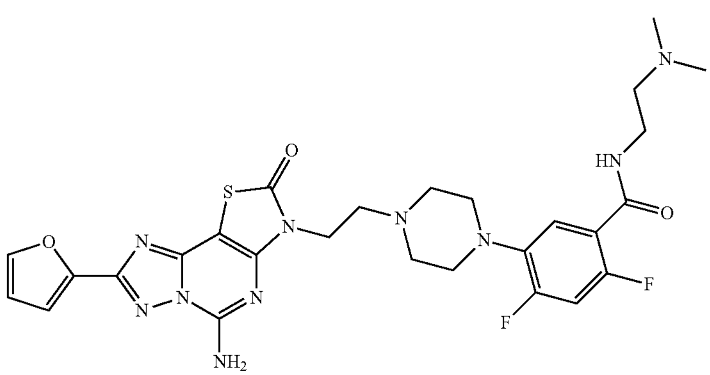 [SMILES: CN(C)CCNC(=O)c1cc(N2CCN(CCn3c(=O)sc4c3nc(N)n3nc(-c5ccco5)nc43)CC2)c(F)cc1F] | 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-2,4-difluorobenzamide | 612.65 |

TABLE 1-continued

| Cpd no | Structure | Chemical name | MW |
|---|---|---|---|
| 82 | 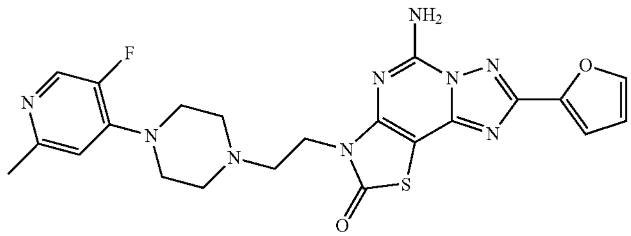 [SMILES: Cc1cc(N2CCN(CCn3c(=O)sc4c3nc(N)n3nc(-c5ccco5)nc43)CC2)c(F)cn1] | 5-amino-3-(2-(4-(5-fluoro-2-methylpyridin-4-yl)piperazin-1-yl)ethyl)-8-(furan-2-yl)thiazolo[5,4-e][1,2,4]triazolo[1,5-c]pyrimidin-2(3H)-one | 495.53 |
| 83 | 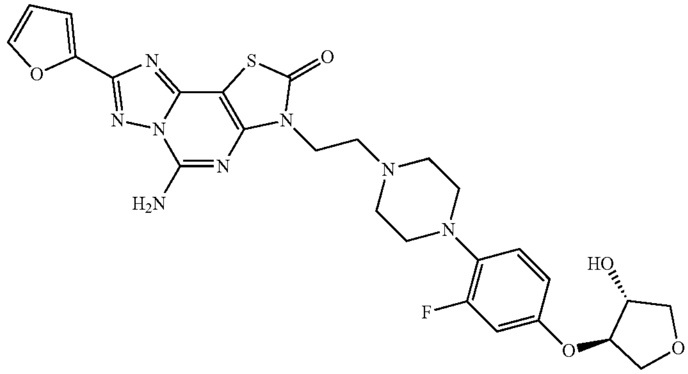 [SMILES: Nc1nc2c(sc(=O)n2CCN2CCN(c3ccc(O[C@@H]4COC[C@H]4O)cc3F)CC2)c2nc(-c3ccco3)nn12] | 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one | 582.61 |
| 84 | 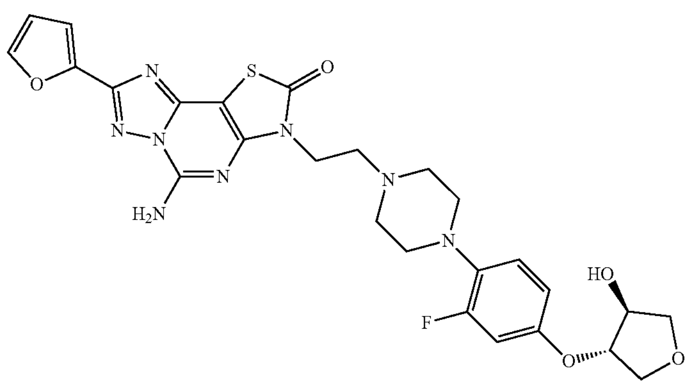 [SMILES: Nc1nc2c(sc(=O)n2CCN2CCN(c3ccc(O[C@H]4COC[C@@H]4O)cc3F)CC2)c2nc(-c3ccco3)nn12] | 5-amino-3-(2-(4-(2-fluoro-4-(((3S,4S)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one | 582.61 |
| 85 | 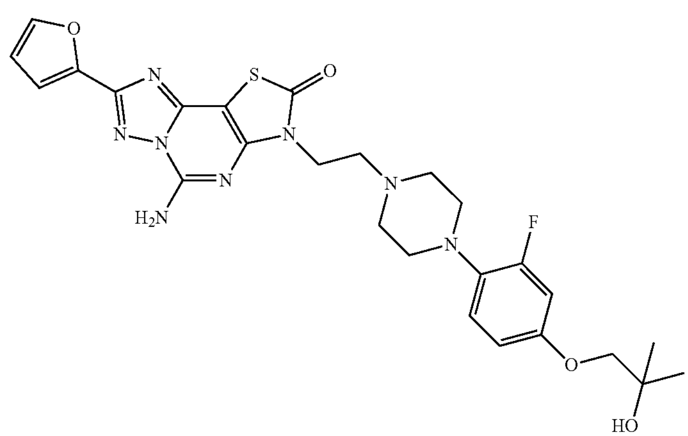 [SMILES: CC(C)(O)COc1ccc(N2CCN(CCn3c(=O)sc4c3nc(N)n3nc(-c5ccco5)nc43)CC2)c(F)c1] | 5-amino-3-(2-(4-(2-fluoro-4-(2-hydroxy-2-methylpropoxy)phenyl)piperazin-1-yl)ethyl)-8-(furan-2-yl)thiazolo[5,4-e][1,2,4]triazolo[1,5-c]pyrimidin-2(3H)-one | 568.62 |

TABLE 1-continued

| Cpd no | Structure | Chemical name | MW |
|---|---|---|---|
| 86 | 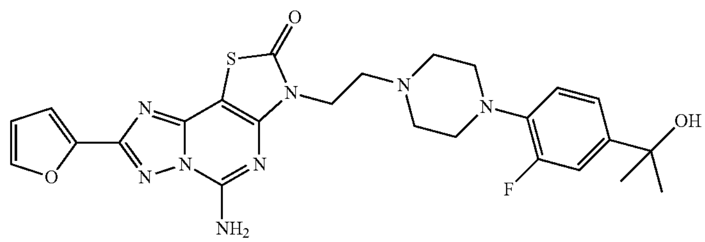 [SMILES: CC(C)(O)c1ccc(N2CCN(CCn3c(=O)sc4c3nc(N)n3nc(-c5ccco5)nc43)CC2)c(F)c1] | 5-amino-3-(2-(4-(2-fluoro-4-(2-hydroxypropan-2-yl)phenyl)piperazin-1-yl)ethyl)-8-(furan-2-yl)thiazolo[5,4-e][1,2,4]triazolo[1,5-c]pyrimidin-2(3H)-one | 538.60 |
| 87 | 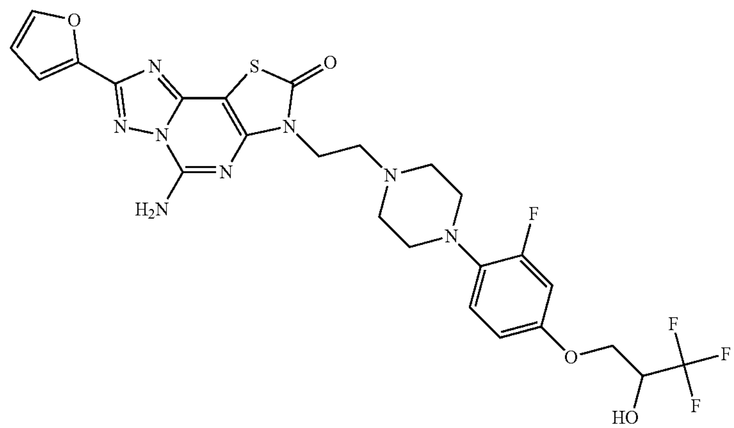 [SMILES: Nc1nc2c(sc(=O)n2CCN2CCN(c3ccc(OCC(O)C(F)(F)F)cc3F)CC2)c2nc(-c3ccco3)nn12] | 5-amino-3-(2-(4-(2-fluoro-4-(3,3,3-trifluoro-2-hydroxypropoxy)phenyl)piperazin-1-yl)ethyl)-8-(furan-2-yl)thiazolo[5,4-e][1,2,4]triazolo[1,5-c]pyrimidin-2(3H)-one | 608.57 |
| 88 | 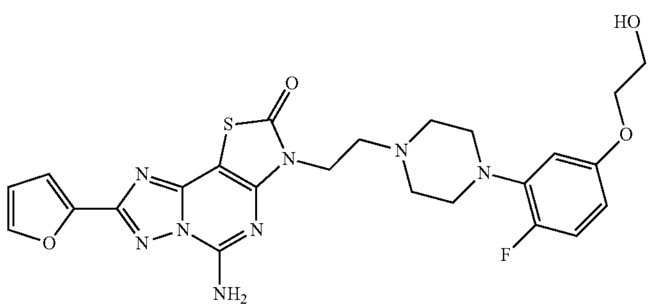 [SMILES: Nc1nc2c(sc(=O)n2CCN2CCN(c3cc(OCCO)ccc3F)CC2)c2nc(-c3ccco3)nn12] | 5-amino-3-(2-(4-(2-fluoro-5-(2-hydroxyethoxy)phenyl)piperazin-1-yl)ethyl)-8-(furan-2-yl)thiazolo[5,4-e][1,2,4]triazolo[1,5-c]pyrimidin-2(3H)-one | 540.57 |
| 89 | 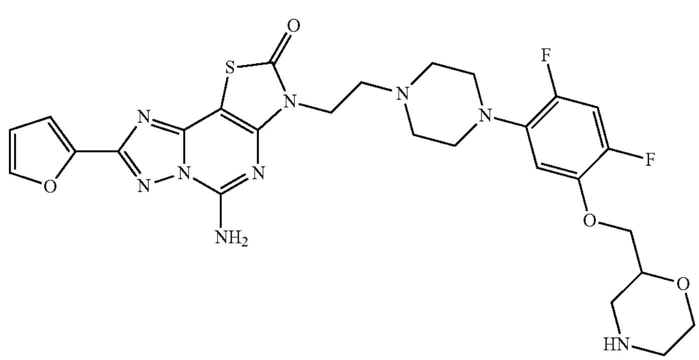 [SMILES: Nc1nc2c(sc(=O)n2CCN2CCN(c3cc(OCC4CNCCO4)c(F)cc3F)CC2)c2nc(-c3ccco3)nn12] | 5-amino-3-(2-(4-(2,4-difluoro-5-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one | 613.64 |

TABLE 1-continued

| Cpd no | Structure | Chemical name | MW |
|---|---|---|---|
| 90 | 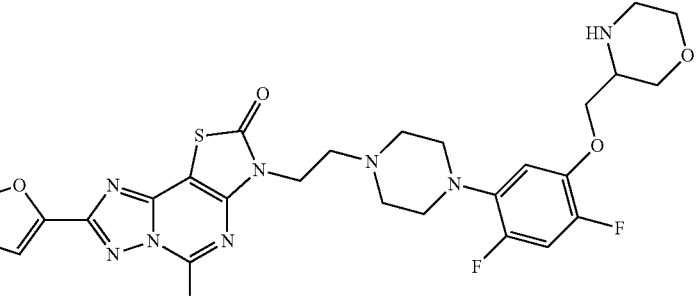 | 5-amino-3-(2-(4-(2,4-difluoro-5-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one | 613.64 |
| 91 | 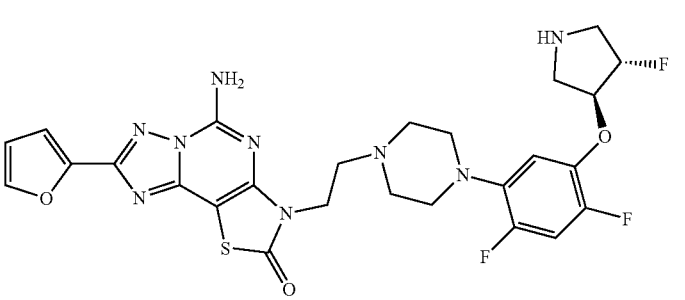 [SMILES: Nc1nc2c(sc(=O)n2CCN2CCN(c3cc(O[C@H]4CNC[C@@H]4F)c(F)cc3F)CC2)c2nc(-c3ccco3)nn12] | 5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |
| 92 | 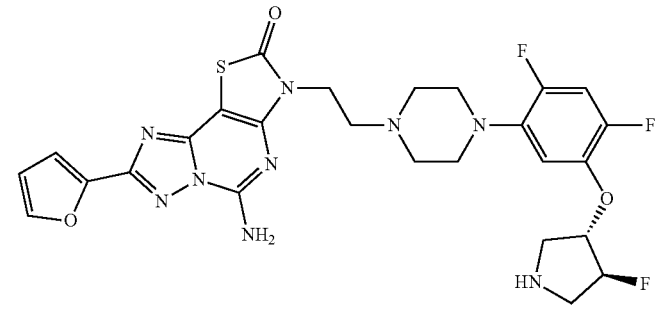 [SMILES: Nc1nc2c(sc(=O)n2CCN2CCN(c3cc(O[C@H]4CNC[C@@H]4F)c(F)cc3F)CC2)c2nc(-c3ccco3)nn12] | 5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |
| 93 | 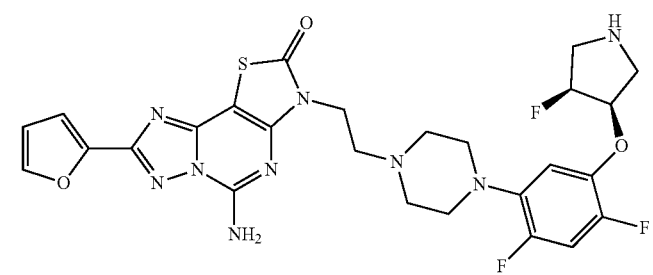 [SMILES: Nc1nc2c(sc(=O)n2CCN2CCN(c3cc(O[C@@H]4CNC[C@@H]4F)c(F)cc3F)CC2)c2nc(-c3ccco3)nn12] | 5-amino-3-(2-(4-(2,4-difluoro-5-(((3R,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |
| 94 | 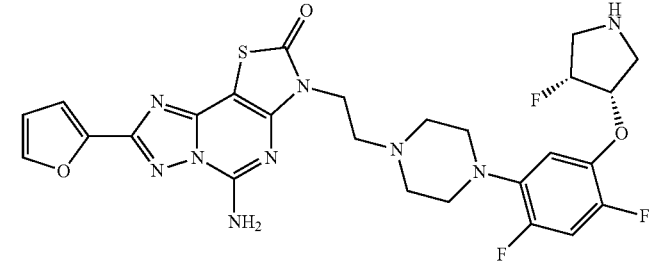 [SMILES: Nc1nc2c(sc(=O)n2CCN2CCN(c3cc(O[C@H]4CNC[C@H]4F)c(F)cc3F)CC2)c2nc(-c3ccco3)nn12] | 5-amino-3-(2-(4-(2,4-difluoro-5-(((3S,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 601.60 |

TABLE 1-continued

| Cpd no | Structure | Chemical name | MW |
|---|---|---|---|
| 95 | 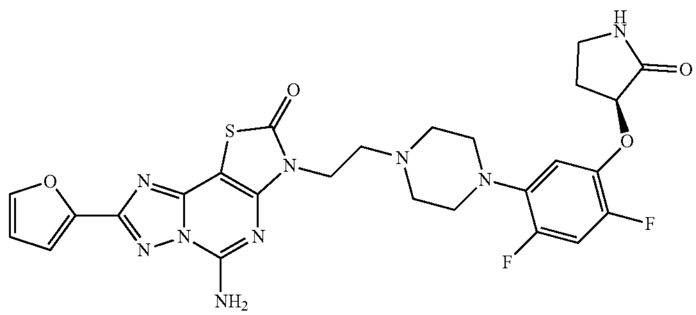 [SMILES: Nc1nc2c(sc(=O)n2CCN2CCN(c3cc(O[C@H]4CCNC4=O)c(F)cc3F)CC2)c2nc(-c3ccco3)nn12] | (S)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 597.60 |
| 96 | 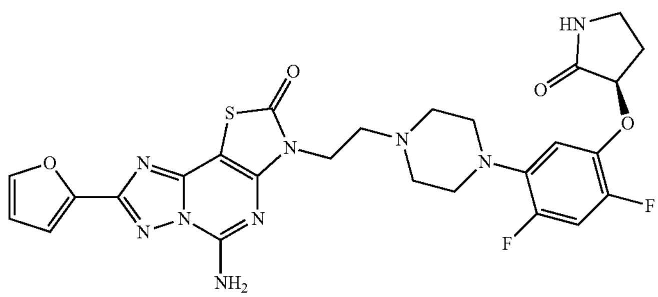 [SMILES: Nc1nc2c(sc(=O)n2CCN2CCN(c3cc(O[C@@H]4CCNC4=O)c(F)cc3F)CC2)c2nc(-c3ccco3)nn12] | (R)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 597.60 |
| 97 | 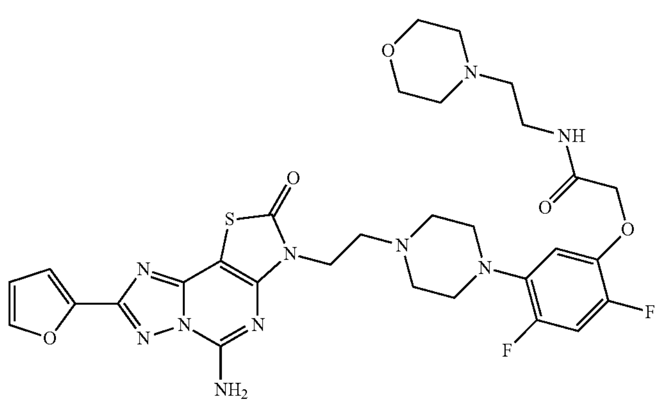 [SMILES: Nc1nc2c(sc(=O)n2CCN2CCN(c3cc(OCC(=O)NCCN4CCOCC4)c(F)cc3F)CC2)c2nc(-c3ccco3)nn12] | 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1--yl)-2,4-difluorophenoxy)-N-(2-morpholinoethyl)acetamide | 684.72 |
| 98 | 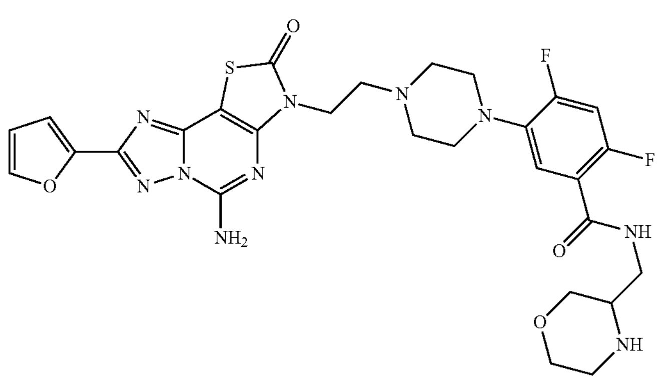 [SMILES: Nc1nc2c(sc(=O)n2CCN2CCN(c3cc(C(=O)NCC4COCCN4)c(F)cc3F)CC2)c2nc(-c3ccco3)nn12] | 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(morpholin-3-ylmethyl)benzamide | 640.66 |

TABLE 1-continued

| Cpd no | Structure | Chemical name | MW |
|---|---|---|---|
| 99 | 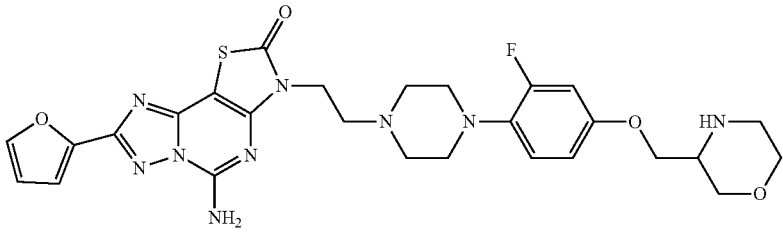 [SMILES: Nc1nc2c(sc(=O)n2CCN2CCN(c3ccc(OCC4COCCN4)cc3F)CC2)c2nc(-c3ccco3)nn12] | 5-amino-3-(2-(4-(2-fluoro-4-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one | 595.65 |
| 100 | 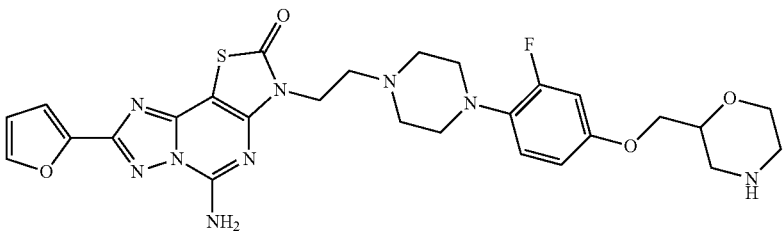 [SMILES: Nc1nc2c(sc(=O)n2CCN2CCN(c3ccc(OCC4CNCCO4)cc3F)CC2)c2nc(-c3ccco3)nn12] | 5-amino-3-(2-(4-(2-fluoro-4-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one | 595.65 |
| 101 | 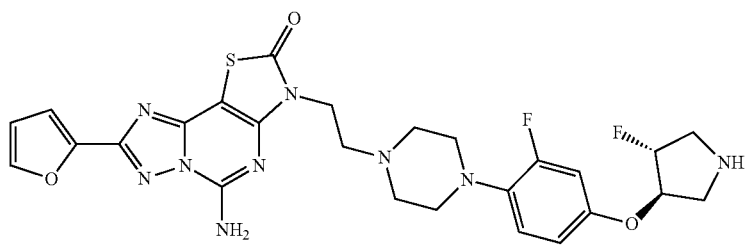 [SMILES: Nc1nc2c(sc(=O)n2CCN2CCN(c3ccc(O[C@@H]4CNC[C@H]4F)cc3F)CC2)c2nc(-c3ccco3)nn12] | 5-amino-3-(2-(4-(2-fluoro-4-(((3R,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |
| 102 | 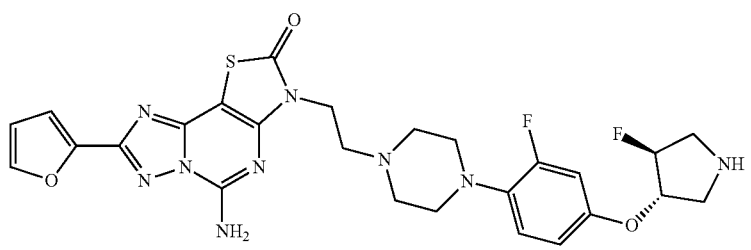 [SMILES: Nc1nc2c(sc(=O)n2CCN2CCN(c3ccc(O[C@H]4CNC[C@@H]4F)cc3F)CC2)c2nc(-c3ccco3)nn12] | 5-amino-3-(2-(4-(2-fluoro-4-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |
| 103 | 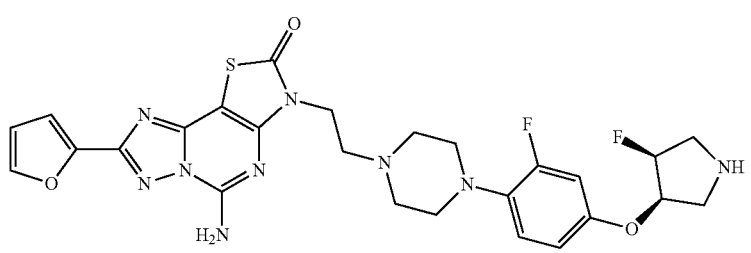 [SMILES: Nc1nc2c(sc(=O)n2CCN2CCN(c3ccc(O[C@@H]4CNC[C@@H]4F)cc3F)CC2)c2nc(-c3ccco3)nn12] | 5-amino-3-(2-(4-(2-fluoro-4-(((3R,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |
| 104 | 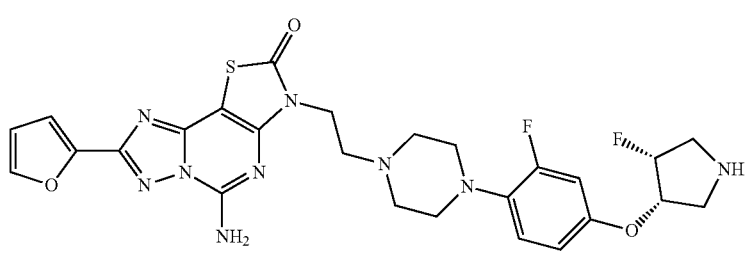 [SMILES: Nc1nc2c(sc(=O)n2CCN2CCN(c3ccc(O[C@H]4CNC[C@H]4F)cc3F)CC2)c2nc(-c3ccco3)nn12] | 5-amino-3-(2-(4-(2-fluoro-4-(((3S,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one | 583.61 |

TABLE 1-continued

| Cpd no | Structure | Chemical name | MW |
|---|---|---|---|
| 105 | 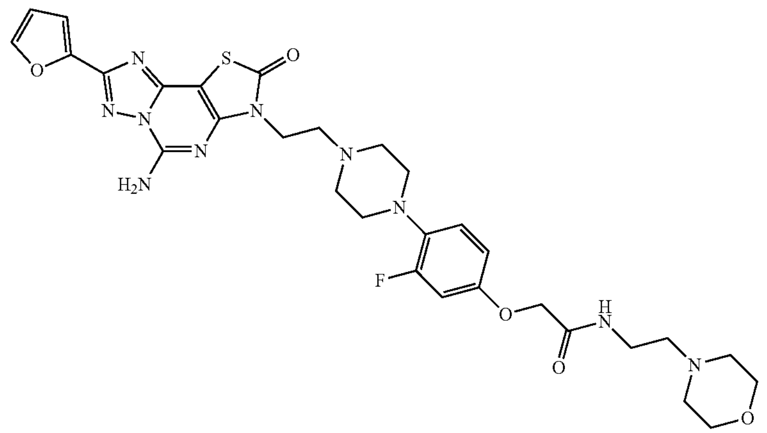 [SMILES: Nc1nc2c(sc(=O)n2CCN2CCN(c3ccc(OCC(=O)NCCN4CCOCC4)cc3F)CC2)c2nc(-c3ccco3)nn12] | 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-morpholinoethyl)acetamide | 666.73 |
| 106 | 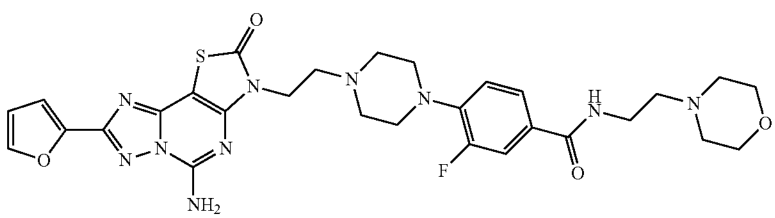 [SMILES: Nc1nc2c(sc(=O)n2CCN2CCN(c3ccc(C(=O)NCCN4CCOCC4)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-morpholinoethyl)benzamide | 636.70 |
| 107 | 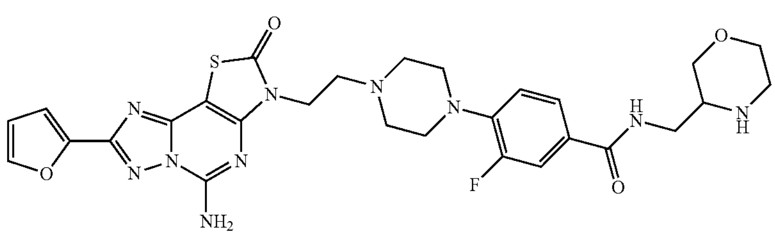 [SMILES: Nc1nc2c(sc(=O)n2CCN2CCN(c3ccc(C(=O)NCC4COCCN4)cc3F)CC2)c2nc(-c3ccco3)nn12] | 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(morpholin-3-ylmethyl)benzamide | 622.67 |
| 108 | 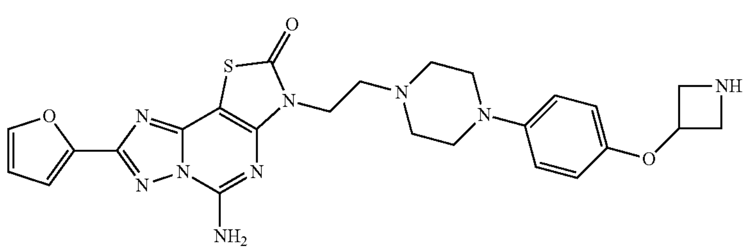 [SMILES: Nc1nc2c(sc(=O)n2CCN2CCN(c3ccc(OC4CNC4)cc3)CC2)c2nc(-c3ccco3)nn12] | 5-amino-3-(2-(4-(4-(azetidin-3-yloxy)phenyl)piperazin-1-yl)ethyl)-8-(furan-2-yl)thiazolo[5,4-e][1,2,4]triazolo[1,5-c]pyrimidin-2(3H)-one | 533.61 |
| 109 | 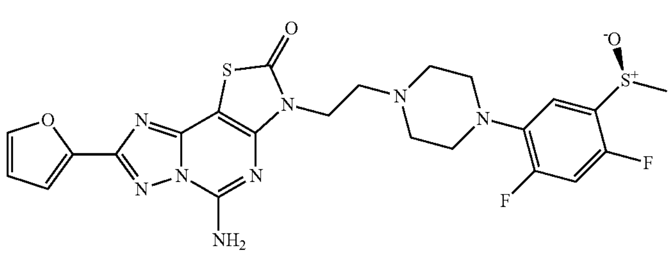 | (S)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one | 560.60 |

TABLE 1-continued

| Cpd no | Chemical name | MW |
|---|---|---|
| 110 | (R)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one | 560.60 |
| 111 | 5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one | 630.69 |
| 112 | 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one | 630.69 |
| 113 | (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide | 631.68 |

TABLE 1-continued

| Cpd no | Structure | Chemical name | MW |
|---|---|---|---|
| 114 | 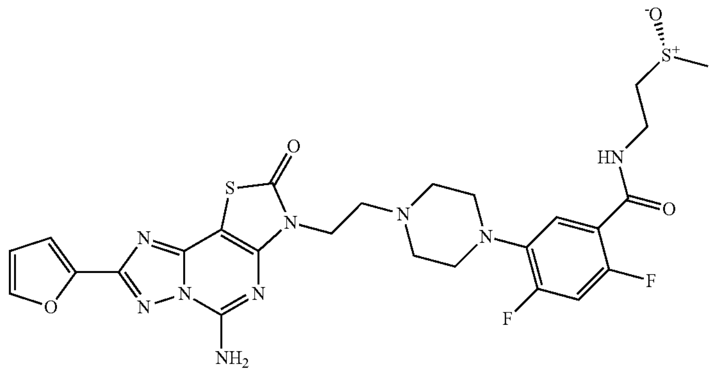 | (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide | 631.68 |
| 115 | 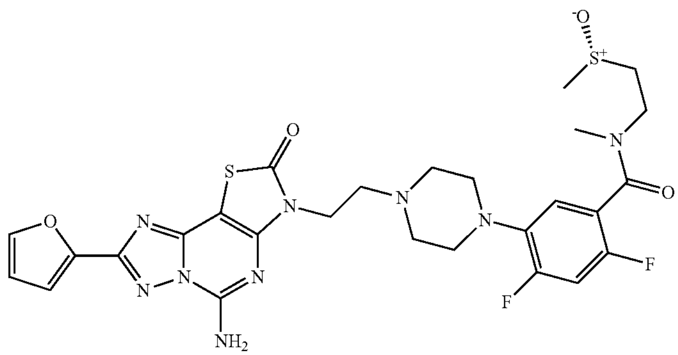 | (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-methyl-N-(2-(methylsulfinyl)ethyl)benzamide | 645.70 |
| 116 | 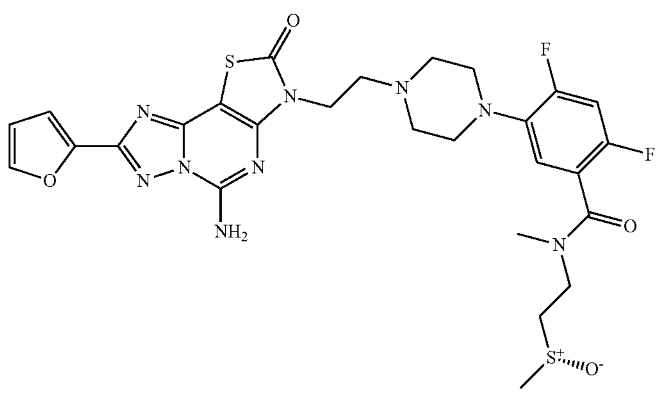 [SMILES: CN(CC[S@@+](C)[O-])C(=O)c1cc(N2CCN(CCn3c(=O)sc4c3nc(N)n3nc(-c5ccco5)nc43)CC2)c(F)cc1F] | (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-methyl-N-(2-(methylsulfinyl)ethyl)benzamide | 645.70 |
| 117 | 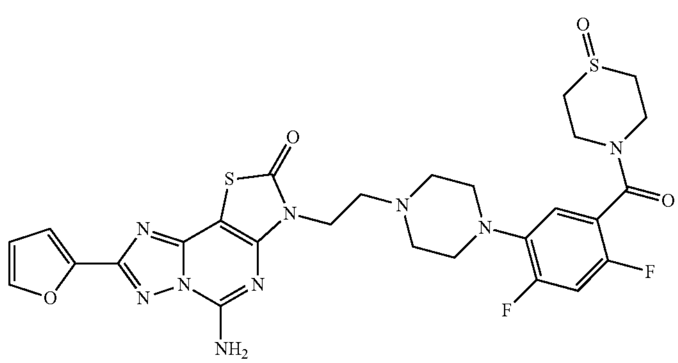 [SMILES: Nc1nc2c(sc(=O)n2CCN2CCN(c3cc(C(=O)N4CCS(=O)CC4)c(F)cc3F)CC2)c2nc(-c3ccco3)nn12] | 5-amino-3-(2-(4-(2,4-difluoro-5-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one | 643.69 |

| Cpd no | Structure | Chemical name | MW |
|---|---|---|---|
| 118 | 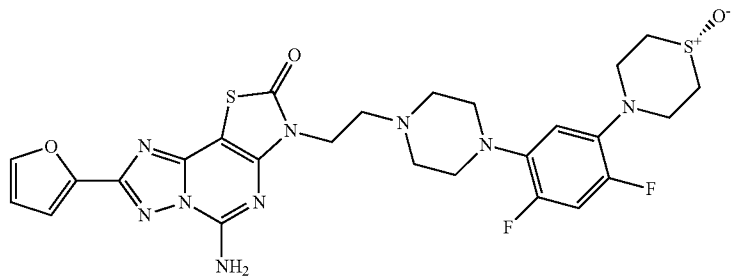 | 5-amino-3-(2-(4-(2,4-difluoro-5-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one | 615.68 |
| 119 | 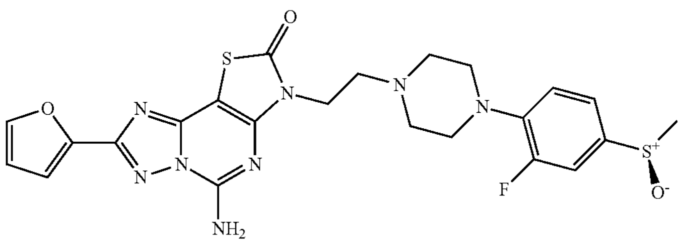 [SMILES: C[S@@+]([O-])c1ccc(N2CCN(CCn3c(=O)sc4c3nc(N)n3nc(-c5ccco5)nc43)CC2)c(F)c1] | (R)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one | 542.61 |
| 120 | 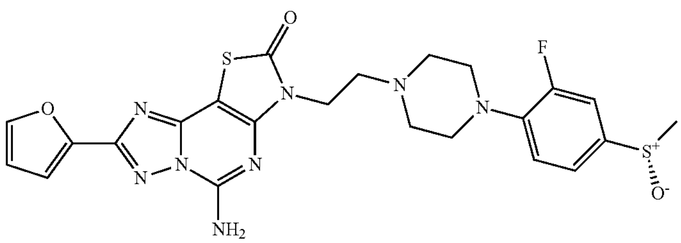 [SMILES: C[S@+]([O-])c1ccc(N2CCN(CCn3c(=O)sc4c3nc(N)n3nc(-c5ccco5)nc43)CC2)c(F)c1] | (S)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one | 542.61 |
| 121 | 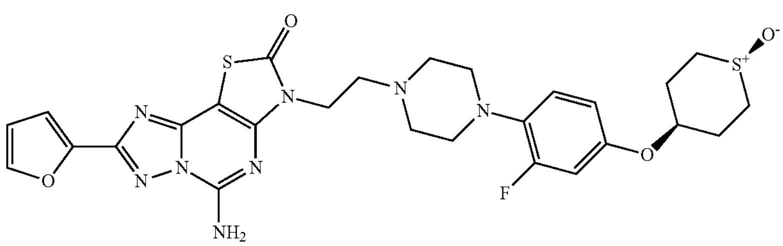 | 5-amino-3-(2-(4-(2-fluoro-4-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one | 612.70 |
| 122 | 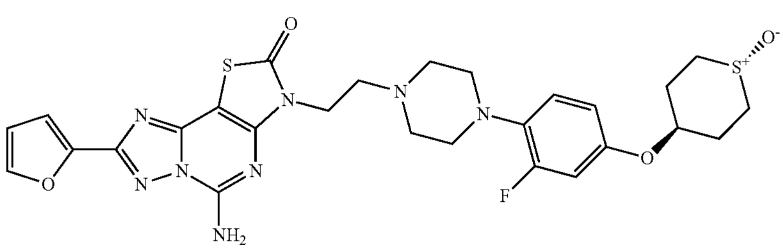 [SMILES: Nc1nc2c(sc(=O)n2CCN2CCN(c3ccc(O[C@H]4CC[S@+]([O-])CC4)cc3F)CC2)c2nc(-c3ccco3)nn12] | 5-amino-3-(2-(4-(2-fluoro-4-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one | 612.70 |
| 123 | 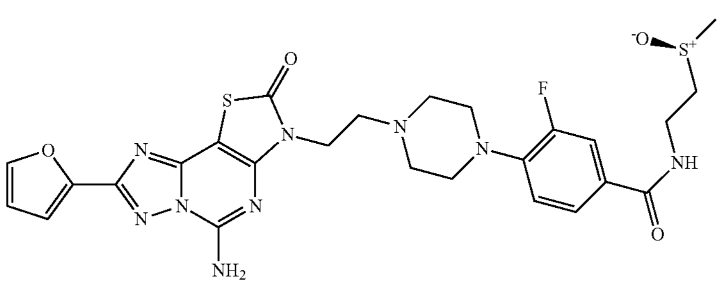 | (S)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide | 613.69 |

TABLE 1-continued

| Cpd no | Structure | Chemical name | MW |
|---|---|---|---|
| 124 | 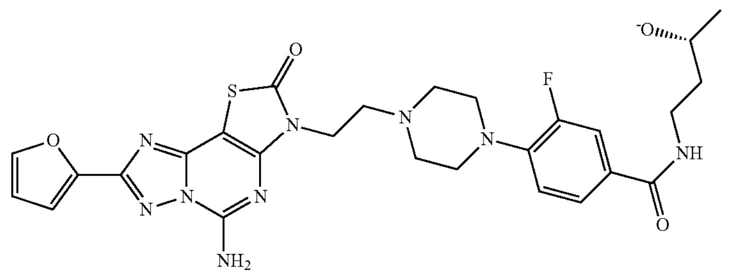 | (R)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide | 613.69 |
| 125 | 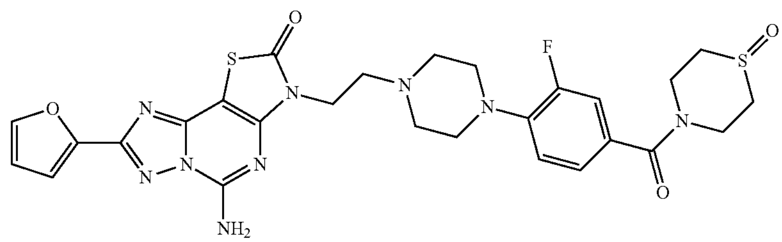 [SMILES: Nc1nc2c(sc(=O)n2CCN2CCN(c3ccc(C(=O)N4CCS(=O)CC4)cc3F)CC2)c2nc(-c3ccco3)nn12] | 5-amino-3-(2-(4-(2-fluoro-4-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one | 625.70 |
| 126 | 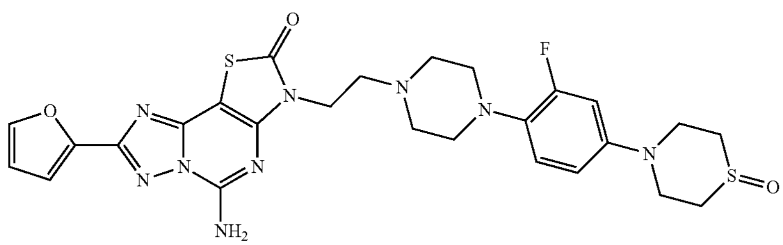 [SMILES: Nc1nc2c(sc(=O)n2CCN2CCN(c3ccc(N4CCS(=O)CC4)cc3F)CC2)c2nc(-c3ccco3)nn12] | 5-amino-3-(2-(4-(2-fluoro-4-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one | 597.69 |
| 127 | 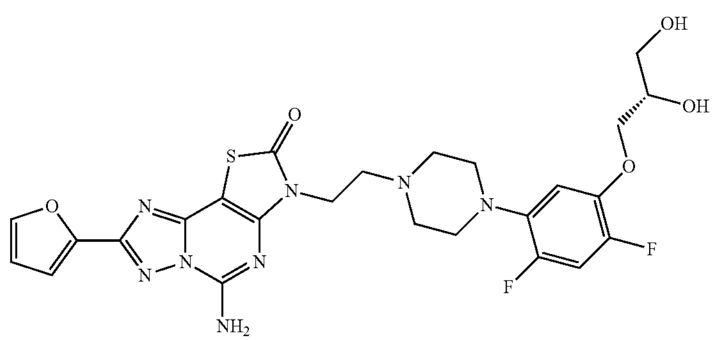 [SMILES: Nc1nc2c(sc(=O)n2CCN2CCN(c3cc(OC[C@@H](O)CO)c(F)cc3F)CC2)c2nc(-c3ccco3)nn12] | (S)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one | 588.59 |
| 128 | 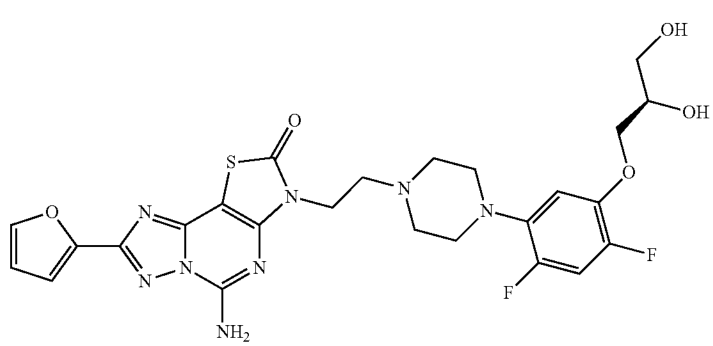 [SMILES: Nc1nc2c(sc(=O)n2CCN2CCN(c3cc(OC[C@H](O)CO)c(F)cc3F)CC2)c2nc(-c3ccco3)nn12] | (R)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one | 588.59 |

TABLE 1-continued

| Cpd no | Structure | Chemical name | MW |
|---|---|---|---|
| 129 | 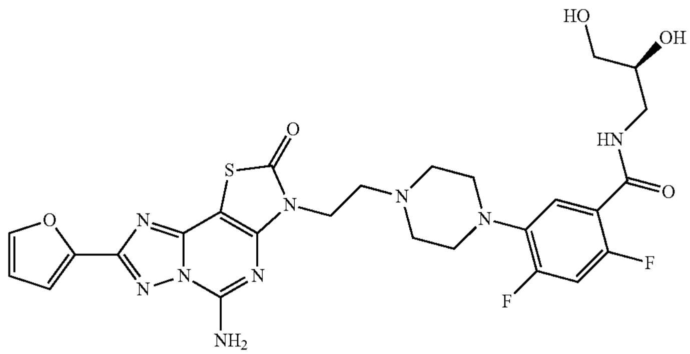 [SMILES: Nc1nc2c(sc(=O)n2CCN2CCN(c3cc(C(=O)NC[C@H](O)CO)c(F)cc3F)CC2)c2nc(-c3ccco3)nn12] | (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-2,4-difluorobenzamide | 615.61 |
| 130 | 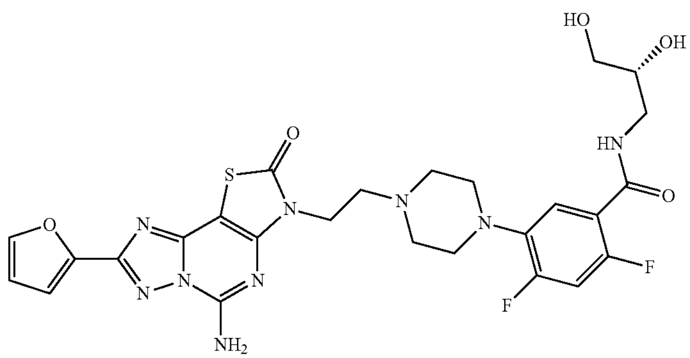 [SMILES: Nc1nc2c(sc(=O)n2CCN2CCN(c3cc(C(=O)NC[C@@H](O)CO)c(F)cc3F)CC2)c2nc(-c3ccco3)nn12] | (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-2,4-difluorobenzamide | 615.61 |
| 131 | 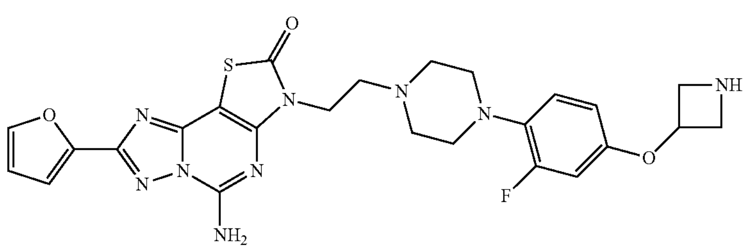 [SMILES: Nc1nc2c(sc(=O)n2CCN2CCN(c3ccc(OC4CNC4)cc3F)CC2)c2nc(-c3ccco3)nn12] | 5-amino-3-(2-(4-(4-(azetidin-3-yloxy)-2-fluorophenyl)piperazin-1-yl)ethyl)-8-(furan-2-yl)thiazolo[5,4-e][1,2,4]triazolo[1,5-c]pyrimidin-2(3H)-one | 551.60 |
| 132 | 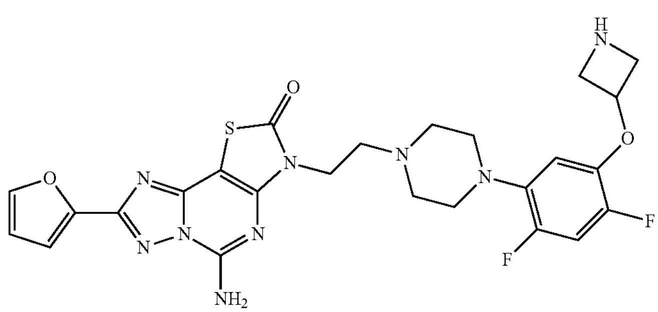 [SMILES: Nc1nc2c(sc(=O)n2CCN2CCN(c3cc(OC4CNC4)c(F)cc3F)CC2)c2nc(-c3ccco3)nn12] | 5-amino-3-(2-(4-(5-(azetidin-3-yloxy)-2,4-difluorophenyl)piperazin-1-yl)ethyl)-8-(furan-2-yl)thiazolo[5,4-e][1,2,4]triazolo[1,5-c]pyrimidin-2(3H)-one | 569.59 |

TABLE 1-continued

| Cpd no | Structure | Chemical name | MW |
|---|---|---|---|
| 133 | | (S)-5-amino-3-(2-(4-(2,4-difluoro-5-(3-(methylsulfinyl)propoxy)phenyl)piperazin-1-yl)ethyl)-8-(furan-2-yl)thiazolo[5,4-e][1,2,4]triazolo[1,5-c]pyrimidin-2(3H)-one | 618.68 | and pharmaceutically acceptable salts and solvates thereof.

In Table 1, the term "Cpd" means compound.

The compounds of Table 1 were named using ChemBioDraw® Ultra version 12.0 (PerkinElmer).

All references to compounds of Formula I and subformulae thereof include references to enantiomers, salts, solvates, polymorphs, multi-component complexes and liquid crystals thereof.

The compounds of the invention include compounds of Formula I and subformulae thereof as hereinbefore defined, including all polymorphs and crystal habits thereof, prodrugs and isomers thereof (including optical, geometric and tautomeric isomers) and isotopically-labeled compounds of Formula I and subformulae thereof.

The compounds of Formula I and subformulae thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of pharmaceutically acceptable salts. Pharmaceutically acceptable salts of the compounds of Formula I and subformulae thereof include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I and subformulae thereof may be prepared by one or more of these methods:
(i) by reacting the compound of Formula I with the desired acid;
(ii) by reacting the compound of Formula I with the desired base;
(iii) by removing an acid- or base-labile protecting group from a suitable precursor of the compound of Formula I or by ring-opening a suitable cyclic precursor, for example, a lactone or lactam, using the desired acid; or
(iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The compounds of the invention may be in the form of pharmaceutically acceptable solvates. Pharmaceutically acceptable solvates of the compounds of Formula I and subformulae thereof contains stoichiometric or sub-stoichiometric amounts of one or more pharmaceutically acceptable solvent molecule such as ethanol or water. The term "hydrate" refers to when the said solvent is water.

The invention also generally covers all pharmaceutically acceptable predrugs and prodrugs of the compounds of Formula I and subformulae thereof.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Process for Manufacturing

The compounds of Formula I can be prepared by different ways with reactions known to a person skilled in the art.

The invention further relates to a process for manufacturing of compounds of Formula (Ia):

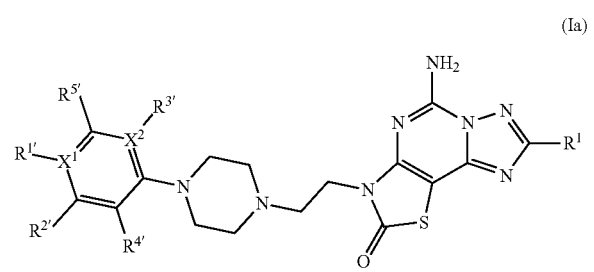

and pharmaceutically acceptable salts and solvates thereof, wherein $X^1$, $X^2$, $R^1$, $R^{1'}$, $R^{2'}$, $R^{3'}$, $R^{4'}$ and $R^{5'}$ are as defined in Formula (Ia);

comprising:
(a1) reacting a compound of Formula (A)

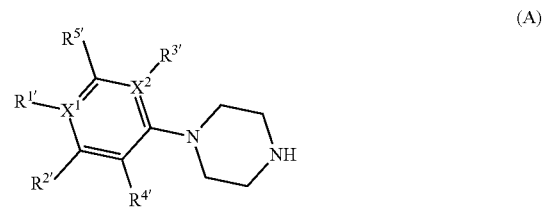

wherein $X^1$, $X^2$, $R^{1'}$, $R^{2'}$, $R^{3'}$, $R^{4'}$ and $R^{5'}$ are as defined in Formula (Ia);
with a compound of Formula (B)

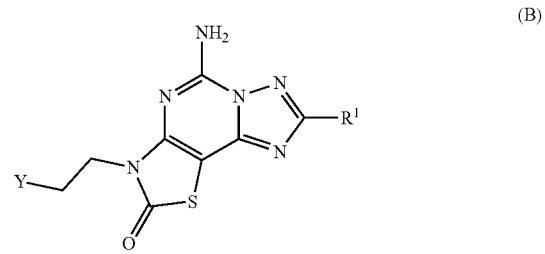

wherein $R^1$ is as defined in Formula (Ia);
Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art.

According to one embodiment, step (a1) of the process of the invention may be performed in the presence or absence of bases. In a specific embodiment, step (a1) of the process of the invention is performed in the presence of bases selected from the group consisting of but not limited to TEA, DIPEA, Pyridine, NaOH, $K_3PO_4$, $K_2CO_3$, $Na_2CO_3$, preferably DIPEA or TEA.

According to one embodiment, step (a1) of the process of the invention may be performed in the presence of a suitable solvent such as but not limited to DMF, dioxane, THF, water or mixtures thereof, preferably in DMF.

According to one embodiment, step (a1) of the process of the invention may be performed at a temperature ranging from 20° C. to about 180° C., with or without microwave irradiation, for a period ranging from 10 minutes to a few hours, e.g. 10 minutes to 24 h.

Compounds of Formula (B) can be prepared according to the following Scheme:

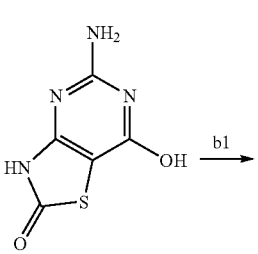

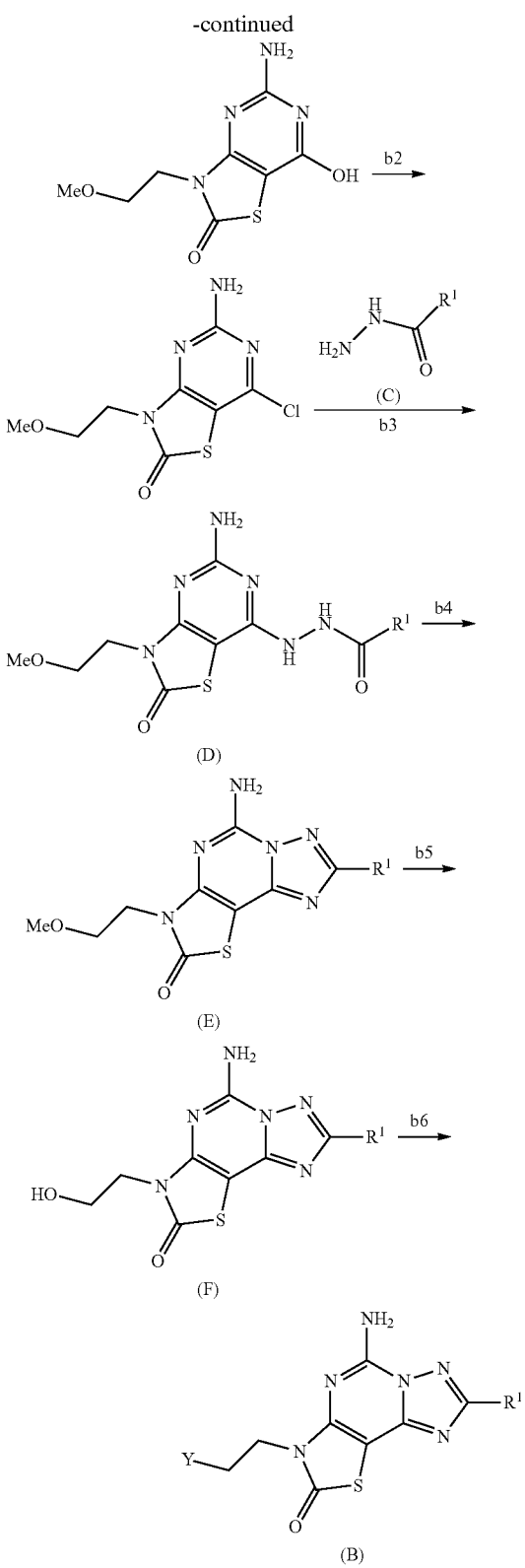

(B)

Step (b1): 5-Aminothiazolo[4,5-d]pyrimidine-2,7(3H,6H)-dione can be converted to 5-amino-7-hydroxy-3-(2-methoxyethyl)-2H,3H-[1,3]thiazolo[4,5-d]pyrimidin-2-one According to one embodiment, step (b1) can be performed by treatment with 1-bromo-2-methoyxy ethane, 1-iodo-2-methoxy ethane, 1-mesyl-2-methoxy ethane or 1-tosyl-2-methoxy ethane, preferably 1-bromo-2-methoyxy ethane.

According to one embodiment, step (b1) of the process of the invention may be performed in the presence or absence of bases. In a specific embodiment, step (b1) is performed in the presence of bases such as but not limited to sodium tert-butoxide, potassium tert-butoxide, NaH, CsOH, NaOH, $K_2CO_3$, $Na_2CO_3$, preferably sodium tert-butoxide, potassium tert-butoxide or NaH.

According to one embodiment, step (b1) of the process of the invention may be performed in the presence of a suitable solvent such as but not limited to DMF, dioxane, THF, DMA, preferably in DMF.

According to one embodiment, step (b1) of the process of the invention may be performed at a temperature ranging from 20° C. to about 180° C., with or without microwave irradiation, for a period ranging from 10 minutes to a few hours, e.g. 10 minutes to 24 h.

Step (b2): 5-amino-7-hydroxy-3-(2-methoxyethyl)-2H,3H-[1,3]thiazolo[4,5-d]pyrimidin-2-one can be converted to 5-amino-7-chloro-3-(2-methoxyethyl)-2H,3H-[1,3]thiazolo[4,5-d]pyrimidin-2-one.

According to one embodiment, step (b2) may be performed in presence of a chlorinating agent, such as but not limited to $POCl_3$, $PCl_5$, $SOCl_2$, preferably $POCl_3$.

According to one embodiment, step (b2) of the process of the invention may be performed in the presence or absence of a suitable solvent, preferably in absence of solvents.

According to one embodiment, step (b2) of the process of the invention may be performed at a temperature ranging from 20° C. to about 180° C., with or without microwave irradiation, for a period ranging from 10 minutes to a few hours, e.g. 10 minutes to 24 h.

Step (b3): 5-amino-7-chloro-3-(2-methoxyethyl)-2H,3H-[1,3]thiazolo[4,5-d]pyrimidin-2-one can be converted to a compound of Formula (D), wherein $R^1$ is as defined in Formula (Ia), by reacting with a compound of Formula (C), wherein $R^1$ is as defined in Formula (Ia).

According to one embodiment, step (b3) of the process of the invention may be performed in the presence of a suitable base.

According to one embodiment, step (b3) of the process of the invention may be performed in the presence or absence of a suitable solvent such as ethanol, propanol, methanol, THF, water, dioxane, or mixtures thereof, preferably in presence of ethanol.

According to one embodiment, step (b3) of the process of the invention may be performed at a temperature ranging from 20° C. to about 180° C., with or without microwave irradiation, for a period ranging from 10 minutes to a few hours, e.g. 10 minutes to 24 h.

Step (b4): Compound of Formula (D), wherein $R^1$ is as defined in Formula (Ia), can be converted to a compound of Formula (E), wherein $R^1$ is as defined in Formula (Ia).

According to one embodiment, step (b4) of the process of the invention may be performed in the presence of N,O-Bis(trimethylsilyl)acetamide, According to one embodiment, step (b4) of the process of the invention may be performed in the presence or absence of hexamethyldisilazane.

According to one embodiment, step (b4) of the process of the invention may be performed in the presence or absence of a suitable solvent, preferably in the absence of solvent.

According to one embodiment, step (b4) of the process of the invention may be performed at a temperature ranging from 20° C. to about 180° C., with or without microwave irradiation, for a period ranging from 1 hour to a few hours, e.g. 1 h to 96 h.

Step (b5): Compound of Formula (E), wherein $R^1$ is as defined in Formula (Ia), can be converted to a compound of Formula (F), wherein $R^1$ is as defined in Formula (Ia).

According to one embodiment, step (b5) of the process of the invention may be performed in the presence of $BBr_3$.

According to one embodiment, step (b5) of the process of the invention may be performed in the presence or absence of a suitable solvent such as DCM, THF, preferably in the presence of DCM.

According to one embodiment, step (b5) of the process of the invention may be performed at a temperature ranging from −20° C. to about 50° C., with or without microwave irradiation, for a period ranging from 10 minutes to a few hours, e.g. 10 minutes to 24 h.

Step (b6): Compound of Formula (F), wherein $R^1$ is as defined in Formula (Ia), can be converted to a compound of Formula (B), wherein $R^1$ and Y are as defined in Formula (Ia).

According to one embodiment, step (b6) of the process of the invention may be performed using any reagent known to those skilled in the art for the conversion of an alcohol to an alkyl halide, or to an alkyl or aryl sulfonic ester, depending on the nature of Y, such as but not limited to tosyl chloride, mesyl chloride, triflic chloride, triflic anhydride, $SOCl_2$, $SO_2Cl_2$, $POCl_3$, $PCl_5$, preferably tosyl chloride or mesyl chloride.

According to one embodiment, step (b6) of the process of the invention may be performed in the presence of a suitable base, such as but not limited to TEA or DIPEA.

According to one embodiment, step (b6) of the process of the invention may be performed in the presence or absence of a suitable solvent such as DMF, DCM, THF, preferably in the presence of DMF.

According to one embodiment, step (b6) of the process of the invention may be performed at a temperature ranging from −20° C. to about 50° C., with or without microwave irradiation, for a period ranging from 10 minutes to a few hours, e.g. 10 minutes to 24 h.

In general, the synthesis pathways for any individual compound of Formula (I) will depend on the specific substituents of each molecule and upon the ready availability of intermediates necessary; again such factors being appreciated by those of ordinary skill in the art.

According to a further general process, compounds of Formula I can be converted to alternative compounds of Formula I, employing suitable interconversion techniques well known by a person skilled in the art.

Compounds of the Formula I and related formulae can furthermore be obtained by liberating compounds of the Formula I from one of their functional derivatives by treatment with a solvolysing or hydrogenolysing agent.

Preferred starting materials for the solvolysis or hydrogenolysis are those which conform to the Formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the Formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, further-more CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter aha, benzyl, 4-methoxybenzyl, p-nitrobenzoyl, p-toluenesulfonyl, tert-butyl and acetyl, where benzyl and tert-butyl are particularly preferred.

The compounds of the Formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolyzed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Intermediates of Synthesis

The invention also relates to intermediates of synthesis of Formula (A)

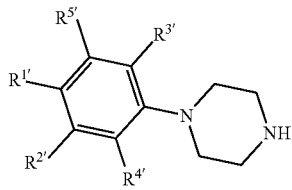

(A-1)

and salts and solvates thereof, wherein:
$R^{1'}$ is absent when $X^1$ is N; or when $X^1$ is C, $R^{1'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl heterocylylsulfonyl alkylsulfonimidoyl, carbonylamino, sulfonylamino or alkylsulfonealkyl;
said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{2'}$ represents H, halo, alkyl, heterocyclyl, alkoxy, cycloalkyloxy, heterocyclyloxy, carbonyl, alkylcarbonyl, aminocarbonyl arbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl;
said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

or $R^{1'}$ and $R^{2'}$ form together with the atoms to which they are attached a 5- or 6-membered aryl ring, a 5- or 6-membered heretoaryl ring, a 5- or 6-membered cycloalkyl ring or a 5- or 6-membered heretocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{3'}$ is absent when $X^2$ is N; or when $X^2$ is C, $R^{3'}$ represents H or halo, preferably H or F;

$R^{4'}$ represents H or halo, preferably H or F; and $R^{5'}$ represents H or halo, preferably H or F.

According to one embodiment, the intermediates of synthesis of Formula (A) used in the process of the invention are selected from the group consisting of:

1-(4-((1H-1,2,3-triazol-5-yl)methoxy)-2-fluorophenyl)piperazine;
1-(2-fluoro-4-(prop-2-yn-1-yloxy)phenyl)piperazine;
2-(2,4-difluoro-5-(piperazin-1-yl)phenoxy)acetamide;
(S)-1-(2-fluoro-4-(2-(methylsulfinyl)ethoxy)phenyl)piperazine;
(R)-1-(2-fluoro-4-(2-(methylsulfinyl)ethoxy)phenyl)piperazine;
(R,S)-1-(2,4-difluoro-5-(2-(methylsulfinyl)ethoxy)phenyl) piperazine;
(S)-1-(2,4-difluoro-5-(2-(methylsulfinyl)ethoxy)phenyl) piperazine; and
(R)-1-(2,4-difluoro-5-(2-(methylsulfinyl)ethoxy)phenyl) piperazine.

Uses

The invention is further directed to the use of the compounds of the invention or pharmaceutically acceptable salts and solvates thereof as A2A inhibitors.

Accordingly, in a particularly preferred embodiment, the invention relates to the use of compounds of Formula I and subformulae in particular those of Table 1 above, or pharmaceutically acceptable salts and solvates thereof, as A2A inhibitors.

Accordingly, in another aspect, the invention relates to the use of these compounds or salts and solvates thereof for the synthesis of pharmaceutical active ingredients, such as A2A inhibitors.

According to a further feature of the present invention there is provided a method for modulating A2A activity, in a patient, preferably a warm-blooded animal, and even more preferably a human, in need of such treatment, which comprises administering to said patient an effective amount of compound of the present invention, or a pharmaceutically acceptable salt and solvate thereof.

In one embodiment, the invention relates to the use of compounds of Formula I and subformulae in particular those of Table 1 above, or pharmaceutically acceptable salts and solvates thereof, for increasing immune recognition and destruction of the cancer cells.

The compounds of the invention are therefore useful as medicaments, in particular for the prevention and/or treatment of cancer.

The invention further relates to a method for treatment or prevention of cancer, which comprises administering to a mammalian species in need thereof a therapeutically effective amount of the compound according to the invention or a pharmaceutically acceptable salt or solvate thereof.

The invention further provides the use of a compound of Formula I or a pharmaceutically acceptable salt and solvate thereof for the manufacture of a medicament for treating and/or preventing cancer.

The invention also provides for a method for delaying in patient the onset of cancer comprising the administration of a pharmaceutically effective amount of a compound of Formula I or pharmaceutically acceptable salt and solvate thereof to a patient in need thereof.

Preferably, the patient is a warm-blooded animal, more preferably a human.

Various cancers are known in the art. The cancer may be metastatic or non-metastatic. The cancer may be may be familial or sporadic. In some embodiments, the cancer is selected from the group consisting of: leukemia and multiple myeloma. Additional cancers that can be treated using the methods of the invention include, for example, benign and malignant solid tumors and benign and malignant non-solid tumors. In a specific embodiment, the cancer is selected from breast, carcinoid, cervical, colorectal, endometrial, glioma, head and neck, liver, lung, melanoma, ovarian, pancreatic, prostate, renal, gastric, thyroid and urothelial cancers. In a specific embodiment, the cancer is breast cancer. In a specific embodiment, the cancer is carcinoid cancer. In a specific embodiment, the cancer is cervical cancer. In a specific embodiment, the cancer is colorectal cancer. In a specific embodiment, the cancer is endometrial cancer. In a specific embodiment, the cancer is glioma. In a specific embodiment, the cancer is head and neck cancer. In a specific embodiment, the cancer is liver cancer. In a specific embodiment, the cancer is lung cancer. In a specific embodiment, the cancer is melanoma. In a specific embodiment, the cancer is ovarian cancer. In a specific embodiment, the cancer is pancreatic cancer. In a specific embodiment, the cancer is prostate cancer. In a specific embodiment, the cancer is renal cancer. In a specific embodiment, the cancer is gastric cancer. In a specific embodiment, the cancer is thyroid cancer. In a specific embodiment, the cancer is urothelial cancer.

Examples of solid tumors include, but are not limited to: biliary tract cancer, brain cancer (including glioblastomas and medulloblastomas), breast cancer, carcinoid, cervical cancer, choriocarcinoma, colon cancer, colorectal cancer, endometrial cancer, esophageal cancer, gastric cancer, glioma, head and neck cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, thyroid cancer (including thyroid adenocarcinoma and medullary carcinoma) and urothelial cancer.

Examples of solid tumors include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, and thyroid cancer (including thyroid adenocarcinoma and medullary carcinoma).

Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

The invention further relates to the use of the compounds according to the invention or pharmaceutically acceptable salts or solvates thereof for the prevention and/or treatment of radiation-induced fibrosis, connective tissue diseases (such as for example Sjogrën syndrome, i.e. scleroderma), chronic bacterial infection (such as for example Helicobacter pylori), abnormal scarring (keloids) and polymicrobial sepsis.

The invention further relates to a method for treatment or prevention of radiation-induced fibrosis, connective tissue diseases (such as for example Sjogrën syndrome, i.e. scleroderma), chronic bacterial infection (such as for example Helicobacter pylori), abnormal scarring (keloids) and polymicrobial sepsis, which comprises administering to a mammalian species in need thereof a therapeutically effective amount of the compound according to the invention or a pharmaceutically acceptable salt or solvate thereof.

The invention further provides the use of a compound of Formula I or a pharmaceutically acceptable salt and solvate thereof for the manufacture of a medicament for treating and/or preventing radiation-induced fibrosis, connective tissue diseases (such as for example Sjogrën syndrome, i.e. scleroderma), chronic bacterial infection (such as for example Helicobacter pylori), abnormal scarring (keloids) and polymicrobial sepsis.

The invention also provides for a method for delaying in patient the onset of radiation-induced fibrosis, connective tissue diseases (such as for example Sjogrën syndrome, i.e. scleroderma), chronic bacterial infection (such as for example Helicobacter pylori), abnormal scarring (keloids) and polymicrobial sepsis, comprising the administration of a pharmaceutically effective amount of a compound of Formula I or pharmaceutically acceptable salt and solvate thereof to a patient in need thereof.

Formulations

The invention also provides pharmaceutical compositions comprising a compound of Formula I or a pharmaceutically acceptable salt and solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt and solvate thereof as active ingredient, additional therapeutic agents and/or active ingredients.

Another object of this invention is a medicament comprising at least one compound of the invention, or a pharmaceutically acceptable salt and solvate thereof, as active ingredient.

According to a further feature of the present invention there is provided the use of a compound of Formula I or a pharmaceutically acceptable salt and solvate thereof for the manufacture of a medicament for modulating A2A activity in a patient, in need of such treatment, which comprises administering to said patient an effective amount of compound of the present invention, or a pharmaceutically acceptable salt and solvate thereof.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

BRIEF DESCRIPTION OF THE DRAWINGS

FIG. 1A relates to whole blood cell cultures stimulated with LPS and FIG. 1B relates to whole blood cell cultures stimulated with anti-CD3/CD28.

EXAMPLES

Figure 1A:
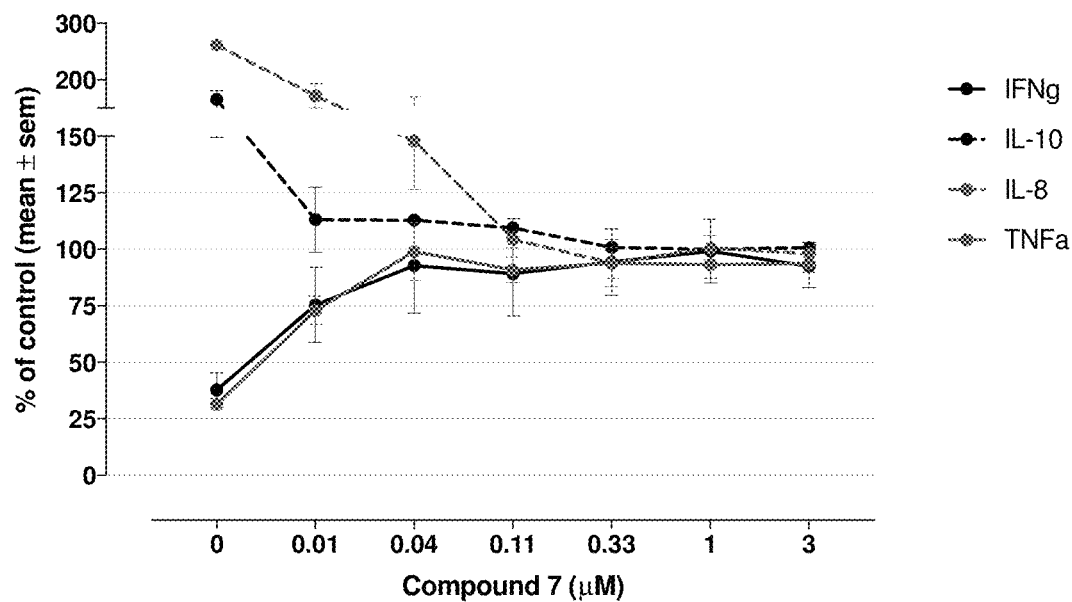
FIG. 1A and FIG. 1B are graphs showing the percentage of cytokines released in peripheral blood lymphocytes, in the presence of A2a agonist CGS24680, over the concentration of compound 7 of the present invention.

The present invention will be better understood with reference to the following examples. These examples are intended to representative of specific embodiments of the invention, and are not intended as limiting the scope of the invention.

The following abbreviations are used:
Boc: tert-Butoxy carbonyl,
BSA: Bis(trimethylsilyl)acetamide or bovine serum albumin, depending on the context,
Cpd: Compound,
DavePhos: 2-Dicyclohexylphosphino-2'-biphenyl,
DCM: Dichloromethane,
DIPEA: N,N-Diisopropylethylamine,
DMF: Dimethylformamide,
DMSO: Dimethyl sulfoxide,
eq.: Equivalent(s),
EtOAc: Ethyl acetate,
g: Gram(s),
h: Hour(s),
HAS: Human serum albumin,
HPLC: High performance liquid chromatography,
HMDS: Hexamethyldisilazane,
L: Liter(s),
LCMS: Liquid chromatography-mass spetrometry
LHMDS: Lithium bistrimethylsilylamide,
M: $mol \cdot L^{-1}$,
MeOH: Methanol,
µg: Microgram(s),
µmol: Micromole(s),
µL: Microliter(s),
mg: Milligram(s),
mL: Milliliter(s),
mmol: Millimole(s),
mM: $mmol \cdot L^{-1}$,
min: Minute(s),
mol: Mole(s),
N: Normality,
$N_2$: Nitrogen,
ng: Nanogram(s),
nM: $nmol \cdot L^{-1}$,
NMP: N-Methyl-2-pyrrolidone,
NMR: Nuclear magnetic resonance spectroscopy,
quant.: Quantitative (yield),
SFC: Supercritical fluid chromatography,
rt or RT: Room temperature,
tBu: tert-Butyl,
TEA: Triethylamine,
TFA: Trifluoroacetic acid,
THF: Tetrahydrofuran,
TLC: Thin layer chromatography,
VTD: Vacuum tray drayer.

I. CHEMISTRY EXAMPLES

The MS data provided in the examples described below were obtained as follows:

LCMS were recorded using Agilent 6130 or 6130B multimode (ESI+APCI)

LCMS Methods:
Column: XBridge C8 (50×4.6 mm) 5 µm; Method: A: 0.1% TFA in $H_2O$, B: 0.1% TFA
in ACN, Flow Rate: 2.0 mL/min.
Column: Zorbax extend C18 (50×4.6 mm) 5 µm; Method: A: 10 mM $NH_4OAc$ in $H_2O$,
B: ACN, Flow Rate: 1.2 mL/min.
Column: Zorbax XDB C18 (50×4.6 mm) 3.5 µm; Method: A: 0.1% HCOOH in $H_2O$,
B: ACN, Flow Rate: 1.5 mL/min.
Column: XBridge C8 (50×4.6 mm) 3.5 µm; Method: A: 10 mM $NH_4HCO_3$ in $H_2O$, B:
ACN, Flow Rate: 1.2 mL/min.

The NMR data provided in the examples described below were obtained as followed: 1H-NMR: Bruker DPX 400 MHz. Abbreviations for multiplicities observed in NMR spectra are as follows: s (singlet), d (doublet), t (triplet), q (quadruplet), m (multiplet), br (broad).

HPLC Purity were evaluated with either of two methods:
Method XB0595TF; COLUMN: XBridge C8 (50×4.6) mm, 3.5 µm; Gradient of eluents from 0.1% TFA in $H_2O$ to 0.1% TFA in ACN, Flow Rate: 2.0 mL/min.
Method: AM9010A3; COLUMN: Phenomenex gemini NX-C18 (150×4.6), 3.0 µm;
Gradient of eluents from 10 mM Ammonium acetate in water to ACN, Flow Rate: 1.0 mL/min.
Method: XB0595NHC; COLUMN: XBridge C8 (50×4.6) mm, 3.5 µm; Gradient of eluents from 10 mM Ammonium bicarbonate in water to ACN, Flow Rate: 1.0 mL/min.

Solvents, reagents and starting materials were purchased and used as received from commercial vendors unless otherwise specified.

The intermediates and compounds described below were named using ChemBioDraw® Ultra version 12.0 (PerkinElmer).

I.1. Synthesis of Intermediate Compounds

Intermediate 1: 2-(5-amino-8-(furan-2-yl)-2-oxothiazolo[5,4-e][1,2,4]triazolo[1,5-c]pyrimidin-3(2H)-yl)ethyl methanesulfonate Step 1: 2,6-diamino-5-thiocyanatopyrimidin-4-ol: To a stirred solution of Acetic acid (27500 mL) in a reactor at 25-30° C. under Nitrogen atmosphere was added 2, 6-diaminopyrimidin-4-ol (500 g). Potassium thiocyanate (1586 g) was added slowly and the temperature was raised to 90±5° C.; until the reaction mass becomes a clear solution. Once it becomes a clear solution, the reaction mixture was cooled to 15±5° C. and bromine (633 g) in acetic acid (750 mL) was added drop wise, stirred for 2 h at the same temperature. After the completion of the reaction, the reaction mixture was neutralised using aqueous ammonia (9000 mL) and stirred for 16 h at 20±5° C. The precipitate formed was filtered and rinsed with water (2500 mL) and methanol (1000 mL). The wet material was dried in VTD at 70° C. for 24 hours to give the title compound as a pale yellow solid (206 g, quant). LCMS: 184.3 $[M+1]^+$. $^1$H-NMR (400 MHz, DMSO-d6): δ 10.36 (s, 1H), 7.03 (s, 2H), 6.64 (bs, 2H).

Step 2: 2,5-diaminothiazolo[4,5-d]pyrimidin-7-ol: To a stirred solution of 2,6-diamino-5-thiocyanatopyrimidin-4-ol (Step-1) (750 g, 4.09 mol) in THF (15 L) was added tetrabutylammonium fluoride (1 M in THF, 6750 mL) and the reaction mass was heated to 64±3° C. for 24 h. After the completion of the reaction, the reaction mixture was cooled to 25±5° C. for 1 h. The precipitate formed was filtered and rinsed with THF (2.25 L). The wet solid was taken up in water (6 L) and concentrated hydrochloric acid (1.5 L) was added. The reaction mixture was stirred for 4 h. The reaction mixture was filtered and the solid residue washed with water (3.75 L) and suck dried for 1 h. The wet material was treated with water (6 L) and sodium bicarbonate (3 kg) was added. The reaction mass was stirred for 4 hours, filtered, washed with water (3.75 L) and dried in VTD for 16 h to afford the title compound as a yellow solid (580 g; 78%). LCMS: 184.2 [M+1]$^+$. $^1$H-NMR (400 MHz, DMSO-d$_6$): δ 10.84 (s, 1H), 7.89 (s, 2H), 6.46 (s, 2H).

Step 3: 5-amino-7-hydroxythiazolo [4,5-d]pyrimidin-2 (3H)-one: A hot (80° C.) mixture of 2,5-diaminothiazolo[4,5-d]pyrimidin-7-ol (Step 2; 570 g, 3.11 mol) and NaNO$_2$ (570 g, 8.26 mol) in water (5700 mL) was slowly added to a hot solution (80° C.) of Conc. HCl (11400 mL, 15 Vol). The reaction mixture was stirred for 2 h and the completion of the reaction was monitored by HPLC. After the completion of the reaction, the mixture was cooled to 15° C. and basified to pH 12 with NaOH pellets. The reaction mass was heated to 80° C. for 2 hours, then cooled to 35° C. and the pH was adjusted to 5-6 using concentrated hydrochloric acid. The solid precipitated was filtered washed with water (5V) and dried in VTD to afford the product as a Pale brown solid (286 g, 51%). LCMS: 185.6 [M+1]$^+$. $^1$H-NMR (400 MHz, DMSO-d$_6$): δ 12.08 (s, 1H), 11.10 (s, 1H), 6.88 (s, 2H).

Step 4: 5-amino-3-(2-methoxyethyl)thiazolo[4,5-d]pyrimidine-2,7 (3H, 4H)-dione: 5-amino-7-hydroxythiazolo[4,5-d]pyrimidin-2(3H)-one (36.2 g, 0.196 mol, 1 eq) was taken in dry DMF (600 mL) and heated to 90° C. in a sealed tube. The reaction mixture was stirred for 30 min at 90° C., then cooled to 30° C. To this reaction mixture was added 60% NaH (10.4 g, 1.1 eq) slowly and stirred for 30 min followed by addition of 1-bromo-2-methoxyethane (32.83 g, 1.1 eq). The reaction mixture was again heated to 100° C. The completion of the reaction was monitored by TLC. After the completion of the reaction, the reaction mixture was cooled to RT, concentrated completely and purified by column chromatography using DCM/Methanol (90:10) to afford as a white solid (20 g, 41%). LCMS: 243.6 [M+1]$^+$. $^1$H-NMR (400 MHz, DMSO-d$_6$): δ 11.10 (s, 1H), 6.92 (bs, 2H), 3.93 (t, J=6 Hz, 2H), 3.57 (t, J=6 Hz, 2H), 3.23 (s, 3H).

Step 5: 5-amino-7-chloro-3-(2-methoxyethyl)thiazolo[4,5-d]pyrimidin-2(3H)-one: 5-amino-7-hydroxy-3-(2-methoxyethyl)thiazolo[4,5-d]pyrimidin-2 (3H)-one (10 g, 0.0412 mol) was treated with POCl$_3$ (100 mL) and heated to 90° C. for 18 h in a sealed tube. After the completion of the reaction as monitored by TLC, the reaction mixture was concentrated and ice cold water was added. The pH of the reaction mixture was adjusted to 7 using NaHCO$_3$ and extracted with DCM. The organic layer was separated, dried over Na$_2$SO$_4$, filtered and concentrated to afford a pale yellow solid which was used as such for the next step without further purification (6.8 g, 63%). LCMS: 261.2 [M+1]$^+$. $^1$H-NMR (400 MHz, DMSO-d$_6$): δ 7.37 (s, 2H), 4.01 (t, J=5.6 Hz, 2H), 3.62 (t, J=5.6 Hz, 2H), 3.23 (s, 3H).

Step 6: N'-(5-amino-3-(2-methoxyethyl)-2-oxo-2,3-dihydrothiazolo[4,5-d] pyrimidin-7-yl)furan-2-carbohydrazide: 5-amino-7-chloro-3-(2-methoxyethyl)thiazole [4,5-d]pyrimidin-2(3H)-one (6.8 g, 0.026 mol) in ethanol was added furoic acid hydrazide (4.9 g, 0.039 mol) and heated to 100° C. in a sealed tube for 19 h. The reaction was monitored by TLC. After the completion of the reaction, the reaction mixture was cooled to RT, concentrated under reduced pressure. To this residue, Petroleum Ether was added to afford a solid which was filtered and was used as such for the next step without further purification (7.2 g, 79%). LCMS: 351.2 [M+1]$^+$.

Step 7: 5-amino-8-(furan-2-yl)-3-(2-methoxyethyl)thiazolo[5,4-e][1,2,4]triazolo[1,5-c]pyrimidin-2(3H)-one: N'-(5-amino-3-(2-methoxyethyl)-2-oxo-2,3-dihydrothiazolo[4,5-d]pyrimidin-7-yl)furan-2-carbohydrazide (7.2 g, 0.20 mol) was treated with BSA (50.8 mL, 11 eq) and HMDS (76 mL, 25 eq). The reaction mixture was heated to 127° C. for 20 h. After the completion of reaction, the reaction mixture was cooled to 0° C. and methanol (30 mL) was added. The solid which precipitated out was filtered and washed with Petroleum ether to afford an Off-White Solid which was used as such for the next step without further purification (5.9 g, 87%). LCMS: 333.2 [M+1]$^+$.

Step 8: 5-amino-8-(furan-2-yl)-3-(2-hydroxyethyl)thiazolo[5,4-e][1,2,4]triazolo[1,5-c]pyrimidin-2(3H)-one: To a solution of 5-amino-8-(furan-2-yl)-3-(2-methoxyethyl)thiazolo[5,4-e][1,2,4]triazolo[1,5-c] pyrimidin-2(3H)-one (5.9 g, 0.017 mol) in dry DCM (100 mL) at −50° C., was added BBr$_3$ (11.5 g, 2.6 eq) slowly and maintained for 19 h at 25-30° C. The reaction was monitored by TLC. After the completion of reaction, the reaction mixture was quenched with chilled water (100 mL) then neutralized with 10% Sodium bicarbonate solution, filtered and washed with water to afford a pale yellow solid which was used as such for the next step without further purification (3.6 g, 65%). LCMS: 319.2 [M+1]$^+$. $^1$H-NMR (400 MHz, DMSO-d$_6$): δ 8.31 (s, 2H), 7.95 (d, J=0.8 Hz, 1H), 7.24 (t, J=2.8 Hz, 1H), 6.74-6.74 (m, 1H), 4.94 (t, J=5.6 Hz, 1H), 4.01 (t, J=6.4 Hz, 2H), 3.71 (t, J=6.0 Hz, 2H).

Step 9: 2-(5-amino-8-(furan-2-yl)-2-oxothiazolo[5,4-e][1,2,4]triazolo[1,5-c]pyrimidin-3(2H)-yl)ethyl methanesulfonate: 5-amino-8-(furan-2-yl)-3-(2-hydroxyethyl)thiazolo[5,4-e][1,2,4]triazolo[1,5-c]pyrimidin-2 (3H)-one (3.6 g, 0.011 mol) was dissolved in dry DMF (95 mL) at 60° C. till the reaction mixture became clear. The reaction mass was cooled to 0° C. and TEA (3 g, 3 eq) was added, followed by Mesyl chloride (1.6 g, 1.3 eq). The reaction mixture was stirred at RT for 48 h. After the completion of reaction, ethyl acetate (100 mL) & water (50 mL) was added and extracted. The organic layer was dried over Na$_2$SO$_4$, filtered and evaporated to afford the compound as a yellow solid which was analytically pure to be used for the next step (3.0 g, 67%). LCMS: 397.2 [M+1]$^+$. $^1$H-NMR (400 MHz, DMSO-d$_6$): δ 8.37 (s, 2H), 7.95 (s, 1H), 7.25 (d, J=3.6 Hz, 1H), 6.74-6.74 (m, 1H), 4.56 (t, J=5.2 Hz, 2H), 4.26 (t, J=4.8 Hz, 2H), 3.16 (s, 3H).

Intermediate 2: 2-(5-amino-8-(furan-2-yl)-2-oxothiazolo[5,4-e][1,2,4]triazolo[1,5-c]pyrimidin-3(2H)-yl)-acetaldehyde To a stirred solution of 5-amino-8-(furan-2-yl)-3-(2-hydroxyethyl)thiazolo[5,4-e][1,2,4]triazolo-[1,5-c]pyrimidin-2(3H)-one (prepared according to the protocol described for Intermediate 1, Step 8, 3.6 g, 10.74 mmol) in THF (150 mL) was added a solution of IBX (15.04 g, 53.72 mmol) in DMSO (35 mL). The resulting mixture was stirred at RT for 6 h. The reaction mixture was diluted with DCM and the layers were separated. The organic layer was washed successively with saturated NaHCO$_3$ solution and saturated brine solution. Then it was dried over anhydrous Na$_2$SO$_4$, filtered and concentrated under reduced pressure. The crude residue (3.0 g, 75%) obtained was used for next step without further purification. LCMS 317 [M+1]$^+$.

95

I.2. Synthesis of Final Compounds

Example 1: 3-(2-(4-(4-((1H-1,2,3-triazolo-1-yl)methoxy-2fluorophenyl)piperazine-1-yl)ethyl)-5-amino-(8-(furan-2-yl)thiazolo[5,4-e][1,2,4]triazolo[1,5-c]pyrimidine-2(3H)-one

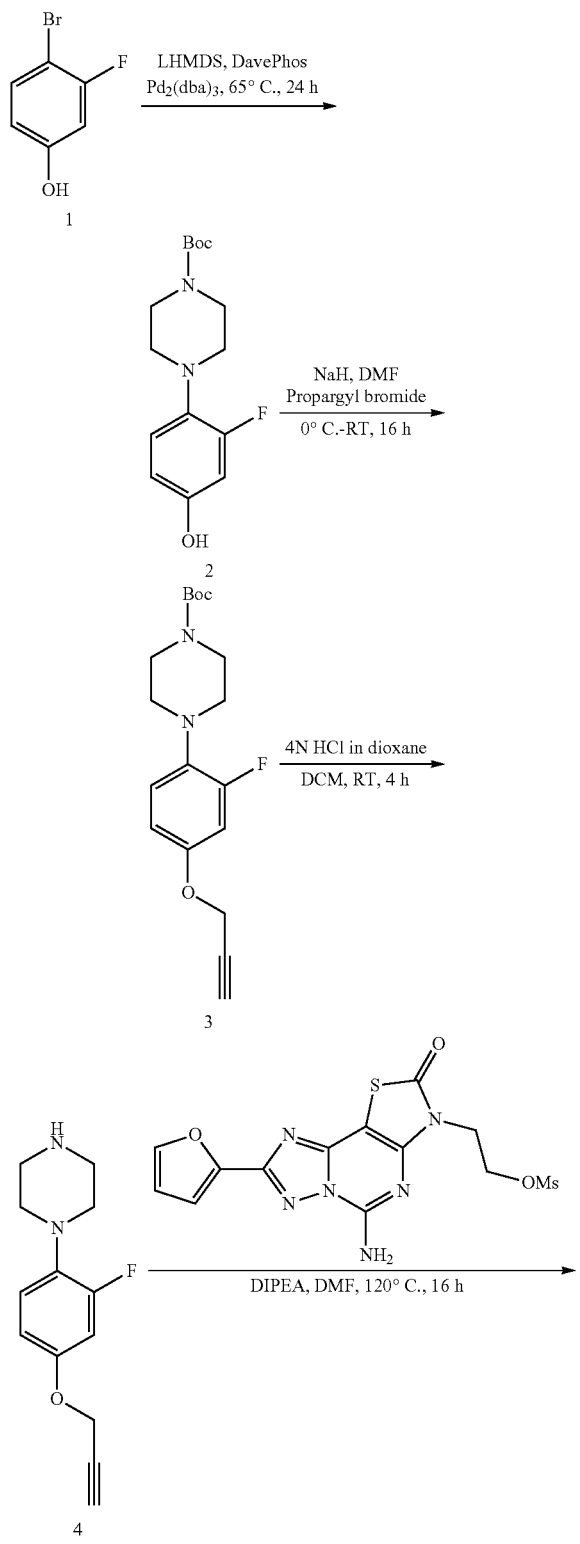

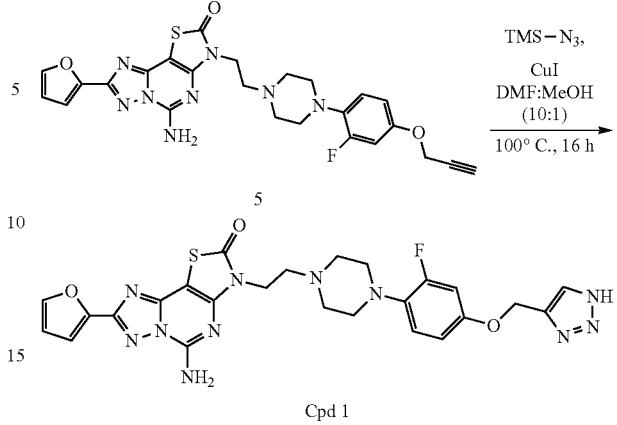

Step 1: tert-butyl 4-(2-fluoro-4-hydroxyphenyl)piperazine-1-carboxylate (2): To a mixture of 4-Bromo-3-fluorophenol (10 g, 0.052 mol), tert-butyl piperazine-1-carboxylate (11.70 g, 0.063 mol), DavePhos (0.515 g, 0.001 mol) and $Pd_2(dba)_3$ (0.958 g, 0.001 mol) was added LHMDS (115 mL of 1.0 M solution in THF, 0.115 mol) at 0° C. under nitrogen. The reaction mixture was heated at 65° C. for 24 h and monitored by TLC. The crude reaction mixture was neutralized with saturated $NH_4Cl$ and extracted with ethyl acetate (2×100 mL). The combined organic layer was concentrated and purified by column chromatography to afford the title compound as off white solid (2.25 g, 14.5%). LCMS (ESI positive ion) m/z: calculated: 296.15; observed: 297.2 (M+1).

Step 2: tert-butyl 4-(2-fluoro-4-(prop-2-yn-1-yloxy)phenyl)piperazine-1-carboxylate (3): To a stirred suspension of sodium hydride (0.7 g, 0.0304 mol) in DMF (10 mL) was added tert-butyl hydroxyphenyl)piperazine-1-carboxylate (2, 4.5 g, 0.0152 mol) in DMF (20 mL) at 0° C. under nitrogen. The reaction mixture was stirred for 15 min at 0° C. and then propargyl bromide (2.71 g, 0.0228 mol) in DMF (10 mL) was added and stirred for 16 h at RT. After the reaction completion (TLC), the reaction mixture was treated with saturated $NH_4Cl$ (20 mL) and extracted with ethyl acetate. Organic layer was washed with saturated brine solution, dried over anhydrous $Na_2SO_4$, filtered and concentrated under reduced pressure. The crude obtained was purified by column chromatography (40% EtOAc/Hexane as eluent) to afford tert-butyl 4-(2-fluoro-4-(prop-2-yn-1-yloxy)phenyl)piperazine-1-carboxylate as brown gummy liquid (3.6 g, 70.8%). LCMS (ESI positive ion) m/z: calculated: 334.17; observed: 335.2 (M+1).

Step 3: 1-(2-fluoro-4-(prop-2-yn-1-yloxy)phenyl) piperazine (4): To a stirred solution of tert-butyl 4-(2-fluoro-4-(prop-2-yn-1-yloxy)phenyl)piperazine-1-carboxylate (3, 3.6 g, 10.8 mmol) in dichloromethane (15 mL) at 0° C., 4 N HCl in dioxane (20 mL) was added dropwise and stirred at RT for 4 h. After the reaction completion (TLC), the reaction mixture was concentrated under reduced pressure. The salt was neutralised with sodium bicarbonate solution, extracted with DCM and the combined organic layers were washed with brine, dried over sodium sulphate and then concentrated under reduced pressure to afford 1-(2-fluoro-4-(prop-2-yn-1-yloxy)phenyl)piperazine as brown solid (2.5 g, 99.2%); LCMS (ESI positive ion) m/z: calculated: 234.12; observed: 235.2 (M+1).

Step 4: 5-amino-3-(2-(4-(2-fluoro-(prop-2yn-1-yloxy)phenyl)piperazine-1-yl)ethyl)-8-(furan-2-yl)thaizolo[5,4-e][1,2,4]triazolo[1,5-c]pyrimidine-2(3H)-one (5): To a mixture of 1-(2-fluoro-4-(prop-2-yn-1-yloxy)phenyl)piperazine (4, 1 g, 4.3 mmol) and 2-(5-amino-8-(furan-2-yl)-2-oxothiazolo[5,4-e][1,2,4]triazolo[1,5-e]pyrimidin-3(2H)-yl)ethyl methane sulfonate (0.9 g, 2.2 mmol) in N,N-Dimethylformamide (15 mL), was added DIPEA (0.6 mL, 6.8 mmol) and the reaction mixture was stirred at 120° C. for 16 h. After completion of the reaction (TLC & LCMS), the reaction mass was concentrated under reduced pressure. The crude product was washed with mixture of diethyl ether and acetonitrile to afford 5-amino-3-(2-(4-(2-fluoro-4-(prop-2yn-1-yloxy)phenyl)piperazin-1-yl)ethyl)-8-(furan-2-yl)thiazolo[5,4-e][1,2,4]triazolo [1,5-c]pyrimidin-2(3H)-one as brown solid (0.7 g, 57.8%); HPLC purity (XB0595TF): 92.63%; LCMS (ESI positive ion) m/z: calculated: 534.16; observed: 534.8 (M+1).

Step 5: 3-(2-(4-(4-((1H-1,2,3-triazolo-1-yl)methoxy-2-fluorophenyl)piperazine-1-yl)ethyl)-5-amino-(8-(furan-2-yl)thaizolo[5,4-e][1,2,4]triazolo[1,5-e]pyrimidine-2(3H)-one (Compound 1): To a stirred solution of 5-amino-3-(2-(4-(2-fluoro-4-(prop-2yn-1-yloxy)phenyl)piperazin-1-yl)ethyl)-8-(furan-2-yl)thiazolo[5,4-e][1,2,4]triazolo[1,5-c]pyrimidin-2(3H)-one (5, 0.4 g, 0.7 moles) in DMF (4.5 mL) and MeOH (0.5 mL) was added copper iodide (0.030 g, 0.014 mmol) at RT. To the reaction mixture trimethylsilyl azide (0.2 mL, 1.4 mmol) was added dropwise under nitrogen atmosphere at 0° C. and was heated to 100° C. for 16 h. After the reaction completion (TLC), the reaction mixture was extracted with ethyl acetate (2×20 mL) and the combined organic layers were washed with brine, dried over sodium sulphate and concentrated under reduced pressure. The product was further enriched by washing with diethyl ether and acetonitrile (50:50) to afford compound 1: 3-(2-(4-(4-((1H-1,2,3-triazol-4-yl)methoxy)-2-fluorophenyl)-piperazin-1-yl)ethyl)-5-amino-8-(furan-2-yl)thiazolo[5,4-e][1,2,4]triazolo[1,5-c]pyrimidin-2(3H)-one as brown solid (0.115 g, 26.6%). HPLC purity (XB0595TF): 92.08%; LCMS (ESI positive ion) m/z: calculated: 577.18; observed: 578.0 (M+1); $^1$H-NMR (400 MHz, DMSO-d6): δ 15.12 (brs, 1H), 8.32 (brs, 2H), 7.96 (s, 2H), 7.24 (d, J=3.2 Hz, 1H), 6.96-6.89 (m, 2H), 6.79-6.73 (m, 2H), 5.13 (s, 2H), 4.08 (t, J=6.0 Hz, 2H), 2.86 (m, 4H), 2.72-2.63 (m, 6H).

Example 2: 5-((4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)methyl)-1,3,4-oxadiazol-2(3H)-one

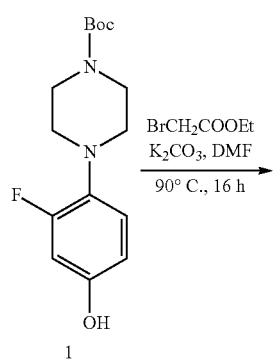

-continued

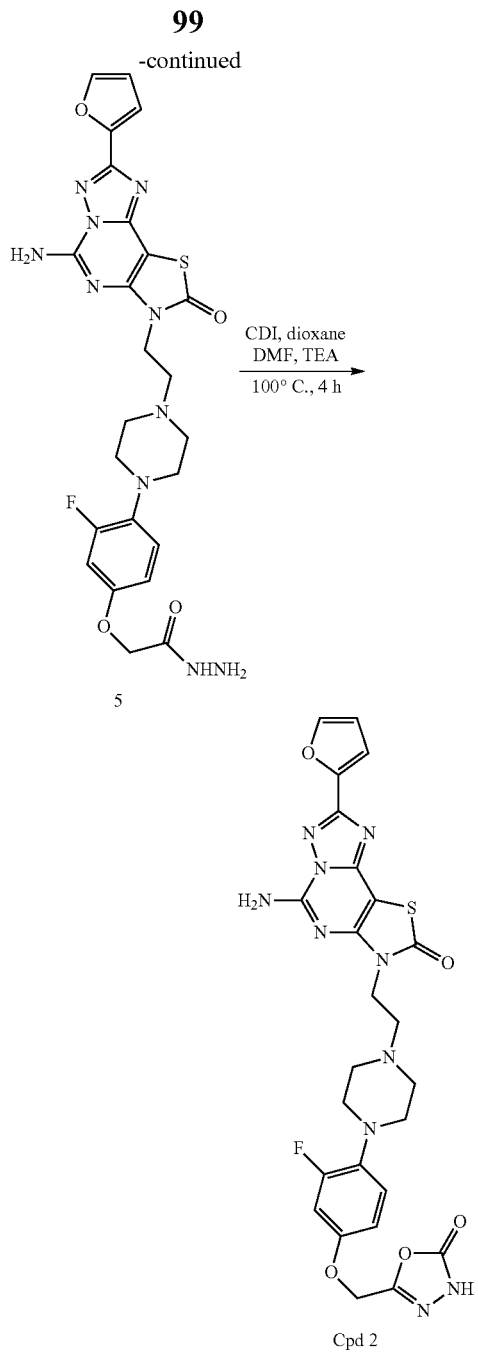

Step 1: tert-butyl 4-(4-(2-ethoxy-2-oxoethoxy)-2-fluorophenyl)piperazine-1-carboxylate (2): To a stirred solution of tert-butyl 4-(2-fluoro-4-hydroxyphenyl)piperazine-1-carboxylate (1, 2 g, 6.75 mmol) and ethyl bromoacetate (1.67 g, 10.0 mmol) in N,N-Dimethylformamide (15 mL) was added $K_2CO_3$ (2.76 g, 20.0 mmol) and the reaction mixture was heated at 90° C. for 16 h. After the reaction completion (TLC), the reaction mixture was diluted with water (20 mL) and extracted with ethyl acetate. Organic layer was washed with saturated brine solution, dried over anhydrous $Na_2SO_4$, filtered and concentrated under reduced pressure. The crude obtained was purified by column chromatography (20% EtOAc/Hexane as eluent) to afford the product as brown liquid (1.9 g, 73.6%); LCMS (ESI positive ion) m/z: calculated: 382.19; observed: 383.0 (M+1).

Step 2: ethyl 2-(3-fluoro-4-(piperazin-1-yl)phenoxy)acetate (3): To an ice cold solution of tert-butyl 4-(4-(2-ethoxy-2-oxoethoxy)-2-fluorophenyl)piperazine-1-carboxylate (2, 1.9 g, 5.0 mmol) in dichloromethane, 4 N HCl in Dioxane (15 mL) was added and the reaction mixture was stirred at RT for 5 h. After the completion of reaction (TLC), reaction mass was quenched with saturated sodium bicarbonate solution and was extracted with ethyl acetate. Organic layer was dried over sodium sulphate, filtered and concentrated under reduced pressure to afford the product as brown liquid (1.00 g, 71.4%); LCMS (ESI positive ion) m/z: calculated: 282.14; observed: 283.1 (M+1).

Step 3: ethyl 2-(4-(4-(2-(5-amino-8-(furan-2-yl)-2-oxothiazolo[5,4-e][1,2,4] triazolo[1,5-c]pyrimidin-3(2H)-yl)ethyl)piperazin-1-yl)-3-fluorophenoxy)acetate (4): To a mixture of ethyl 2-(3-fluoro-4-(piperazin-1-yl)phenoxy)acetate (3, 1.0 g, 3.52 mmol) and 2-(5-amino-8-(furan-2-yl)-2-oxothiazolo[5,4-e][1,2,4]triazolo[1,5-c]pyrimidin-3(2H)-yl)ethyl methane sulfonate (1.12 g, 2.82 mmol) in N,N-Dimethylformamide (15 mL), was added DIPEA (1.3 g, 11.0 mmol) and the reaction mixture was stirred at 120° C. for 16 h. After the completion of reaction (TLC & LCMS), the solvent was removed under reduced pressure and purified by recrystallization with diethyl ether:acetonitrile (1:1) mixture to get the title compound as dark brown solid (0.70 g, 42.5%); LCMS (ESI positive ion) m/z: calculated: 582.18; observed: 583.0 (M+1).

Step 4: 2-(4-(4-(2-(5-amino-8-(furan-2-yl)-2-oxothiazolo[5,4-e][1,2,4]triazolo [1,5-c]pyrimidin-3(2H)-yl)ethyl)piperazin-1-yl)-3-fluorophenoxy)acetohydrazide (5): To a solution of Ethyl 2-(4-(4-(2-(5-amino-8-(furan-2-yl)-2-oxothiazolo[5,4-e][1,2,4]-triazolo[1,5-c]pyrimidin-3(2H)-yl)ethyl)piperazin-1-yl)-3-fluorophenoxy)acetate (4, 0.2 g, 0.34 mmol) in ethanol (20 mL), was added hydrazine hydrate (50 mg, 1.0 mmol) and the reaction mixture was stirred at 90° C. for 16 h. After the completion of reaction (TLC & LCMS), the solvent was removed under reduced pressure and purified by recrystallization with diethylether and acetonitrile mixture to get the title compound as white solid (150 mg, 76.9%); LCMS (ESI positive ion) m/z: calculated: 568.18; observed: 569.0 (M+1).

Step 5: 5-((4-(4-(2-(5-amino-8-(furan-2-yl)-2-oxothiazolo[5,4-e][1,2,4]tri-azolo [1,5-c]pyrimidin-3(2H)-yl)ethyl)piperazin-1-yl)-3-fluorophenoxy)methyl)-1,3,4-oxadiazol-2(3H)-one (Compound 2): To a suspension of compound 5 (0.158 g, 0.27 mol) in 1,4-Dioxane (10 mL) and DMF (1 mL), TEA (0.084 g, 0.83 mol) was added and the reaction mixture was stirred at 100° C. for 4 h. After the completion of reaction (TLC & LCMS), solvent was removed under reduced pressure and purified by prep. HPLC purification to get title compound 2 as white solid (21 mg, 12.7%); HPLC purity (XB0595TF): 95.33%; LCMS (ESI positive ion) m/z: calculated: 594.16; observed: 595.1 (M+1); $^1$H-NMR (400 MHz, DMSO-d6): δ 12.52 (brs, 1H), 8.32 (brs, 2H), 7.96 (d, J=0.80 Hz, 1H), 7.25 (d, J=3.20 Hz, 1H), 6.99-6.92 (m, 2H), 6.78 (dd, J=2.0 & 8.8 Hz, 1H), 6.74 (dd, J=1.6 & 3.2 Hz, 1H), 5.01 (s, 2H), 4.08 (t, J=6.40 Hz, 2H), 2.87 (m, 4H), 2.72-2.63 (m, 6H).

Example 3: 5-amino-3-(2-(4-(3-fluoropyridin-4-yl)piperazin-1-yl)ethyl)-8-(furan-2-yl)thiazolo[5,4-e][1,2,4]triazolo[1,5-c]pyrimidin-2(3H)-one

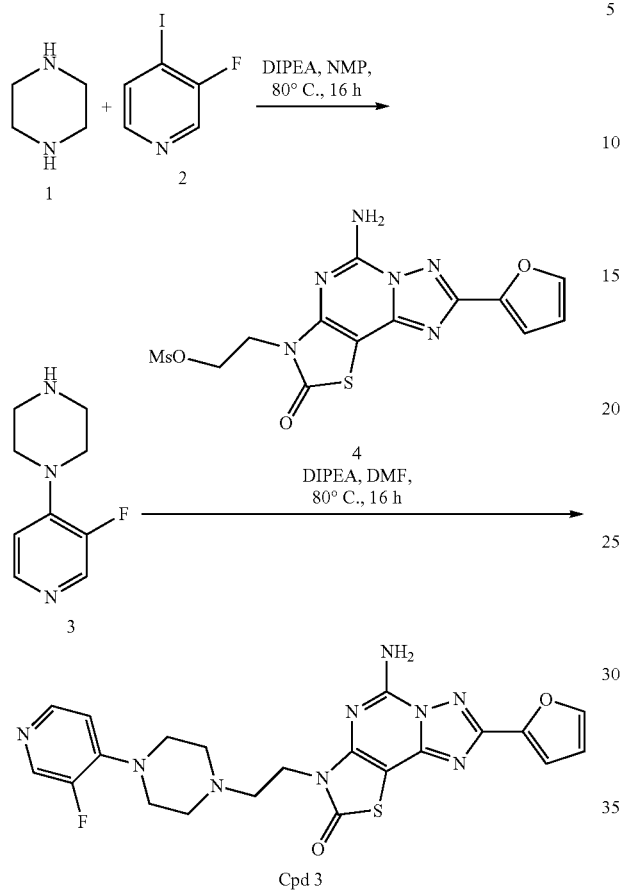

Example 4: 2-(5-(4-(2-(5-amino-8-(furan-2-yl)-2-oxothiazolo[5,4-e][1,2,4]triazolo [1,5-c]pyrimidin-3(2H)-yl)ethyl)piperazin-1-yl)-2,4-difluorophenoxy)acetamide

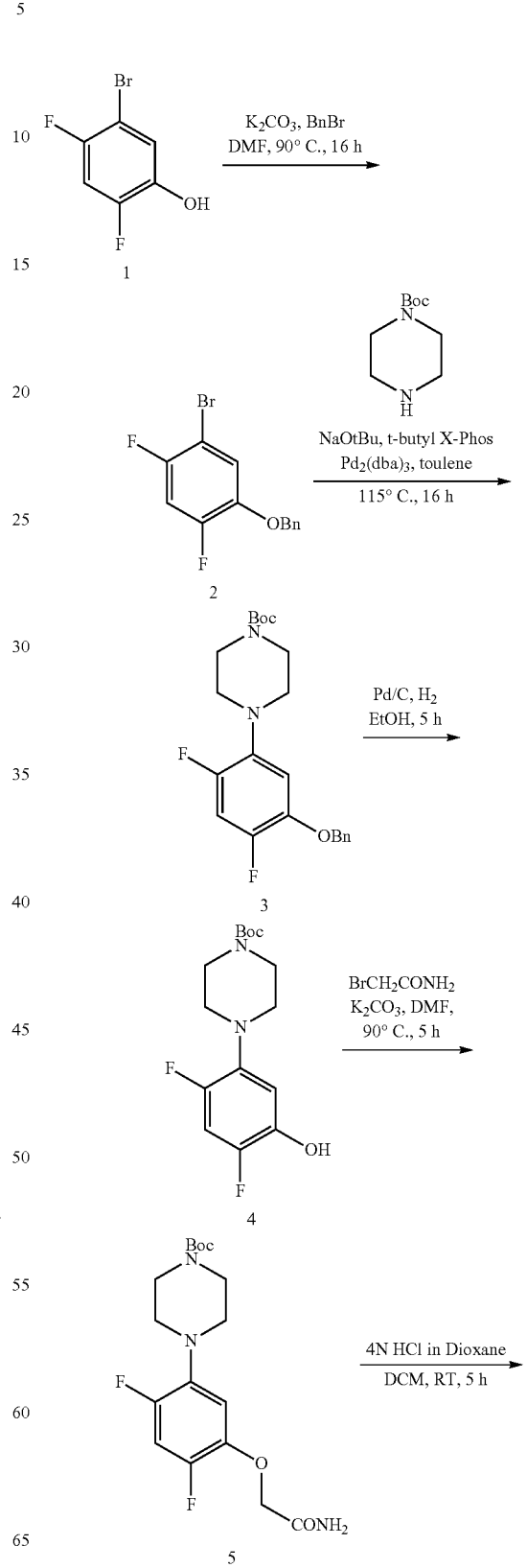

Step 1: 1-(3-fluoropyridin-4-yl)piperazine (3): To a stirred solution of 3-fluoro-4-iodopyridine (2, 2 g, 4.48 mmol, 1 eq) in NMP (20 mL), DIPEA (0.694 g, 5.38 mmol, 1.2 eq) and piperazine (1, 0.484 g, 6.72 mmol, 1.5 eq) were added at RT. The resulting mixture was stirred at 80° C. for 16 h. After the completion, the reaction mixture was concentrated under reduced pressure. The residue was taken in water and lyophilized. The gummy solid obtained was triturated with diethyl ether and n-pentane to afford 1-(3-fluoropyridin-4-yl)piperazine, 3 (0.750 g, 92%) as light yellow colour solid. LCMS (ESI positive ion) m/z: calculated: 181.21; Observed; 182.2 (M+1).

Step 2: 5-amino-3-(2-(4-(3-fluoropyridin-4-yl)piperazin-1-yl)ethyl)-8-(furan-2-yl)thiazolo[5,4-e][1,2,4]triazolo[1,5-c]pyrimidin-2(3H)-one (Compound 3): To a solution of 1-(3-fluoropyridin-4-yl)piperazine (3, 0.071 g, 0.392 mmol, 1 eq) in DMF (2 mL), 2-(5-amino-8-(furan-2-yl)-2-oxothiazolo[4,5-e][1,2,4]triazolo[1,5-c]-pyrimidin-1(2H)-yl)ethyl methane sulfonate (4, 0.150 g, 0.392 mmol, 1.03 eq) and DIPEA (0.100 g, 0.775 mmol, 2 eq) was added at RT. The reaction was stirred at 80° C. for 16 h. After completion, the reaction mixture was concentrated under reduced pressure. The residue obtained was diluted with water and extracted with ethyl acetate (2×30 mL). Combined organic phases were dried (anhydrous $Na_2SO_4$), filtered and concentrated under reduced pressure. The crude product obtained was purified by reverse phase preparative HPLC to afford title compound 3 as brown colour solid (0.013 g, 7%). LCMS (ESI positive ion) m/z: calculated: 481.51; Observed; 482 (M+1). HPLC purity (XB0595TF.M): 97.75%.

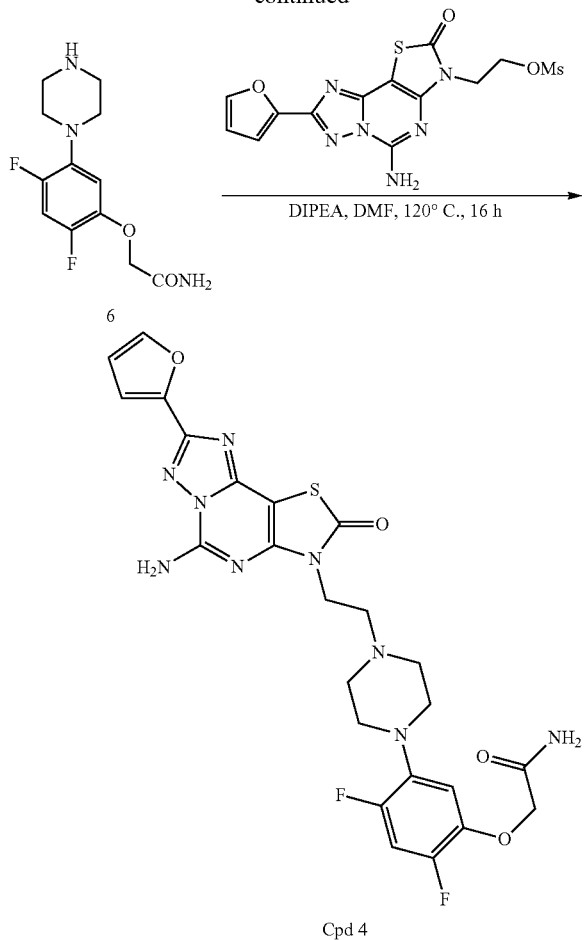

Cpd 4

Step 1: Preparation of 1-(benzyloxy)-5-bromo-2,4-difluorobenzene (2): To a solution of 5-bromo-2,4-difluorophenol (1, 20 g, 95.69 mmol) and benzyl bromide (18 g, 105.26 mmol) in N,N-dimethylformamide (200 mL), was added $K_2CO_3$ (39.62 g, 287.08 mmol) and the reaction mixture was heated at 90° C. for 16 h. After the reaction completion (TLC), the reaction mixture was diluted with water (200 mL) and extracted with ethyl acetate. Organic layer was washed with saturated brine solution, dried over anhydrous $Na_2SO_4$, filtered and concentrated under reduced pressure. The crude obtained was purified by column chromatography (5% EtOAc/Hexane as eluent) to afford the product as off white solid (24 g, 85%). LCMS (ESI negative ion); m/z: calculated: 297.98; Observed; 296.8 (M−1); $^1$H-NMR (400 MHz, DMSO-d6): δ 7.60-7.67 (m, 1H), 7.55-7.58 (m, 1H), 7.37-7.44 (m, 5H), and 5.20 (s, 2H).

Step 2: Preparation of tert-butyl 4-(5-(benzyloxy)-2,4-difluorophenyl)piperazine-1-carboxylate (3): To a solution of 1-(benzyloxy)-5-bromo-2,4-difluorobenzene (2, 24 g, 80.08 mmol), N-Boc piperazine (16.55 g, 88.88 mmol) and sodium tert-butoxide (17.06 g, 177.77 mmol) in toluene (200 mL), t-Bu Xphos (3.43 g, 8.08 mmol) were added. The reaction mixture was purged with $N_2$ and $Pd_2(dba)_3$ (3.69 g, 4.04 mmol) was added. The reaction mixture was heated at 115° C. for 16 h and after completion (TLC), the reaction mixture was cooled and filtered through celite. The filtrate was concentrated and purified by column chromatography (12-15% EtOAc/Hexane) to get the title compound as light brown oil (18 g, 55.14%); LCMS (ESI positive ion); m/z: calculated: 404.19; Observed; 405 (M+1); $^1$H-NMR (400 MHz, DMSO-d6): δ 7.34-7.38 (m, 5H), 7.26 (t, J=11.60 Hz, 1H), 6.94 (t, J=8.80 Hz, 1H), 5.16 (s, 2H), 3.45 (m, 4H), 2.90 (t, J=4.8 Hz, 4H), and 1.42 (s, 9H).

Step 3: tert-butyl 4-(2,4-difluoro-5-hydroxyphenyl)piperazine-1-carboxylate (4): To a clear solution of tert-butyl 4-(5-(benzyloxy)-2,4-difluorophenyl)piperazine-1-carboxylate (3, 18 g, 44.55 mmol) in ethanol (180 mL), 10% Pd-C (2.7 g, 15% Wt.) was added and the reaction mixture was stirred under $H_2$ atmosphere at RT for 5 h. After completion (TLC), the reaction mixture was filtered through celite and washed with methanol (500 mL). The filtrate was concentrated and triturated with diethyl ether to get the title compound as off white solid (13 g, 92.6%); LCMS (ESI positive ion); m/z: calculated: 314.14; Observed; 315.2 (M+1); $^1$H-NMR (400 MHz, $CD_3OD$): δ 6.92 (t, J=8.8 Hz, 1H), 6.56-6.51 (m, 2H), 3.57 (m, 4H), 2.91 (t, J=4.80 Hz, 4H), and 1.49 (s, 9H).

Step 4: tert-butyl 4-(5-(2-amino-2-oxoethoxy)-2,4-difluorophenyl)piperazine-1-carboxylate (5): To a suspension of tert-butyl 4-(2,4-difluoro-5-hydroxyphenyl)piperazine-1-carboxylate (4, 10 g, 31.7 mmol) and bromoacetamide (5.25 g, 38.09 mmol) in N,N-Dimethyl formamide (100 mL), $K_2CO_3$ (13.14 g, 95.23 mmol) was added. The reaction mixture was stirred at 90° C. for 5 h and monitored by TLC. After completion, the reaction mixture was diluted with water (100 mL) and the crude product was extracted with ethyl acetate. Organic layer was washed with saturated brine solution, dried over anhydrous $Na_2SO_4$, filtered, concentrated and triturated with diethyl ether to get the title compound as off light brown solid (9.5 g, 80.7%); LCMS (ESI positive ion); m/z: calculated: 371.17; Observed; 372.2 (M+1); $^1$H-NMR (400 MHz, $CDCl_3$): δ 6.92 (t, J=11.2 Hz, 1H), 6.92 (m, 2H), 5.66 (brs, 1H), 4.53 (s, 2H), 3.61 (t, J=5.20 Hz, 4H), 2.98 (t, J=4.40 Hz, 4H), and 1.51 (s, 9H).

Step 5: 2-(2, 4-difluoro-5-(piperazin-1-yl)phenoxy)acetamide (6): To an ice cold solution of tert-butyl 4-(5-(2-amino-2-oxoethoxy)-2,4-difluorophenyl)-piperazine-1-carboxylate (5, 8.0 g, 21.5 mmol) in DCM, 4 N HCl in Dioxane (80 mL) was added and the reaction mixture was stirred at RT for 5 h. After completion of the reaction (TLC), the HCl salt was filtered. The salt was dissolved in methanol and neutralized using Tosic acid scavenger resin to get the free base as the off white solid (3.5 g, 59.9%); LCMS (ESI positive ion); m/z: calculated: 271.11; Observed; 272.1 (M+1); $^1$H-NMR (400 MHz, DMSO-d6): δ 7.49 (brs, 1H), 7.43 (brs, 1H), 7.25 (t, J=11.60 Hz, 1H), 6.75 (t, J=8.80 Hz, 1H), 4.51 (s, 2H), and 2.81-2.86 (m, 8H).

Step 6: 2-(5-(4-(2-(5-amino-8-(furan-2-yl)-2-oxothiazolo[5,4-e][1,2,4]triazolo [1,5-c]pyrimidin-3(2H)-yl)ethyl)piperazin-1-yl)-2,4-difluorophenoxy)acetamide (Compound 4): To a mixture of 2-(2,4-difluoro-5-(piperazin-1-yl)phenoxy)acetamide (6, 3.5 g, 12.91 mmol) and 2-(5-amino-8-(furan-2-yl)-2-oxothiazolo[5,4-e][1,2,4]triazolo[1,5-c]pyrimidin-3(2H)-yl)-ethyl methane sulfonate (5.88 g, 14.84 mmol) in N,N-Dimethyl formamide (70 mL), was added DIPEA (8.33 g, 64.57 mmol) and the reaction mixture was stirred at 120° C. for 16 h. After completion of the reaction (TLC & LCMS), the reaction mass was concentrated to half of the volume under reduced pressure and cooled to 0° C. The product was precipitated as pale yellow solid. It was filtered and dried. As the purity was not good, it was suspended in DMSO (150 mL) and heated at 110° C. for 1 h and filtered in hot condition. The filtrate was cooled to 0° C., diluted with MeOH and then water was added slowly to facilitate the precipitation. The mixture was stirred at RT for 1 h and filtered. The solid was washed with water and methanol to get compound 4 as light yellow solid (2.5 g, 34%). HPLC purity (XB_0595TF.M): 92.4%; LCMS (ESI positive ion) m/z: calculated: 571.16; Observed; 572.0 (M+1); $^1$H-NMR (400 MHz, DMSO-d6): δ 8.31 (brs, 2H), 7.95 (t, J=0.8 Hz, 1H), 7.44 (brs, 1H), 7.40 (brs, 1H), 7.27-7.21 (m, 2H), 6.76-6.72 (m, 2H), 4.49 (s, 2H), 4.08 (t, J=6.0 Hz, 2H), 2.90 (m, 4H), 2.71 (t, J=6.00 Hz, 2H), and 2.63 (m, 4H).

Examples 5 and 6: (S)-5-amino-3-(2-(4-(2-fluoro-4-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one and (R)-5-amino-3-(2-(4-(2-fluoro-4-(2-(methylsulfinyl)ethoxy)phenyl)-piperazin-1-yl)ethyl)-8-(furan-2-yl)thiazolo[5,4-e][1,2,4]triazolo[1,5-c]pyrimidin-2(3H)-one
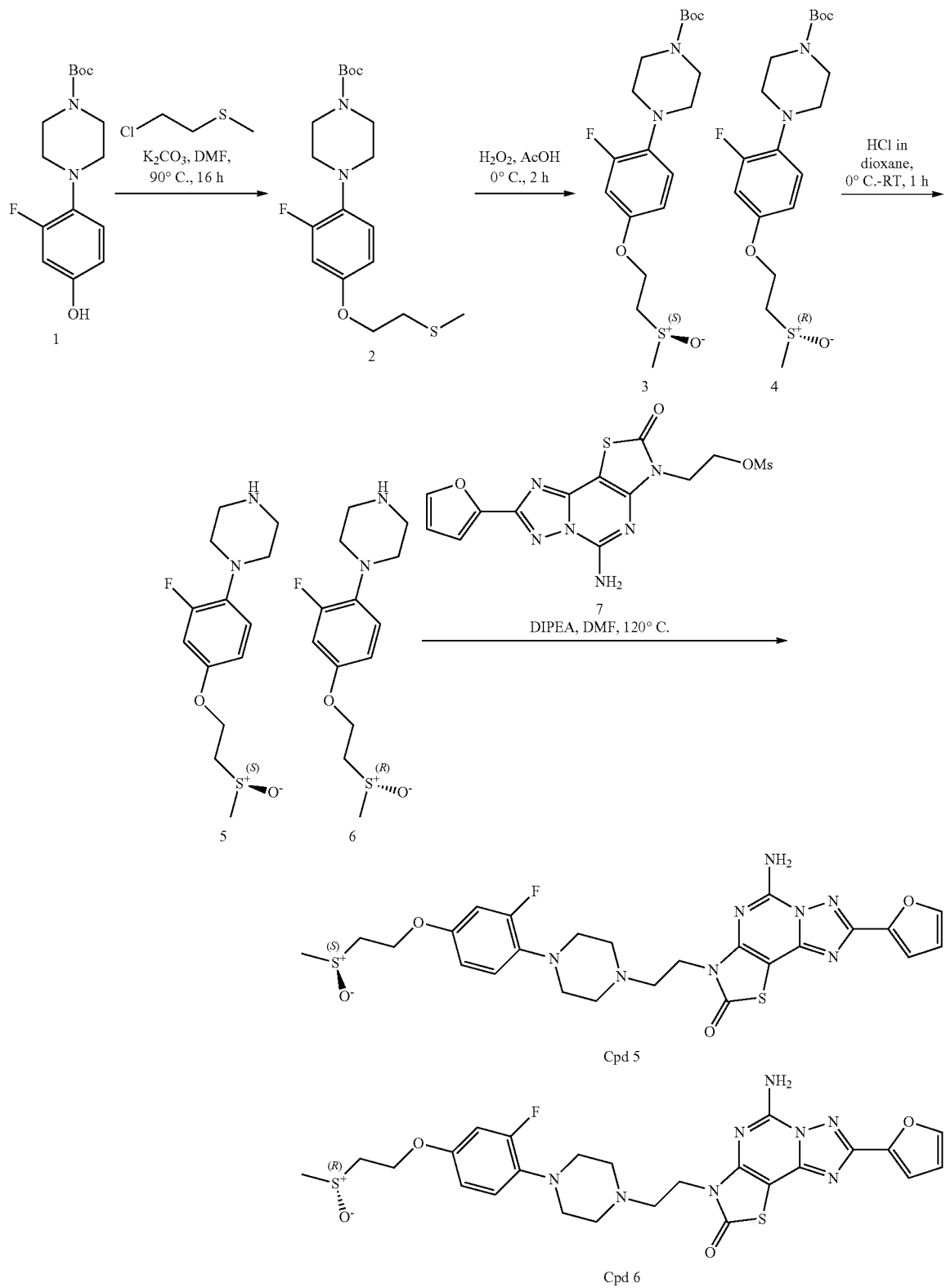

Step 1: Synthesis of tert-butyl 4-(2-fluoro-4-(2-(methylthio)ethoxy)phenyl)piperazine-1-carboxylate (2): To a solution of tert-butyl 4-(2-fluoro-4-hydroxyphenyl)piperazine-1-carboxylate (1, 0.3 g, 1.102 mmol, 1 eq) and 1-chloro-2-methylsulfanyl-ethane (0.168 g, 1.519 mmol, 1 eq) in N,N-dimethylformamide (3 mL), $K_2CO_3$ (0.419 g, 3.027 mmol, 2 eq) was added and the reaction mixture was heated at 90° C. for 16 h. After the reaction completion (TLC), the reaction mixture was diluted with water (10 mL) and extracted with ethyl acetate. Organic layer was washed with saturated brine solution, dried over anhydrous $Na_2SO_4$, filtered and concentrated under reduced pressure. The crude residue obtained was purified by column chromatography (50% EtOAc/Hexane as eluent) to afford the product as off white solid (0.3 g, 53%). LCMS (ESI positive ion) m/z: calculated: 370.48; Observed; 370.9 (M+). 1H-NMR (400 MHz, DMSO-d6): δ 7.02 (m, 1H), 6.85 (m, 1H), 6.72 (m, 1H), 4.09-4.12 (m, 2H), 3.45 (d, J=4.40 Hz, 4H), 2.80-2.86 (m, 6H), 2.14 (s, 3H), and 1.42 (s, 9H).

Step 2: Synthesis of tert-butyl 4-(2-fluoro-4-(2-(methylsulfinyl)ethoxy)phenyl)piperazine-1-carboxylate (3, 4): To an ice cold solution of tert-butyl 4-(2-fluoro-4-(2-(methylthio)ethoxy)phenyl)piperazine-1-carboxylate (2, 0.3 g, 0.809 mmol, 1 eq) in acetic acid (10 mL), hydrogen peroxide (0.187 mL) was added drop wise and stirred at same temperature for 2 h. After the reaction of completion (TLC), the reaction mixture poured in to 4N NaOH solution (20 mL) and extracted with ethyl acetate. Organic layer was washed with saturated brine solution, dried over anhydrous $Na_2SO_4$, filtered and concentrated under reduced pressure. The crude obtained was purified by column chromatography (80% EtOAc/Hexane as eluent) to afford the product as off white solid. (0.29 g, 93%). LCMS (ESI positive ion) m/z: calculated: 386.48; Observed; 387.9 (M+1). 1H-NMR (400 MHz, DMSO-d6): δ 7.02-7.04 (m, 1H), 6.88-6.92 (m, 1H), 6.75-6.78 (m, 1H), 4.28-4.35 (m, 2H), 3.45 (d, J=4.52 Hz, 4H), 3.21-3.27 (m, 1H), 3.00-3.05 (m, 1H), 2.85-2.87 (m, 4H), 2.63 (s, 3H), and 1.41 (s, 9H).

Racemic mixture (0.29 g) was subjected to chiral separation by SFC (0.29 g sample was dissolved in 3 mL of methanol), column—Lux A1 mobile phase: 70:30 (A:B), A=liquid $CO_2$, B=methanol, flow rate: 0.9 mL/min; wave length: 220 nm) to yield 130 mg of peak 1 (3) and 130 mg of peak 2 (4) as off white solid respectively. Note: Peak 1 from SFC purification was arbitrarily considered as (S) isomer and peak 2 was considered as (R) isomer.

Synthesis of Compound 5

Step 3: Synthesis of (S)-1-(2-fluoro-4-(2-(methylsulfinyl)ethoxy)phenyl)piperazine (5): To an ice cold solution of tert-butyl (S)-4-(2-fluoro-4-(2-(methylsulfinyl)ethoxy)phenyl)-piperazine-1-carboxylate (3, 0.13 g) in dichloromethane (1 mL), 4M HCl in dioxane (1 mL) was added and the reaction mixture was stirred at 0° C. for 1 h. After completion, the reaction mixture was concentrated under reduced pressure at room temperature. The residue obtained was triturated with diethyl ether. Then it was dissolved in methanol, passed through Si-Carbonate resin for making free base 5 (0.094 g, 59%). LCMS (ESI positive ion) m/z: calculated: 286.37; Observed; 287 (M+1).

Step 4: Synthesis of (S)-5-amino-3-(2-(4-(2-fluoro-4-(2-(methylsulfinyl)ethoxy)phenyl)-piperazin-1-yl)ethyl)-8-(furan-2-yl)thiazolo[5,4-e][1,2,4]triazolo[1,5-c]pyrimidin-2(3H)-one (Compound 5): A mixture of 2-(5-amino-8-(furan-2-yl)-2-oxothiazolo[5,4-e][1,2,4]triazolo[1,5-c]pyrimidin-3(2H)-yl)ethyl methane sulfonate (7, 0.11 g, 0.303 mmol, 1 eq), (S)-1-(2-fluoro-4-(2(methylsulfinyl)-ethoxy)phenyl)piperazine (5, 0.094 g, 0.33 mmol, 1.1 eq) and diisopropyl ethyl amine (0.195 g, 1.514 mmol, 5 eq) in N,N-dimethylformamide (2 mL) was stirred at 120° C. for 16 h. The reaction progress was monitored by TLC. After completion, the reaction mixture was diluted with water (10 mL) and extracted with ethyl acetate. Organic layer was washed with saturated brine solution, dried over anhydrous $Na_2SO_4$, filtered, concentrated. The crude residue obtained was subjected to preparative HPLC purification to afford compound 5 as off white solid (5 mg). LCMS (ESI positive ion) m/z: calculated: 586.66; Observed; 587.2 (M+1). HPLC purity (XB0595TF.M): 91.67%. 1H-NMR (400 MHz, DMSO-d6): δ 8.32 (s, 2H), 7.95-7.96 (m, 1H), 7.24-7.25 (m, 1H), 6.93-6.98 (m, 1H), 6.85-6.89 (m, 1H), 6.73-6.74 (m, 2H), 4.25-4.30 (m, 2H), 4.09 (s, 2H), 3.22-3.27 (m, 1H), 3.02 (m, 1H), 2.87 (m, 5H), and 2.63 (m, 8H).

Synthesis of Compound 6

Step 1: (R)-1-(2-fluoro-4-(2-(methylsulfinyl)ethoxy)phenyl)piperazine (6): To an ice-cold solution of tert-butyl (R)-4-(2-fluoro-4-(2-(methylsulfinyl)ethoxy)-phenyl)piperazine-1-carboxylate (4, 0.13 g,) in dichloromethane (1 mL), 4M HCl in dioxane (0.5 mL) was added and the reaction mixture was stirred at 0° C. for 1 h. After completion (TLC), the reaction mixture was concentrated under reduced pressure at room temperature. The crude residue obtained was triturated with diethyl ether. Then it was dissolved in methanol, passed through Si-Carbonate resin for making free base 6, (0.094 g). LCMS (ESI positive ion) m/z: calculated: 286.37; Observed; 287 (M+1).

Step 2: (R)-5-amino-3-(2-(4-(2-fluoro-4-(2-(methylsulfinyl)ethoxy)phenyl)-piperazin-1-yl)ethyl)-8-(furan-2-yl)thiazolo[5,4-e][1,2,4]triazolo[1,5-c]pyrimidin-2(3H)-one (Compound 6): A mixture of 2-(5-amino-8-(furan-2-yl)-2-oxothiazolo[5,4-e][1,2,4]triazolo[1,5-c]pyrimidin-3(2H)-yl) ethyl methane sulfonate (7, 0.11 g, 0.303 mmol, 1 eq), (R)-1-(2-fluoro-4-(2-(methylsulfinyl)-ethoxy)phenyl)piperazine (6, 0.094 g, 0.33 mmol, 1.1 eq) and diisopropyl ethyl amine (0.195 g, 1.514 mmol, 5 eq) in N,N-dimethylformamide (2 mL) was stirred at 120° C. for 16 h. The reaction progress was monitored by TLC. After completion, the reaction mixture was diluted with water (10 mL) and extracted with ethyl acetate. Organic layer was washed with saturated brine solution, dried over anhydrous $Na_2SO_4$, filtered, concentrated. The crude product obtained was subjected to reverse phase preparative HPLC purification to afford compound 6 as off white solid. (3 mg). LCMS (ESI positive ion) m/z: calculated: 586.66; Observed; 587.2 (M+1). HPLC purity (XB0595TF.M): 96.6%. 1H-NMR (400 MHz, DMSO-d6): δ 8.31 (broad s, 2H), 7.95-7.95 (s, 1H), 7.24-7.25 (m, 1H), 7.00-6.88 (m, 1H), 6.85 (m, 1H), 6.71-6.74 (m, 2H), 4.25-4.31 (m, 2H), 4.08 (t, J=6.00 Hz, 2H), 3.22-3.29 (m, 2H), 3.00-3.03 (m, 1H), 2.86 (s, 4H), and 2.62-2.70 (m, 8H).

Examples 7, 8a and 8b: (R,S)-5-amino-3-(2-(4-(2,4-difluoro-5-(2-(methylsulfinyl)ethoxy)-phenyl)-piperazin-1-yl)ethyl)-8-(furan-2-yl)thiazolo[5,4-e][1,2,4]triazolo[1,5-c]-pyrimidin-2(3H)-one, (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one and (−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one

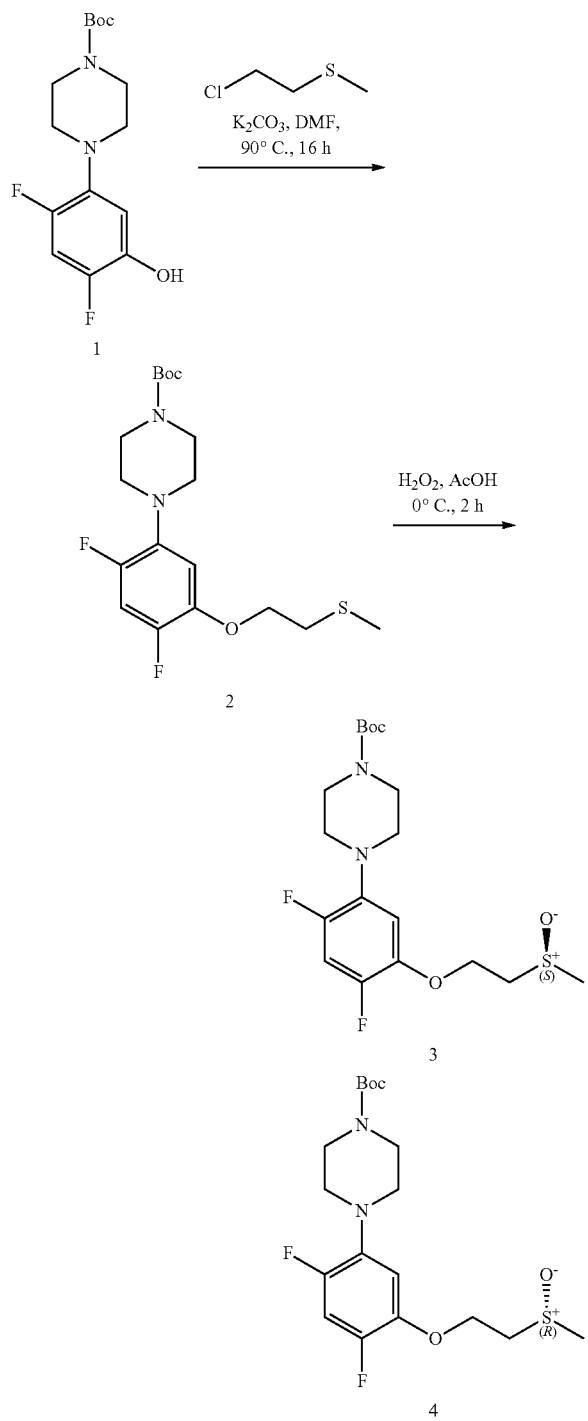

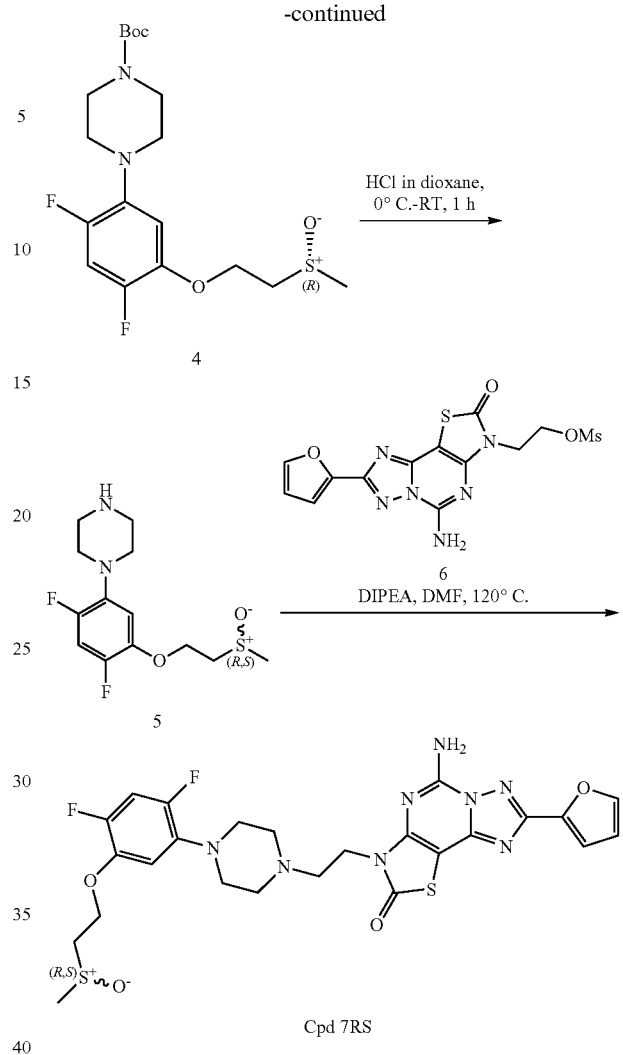

Cpd 7RS

Step 1: Synthesis of tert-butyl 4-(2,4-difluoro-5-(2-(methylthio)ethoxy)-phenyl)piperazine-1-carboxylate (2): To a solution of tert-butyl 4-(2,4-difluoro-5-hydroxyphenyl)piperazine-1-carboxylate (1, 0.5 g, 1.591 mmol, 1 eq) and 1-chloro-2-methylsulfanyl-ethane (0.264 g, 2.386 mmol, 1.5 eq) in N,N-dimethylformamide (5 mL), $K_2CO_3$ (0.439 g, 3.181 mmol, 2 eq) was added and the reaction mixture was heated at 90° C. for 16 h. After the reaction completion (TLC), the reaction mixture was diluted with water (10 mL) and extracted with ethyl acetate. Organic layer was washed with saturated brine solution, dried over anhydrous $Na_2SO_4$, filtered and concentrated under reduced pressure. The crude obtained was purified by column chromatography (50% EtOAc/Hexane as eluent) to afford the product as off white solid (2, 0.5 g, 77%). LCMS (ESI positive ion) m/z: calculated: 388.47; Observed; 389 (M+1).

Step 2: Synthesis of tert-butyl 4-(2,4-difluoro-5-(2-(methylsulfinyl)ethoxy)phenyl)-piperazine-1-carboxylate (3, 4): To an ice cold solution of tert-butyl 4-(2,4-difluoro-5-(2-(methylthio)ethoxy)-phenyl)piperazine-1-carboxylate (2, 0.5 g, 0.001 mmol, 1 eq) in acetic acid (10 mL), hydrogen peroxide (0.312 mL) was added drop wise and stirred at same temperature for 2 h. After the reaction completion (TLC), the reaction mixture poured in to 4N NaOH solution (20 mL) and extracted with ethyl acetate. Organic layer was washed with saturated brine solution, dried over anhydrous Na$_2$SO$_4$, filtered and concentrated under reduced pressure. The crude obtained was purified by column chromatography (80% EtOAc/Hexane as eluent) to afford the product as off white solid (0.38 g, 86%). LCMS (ESI positive ion) m/z: calculated: 404.47; Observed; 348.9 (M-t-butyl). 1H-NMR (400 MHz, DMSO-d6): δ 7.24-7.32 (m, 1H), 6.89-6.94 (m, 1H), 4.39-4.45 (m, 2H), 3.47 (s, 4H), 3.05 (m, 2H), 2.94 (s, 4H), 2.64 (s, 3H), and 1.42 (s, 9H). The above racemic compound (0.38 g) was subjected to chiral separation by SFC (0.38 g sample was dissolved in 5 mL of methanol, column—Lux A1 mobile phase: 70:30 (A:B), A=liquid CO$_2$, B=methanol, flow rate: 0.9 mL/min; wave length: 220 nm) to yield 150 mg of peak 1 (3, [α]$_D$=+50.7°, c=1.1, MeOH) and 150 mg of peak 2 (4, [α]$_D$=−45.2°, c=1.1, MeOH) as off white solids respectively.

Step 3: Synthesis of (R,S)-1-(2,4-difluoro-5-(2-(methylsulfinyl)ethoxy)phenyl)piperazine (5RS): To an ice cold solution of tert-butyl (R,S)-4-(2,4-difluoro-5-(2-(methylsulfinyl)ethoxy)phenyl)-piperazine-1-carboxylate (racemic mixture of 3 and 4, 0.15 g, 0.371 mmol, 1 eq) in dichloromethane (2 mL), 4M HCl in dioxane (0.5 mL) was added and the reaction mixture was stirred at 0° C. for 1 h. After completion (TLC), the reaction mixture was concentrated under reduced pressure at room temperature. The residue obtained was triturated with diethyl ether to afford the racemic product. Then it was dissolved in methanol, passed through Si-Carbonate resin for making free base (0.09 g). LCMS (ESI positive ion) m/z: calculated: 304.36; Observed; 305 (M+1).

Step 4 for Compound 7: Synthesis of (R,S)-5-amino-3-(2-(4-(2,4-difluoro-5-(2-(methylsulfinyl)ethoxy)-phenyl)-piperazin-1-yl)ethyl)-8-(furan-2-yl)thiazolo[5,4-e][1,2,4]triazolo[1,5-c]-pyrimidin-2(3H)-one: To a solution of 2-(5-amino-8-(furan-2-yl)-2-oxothiazolo[5,4-e][1,2,4]triazolo[1,5-c]pyrimidin-3(2H)-yl)ethyl methane sulfonate (6, 105 mg, 0.265 mmol, 1.0 eq) in DMF (2 mL), (R)-1-(2,4-difluoro-5-(2-(methylsulfinyl)ethoxy)phenyl)piperazine (5RS, 86.46 mg, 0.278 mmol) and DIPEA (170.85 mg, 0.001 mmol, 5 eq) were added. The reaction mass was degassed with nitrogen and heated to 120° C. for 16 h. The progress of the reaction was monitored by LCMS analysis. After completion, the reaction mixture was concentrated under reduced pressure. The crude product obtained was purified by grace column chromatography with 5% Methanol in DCM to afford the required racemic compound. It was purified further by preparative HPLC to afford title compound 7 (6 mg, purity 96%). LCMS (ESI positive ion) m/z: calculated: 604.65; Observed; 605.2 (M+1). HPLC purity (XB0595TF.M): 96.68%. 1H-NMR (400 MHz, DMSO-d6): δ 8.31 (s, 1H), 7.50 (m, 1H), 7.27-6.97 (m, 3H), 6.83 (m, 1H), 6.73-6.74 (m, 1H), 4.36-4.45 (m, 2H), 4.08 (m, 2H), 3.25-3.38 (m, 2H), 3.00-3.06 (m, 2H), 2.94 (s, 3H), 2.63-2.71 (m, 2H), and 2.53-2.58 (m, 6H).

Step 3': Synthesis of (+)-1-(2,4-difluoro-5-(2-(methylsulfinyl)ethoxy)phenyl)piperazine: To an ice cold stirred solution of tert-butyl (+)-4-(2,4-difluoro-5-(2-(methylsulfinyl)ethoxy)-phenyl)piperazine-1-carboxylate (4, 500 mg, 1.23 mmol) in ethyl acetate (3 mL), SnCl$_4$ (644 mg, 2.47 mmol) was added. The resulting mixture was stirred at RT for 2 h. The reaction mixture was concentrated under reduced pressure. The residue obtained was triturated with cold ethyl acetate (2×10 mL) to afford the crude product (580 mg), which was used as such for the next step. LCMS (M+H) 305.1. [α]$_D$=+24°, c=0.5, MeOH.

Step 4' for Compound 8a: Synthesis of (+)-5-amino-3-(2-(4-(2,4-difluoro-5-(2-(methylsulfinyl)ethoxy)-phenyl)-piperazin-1-yl)ethyl)-8-(furan-2-yl)thiazolo[5,4-e][1,2,4]triazolo[1,5-c]-pyrimidin-2(3H)-one was prepared according to the same procedure described for Compound 7, starting from (+)-1-(2,4-difluoro-5-(2-(methylsulfinyl)ethoxy)phenyl)piperazine. 1H-NMR (400 MHz, DMSO-d6): δ 8.31 (s, 1H), 7.50 (m, 1H), 7.27-6.97 (m, 3H), 6.83 (m, 1H), 6.73-6.74 (m, 1H), 4.36-4.45 (m, 2H), 4.08 (m, 2H), 3.25-3.38 (m, 2H), 3.00-3.06 (m, 2H), 2.94 (s, 3H), 2.63-2.71 (m, 2H), and 2.53-2.58 (m, 6H). [α]$_D$=+24°, c=0.1, AcOH. Absolute stereochemistry of the chiral center is unknown.

Steps 3" and 4" for Compound 8b: (−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one was prepared according to the same procedure described for Compound 7, starting from (−)-4-(2,4-difluoro-5-(2-(methylsulfinyl)ethoxy)phenyl)-piperazine-1-carboxylate (3) leading by a step 3" to the (−)-1-(2,4-difluoro-5-(2-(methylsulfinyl)ethoxy)phenyl) piperazine. LCMS (ESI positive ion) m/z: calculated: 604.65; Observed; 605.2 (M+1); HPLC purity (XB0595TF): 98.81%; $^1$H NMR (400 MHz, DMSO-d6): δ 8.32 (brs, 1H), 7.96 (s, 1H), 7.22-7.28 (m, 2H), 6.74-6.85 (m, 2H), 6.73-6.74 (m, 1H), 4.36-4.45 (m, 2H), 4.09 (s, 2H), 3.28-3.30 (m, 1H), 3.23-3.26 (m, 1H), 3.00-3.06 (m, 4H), 2.71-2.94 (m, 3H), and 2.64 (s, 6H). [α]$_D$=−39°, c=0.1, AcOH. Absolute stereochemistry of the chiral center is unknown.

Example 77: 5-amino-3-(2-(4-(2,4-difluoro-5-(2-(methylsulfonyl)ethoxy)phenyl)piperazin-1-yl) ethyl)-8-(furan-2-yl)thiazolo[5,4-e][1,2,4]triazolo[1,5-c]pyrimidin-2(3H)-one Step 1: Synthesis of tert-butyl 4-(2,4-difluoro-5-(2-(methylsulfonyl)ethoxy)phenyl)-piperazine-1-carboxylate: In an open vial tert-butyl 4-(2,4-difluoro-5-(2-(methylthio)ethoxy)phenyl)-piperazine-1-carboxylate (20 g, 51.48 mmol, prepared as described in Example 7, Step 1) and urea hydrogen peroxide (21.78 g, 231.68 mmol) were heated to 90° C. After 1 hour the reaction mixture was allowed to room temperature. About 500 mL of ethyl acetate was added and stirred for 0.5 h, then filtered. Concentration of the filtrate afforded the crude product. It was purified by column chromatography using 50% ethyl acetate in petroleum ether to afford the product as off white solid (9 gram, 42%) LCMS (ESI positive ion) m/z: 421.

Step 2: Synthesis of 1-(2,4-difluoro-5-(2-(methylsulfonyl)ethoxy)phenyl)piperazine hydrochloride (7): To an ice cold solution of tert-butyl 4-(2,4-difluoro-5-(2-(methylsulfonyl)ethoxy)phenyl) piperazine-1-carboxylate (9 g, 21.40 mmol) in dichloromethane (50 mL) was added a solution of HCl in in diethyl ether (50 mL). After stirring at 0° C. for 0.5 h, it was allowed to reach room temperature and stirred for 16 h. The reaction mixture was concentrated under reduced pressure at room temperature. The residue obtained was triturated with diethyl ether to afford the pure product (10 g). LCMS (ESI positive ion) m/z: 321 (M+1).

Step 3: To a stirred suspension of 1-(2,4-difluoro-5-(2-(methylsulfonyl)ethoxy)phenyl)piperazine hydrochloride (7 g, 22.13 mmol) in dry dichloroethane (70 mL), triethyl amine (6.259 g, 61.97 mmol) and freshly prepared 2-(5-amino-8-(furan-2-yl)-2-oxothiazolo[5,4-e][1,2,4]triazolo[1,5-c]pyrimidin-3(2H)-yl)-acetaldehyde (7 g, 22.13 mmol) were added. After stirring at room temperature for 3 h, sodium triacetoxy borohydride (9.339 g, 44.26 mmol) was added. The resulting mixture was stirred at room temperature for 24 h. After completion, the reaction mixture was diluted with dichloromethane. The organic layer separated was washed successively with saturated bicarbonate solution and saturated brineution. Then it was dried over anhydrous Na$_2$SO$_4$, filtered and concentrated under reduced pressure. The crude obtained was purified by column chromatography (230-400 silica gel, 5% methanol/dichloromethane as an eluent) to afford the product as off white solid (3.2 g, 26%). LCMS (ESI positive ion) m/z: 621 (M+1). ¹H-NMR (400 MHz, DMSO-d6): δ 8.31 (s, 2H), 7.95 (d, J=0.92 Hz, 1H), 7.23-7.29 (m, 2H), 6.82 (t, J=8.60 Hz, 1H), 6.73-6.74 (m, 1H), 4.40 (t, J=5.64 Hz, 2H), 4.08 (t, J=5.96 Hz, 2H), 3.62 (t, J=5.44 Hz, 2H), 3.07 (s, 3H), 2.94 (s, 4H), 2.71 (t, J=6.04 Hz, 2H), and 2.67-2.68 (m, 4H), Example 78: 5-amino-3-(2-(4-(2-fluoro-4-(2-(methylsulfonyl)ethoxy)phenyl)piperazin-1-yl)ethyl)-8-(furan-2-yl)thiazolo[5,4-e][1,2,4]triazolo[1,5-c]pyrimidin-2(3H)-one

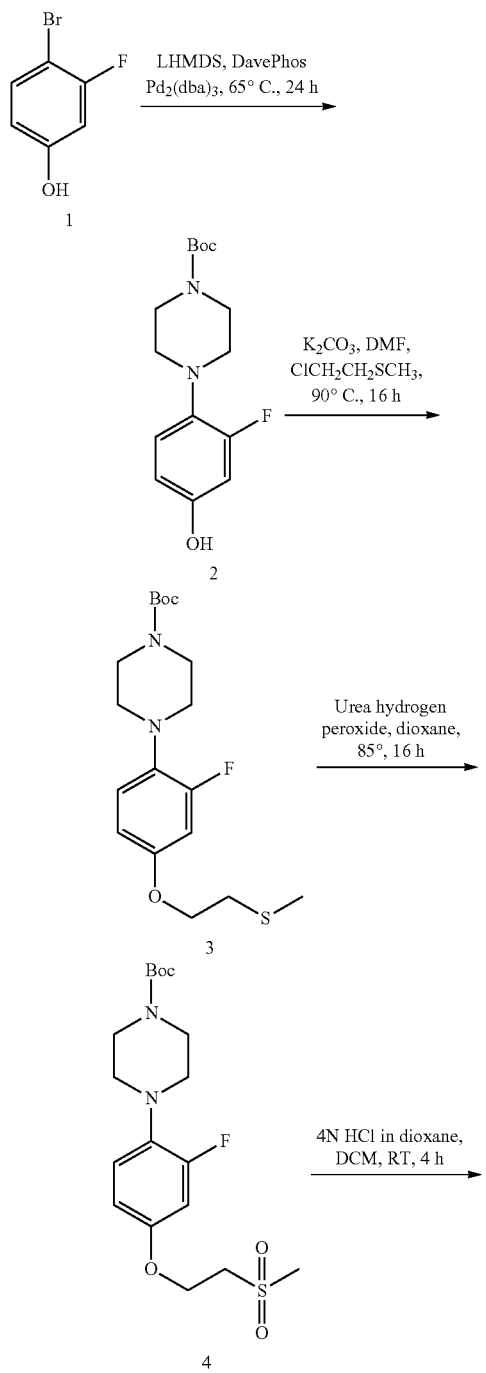

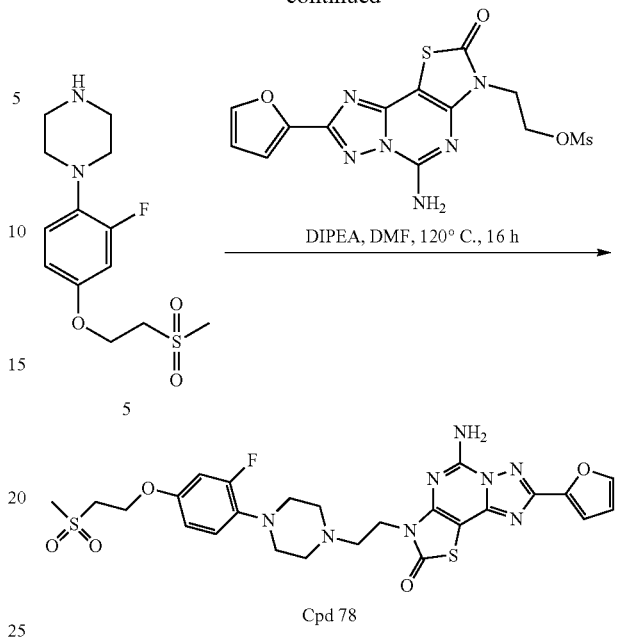

Step 1: Synthesis of tert-butyl 4-(2-fluoro-4-hydroxyphenyl)piperazine-1-carboxylate (2): To a mixture of 4-Bromo-3-fluorophenol (1, 10 g, 0.052 mol), tert-butyl piperazine-1-carboxylate (11.70 g, 0.063 mol), DavePhos (0.515 g, 0.001 mol) and Pd₂(dba)₃ (0.958 g, 0.001 mol) was added LHMDS (115 mL of 1.0 M solution in THF, 0.115 mol) at 0° C. under nitrogen. The reaction mixture was heated at 65° C. for 24 h and monitored by TLC. The crude reaction mixture was neutralized with saturated NH₄Cl and extracted with ethyl acetate (2×100 mL). The combined organic layer was concentrated and purified by column chromatography to afford the title compound as off white solid (2.25 g, 14.5%). LCMS (ESI positive ion) m/z: calculated: 296.15; observed: 297.2 (M+1).

Step 2: Synthesis of tert-butyl 4-(2-fluoro-4-(2-(methylthio)ethoxy)phenyl)piperazine-1-carboxylate (3): To a mixture of tert-butyl 4-(2-fluoro-4-(2-(methylthio)ethoxy)phenyl)piperazine-1-carboxylate (2, 0.3 g, 1.102 mmol) and 1-chloro-2-methylsulfanyl-ethane (0.168 g, 1.519 mmol) in N,N-Dimethylformamide (3 mL), was added potassium carbonate (0.419 g, 3.027 mmol) and the reaction mixture was heated at 90° C. for 16 h. After the reaction completion (TLC), the reaction mixture was diluted with water (10 mL) and extracted with ethyl acetate. Combined organic layer was washed with saturated brine solution, dried over anhydrous Na₂SO₄, filtered and concentrated under reduced pressure. The crude obtained was purified by column chromatography (50% EtOAc/Hexane as eluent) to afford the product as off white solid (0.3 g, 52.8%). LCMS (ESI positive ion) m/z: calculated: 370.48; observed: 370.9 (M+). ¹H-NMR (400 MHz, DMSO-d6):δ 7.02 (m, 1H), 6.85 (d, J=2.80 Hz, 1H), 6.72 (d, J=2.00 Hz, 1H), 4.09-4.12 (m, 2H), 3.45 (d, J=4.40 Hz, 4H), 2.80-2.86 (m, 6H), 2.14 (s, 3H), and 1.42 (s, 9H).

Step 3: Synthesis of tert-butyl 4-(2-fluoro-4-(2-(methylsulfonyl)ethoxy)phenyl)-piperazine-1-carboxylate (4): To a solution of tert-butyl 4-[2-fluoro-4-(2-methylsulfanylethoxy)phenyl]piperazine-1-carboxylate (3, 0.5 g, 0.001 mmol) in 1,4-Dioxane (2 mL), Urea hydrogen peroxide (507.49 g, 0.005 mmol) was added. The mixture was heated to 85° C. for 16 h. After the completion of the reaction, it was concentrated under reduced pressure. The residue was taken in ethyl acetate and filtered. The filtrate was washed with water, dried over $Na_2SO_4$ and concentrated under reduced pressure. The crude product obtained was subjected to column chromatography (1% Methanol in DCM solvent mixture as eluent) to afford the product tert-butyl 4-(2-fluoro-4-(2-(methylsulfonyl)ethoxy)phenyl)piperazine-1-carboxylate (0.22 g, 40%). LCMS (ESI positive ion) m/z: calculated: 402.48; observed: 403.3 (M+1). 1H-NMR (400 MHz, DMSO-d6): δ 7.02 (broad s, 1H), 6.65-6.72 (m, 2H), 4.41 (t, J=5.60 Hz, 2H), 3.64 (s, 4H), 3.44 (t, J=5.20 Hz, 2H), 3.07 (s, 3H), 3.00 (s, 4H), and 1.50 (s, 9H).

Step 4: Synthesis of 1-(2-fluoro-4-(2-(methylsulfonyl)ethoxy)phenyl)piperazine (5): To an ice cold solution of tert-butyl 4-[2-fluoro-4-(2-methylsulfonyl)ethoxy)phenyl]piperazine-1-carboxylate (4, 0.22 g, 0.547 mmol) in dichloromethane (5 mL), 2M HCl in diethyl ether (2 mL) was added and the reaction mixture was stirred at 0° C. for 1 h. After completion (TLC), the reaction mixture was concentrated under reduced pressure at room temperature. The residue obtained was triturated with diethyl ether to afford the pure product. Then it was dissolved in methanol, passed through Si-Carbonate resin for making free base (0.105 g crude compound) directly used for the next step.

Step 5: Synthesis of 5-amino-3-(2-(4-(2-fluoro-4-(2-(methylsulfonyl)ethoxy)phenyl)-piperazin-1-yl)ethyl)-8-(furan-2-yl)thiazolo[5,4-e][1,2,4]triazolo[1,5-c]pyrimidin-2(3H)-one (Compound 78): To a mixture of 1-[2-fluoro-4-(2-methylsulfinylethoxy)phenyl]piperazine (5, 105 mg, 0.347 mmol) and 2-(5-amino-8-(furan-2-yl)-2-oxothiazolo[5,4-e][1,2,4]triazolo[1,5-c]pyrimidin-3(2H)-yl)ethyl methane sulfonate (125 mg, 0.315 mmol) in N,N-Dimethylformamide (2 mL), was added DIPEA (204 mg, 1.577 mmol) and the reaction mixture was stirred at 120° C. for 16 h. After completion of the reaction (TLC & LCMS), the reaction mass was concentrated under reduced pressure. The crude product was purified by column chromatography with 5% Methanol in DCM to afford the product. It was further purified by RP preparative HPLC to afford the the title compound. LCMS (ESI positive ion) m/z: calculated: 602.66; observed: 603 (M+1). HPLC purity (PG_AM9010A3): 93.64%. 1H-NMR (400 MHz, DMSO-d6): δ 8.31 (broad s, 2H), 7.95 (s, 1H), 7.24 (d, J=3.20 Hz, 1H), 6.87-6.98 (m, 2H), 6.73-6.74 (m, 2H), 4.29 (t, J=5.60 Hz, 2H), 4.08 (t, J=5.60 Hz, 2H), 3.58 (t, J=5.60 Hz, 2H), 3.05 (s, 3H), 2.86 (s, 4H), and 2.68-2.72 (m, 6H).

Example 80: 5-amino-3-(2-(4-(2-fluoro-4-(S-methylsulfonimidoyl)phenyl)piperazin-1-yl)ethyl)-8-(furan-2-yl)thiazolo[5,4-e][1,2,4]triazolo[1,5-c]pyrimidin-2(3H)-one

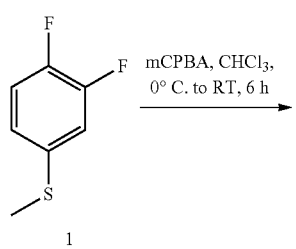

Step 1: Synthesis of 1,2-difluoro-4-(methylsulfinyl)benzene (2): To an ice cold solution of (3,4-difluorophenyl)

(methyl)sulfane (1, 3.0 g, 18.73 mmol) in DCM, was added 3-chloroperbenzoic acid (6.78 g, 39.33 mmol) and stirred the reaction mixture at RT for 16 h. After the reaction completion (TLC), the reaction mixture was diluted with ice cold water (30 mL) and the crude product was extracted with DCM. Organic layer was successively washed with aqueous sodium thiosulphate, 10% NaHCO$_3$, brine solution, dried over anhydrous Na$_2$SO$_4$, filtered and concentrated under reduced pressure. The crude product obtained was purified by column chromatography (50% EtOAc/Hexane as eluent) to afford the title product 2 as off white solid (2.8 g, 85%); LCMS (ESI positive ion) m/z: calculated: 176.18; Observed; 177.1 (M+1); 1H-NMR (400 MHz, DMSO-d6): δ 7.83-7.79 (m, 1H), 7.73-7.66 (m, 1H), 7.60-7.57 (m, 1H), 2.78 (s, 1H).

Step 2: Synthesis of (3,4-difluorophenyl)(imino)(methyl)-l6-sulfanone (3): To a solution of 1,2-difluoro-4-(methylsulfinyl)benzene (2, 2.8 g, 15.89 mmol) in dichloromethane (60 mL) was added trifluoroacetamide (3.59 g, 31.79 mmol), magnesium oxide (2.54 g, 63.57 mmol) and rhodium diacetate dimer (0.172 g, 0.429 mmol) and the reaction mixture was purged with N$_2$ for 2 min. Iodobenzene diacetate (10.23 g, 31.79 mmol) was added and the reaction mixture was stirred at RT for 16 h. After the reaction completion (TLC), the reaction mixture was filtered through celite bed, concentrated and purified by preparative column chromatography to afford the title compound 3 as off white solid (0.7 g, 23.0%); LCMS (ESI positive ion) m/z: calculated: 191.20; Observed; 192.1 (M+1); 1H-NMR (400 MHz, DMSO-d6): δ 8.07-8.02 (m, 1H), 7.86-7.83 (m, 1H), 7.75-7.71 (m, 1H), 3.28 (s, 3H).

Step 3: Synthesis of (3-fluoro-4-(piperazin-1-yl)phenyl)(imino)(methyl)-l6-sulfanone (4): To a solution of (3,4-difluorophenyl)(imino)(methyl)-l6-sulfanone (0.7 g, 3.66 mmol) in N,N-Dimethylformamide (10 mL), was added Piperazine (0.32 g, 3.66 mmol), Potassium carbonate (1.51 g, 10.98 mmol) and the reaction mixture was heated at 100° C. for 16 h. After the reaction completion (TLC), reaction mixture diluted with water and the crude product was extracted with ethyl acetate, washed with brine, dried over Na$_2$SO$_4$, filtered and concentrated under reduced pressure. The crude obtained was purified by preparative column chromatography to afford the desired product 4 as off white solid. LCMS (ESI positive ion) m/z: calculated: 257.33; Observed; 258.1 (M+1).

Step 4: Synthesis of 5-amino-3-(2-(4-(2-fluoro-4-(S-methylsulfonimidoyl) phenyl) piperazin-1-yl)ethyl)-8-(furan-2-yl)thiazolo[5,4-e][1,2,4]triazolo[1,5-c] pyrimidin-2 (3H)-one (Compound 80): A mixture of (3-fluoro-4-(piperazin-1-yl)phenyl) (imino)(methyl)-l6-sulfanone (4, 0.14 g, 0.545 mmol), 2-(5-amino-8-(furan-2-yl)-2-oxothiazolo[5,4-e][1,2,4] triazolo[1,5-c] pyrimidin-3(2H)-yl)ethyl methanesulfonate (0.18 g, 0.45 mmol) and DIPEA (0.176 g, 1.36 mmol) in N,N-Dimethylformamide (2 mL), was stirred at 120° C. for 16 h. After the reaction completion (TLC), reaction mixture diluted with water and the crude product was extracted with ethyl acetate, washed with brine, dried over Na$_2$SO$_4$, filtered, concentrated and purified by preparative HPLC to afford the title compound as off white solid. LCMS (ESI positive ion) m/z: calculated: 557.62; Observed; 558.1 (M+1). HPLC purity (XB_0595TF.M): 93.12%. 1H-NMR (400 MHz, DMSO-d6): δ 8.31 (brs, 2H), 7.95 (s, 1H), 7.61-7.57 (m, 2H), 7.24 (d, J=4.8 Hz, 1H), 7.15 (t, J=9.2 Hz, 1H), 6.73-6.72 (m, 1H), 4.10 (s, 1H), 4.10 (t, J=6.00 Hz, 2H), 3.08 (m, 4H), 3.03 (s, 3H), 2.73 (t, J=6.00 Hz, 2H), 2.67-2.65 (m, 4H).

Example 81: 5-(4-(2-(5-amino-8-(furan-2-yl)-2-oxothiazolo[5,4-e][1,2,4]triazolo[1,5-c]pyrimidin-3 (2H)-yl)ethyl)piperazin-1-yl)-N-(2-(dimethylamino) ethyl)-2,4-difluorobenzamide

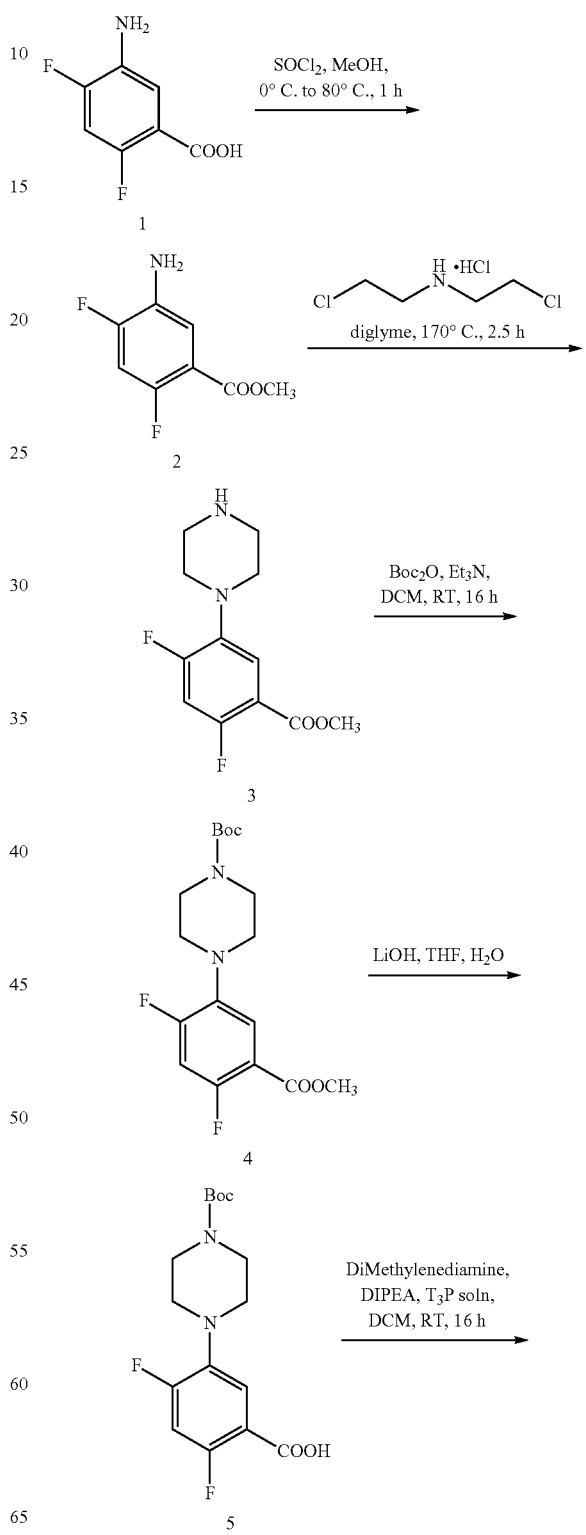

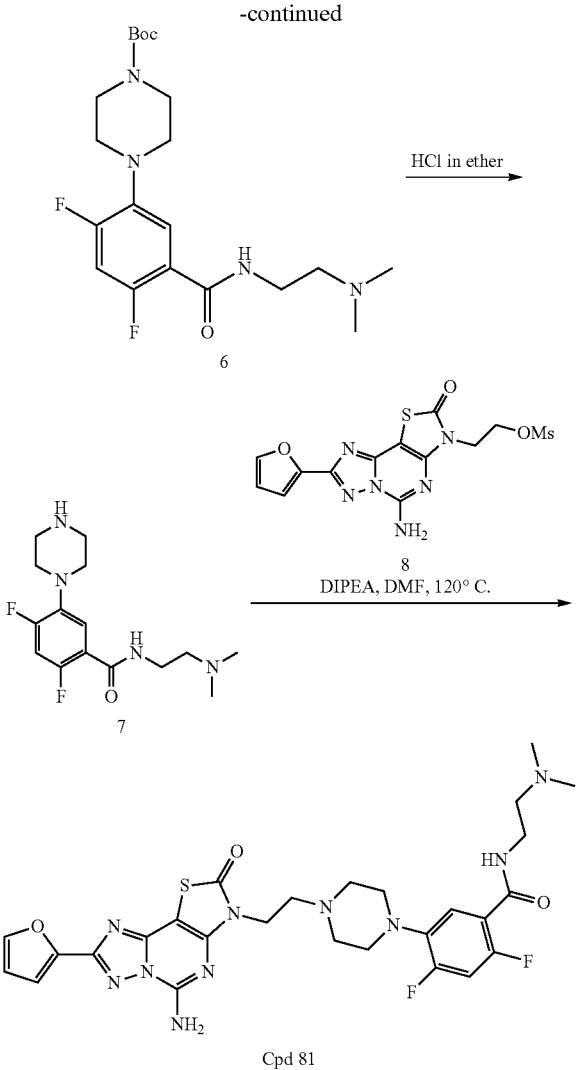

Cpd 81

Step 1: Synthesis of methyl 5-amino-2,4-difluorobenzoate (2): To an ice cold solution of 5-amino-2,4-difluoro-benzoic acid (1, 0 g, 0.017 mol) in methanol (20.0 mL), thionyl chloride (2.514 mL, 0.035 mol) was added. The resulting mixture was heated at 80° C. for 1 h. Progress of the reaction was monitored by TLC. The reaction mixture was concentrated under reduced pressure. DCM and water was added to the reaction mixture. Combined organic layer was dried over sodium sulphate, concentrated under reduced pressure to afford the product methyl 5-amino-2,4-difluoro-benzoate (2.8 g, 86.0%). LCMS (ESI positive ion) m/z: calculated: 187.15; Observed; 188.2 (M+1). 1H-NMR (400 MHz, CDCl3): δ 7.35-7.39 (m, 1H), 6.82-6.87 (m, 1H), and 3.92 (s, 3H).

Step 2: Synthesis of methyl 2,4-difluoro-5-(piperazin-1-yl)benzoate (3): A mixture of methyl 5-amino-2,4-difluoro-benzoate (2, 3.0 g, 0.016 mol) and 2-chloro-N-(2-chloroethyl)ethanamine hydrochloride (3.719 g, 0.021 mol) in diethylene glycol monomethyl ether (12 mL) was heated to 170° C. for 2.5 h. Progress of the reaction was monitored by TLC. Water was added to the reaction mixture and extracted with ethyl acetate. The organic part was discarded. Then pH of the aqueous part was adjusted with sodium bicarbonate and extracted with ethyl acetate. Combined organic part was dried over anhydrous sodium sulphate, and concentrated under reduced pressure. The crude product obtained was purified by column chromatography to afford the product (1.5 g, 29.9%). LCMS (ESI positive ion) m/z: calculated: 256.25; Observed; 257.0 (M+1).

Step 3: Synthesis of tert-butyl 4-(2,4-difluoro-5-(methoxycarbonyl)phenyl)piperazine-1-carboxylate (4): To an ice cold solution of methyl 2,4-difluoro-5-piperazin-1-yl-benzoate (3, 1.0 g, 0.009 mol) in DCM (10 mL), triethyl amine (1.510 mL, 0.012 mol) and boc anhydride (1.278 mL, 0.006 mol) were added. The resulting mixture was stirred at room temperature for 16 h. Progress of the reaction was monitored by TLC. The reaction mixture was diluted with water and extracted with ethyl acetate. The combined organic part was washed with saturated brine solution, dried over anhydrous sodium sulphate, concentrated under reduced pressure to afford the product (0.800 g, 58%). LCMS (ESI positive ion) m/z: calculated: 356.37; Observed; 357.2 (M+1).

Step 4: Synthesis of 5-(4-(tert-butoxycarbonyl)piperazin-1-yl)-2,4-difluorobenzoic acid (5): To a stirred solution of tert-butyl 4-(2,4-difluoro-5-(methoxycarbonyl)phenyl)piperazine-1-carboxylate (4, 1.0 g, 0.003 mol) in THF: water (20 mL, 3:1), lithium hydroxide (0.176 g, 0.004 mol) was added and reaction mixture was stirred at RT for 16 h. Progress of the reaction was monitored by TLC. The reaction mixture was concentrated to remove THF. 1.5N HCl was added to make the pH acidic. The solid formed was filtered to afford 5-(4-(tert-butoxycarbonyl)piperazin-1-yl)-2,4-difluorobenzoic acid (0.800 g, 97%). LCMS (ESI negative ion) m/z: calculated: 342.34; Observed; 341.0 (M−1).

Step 5: Synthesis of tert-butyl 4-(5-((2-(dimethylamino)ethyl)carbamoyl)-2,4-difluorophenyl)piperazine-1-carboxylate (6): To a stirred solution of 5-(4-(tert-butoxycarbonyl)piperazin-1-yl)-2,4-difluorobenzoic acid (5, 0.200 g, 0.0005 mol) in DCM (10 mL), N1,N1-dimethylethane-1,2-diamine (0.062 g, 0.0007 mol), DIPEA (0.306 mL, 0.002 mol) and T3P solution (0.438 mL, 0.001 mol) were successively added. The resulting mixture was stirred at RT for 16 h. Progress of the reaction was monitored by TLC. Water was added to the reaction mixture and extracted with dichloromethane. Combined organic part was dried over anhydrous sodium sulphate and concentrated under reduced pressure to afford the product (0.13 g, 46.4%). LCMS (ESI positive ion) m/z: calculated: 412.48; Observed; 413.6 (M+1).

Step 6: Synthesis of N-(2-(dimethylamino)ethyl)-2,4-difluoro-5-(piperazin-1-yl)-benzamide (7): To an ice cold solution of tert-butyl 4-(5-((2-(dimethylamino)ethyl)carbamoyl)-2,4-difluorophenyl)piperazine-1-carboxylate (6, 0.200 g, 0.0004 mol) in DCM (10 mL), HCl in diethyl ether solution (0.121 mL, 4M soln) was added. The resulting mixture was stirred at RT for 16 h. Progress of the reaction was monitored by TLC. The reaction mixture was concentrated under reduced pressure. The residue was neutralized with sodium bicarbonate and extracted with DCM. The organic part was concentrated to afford N-(2-(dimethylamino)-ethyl)-2,4-difluoro-5-(piperazin-1-yl)benzamide (0.130 g, 62.28%). LCMS (ESI positive ion) m/z: calculated: 312.36; Observed; 313.2 (M+1).

Step 7: Synthesis of 5-(4-(2-(5-amino-8-(furan-2-yl)-2-oxothiazolo[5,4-e][1,2,4]triazolo-[1,5-c]pyrimidin-3(2H)-yl)ethyl)piperazin-1-yl)-N-(2-(dimethylamino)ethyl)-2,4- difluorobenzamide (Compound 81): To a stirred mixture of 2-(5-amino-8-(furan-2-yl)-2-oxothiazolo[5,4-e][1,2,4]triazolo[1,5-c]pyrimidin-3(2H)-yl)ethyl methane sulfonate (8, 120 mg, 0.0003 mol) and N-[2-(dimethylamino)ethyl]-2,4-difluoro-5-piperazin-1-yl-benzamide (7, 113 mg, 0.00036 mol) in DMF (5 mL), DIPEA (0.129 mL, 0.0009 mol) was added. The resulting mixture was heated to 120° C. for 16 h. After the completion of the reaction, the reaction mixture was concentrated under reduced pressure. The crude residue obtained was purified by reverse phase preparative HPLC purification to afford the product. LCMS (ESI positive ion) m/z: calculated: 612.66; Observed; 613.2 (M+1). HPLC purity (XB_0595TF): 92.76%. 1H-NMR (400 MHz, DMSO-d6): δ 7.72 (s, 1H), 7.52-7.56 (m, 1H), 7.20 (s, 1H), 7.11-7.17 (m, 1H), 6.63 (t, J=2.00 Hz, 1H), 4.31 (bs, 2H), 3.91 (t, J=7.84 Hz, 2H), 3.83 (m, 4H), 3.63 (t, J=6.12 Hz, 3H), 2.85 (m, 5H), and 2.56 (broad s, 6H).

Examples 83 and 84: 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one and 5-amino-3-(2-(4-(2-fluoro-4-(((3S,4S)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one

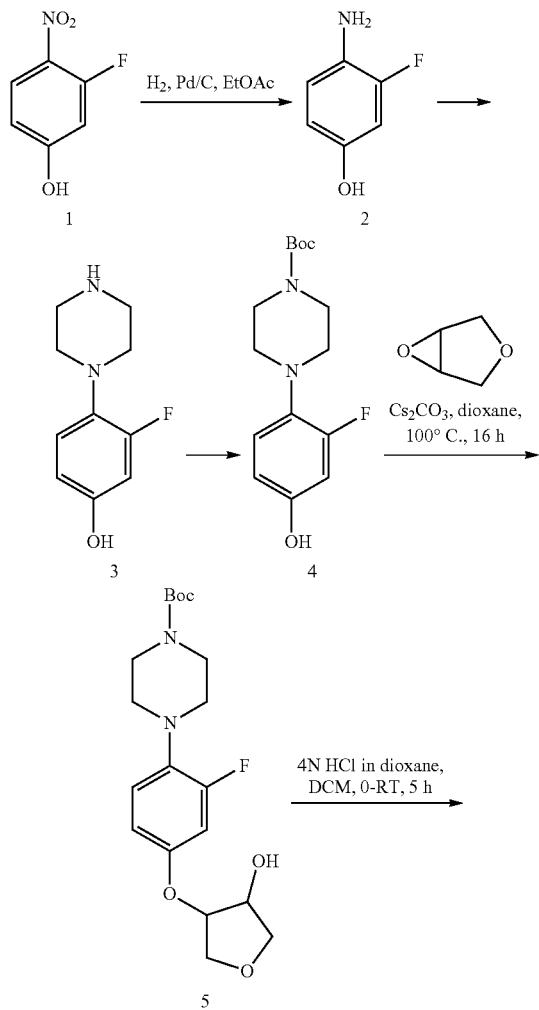

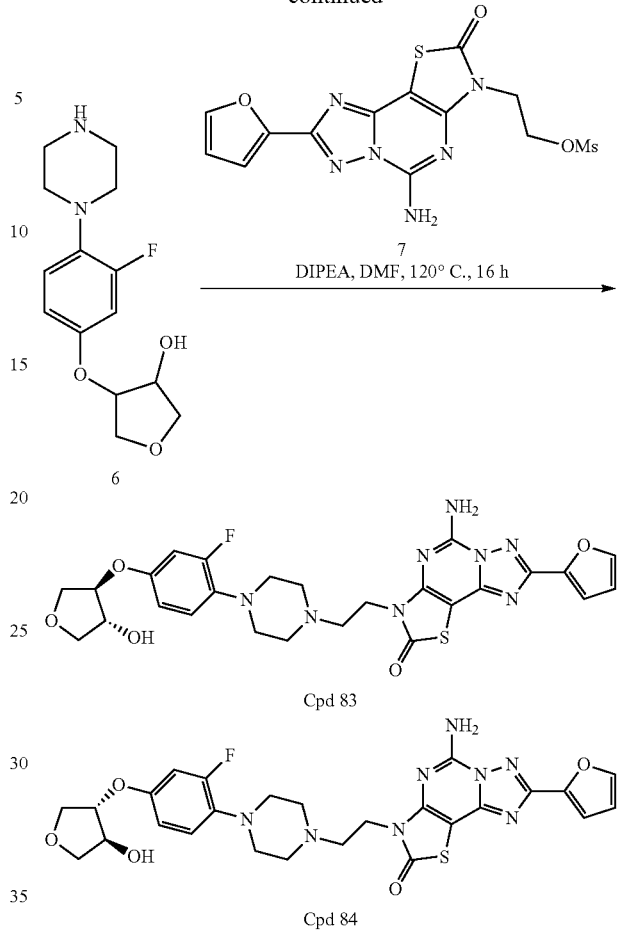

Cpd 83

Cpd 84

Step 1: Synthesis of 4-amino-3-fluorophenol (2): To a stirred solution of 3-fluoro-4-nitrophenol (1, 10 g, 0.064 mol) in ethyl acetate (140 mL), Pd/C (4.0 g, 0.038 mol) was added under nitrogen atmosphere. The reaction mixture was stirred under hydrogen bladder pressure for 16 h. The progress of the reaction was monitored by TLC. The reaction mixture was filtered through Celite bed, and the filtrate was concentrated under reduced pressure to afford 4-amino-3-fluorophenol as light pink colored solid (6.9 g, 94%). LCMS (ESI positive ion); m/z: calculated: 127.12; Observed; 128.2 (M+1).

Step 2: Synthesis of 3-fluoro-4-(piperazin-1-yl)phenol hydrochloride (3): To a stirred solution of 4-amino-3-fluorophenol (2, 6.9 g, 0.054 mol) in sulfolane (15 mL), bis(2-chloroethyl)amine hydrochloride (13.56 g, 0.076 mol) was added. The reaction mixture was heated at 150° C. for 16 h. After the completion of the reaction, the reaction mixture was cooled to RT. About 30 mL of cold acetone was added and stirred at 0° C. for 0.5 h. The solid formed was filtered, and dried to afford the 3-fluoro-4-(piperazin-1-yl)phenol hydrochloride as black colored solid (10 g, 98%). LCMS (ESI positive ion); m/z: calculated: 196.23; Observed; 197.1 (M+1).

Step 3: Synthesis of tert-butyl 4-(2-fluoro-4-hydroxyphenyl)piperazine-1-carboxylate (4): To an ice cold stirred solution of 3-fluoro-4-(piperazin-1-yl)phenol hydrochloride (3, 3.0 g, 0.015 mol) in DMF (30 mL), triethyl amine was added till it becomes basic. Then BOC anhydride (3.0 mL, 0.041 mol) was added and the reaction was kept at 0° C. for 0.5 h. After the reaction completion it was diluted with ethyl acetate and water. The organic layer was dried over anhydrous sodium sulphate and concentrated under reduced pressure. The crude product obtained was purified by column chromatography to afford tert-butyl 4-(2-fluoro-4-hydroxyphenyl)piperazine-1-carboxylate (1.5 g, 86%). LCMS (ESI positive ion); m/z: calculated: 296.34; Observed; 297.1 (M+1).

Step 4: Synthesis of tert-butyl 4-(2-fluoro-4-((4-hydroxytetrahydrofuran-3-yl)oxy)-phenyl)piperazine-1-carboxylate (5): To a stirred solution of tert-butyl 4-(2-fluoro-4-hydroxyphenyl)piperazine-1-carboxylate (4, 1.5 g, 0.005 mol) in dioxane (25 mL), 3,6-dioxabicyclo[3.1.0]hexane (1.089 g, 0.013 mol) and cesium carbonate (2.47 g, 0.008 mol) were added. The reaction mixture was heated at 100° C. for 16 h. Progress of the reaction was monitored by TLC. Then reaction mixture was diluted with 10 mL of water and extracted with ethyl acetate (10 mL×2). The combine organic layer was dried over anhydrous $MgSO_4$, concentrated under reduced pressure to afford the tert-butyl 4-(2-fluoro-4-((4-hydroxytetrahydrofuran-3-yl)oxy)phenyl)piperazine-1-carboxylate as brown colored solid (0.800 g, 98%). LCMS (ESI positive ion); m/z: calculated: 382.43; Observed; 383.1 (M+1).

Step 5: Synthesis of 4-(3-fluoro-4-(piperazin-1-yl)phenoxy)tetrahydrofuran-3-ol (6): To an ice cold solution of tert-butyl 4-(2-fluoro-4-((4-hydroxytetrahydrofuran-3-yl)oxy)-phenyl)piperazine-1-carboxylate (5, 0.500 g, 0.001 mol) in dioxane (10 mL), HCl in dioxane solution (4M solution, 1 mL) was added. After stirring for 16 h at room temperature, the reaction mixture was concentrated under reduced pressure. The residue was neutralized with 10% sodium bicarbonate solution and extracted with DCM. Concentration of the organic part afford 4-(3-fluoro-4-(piperazin-1-yl)phenoxy)tetrahydrofuran-3-ol (0.250 g, 88%). LCMS (ESI positive ion); m/z: calculated: 282.3; Observed; 283.2 (M+).

Step 6: Synthesis of 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)thiazolo[5,4-e][1,2,4]triazolo[1,5-c]-pyrimidin-2(3H)-one (Compound 83) and 5-amino-3-(2-(4-(2-fluoro-4-(((3S,4S)-4-hydroxy-tetrahydrofuran-3-yl)oxy)phenyl)piperazin-1-yl)ethyl)-8-(furan-2-yl)thiazolo[5,4-e]-[1,2,4]triazolo[1,5-c]pyrimidin-2(3H)-one (Compounds 84): To a stirred solution of 2-(5-amino-8-(furan-2-yl)-2-oxothiazolo[5,4-e][1,2,4]triazolo[1,5-c]pyrimidin-3(2H)-yl)-ethyl methane sulfonate (7, 0.320 g, 0.00080 mol) in DMF (8 mL), 4-(3-fluoro-4-(piperazin-1-yl)phenoxy)tetrahydrofuran-3-ol (6, 0.273 g, 0.0009 mol) and N-ethyl-N-isopropylpropan-2-amine (0.218 mL, 0.002 mol) were added. The reaction mixture was heated at 120° C. for 16 h. After the completion of the reaction, the reaction mixture was concentrated and the residue was purified by preparative HPLC purification. The pure product was then purified by chiral SFC purification to afford two isomers 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one (5.29 mg) and 5-amino-3-(2-(4-(2-fluoro-4-(((3S,4S)-4-hydroxytetrahydrofuran-3-yl)oxy)phenyl)piperazin-1-yl) ethyl)-8-(furan-2-yl)thiazolo[5,4-e][1,2,4]triazolo[1,5-c]pyrimidin-2(3H)-one First eluting enantiomer: LCMS (ESI positive ion); m/z: calculated: 582.61; Observed; 583.2 (M+1). HPLC purity (XB_0595TF): 96.23%. 1H-NMR (400 MHz, DMSO-d6): δ 8.30 (bs, 2H), 7.95 (s, 1H), 7.23 (d, J=3.20 Hz, 1H), 6.92-6.96 (m, 1H), 6.83-6.87 (m, 1H), 6.70-6.74 (m, 2H), 5.48 (bs, 1H), 4.58 (d, J=4.00 Hz, 1H), 4.58 (d, J=4.00 Hz, 1H), 4.07 (t, J=6.40 Hz, 2H), 3.99-4.03 (m, 1H), 3.85-3.89 (m, 1H), 3.71-3.74 (m, 1H), 3.55-3.58 (m, 1H), 2.61 (s, 4H), 2.708 (m, 2H), and 2.67 (m, 4H).

Second-eluting enantiomer: LCMS (ESI positive ion); m/z: calculated: 582.61; Observed; 583.2 (M+1). HPLC purity (XB_0595TF): 93.44%. 1H-NMR (400 MHz, DMSO-d6): δ 8.31 (bs, 2H), 7.96 (s, 1H), 7.24 (d, J=3.32 Hz, 1H), 6.94 (t, J=9.36 Hz, 1H), 6.83-6.87 (m, 1H), 6.70-6.74 (m, 2H), 5.46 (d, J=3.84 Hz, 1H), 4.58 (d, J=3.40 Hz, 1H), 4.16 (s, 1H), 4.08 (t, J=6.24 Hz, 2H), 4.02-4.03 (m, 1H), 3.86-3.89 (m, 1H), 3.72 (d, J=9.96 Hz, 1H), 3.57 (d, J=9.60 Hz, 1H), 2.9277 (m, 4H), 2.9363 (m, 2H), and 2.7029 (s, 4H).

Example 88: 5-amino-3-(2-(4-(2-fluoro-5-(2-hydroxyethoxy)phenyl)piperazin-1-yl)ethyl)-8-(furan-2-yl)thiazolo[5,4-e][1,2,4]triazolo[1,5-c]pyrimidin-2 (3H)-one

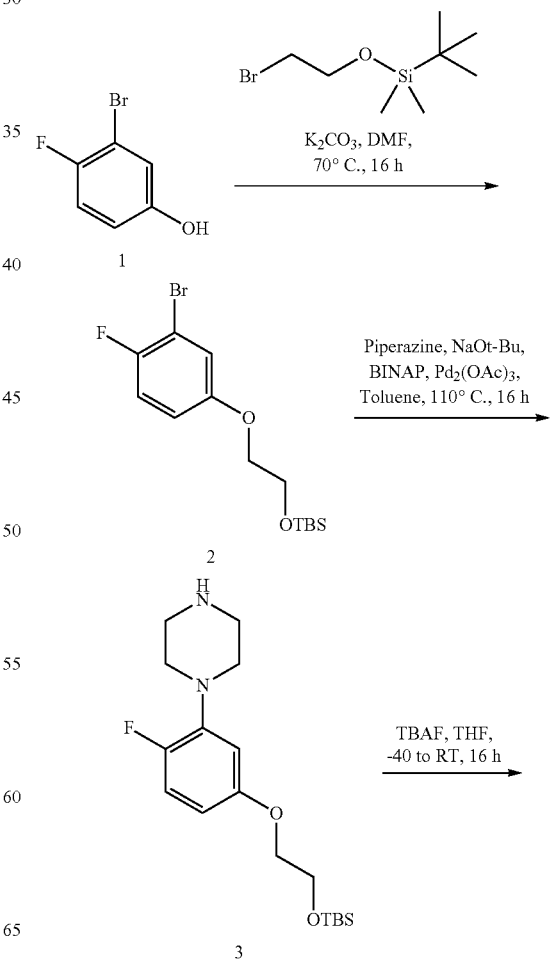

-continued

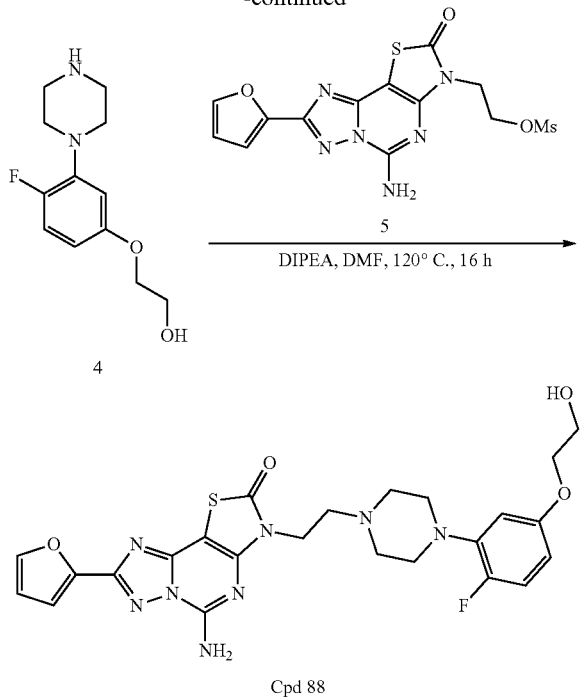

Cpd 88

Step 1: Synthesis of (2-(3-bromo-4-fluorophenoxy) ethoxy)(tert-butyl)dimethylsilane (2): A mixture of 3-bromo-4-fluorophenol (1, 2.3 g, 0.012 mol), (2-bromoethoxy)(tert-butyl)dimethylsilane (3.74 g, 0.016 mol) in DMF (30 mL), K2CO3 (2.49 g, 0.018 mol) was heated to 70° C. for 16 h. Progress of the reaction was monitored by TLC. After the reaction completion, water (20 mL) was added to the reaction mixture and extracted with dichloromethane (30 mL×2). The combined organic part was washed with saturated brine solution, dried over anhydrous sodium sulfate and concentrated under reduced pressure to afford the title compound (2 g, 29%), which was used as such for the next step.

Step 2: Synthesis of 1-(5-(2-((tert-butyldimethylsilyl) oxy)ethoxy)-2-fluorophenyl)-piperazine (3): To a stirred solution of 2-(3-bromo-4-fluoro-phenoxy)ethoxy-tert-butyl-dimethyl-silane (2, 1.0 g, 0.003 mol) and piperazine (499 mg, 0.006 mol)) in toluene (15 mL), NaOBu-t (412 mg) was added. The resulting mixture was degassed with nitrogen. Then BINAP (107 mg, 0.00017 mol), and palladium acetate (262 mg, 0.0003 mol) were added and the resulting mixture was heated to 110° C. for 16 h. After the completion, the reaction mixture was filtered, and filtrate was concentrated under reduced pressure. The crude residue obtained was purified by column chromatography to afford the title compound (0.3 g, 29.5%). LCMS (ESI positive ion) m/z: calculated: 354.54; observed: 355.3 (M+1).

Step 3: Synthesis of 2-(4-fluoro-3-(piperazin-1-yl)phenoxy)ethan-1-ol (4): To an ice cold solution of 1-(5-(2-((tert-butyldimethylsilyl)oxy)ethoxy)-2-fluorophenyl)-piperazine (3, 0.354 g, 0.0009 mol) in THF (10 mL), TBAF (0.499 mL, 4 M in THF) was added slowly. The resulting mixture was allowed to reach RT and stirred there for 16 h. After reaction completion, the reaction mixture was diluted with water and ethyl acetate. The organic layer separated was dried over anhydrous sodium sulphate, concentrated under reduced pressure. The crude product obtained was purified by column chromatography to afford the title compound (0.240 g, 98.99%). LCMS (ESI positive ion) m/z: calculated: 240.28; observed: 241.2 (M+1).

Step 4: Synthesis of 5-amino-3-(2-(4-(2-fluoro-5-(2-hydroxyethoxy)phenyl)piperazin-1-yl)ethyl)-8-(furan-2-yl) thiazolo[5,4-e][1,2,4]triazolo[1,5-c]pyrimidin-2(3H)-one (Compound 88): To a stirred solution of 2-(5-amino-8-(furan-2-yl)-2-oxothiazolo[5,4-e][1,2,4]triazolo[1,5-c]pyrimidin-3(2H)-yl)ethyl methane sulfonate (0.300 g, 0.0007 mol) in DMF (8 mL), 2-(4-fluoro-3-(piperazin-1-yl)phenoxy)ethan-1-ol (4, 0.218 g, 0.0009 mol) and DIPEA (0.397 mL, 0.002 mol) were added. The reaction mixture was heated to 120° C. for 16 h. After the completion, the reaction mixture was concentrated and the crude product obtained was purified by reverse phase preparative HPLC purification to afford the title compound as off white solid. HPLC purity (XB_0595TF): 98.29%; LCMS (ESI positive ion) m/z: calculated: 540.57; observed: 541.0 (M+1). 1H-NMR (400 MHz, DMSO-d6): δ 9.19 (s, 1H), 8.39-8.45 (bs, 2H), 7.97 (s, 1H), 7.11 (m, 1H), 6.75 (s, 1H), 6.59 (m, 2H), 4.86 (m, 1H), 4.32 (m, 2H), 3.95-3.98 (m, 4H), 3.68-3.70 (m, 2H), 3.63 (m, 3H), 2.94-3.00 (m, 2H), and 3.69 (s, 2H).

Example 90: 5-amino-3-(2-(4-(2,4-difluoro-5-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one

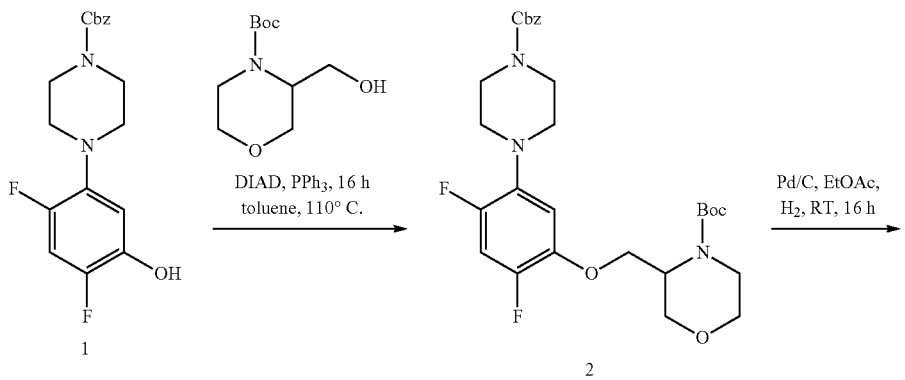

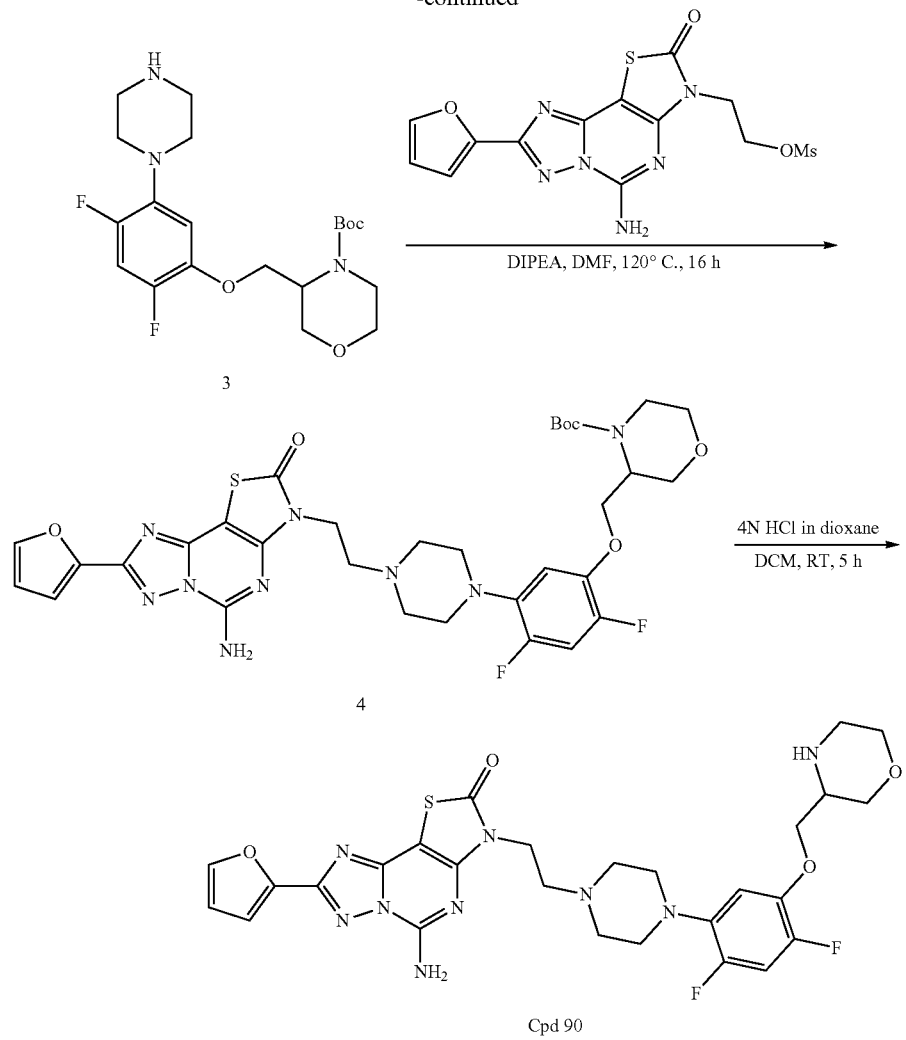

Step 1: Synthesis of tert-butyl 3-((5-(4-((benzyloxy)carbonyl)piperazin-1-yl)-2,4-difluorophenoxy)methyl)morpholine-4-carboxylate (2): To a stirred solution of benzyl 4-(2,4-difluoro-5-hydroxyphenyl)piperazine-1-carboxylate (1, 1.2 g, 2.9 mmol) and tert-butyl 3-(hydroxymethyl)morpholine-4-carboxylate (1.1 g, 4.3 mmol) in toluene (10 mL) was added triphenyl phosphine (1.8 g, 6.9 mol) followed by the drop-wise addition of DIAD (1.39 g, 6.9 mmol) at 0° C. Reaction mixture was stirred at 110° C. for 16 h. After the reaction completion (TLC), the reaction mixture was diluted with water (20 mL) and extracted with ethyl acetate. Organic layer was washed with saturated brine solution, dried over anhydrous $Na_2SO_4$, filtered and concentrated under reduced pressure. The crude obtained was purified by column chromatography (20% EtOAc/Hexane) to afford the title compound as brown liquid (1.4 g, 63.8%); LCMS (ESI positive ion) m/z: calculated: 547.25; observed: 548.1 (M+1).

Step 2: Synthesis of tert-butyl 3-((2,4-difluoro-5-(piperazin-1-yl)phenoxy)methyl) morpholine-4-carboxylate (3): To stirred solution of tert-butyl 3-((5-(4-((benzyloxy)carbonyl)piperazin-1-yl)-2,4-difluorophenoxy)methyl)morpholine-4-carboxylate (0.5 g, 0.91 mmol) in EtOAc (20 mL) was added 10% Pd/C (0.2 g) under nitrogen atmosphere. The reaction mixture was stirred under hydrogenation atmosphere at room temperature for 16 h. The reaction progress was monitored by TLC. After completion, the reaction mixture was filtered using celite to remove the Pd/C. The combined organic layer was dried over anhydrous $Na_2SO_4$ and concentrated under reduced pressure to afford the title compound as brown gummy solid (280 mg, 73.5%); LCMS (ESI positive ion) m/z: calculated: 413.21; observed: 414.3 (M+1).

Step 3: Synthesis of tert-butyl 3-((5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-methyl) morpholine-4-carboxylate (4): To a stirred solution of tert-butyl 3-((2,4-difluoro-5-(piperazin-1-yl)phenoxy)methyl)-morpholine-4-carboxylate (3, 100 mg, 0.242 mmol) and 2-(5-amino-8-(furan-2-yl)-2-oxothiazolo[5,4-e][1,2,4]triazolo[1,5-c]pyrimidin-3(2H)-yl)ethyl methane sulfonate (86 mg, 0.218 mmol) in N,N-dimethylformamide (10 mL) in 50 mL sealed tube was added DIPEA (94 mg, 0.726 mmol) and the reaction mixture was stirred at 120° C. for 16 h. After completion of the reaction (TLC & LCMS), the solvent was removed under reduced pressure. The reaction mass was treated with water and extracted with ethyl acetate. Organic layer was washed with saturated brine solution, dried over anhydrous $Na_2SO_4$, filtered and concentrated under reduced pressure. The crude product was purified by preparative TLC to afford the title compound as dark brown solid (25 mg, 14.4%); LCMS (ESI positive ion) m/z: calculated: 713.26; observed: 714.1 (M+1).

Step 4: Synthesis of 5-amino-3-(2-(4-(2,4-difluoro-5-(morpholin-3-ylmethoxy)-phenyl)piperazin-1-yl)ethyl)-8-(furan-2-yl)thiazolo[5,4-e][1,2,4]triazolo[1,5-c]pyrimidin-2(3H)-one (Compound 90): To a stirred solution of tert-butyl 3-((3-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-4,5-difluorophenoxy)-methyl)-morpholine-4-carboxylate (4, 25 mg, 0.035 mmol) in DCM (5 mL) at 0° C., 4 N HCl in dioxane (1.5 mL) was added and the reaction mixture was stirred at RT for 5 h. After the completion of reaction (TLC), the reaction mixture was concentrated under reduced pressure to get the crude product, which was washed with acetonitrile to afford title compound as brown solid (16 mg, 73.3%); HPLC purity (AM9010A3): 98.49%; LCMS (ESI positive ion) m/z: calculated: 613.20; observed: 614.1 (M+1); $^1$H-NMR (400 MHz, DMSO-d6): δ 10.33 (brs, 1H), 9.53 (brs, 2H), 8.41 (brs, 2H), 7.97 (s, 1H), 7.40 (t, J=11.20 Hz, 1H), 7.26 (d, J=3.20 Hz, 1H), 7.01 (t, J=7.60 Hz, 1H), 6.75-6.74 (m, 1H), 4.33-4.23 (m, 4H), 4.02-3.93 (m, 4H), 3.69-3.62 (m, 6H), 3.27 (m, 3H), 2.98 (m, 4H).

Example 91: 5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one

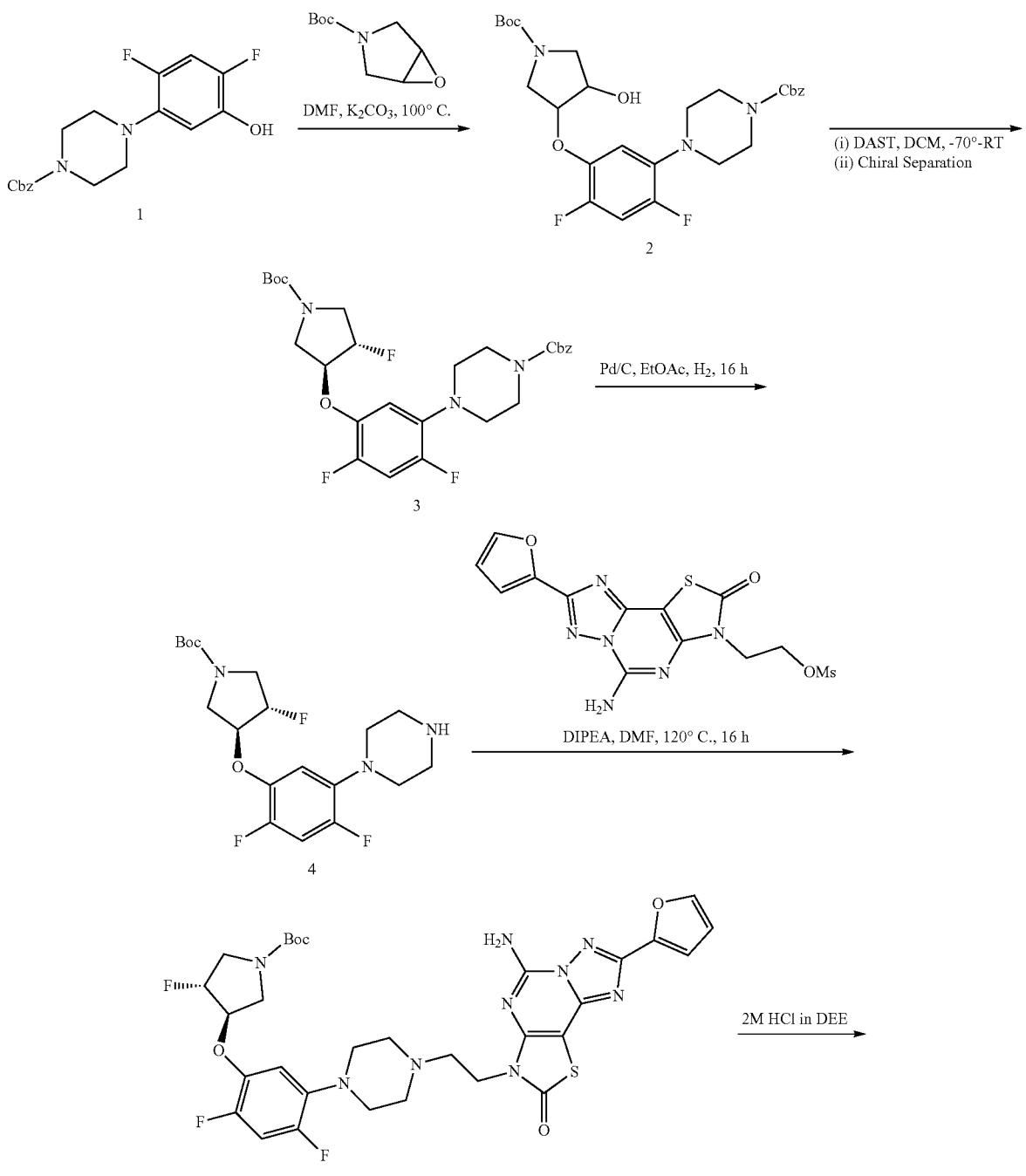

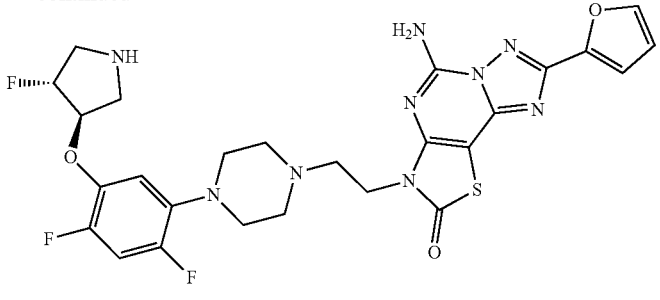

Cpd 91

Step 1: Synthesis of benzyl 4-(5-((1-(tert-butoxycarbonyl)-4-hydroxypyrrolidin-3-yl)oxy)-2,4-difluorophenyl)piperazine-1-carboxylate (2): To a suspension of benzyl 4-(2,4-difluoro-5-hydroxyphenyl)piperazine-1-carboxylate (6.0 g, 17.22 mmol) and tert-butyl 6-oxa-3-azabicyclo[3.1.0]hexane-3-carboxylate (3.82 g, 20.67 mmol) in dry DMF (30 mL), was added $K_2CO_3$ (7.13 g, 51.67 mmol) and the reaction mixture was heated at 100° C. for 16 h. After completion of reaction (TLC), the reaction mixture was concentrated under reduced pressure and the crude was purified by column chromatography to afford the title compound 2 as color less liquid (3.5 g, 36%); LCMS (ESI positive ion); m/z: calculated: 533.57; Observed: 534.1 (M+1); 1H-NMR (400 MHz, DMSO-d6): δ 7.38-7.28 (m, 6H), 6.89-6.88 (m, 1H), 5.49-5.48 (m, 1H), 5.10-4.65 (m, 2H), 4.15 (m, 1H), 4.05-4.03 (m, 1H), 3.59-3.49 (m, 6H), 2.96-2.88 (m, 4H), 1.40 (s, 9H).

Step 2: Synthesis of benzyl 4-(5-(((3S,4S)-1-(tert-butoxycarbonyl)-4-fluoropyrrolidin-3-yl)oxy)-2,4-difluorophenyl)piperazine-1-carboxylate (3): A solution of benzyl 4-(5-((1-(tert-butoxycarbonyl)-4-hydroxypyrrolidin-3-yl)oxy)-2,4-difluorophenyl) piperazine-1-carboxylate (3.5 g, 6.56 mmol) in dichloromethane (60 mL) was cooled to –70° C. and DAST (2.11 g, 0.013 mmol) was added slowly, and the reaction mixture was stirred at RT for 16 h. After the reaction completion (TLC) the reaction mixture was diluted with water and the crude product was extracted with dichloromethane. The organic layer was successively washed with 10% $NaHCO_3$, water, brine, dried over $Na_2SO_4$, filtered and concentrated to afford the crude product. The diastereomers formed were separated by normal silica column chromatography as peak 1 and peak 2. The enantiomers present in the peak 1 were separated through SFC chiral column; Method: YMC cellulose SC_IPA; 70:30 (A:B), A=liquid $CO_2$, B=IPA, flow rate: 0.9 mL/min; wave length: 220 nm. The first peak eluted out of chiral column was concentrated to afford the title compound 3 as off white solid (0.7 g, 19%); LCMS (ESI positive ion); m/z: calculated: 535.56; Observed: 536.2 (M+1); 1H-NMR (400 MHz, DMSO-d6): δ 7.38-7.29 (m, 6H), 6.97-6.95 (m, 1H), 5.38-5.25 (m, 1H), 5.11-5.04 (m, 2H), 3.84-3.79 (m, 7H), 3.22-3.16 (m, 4H), 1.42 (s, 9H).

Step 3: Synthesis of tert-butyl (3S, 4S)-3-(2,4-difluoro-5-(piperazin-1-yl)phenoxy)-4-fluoropyrrolidine-1-carboxylate (4): A suspension of benzyl 4-(5-(((3S,4S)-1-(tert-butoxycarbonyl)-4-fluoropyrrolidin-3-yl)oxy)-2,4-difluorophenyl)piperazine-1-carboxylate (0.23 g, 0.429 mmol) in ethyl acetate (10 mL) was charged with 10% Palladium on carbon (0.049 g) and stirred under hydrogen bladder pressure for 5 h at room temperature. After completion of reaction (TLC), the reaction mass was filtered through pad of celite and concentrated to afford the title compound 4 as pale brown solid (0.16 g, 92.8%); LCMS (ESI positive ion); m/z: calculated: 401.43; Observed; 402.2 (M+1); 1H-NMR (400 MHz, $CD_3OD$): δ 6.92 (t, J=8.8 Hz, 1H), 6.56-6.51 (m, 2H), 3.57 (m, 4H), 2.91 (t, J=4.80 Hz, 4H), 1.49 (s, 9H).

Step 4: Synthesis of tert-butyl (3R,4R)-3-(5-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-2,4-difluorophenoxy)-4-fluoropyrrolidine-1-carboxylate (5): To a solution of tert-butyl (3S, 4S)-3-(2,4-difluoro-5-(piperazin-1-yl)phenoxy)-4-fluoropyrrolidine-1-carboxylate (0.16 g, 0.399 mmol) and 2-(5-amino-8-(furan-2-yl)-2-oxothiazolo [5,4-e][1,2,4]triazolo[1,5-c] pyrimidin-3(2H)-yl)ethyl methane sulfonate (0.15 g, 0.39 mmol) in dry DMF (3 mL), was added N,N-Di isopropyl ethylamine (0.13 g, 0.83 mmol) and the reaction mixture was heated in a sealed tube at 120° C. for 16 h. After completion of reaction (LCMS), the reaction mixture was concentrated under reduced pressure and purified by preparatory HPLC to afford the title compound 5 as off white solid (0.06 g, 21.4%). LCMS (ESI positive ion); m/z: calculated: 701.73; Observed; 702.3 (M+1); 1H-NMR (400 MHz, DMSO-d6): δ 8.30 (s, 2H), 7.95 (t, J=0.80 Hz, 1H), 7.30-7.23 (m, 2H), 6.88 (t, J=8 Hz, 1H), 6.73-6.72 (m, 1H), 5.32 (s, 1H), 5.06-5.04 (m, 1H), 4.06 (t, J=12 Hz, 2H), 3.60-3.49 (m, 4H), 2.92 (s, 4H), 2.73-2.68 (m, 2H), 2.67-2.51 (m, 4H), 1.41 (s, 9H).

Step 5: Synthesis of 5-amino-3-(2-(4-(2,4-difluoro-5-(((3R,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one (Compound 91): To an ice cooled solution of tert-butyl (3R,4R)-3-(5-(4-(2-(5-amino-8-(furan-2-yl)-2-oxothiazolo[5,4-e][1,2,4]triazolo[1,5-c]pyrimidin-3 (2H)-yl)ethyl)piperazin-1-yl)-2,4-difluorophenoxy)-4-fluoropyrrolidine-1-carboxylate (0.06 g, 0.086 mmol) in dichloromethane (3 mL), was added 2M HCl in diethyl ether (3 mL) under nitrogen pressure. The reaction mixture was stirred at RT for 3 h. After completion of reaction, the reaction mixture was concentrated under reduced pressure, triturated with diethyl ether and dried to afford title compound 91 as off white solid (0.02 g, 38.9%). LCMS (ESI positive ion); m/z: calculated: 601.61; Observed; 602.2 (M+1); HPLC purity (XB_0595TF): 97.51%; 1H-NMR (400 MHz, DMSO-d6): 10.26 (brs, 1H), 9.83 (brs, 2H), 8.41 (brs, 2H), 7.96 (d, J=0.30 Hz, 1H), 7.46-7.43 (m, 1H), 7.40-7.26 (m, 1H), 7.25-7.08 (m, 1H), 6.75-6.74 (m, 1H), 5.42 (s, 1H), 5.26-5.24 (m, 1H), 4.33 (m, 2H), 3.94-3.91 (m, 2H), 3.64-3.55 (m, 10H), 3.39-3.27 (m, 2H), 3.17-3.05 (m, 2H).

Example 95: (S)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one

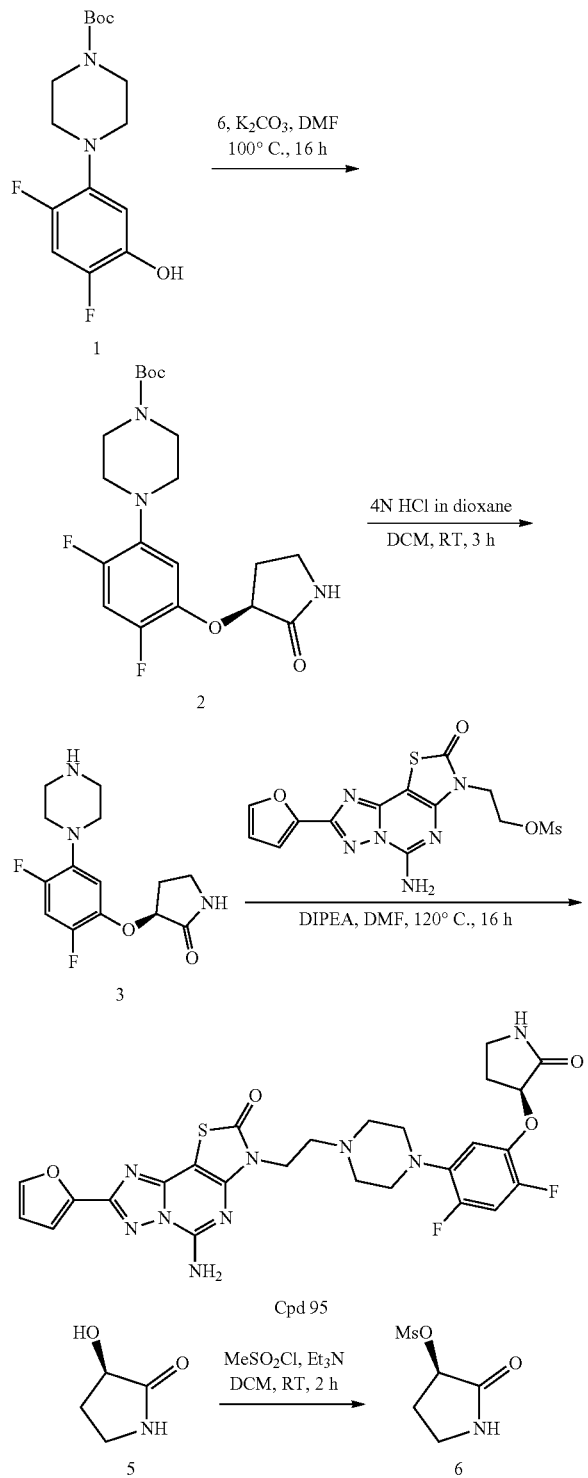

Step 1: Synthesis of (R)-2-oxopyrrolidin-3-yl methanesulfonate (6): To a stirred solution of (3R)-3-hydroxypyrrolidin-2-one (5, 1.0 g, 9.9 mmol) in DCM (15 mL) was added TEA (2.0 g, 19.8 mmol) and mesyl chloride (1.36 g, 11.9 mmol) at 0° C. Resulting reaction mixture was stirred at RT for 2 h. After completion of the reaction, reaction mixture was quenched with NH$_4$Cl solution and extracted with DCM. Organic layer was washed with saturated brine solution, dried over anhydrous Na$_2$SO$_4$, filtered and concentrated under reduced pressure. The crude was purified by column chromatography to get pure product (1.2 g, 67.0%); $^1$H-NMR (400 MHz, CDCl$_3$): δ 5.17 (t, J=7.96 Hz, 1H), 3.53-3.50 (m, 1H), 3.43-3.38 (m, 1H), 3.27 (s, 3H), 2.69-2.64 (m, 1H), 2.43-2.36 (m, 1H).

Step 2: Synthesis of tert-butyl (S)-4-(2,4-difluoro-5-((2-oxopyrrolidin-3-yl)oxy)phenyl) piperazine-1-carboxylate (2): To a stirred solution of tert-butyl 4-(2,4-difluoro-5-hydroxyphenyl)piperazine-1-carboxylate (1, 900 mg, 2.86 mmol) in DMF (20 mL) was added K$_2$CO$_3$ (791 mg, 5.73 mmol) and (R)-2-oxopyrrolidin-3-yl methanesulfonate (6, 769 mg, 4.3 mmol) and heated at 80° C. for 16 h. After completion of the reaction, the reaction mixture was treated with saturated NH$_4$Cl solution and extracted with ethyl acetate. Organic layer was washed with saturated brine solution, dried over anhydrous Na$_2$SO$_4$, filtered and concentrated under reduced pressure. The crude reaction mixture was purified by column chromatography to afford the title compound (900 mg, 78%); LCMS (ESI positive ion) m/z: calculated: 397.18; observed: 398.1 (M+1).

Step 3: Synthesis of (S)-3-(2,4-difluoro-5-(piperazin-1-yl)phenoxy)pyrrolidin-2-one (3): To a stirred solution of tert-butyl (S)-4-(2,4-difluoro-5-((2-oxopyrrolidin-3-yl)oxy)phenyl) piperazine-1-carboxylate (2, 900 mg, 2.26 mmol) in dichloromethane (20 mL) at 0° C., 4 N HCl in dioxane (2.5 mL) was added dropwise and stirred at RT for 3 h. After the reaction completion (TLC), the reaction mixture was concentrated under reduced pressure. The salt was dissolved in methanol and neutralized using tosic acid scavenger resin to get the free base as the off white gum (400 mg, 58.2%); LCMS (ESI positive ion) m/z: calculated: 297.13; observed: 298.1 (M+1).

Step 4: Synthesis of (S)-5-amino-3-(2-(4-(2,4-difluoro-5-((2-oxopyrrolidin-3-yl)oxy)-phenyl)piperazin-1-yl)ethyl)-8-(furan-2-yl)thiazolo[5,4-e][1,2,4]triazolo[1,5-c]pyri-midin-2(3H)-one (Compound 95): To a stirred solution of (S)-3-(2,4-difluoro-5-(piperazin-1-yl)phenoxy)pyrrolidin-2-one (3, 350 mg, 1.18 mmol) in DMF (10 mL) was added DIPEA (608 mg, 4.71 mmol) and 2-(5-amino-8-(furan-2-yl)-2-oxothiazolo[5,4-e][1,2,4]triazolo[1,5-c]pyrimidin-3(2H)-yl) ethylmethane sulfonate (420 mg, 1.06 mmol). The reaction mixture was stirred at 120° C. for 16 h. After completion of reaction (TLC & LCMS), the solvent was removed under reduced pressure and the reaction mixture was partitioned between water and ethyl acetate. The separated organic layer was washed with brine solution, dried over anhydrous Na$_2$SO$_4$ and filtered. The filtrate was concentrate under reduced pressure and purified by flash column chromatography using (3% methanol/dichloromethane) to afford the title compound (250 mg, 34.1%); HPLC purity (XB0595TF): 96.08%; LCMS (ESI positive ion) m/z: calculated: 597.17; observed: 598.0 (M+1); $^1$H-NMR (400 MHz, DMSO-d6): δ 8.31 (brs, 2H), 8.08 (s, 1H), 7.95 (s, 1H), 7.24-7.18 (m, 2H), 6.97 (t, J=8.80 Hz, 1H), 6.74-6.73 (m, 1H), 4.92 (t, J=7.60 Hz, 1H), 4.08 (t, J=6.00 Hz, 2H), 3.27-3.18 (m, 2H), 2.91 (m, 4H), 2.73-2.64 (m, 6H), 2.03-1.98 (m, 1H).

Example 96: (R)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one

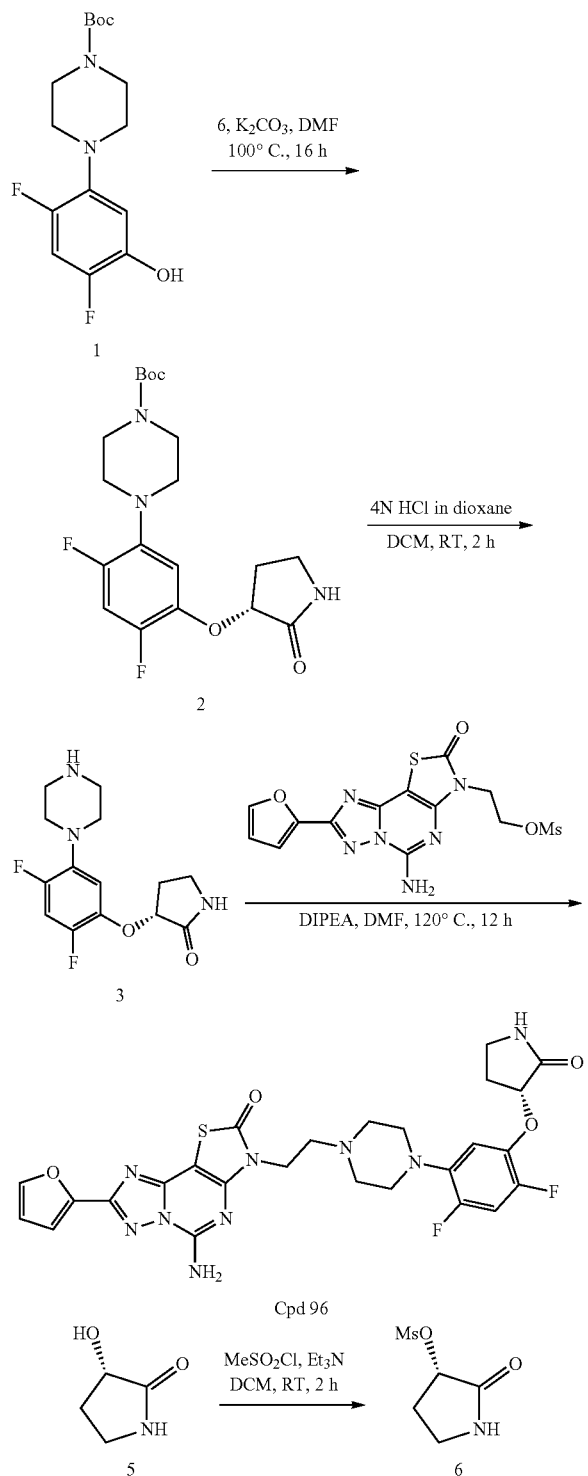

Step 1: Synthesis of (S)-2-oxopyrrolidin-3-yl methanesulfonate (6): To a solution of (S)-3-hydroxypyrrolidin-2-one (5, 2.0 g, 0.02 mol) in DCM (10 mL) was added triethylamine (4.0 g, 0.04 mol) and mesyl chloride (2.49 g, 0.022 mol) at 0° C. Resulting reaction mixture was stirred at RT for 2 h. After completion of the reaction, reaction mixture was quenched with NH$_4$Cl solution and extracted with DCM. Organic layer was washed with saturated brine solution, dried over anhydrous Na$_2$SO$_4$, filtered and concentrated under reduced pressure to afford (S)-2-oxopyrrolidin-3-yl methanesulfonate as pale yellow liquid (1.4 g, 39.5%); LCMS (ESI positive ion) m/z: calculated: 179.03; observed: 180.1 (M+1).

Step 2: Synthesis of tert-butyl (R)-4-(2,4-difluoro-5-((2-oxopyrrolidin-3-yl)oxy)phenyl) piperazine-1-carboxylate (2): To a solution of tert-butyl 4-(2,4-difluoro-5-hydroxyphenyl)piperazine-1-carboxylate (1, 1.5 g, 4.8 mmol) in DMF (20 mL) was added (S)-2-oxopyrrolidin-3-yl methanesulfonate (6, 1.3 g, 7.2 mmol) and K$_2$CO$_3$ (1.32 g, 9.6 mmol) and heated to 90° C. for 16 h. After completion of the reaction, the reaction mixture was treated with saturated NH$_4$Cl solution and extracted with ethyl acetate. Organic layer was washed with saturated brine solution, dried over anhydrous Na$_2$SO$_4$, filtered and concentrated under reduced pressure. The crude reaction mixture was purified by column chromatography to afford the title compound as pale brown solid (1.0 g 45.8%); LCMS (ESI positive ion) m/z: calculated: 397.18; observed: 398.1 (M+1).

Step 3: Synthesis of (R)-3-(2,4-difluoro-5-(piperazin-1-yl)phenoxy)pyrrolidin-2-one (3): To a stirred solution of tert-butyl 4-[2,4-difluoro-5-[(3R)-2-oxopyrrolidin-3-yl]oxy)phenyl] piperazine-1-carboxylate (2, 1.0 g, 2.5 mmol) in dichloromethane (15 mL) at 0° C., 4 N HCl in dioxane (10 mL) was added dropwise and stirred at RT for 2 h. After the reaction completion (TLC), the reaction mixture was concentrated under reduced pressure. The salt was dissolved in methanol and neutralized using Tosic acid scavenger resin to get the free base as the off white gum (600 mg 72.9%); LCMS (ESI positive ion) m/z: calculated: 297.13; observed: 298.2 (M+1).

Step 4: Synthesis of (R)-5-amino-3-(2-(4-(2,4-difluoro-5-((2-oxopyrrolidin-3-yl)oxy)-phenyl)piperazin-1-yl)ethyl)-8-(furan-2-yl)thiazolo[5,4-e][1,2,4]triazolo[1,5-c]pyrimidin-2(3H)-one (Compound 96): To a solution of 2-(5-amino-8-(furan-2-yl)-2-oxothiazolo[5,4-e][1,2,4]triazolo[1,5-c] pyrimidin-3(2H)-yl)ethyl methane sulfonate (300 mg, 0.76 mmol) in DMF (10 mL) was added DIPEA (0.49 g, 3.79 mmol) and (R)-3-(2,4-difluoro-5-(piperazin-1-yl)phenoxy) pyrrolidin-2-one (337 mg, 1.14 mmol). The reaction mixture was stirred at 120° C. for 16 h. After completion of reaction (TLC & LCMS), the solvent was removed under reduced pressure and the reaction mixture was partitioned between water and ethyl acetate. The separated organic layer was washed with brine solution, dried over anhydrous Na$_2$SO$_4$ and filtered. The filtrate was concentrate under reduced pressure and purified by flash column chromatography using (3% methanol/dichloromethane) to afford the title compound. HPLC purity (XB0595TF): 97.73%; LCMS (ESI positive ion) m/z: calculated: 597.17; observed: 598.0 (M+1); $^1$H-NMR (400 MHz, DMSO-d6): δ 8.32 (brs, 2H), 8.09 (s, 1H), 7.95 (s, 1H), 7.19-7.25 (m, 2H), 6.97 (t, J=8.64 Hz, 1H), 6.74 (s, 1H), 4.93 (t, J=7.56 Hz, 2H), 4.08 (t, J=6.00 Hz, 2H), 3.18-3.26 (m, 2H), 2.91 (m, 4H), 2.64-2.73 (m, 6H), 1.98-2.03 (m, 1H).

Example 99: 5-amino-3-(2-(4-(2-fluoro-4-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one

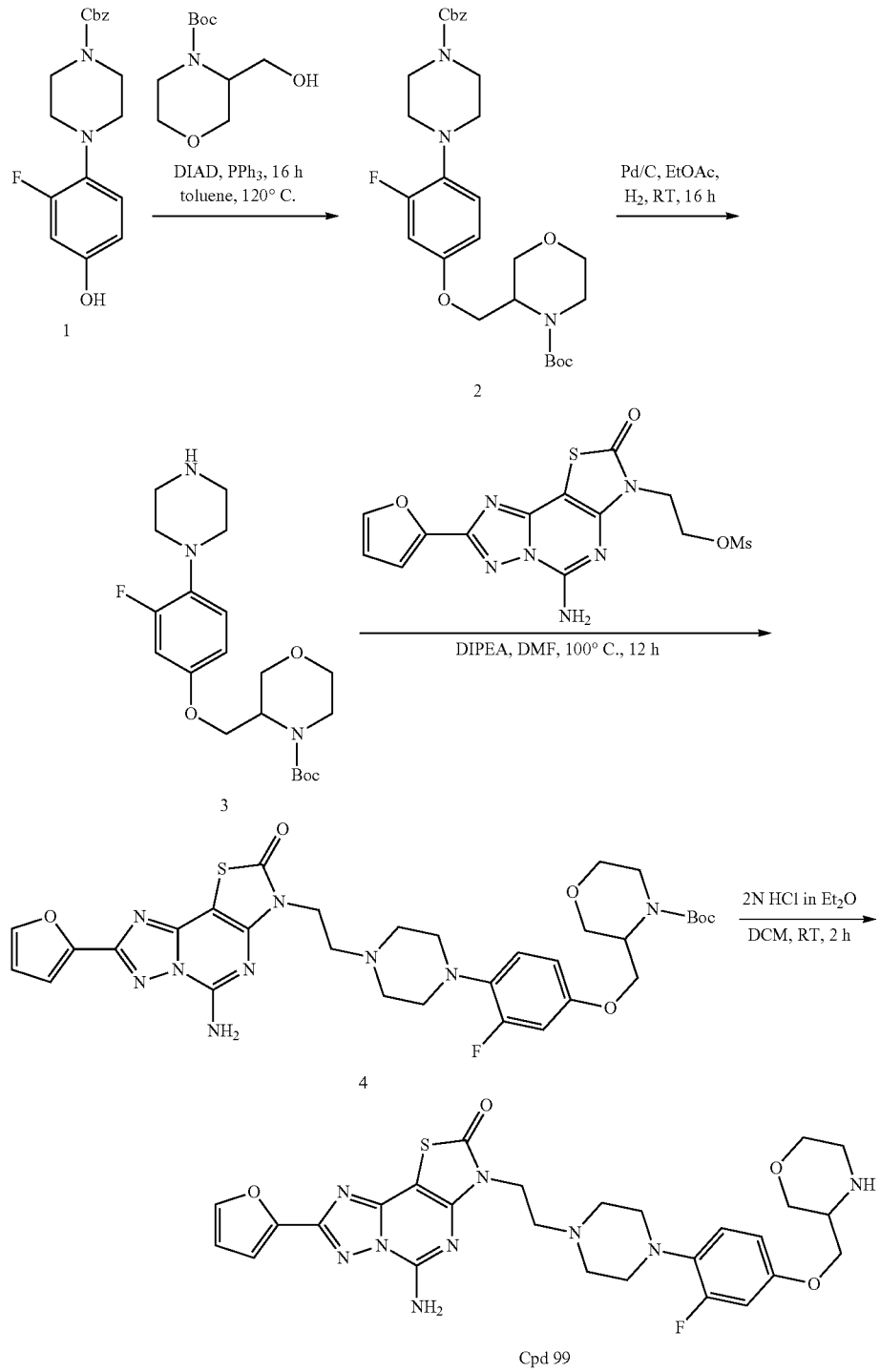

Step 1: Synthesis of tert-butyl 3-((4-(4-(((benzyloxy)carbonyl)piperazin-1-yl)-3-fluorophenoxy)methyl)morpholine-4-carboxylate (2): To a stirred solution of benzyl 4-(2-fluoro-4-hydroxyphenyl)piperazine-1-carboxylate (1, 2.0 g, 6.05 mmol) in toluene (20 mL) was added tert-butyl 3-(hydroxymethyl)morpholine-4-carboxylate (2.63 g, 12.1 mmol), triphenyl phosphine (4.76 g, 12.1 mmol) and DIAD (2.45 g, 12.1 mmol) at RT. The reaction mixture was stirred at 120° C. in seal tube for 16 h. Reaction progress was monitored by TLC. After completion of the reaction, reaction mixture was partitioned between water and ethyl acetate and separated organic layer was washed with brine solution dried over anhydrous Na$_2$SO$_4$, and concentrated under vacuum to afford as a crude product. The crude obtained was purified by column chromatography (20% EtOAc/Hexane) to afford tert-butyl tert-butyl 3-((4-(4-((benzyloxy)carbonyl)piperazin-1-yl)-3-fluorophenoxy)-methyl)morpholine-4-carboxylate (1.0 g, 31.2%); LCMS (ESI positive ion) m/z: calculated: 529.26; observed: 530.1 (M+1).

Step 2: Synthesis of tert-butyl 3-((3-fluoro-4-(piperazin-1-yl)phenoxy)methyl)-morpholine-4-carboxylate (3): To a stirred solution of tert-butyl 3-((4-(4-((benzyloxy)carbonyl)piperazin-1-yl)-3-fluorophenoxy)methyl)morpholine-4-carboxylate (2, 600 mg, 1.1 mmol) in ethyl acetate (10 mL) was added 10% Pd/C (120 mg) at RT and stirred under hydrogen atmosphere for 16 h. After completion, the reaction mixture was filtered using celite to remove the Pd/C. The combined organic layer was dried over anhydrous Na$_2$SO$_4$ and concentrated under reduced pressure to afford tert-butyl 3-((3-fluoro-4-(piperazin-1-yl)phenoxy)methyl)-morpholine-4-carboxylate as gummy solid (350 mg, 61.7%); LCMS (ESI positive ion) m/z: calculated: 395.22; observed: 396.1 (M+1).

Step 3: Synthesis of tert-butyl 3-((4-(4-(2-(5-amino-8-(furan-2-yl)-2-oxothiazolo[5,4-e]-[1,2,4]triazolo[1,5-c]pyrimidin-3(2H)-yl)ethyl)piperazin-1-yl)-3-fluorophenoxy)-methyl)-morpholine-4-carboxylate (4): To a stirred solution of 2-(5-amino-8-(furan-2-yl)-2-oxothiazolo[5,4-e][1,2,4]triazolo[1,5-c]pyrimidin-3(2H)-yl)ethyl methane sulfonate (200 mg, 0.631 mmol) and tert-butyl tert-butyl 3-((3-fluoro-4-(piperazin-1-yl)phenoxy)methyl)morpholine-4-carboxylate (300 mg, 0.756 mmol) in DMF (10 mL) was added DIPEA (292 mg, 2.27 mmol) and the reaction mixture was stirred at 100° C. for 16 h. Reaction progress was monitored by TLC, the reaction mixture was partitioned between water and ethyl acetate. The separated organic layer was washed with NaHCO$_3$ solution, brine solution, dried over anhydrous Na$_2$SO$_4$ and concentrated under reduced pressure to afford crude product. The crude product was purified by preparative HPLC to get pure tert-butyl 3-((4-(4-(2-(5-amino-8-(furan-2-yl)-2-oxothiazolo[5,4-e][1,2,4]-triazolo[1,5-c]pyrimidin-3 (2H)yl) ethyl)piperazin-1-yl)-3-fluorophenoxy) methyl)morpholine-4-carboxylate (80 mg, 21.4%); LCMS (ESI positive ion) m/z: calculated: 695.26; observed: 696.1 (M+1).

Step 4: Synthesis of 5-amino-3-(2-(4-(2-fluoro-4-(morpholin-3-ylmethoxy)phenyl)-piperazin-1-yl)ethyl)-8-(furan-2-yl)thiazolo[5,4-e][1,2,4]triazolo[1,5-c]pyrimidin-2(3H)-one (Compound 99): To a stirred solution of tert-butyl 3-((4-(4-(2-(5-amino-8-(furan-2-yl)-2-oxothiazolo[5,4-e]-[1,2,4]triazolo[1,5-c]pyrimidin-3(2H)-yl)ethyl)piperazin-1-yl)-3-fluorophenoxy)methyl) morpholine-4-carboxylate (4, 80 mg, 0.11 mmol) in DCM (5 mL) was added 2 N HCl in diethyl ether (2 mL) and the resulting reaction mixture was stirred at RT for 2 h. After completion of the reaction, reaction mixture was concentrated under reduced pressure to get crude compound and it was purified by preparative HPLC to get pure 5-amino-3-(2-(4-(2-fluoro-4-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one as off white solid (15 mg, 22%); HPLC purity (XB0595TF): 95.90%; LCMS (ESI positive ion) m/z: calculated: 595.21; observed: 596.1 (M+1); $^1$H-NMR (400 MHz, DMSO-d6): δ 8.31 (brs, 2H), 7.95 (m, 1H), 7.24 (dd, J=0.80 Hz and 3.40 Hz, 1H), 6.92 (t, J=10.00 Hz, 1H), 6.80 (dd, J=2.80 Hz and 14.00 Hz, 1H), 6.73 (dd, J=2.00 Hz and 3.40 Hz, 1H), 6.67 (dd, J=2.40 Hz and 8.80 Hz, 1H), 4.08 (t, J=6.40 Hz, 2H), 3.81-3.74 (m, 3H), 3.67-3.64 (m, 1H), 3.34 (m, 1H), 3.18 (t, J=10.80 Hz, 1H), 3.01-2.98 (m, 1H), 2.85 (m, 4H), 2.77-2.67 (m, 4H), 2.63 (m, 4H).

Example 100: 5-amino-3-(2-(4-(2-fluoro-4-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one

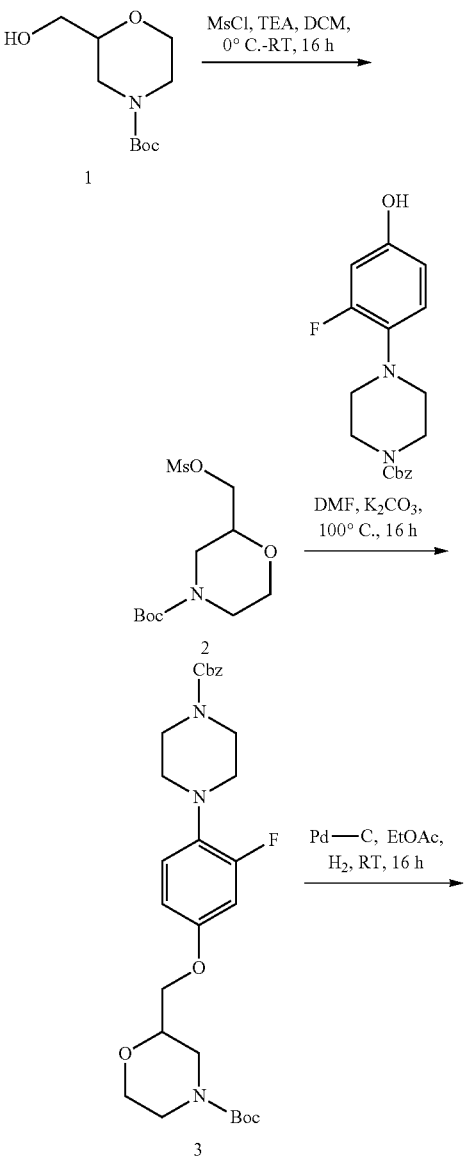

-continued

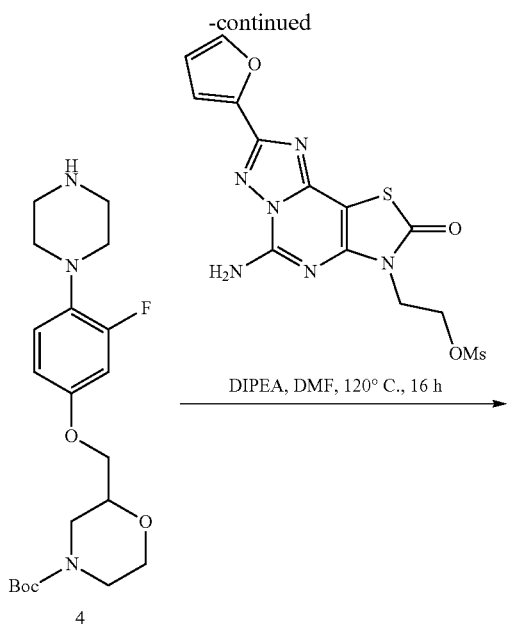

4

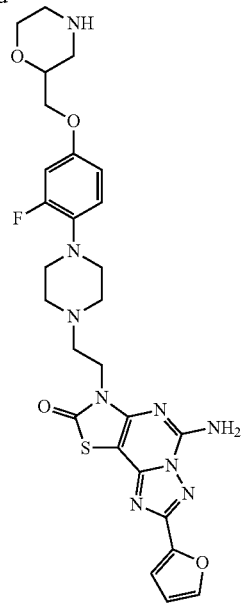

DIPEA, DMF, 120° C., 16 h
→

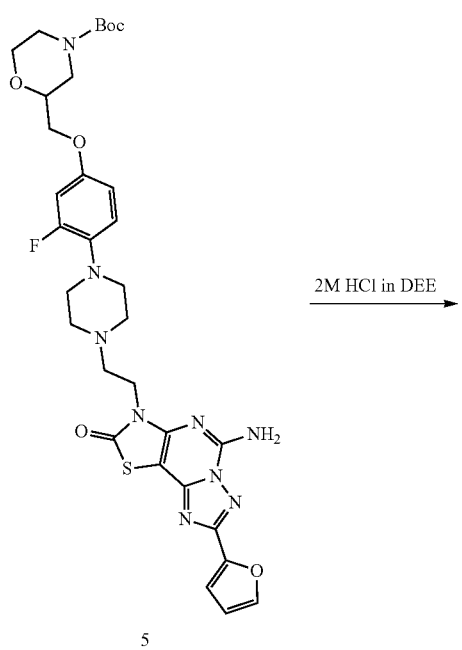

5

2M HCl in DEE
→

-continued

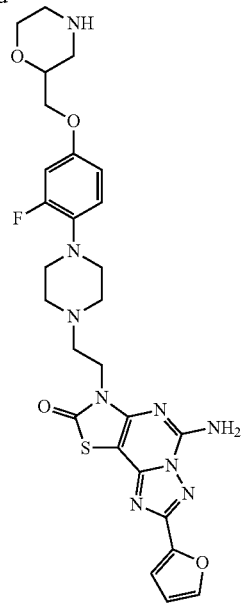

Cpd 100

Step 1: Synthesis of tert-butyl 2-(((methylsulfonyl)oxy)methyl)morpholine-4-carboxylate (2): To a cooled suspension of tert-butyl 2-(hydroxymethyl) morpholine-4-carboxylate (1, 5.0 g, 23.01 mmol) in dry DCM (50 mL) was added methane sulfonyl chloride drop wise (3.42 g, 29.92 mmol) and the reaction mixture was stirred at RT for 16 h. After the completion of reaction the reaction (TLC), the reaction mixture was diluted with water and the crude product was extracted with DCM, concentrated and purified by column chromatography (30% EtOAc/Hexane as eluent) to afford the title compound 2 as light yellow gum (6.0 g, 87%). LCMS (ESI positive ion) m/z: calculated: 295.35; Observed; 196.1 (M+1-100).

Step 2: Synthesis of tert-butyl 2-((4-(4-((benzyloxy)carbonyl)piperazin-1-yl)-3-fluorophenoxy)methyl)morpholine-4-carboxylate (3): To a suspension of benzyl 4-(2-fluoro-4-hydroxyphenyl) piperazine-1-carboxylate (2, 0.5 g, 1.51 mmol) and tert-butyl 2-(((methylsulfonyl)oxy)methyl) morpholine-4-carboxylate (0.53 g, 1.81 mmol) in dry DMF (10 mL) was added $K_2CO_3$ (0.63 g, 4.54 mmol) and the reaction mixture was heated at 100° C. for 16 h. After the completion of reaction the reaction (TLC), reaction mass was filtered through pad of celite and the filtrate was concentrated and purified by column chromatography (30% EtOAc/Hexane as eluent) to afford the title compound 3 as off white solid (0.35 g, 39%); LCMS (ESI positive ion) m/z: calculated: 529.61; observed: 530.3 (M+1). 1H-NMR (400 MHz, DMSO-d6): δ 7.39-7.35 (m, 5H), 7.32-7.00 (m, 1H), 6.97-6.85 (m, 1H), 6.84-6.72 (m, 1H), 5.11 (s, 2H), 3.98-3.96 (m, 2H), 3.86-3.73 (m, 2H), 3.70-3.66 (m, 2H), 3.64-3.43 (m, 2H), 3.38-3.34 (m, 4H), 3.32 (m, 1H), 2.89 (m, 4H), Step 3: Synthesis of tert-butyl 2-((3-fluoro-4-(piperazin-1-yl)phenoxy)methyl) morpholine-4-carboxylate (4): A solution of of tert-butyl 2-((4-(4-((benzyloxy)carbonyl)piperazin-1-yl)-3-fluorophenoxy) methyl) morpholine-4-carboxylate (3, 0.33 g, 0.62 mmol) in ethyl acetate (6 mL) was charged with 10% Palladium on Carbon (0.060 g) and the reaction mixture was stirred under hydrogen bladder pressure at room temperature for 16 h. After the reaction completion (TLC) the reaction mixture was filtered through pad of celite and the filtrate was concentrated under reduced pressure to afford tert-butyl the title compound 4 as light brown solid (0.18 g, 65%); LCMS (ESI positive ion) m/z: calculated: 395.48; observed: 396.3 (M+1). 1H-NMR (400

MHz, DMSO-d6): δ 6.95 (t, J=10.00 Hz, 1H), 6.84-6.80 (m, 1H), 6.72-6.70 (m, 1H), 3.96-3.95 (m, 2H), 3.92-3.83 (m, 2H), 3.74-3.67 (m, 2H), 3.65-3.64 (m, 1H), 3.33-2.99 (m, 9H), 1.42 (s, 9H).

Step 4: Synthesis of tert-butyl 2-((4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-methyl)-orpholine-4-carboxylate (5): A mixture of 2-(5-amino-8-(furan-2-yl)-2-oxothiazolo[5,4-e][1,2,4]triazolo[1,5-c]pyrimidin-3(2H)-yl)ethyl methanesulfonate (0.16 g, 0.40 mmol), tert-butyl 2-((3-fluoro-4-(piperazin-1-yl)phenoxy)methyl) morpholine-4-carboxylate (4, 0.176 g, 0.444 mmol) and DIPEA (0.26 g, 2.01 mmol) in dry DMF (3 mL) was heated at 120° C. for 16 h in a sealed tube. After completion (TLC), the reaction mixture was cooled to RT, diluted with water and the crude solid was filtered and purified by column chromatography (70% EtOAc/Hexane as eluent) to afford the title compound 5 as off white solid (0.05 g, 16.4%); LCMS (ESI positive ion) m/z: calculated: 695.77; observed: 696.0 (M+1). 1H-NMR (400 MHz, DMSO-d6): δ 8.30 (brs, 2H), 7.95 (brs, 1H), 7.24 (s, 1H), 6.92 (m, 1H), 6.83-6.73 (m, 1H), 6.69 (d, J=8.80 Hz, 2H), 4.08-3.95 (m, 2H), 3.85-3.83 (m, 2H), 3.70 (m, 2H), 3.43 (m, 2H), 3.33 (m, 1H), 2.85 (m, 4H), 2.68-2.63 (m, 4H), 2.45-2.33 (m, 4H), 1.41 (s, 9H).

Step 5: Synthesis of 5-amino-3-(2-(4-(2-fluoro-4-(morpholin-2-ylmethoxy)phenyl) piperazin-1-yl)ethyl)-8-(furan-2-yl)thiazolo[5,4-e][1,2,4]triazolo[1,5-c]pyrimidin-2(3H)-one (Compound 100): To an ice cold solution of tert-butyl 2-((4-(4-(2-(5-amino-8-(furan-2-yl)-2-oxothiazolo[5,4-e][1,2,4] triazolo[1,5-c]pyrimidin-3(2H)-yl)ethyl) piperazin-1-yl)-3-fluorophenoxy) methyl) morpholine-4-carboxylate (5, 0.04 g, 0.057 mmol) in dichloromethane (1 mL) was added 2 M HCl in Diethylether (1 mL) and the reaction mixture was stirred at RT for 2 h. After completion of the reaction (TLC), the solid formed (HCl salt) was filtered, dried under reduced pressure to afford the title compound 100 as off white solid (0.014 g, 36%); HPLC purity (XB_0595TF.M): 95.72%; LCMS (ESI positive ion) m/z: calculated: 595.35; observed: 596.2 (M+1); 1H-NMR (400 MHz, DMSO-d6): δ 10.11 (brs, 1H), 9.39-9.41 (m, 2H), 8.42 (brs, 2H), 7.97 (s, 1H), 7.26-7.27 (m, 1H), 7.04 (t, J=9.64 Hz, 1H), 6.90-6.94 (m, 1H), 6.74-6.77 (m, 2H), 4.14 (t, J=3.32 Hz, 2H), 3.99-4.03 (m, 4H), 3.91-3.94 (m, 2H), 3.78 (t, J=12.12 Hz, 1H), 3.60-3.61 (m, 2H), 3.30-3.48 (m, 3H), 3.271-3.198 (m, 2H), 3.17-3.00 (m, 4H).

Examples 101 and 102: 5-amino-3-(2-(4-(2-fluoro-4-(((3R,4R)-4-fluoropyrrolidin-3-yl)oxy)phenyl) piperazin-1-yl)ethyl)-8-(furan-2-yl)thiazolo[5,4-e][1,2,4]triazolo[1,5-c]pyrimidin-2(3H)-one and 5-amino-3-(2-(4-(2-fluoro-4-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one

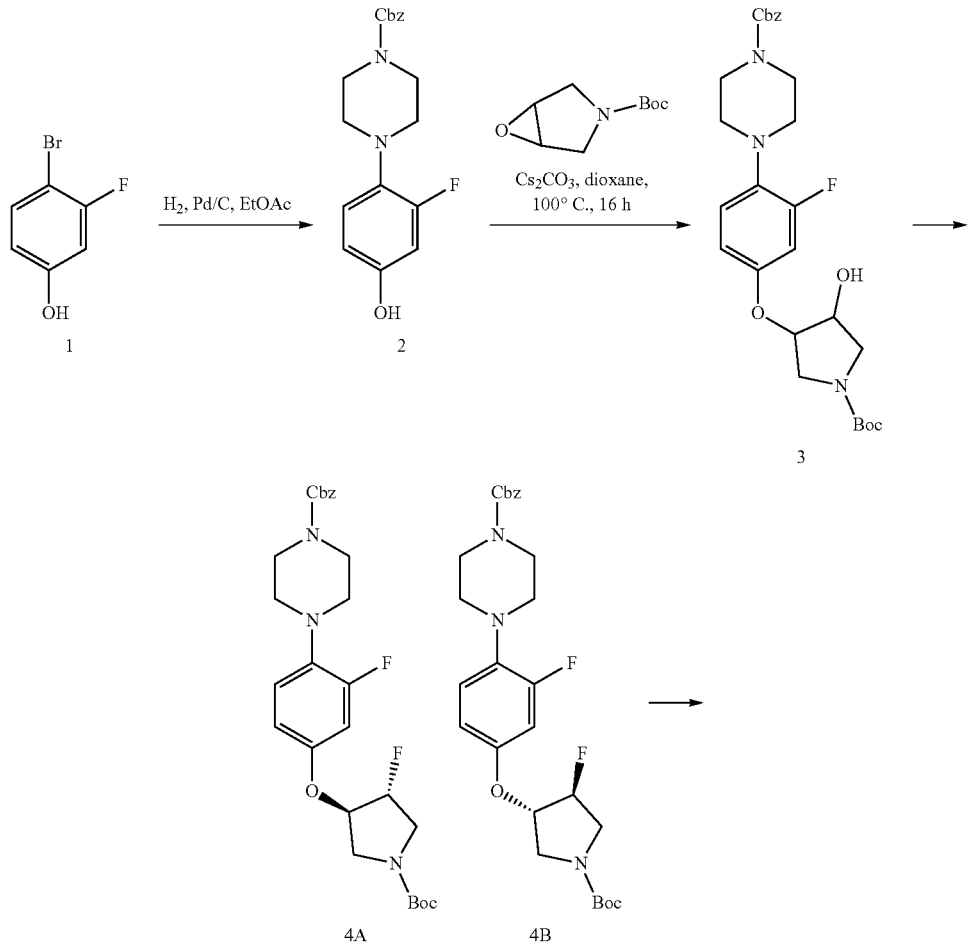

-continued
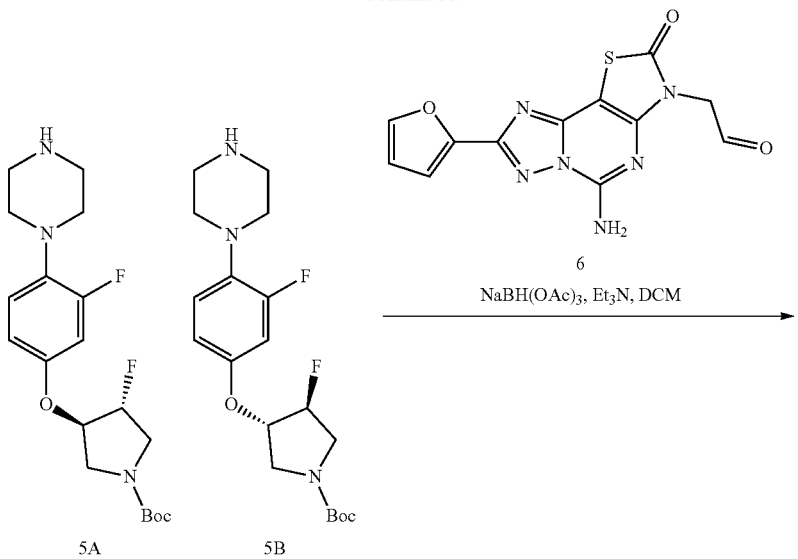
5A     5B
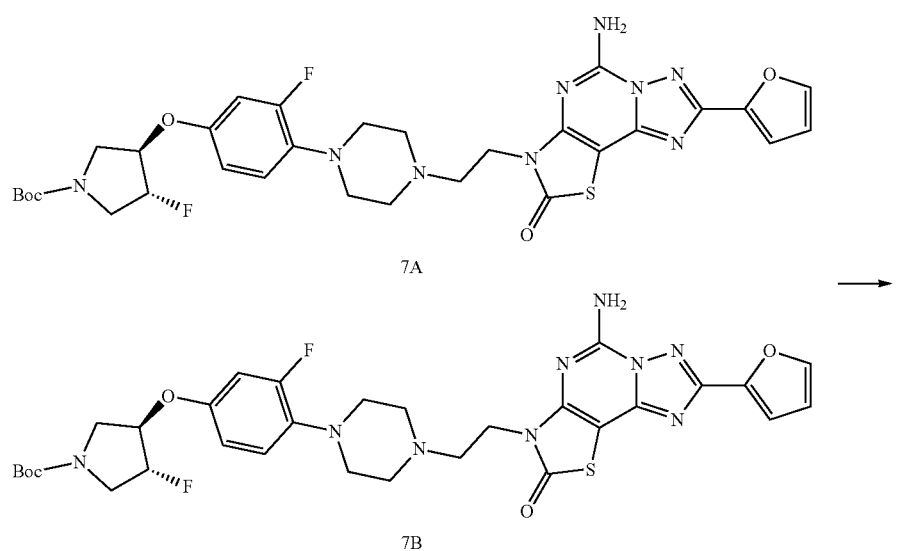
7A
7B
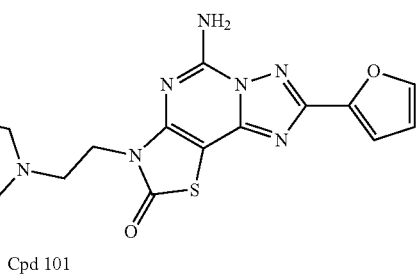
Cpd 101
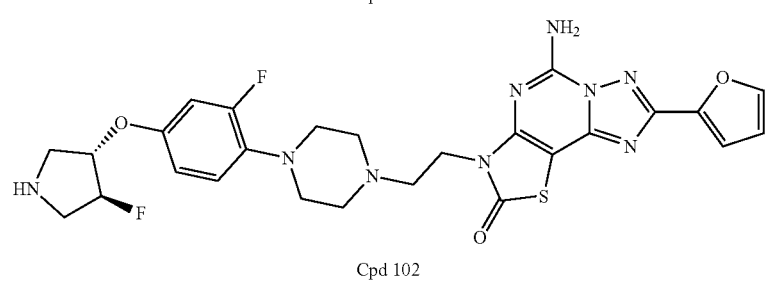
Cpd 102

Step 1: Synthesis of benzyl 4-(2-fluoro-4-hydroxyphenyl)piperazine-1-carboxylate (2): To an ice cold stirred solution of 4-bromo-3-fluorophenol (1, 15 g, 0.079 mol), benzyl piperazine-1-carboxylate (20.76 g, 0.094 mol), DavePhos (3.704 g, 0.009 mol), $Pd_2(dba)_3$ (7.186 g, 0.008 mol) in THF (100 mL), LHMDS (100 mL) was added. After addition, the reaction was allowed to reach room temperature. Then it was heated to 65° C. for 24 h. After the completion, the reaction mixture was quenched with saturated ammonium chloride solution and extracted with ethyl acetate. Combined organic layer was washed with saturated brine solution, dried over anhydrous Na2SO4, filtered and concentrated under reduced pressure. The crude obtained was purified by column chromatography (230-400 silica gel (30% EA/Pet ether as an eluent) to afford the product as off white solid (10.00 g, 30.1%). LCMS (ESI positive ion) m/z: calculated: 330.36; observed: 331.1 (M+1).

Step 2: Synthesis of benzyl 4-(4-((1-(tert-butoxycarbonyl)-4-fluoropyrrolidin-3-yl)oxy)-2-fluorophenyl)piperazine-1-carboxylate (3): To a stirred solution of benzyl 4-(2-fluoro-4-hydroxyphenyl)piperazine-1-carboxylate (6.8 g, 20.58 mmol), tert-butyl 6-oxa-3-azabicyclo[3.1.0]hexane-3-carboxylate (4.986 g, 26.76 mmol) in 1,4-dioxane (20 mL), Cs2CO3 (10.3 g, 30.88 mmol) was added. The resulting mixture was stirred at 100° C. for 16 h. Then it was filtered to remove the inorganic. The crude residue obtained on concentration of the filtrate was purified by column chromatography (230-400 silica gel (30% EA/Pet ether as an eluent) to afford an off-white solid (6.00 g, 56.0%). LCMS (ESI positive ion) m/z: calculated: 515.58; observed: 516.2 (M+1).

Step 3: Synthesis of benzyl 4-(4-((-1-(tert-butoxycarbonyl)-4-fluoropyrrolidin-3-yl)oxy)-2-fluorophenyl)piperazine-1-carboxylate (4A & 4B): To an ice cold stirred solution of benzyl 4-(4-((1-(tert-butoxycarbonyl)-4-hydroxypyrrolidin-3-yl)oxy)-2-fluorophenyl)piperazine-1-carboxylate (3, 6 g, 11.64 mmol) in DCM (30 mL), DAST (5.816 g, 34.91 mmol) was added to the reaction mixture at −20° C. The resulting mixture was stirred at −20° C. for 0.5 h and then RT for 16 h. After the completion of the reaction, the reaction mixture quenched with saturated $NaHCO_3$ solution and extracted with DCM. Combined organic layer was dried over anhydrous Na2SO4, filtered and concentrated under reduced pressure. The crude obtained was purified by column chromatography (230-400 silica gel (30% EA/hexane as an eluent) to afford two fractions of product. Fraction-1-1.4 g, Fraction-2-900 mg. LCMS (ESI positive ion) m/z: calculated: 517.57; observed: 518.2 (M+1).

The two fractions were further purified by chiral SFC purification (0.5% DEA in IPA, YMC Cellulose-SC) to afford enantiomers 4A and 4B Step 4: Synthesis of tert-butyl (3R,4R)-3-fluoro-4-(3-fluoro-4-(piperazin-1-yl)phenoxy)-pyrrolidine-1-carboxylate (5A): To a stirred solution of benzyl 4-(4-(((3R,4R)-1-(tert-butoxycarbonyl)-4-fluoropyrrolidin-3-yl)oxy)-2-fluorophenyl)piperazine-1-carboxylate (4A, 430 mg, 0.831 mmol), in ethyl acetate (10 mL), Pd/C 10% (200 mg) was added under nitrogen atmosphere. The resulting mixture was stirred at RT under hydrogen atmosphere for 32 h. Then it was filtered through celite pad to remove the Pd/C. The crude residue obtained on concentration of the filtrate to afford as sticky material. The crude material was taken next step without purification (0.23 g, 69.3%). LCMS (ESI positive ion) m/z: calculated: 383.44; observed: 384.3 (M+1).

Step 5: Synthesis of tert-butyl (3R,4R)-3-(4-(4-(2-(5-amino-8-(furan-2-yl)-2-oxothiazolo-[5,4-e][1,2,4]triazolo[1,5-c]pyrimidin-3(2H)-yl)ethyl)piperazin-1-yl)-3-fluorophenoxy)-4-fluoropyrrolidine-1-carboxylate (7A): To a stirred solution of tert-butyl (3R,4R)-3-(4-(4-(2-(5-amino-8-(furan-2-yl)-2-oxothiazolo-[5,4-e][1,2,4]triazolo[1,5-c]pyrimidin-3(2H)-yl)ethyl)piperazin-1-yl)-3-fluorophenoxy)-4-fluoropyrrolidine-1-carboxylate (5A, 100 mg, 0.261 mmol) in DCM (10 mL), 2-(5-amino-8-(furan-2-yl)-2-oxothiazolo[5,4-e][1,2,4]triazolo[1,5-c]pyrimidin-3(2H)-yl)acetaldehyde (82 mg, 0.261 mmol), and $Et_3N$ (52 mg, 0.552 mmol) were added. The resulting mixture was stirred at room temperature for 3 h. Then $NaBH(OAc)_3$ (165 mg 0.522 mmol) was added and the resulting mixture was stirred at room temperature for 24 h. After completion, the reaction mixture was diluted with DCM. The organic part separated was washed successively with saturated bicarbonate solution, saturated brine solution. After drying over anhydrous $Na_2SO_4$, it was filtered and concentrated under reduced pressure. The crude obtained was purified by column chromatography (230-400 silica gel (5% MeOH/DCM as an eluent) to afford the product as off white solid (0.025 g, 14.0%). LCMS (ESI positive ion) m/z: calculated: 683.74; observed: 684.3 (M+1).

Step 6: Synthesis of 5-amino-3-(2-(4-(2-fluoro-4-(((3R,4R)-4-fluoropyrrolidin-3-yl)oxy)phenyl)piperazin-1-yl) ethyl)-8-(furan-2-yl)thiazolo[5,4-e][1,2,4]triazolo[1,5-c]pyrimidin-2(3H)-one (Compound 101): To an ice cold stirred solution of tert-butyl (3R,4R)-3-(4-(4-(2-(5-amino-8-(furan-2-yl)-2-oxothiazolo[5,4-e][1,2,4]triazolo[1,5-c]pyrimidin-3 (2H)-yl)ethyl)piperazin-1-yl)-3-fluorophenoxy)-4-fluoropyrrolidine-1-carboxylate (7A, 25 mg, 0.037 mmol) in DCM (1 mL), HCl in ether (0.073 mL) was added. The resulting mixture was stirred at 0° C. for 1 h. After the completion of reaction, the reaction mixture was concentrated under reduced pressure. The crude product obtained was triturated with ether to afford product as off white solid (0.013 g, 52.75%). LCMS (ESI positive ion) m/z: calculated: 583.62; observed: 584.0 (M+1). HPLC purity (XB0595TF): 92.31%. 1H-NMR (400 MHz, DMSO-d6): δ 9.86 (broad s, 1H), 9.69 (broad s, 1H), 9.47 (broad s, 1H), 8.42 (m, 2H), 7.97 (s, 1H), 7.26 (d, J=3.60 Hz, 1H), 7.06-7.10 (m, 2H), 6.87 (d, J=8.40 Hz, 1H), 6.74-6.76 (m, 1H), 5.49 (m, 1H), 5.07-5.13 (m, 1H), 4.32 (brs, 2H), 3.72-3.92 (m, 2H) 3.62 (d, J=5.20 Hz, 2H), 3.39 (t, J=5.20 Hz, 5H), and 3.02 (brs, 5H).

Step 4: Synthesis of tert-butyl (3S,4S)-3-fluoro-4-(3-fluoro-4-(piperazin-1-yl)phenoxy)-pyrrolidine-1-carboxylate (5B): To a stirred solution of benzyl 4-(4-(((3S,4S)-1-(tert-butoxycarbonyl)-4-fluoropyrrolidin-3-yl)oxy)-2-fluorophenyl)piperazine-1-carboxylate (4B, 380 mg, 0.734 mmol), in ethyl acetate (10 mL), Pd/C 10% (200 mg) was added under nitrogen atmosphere. The resulting mixture was stirred at RT under hydrogen atmosphere for 32 h. Then it was filtered through celite pad to remove the Pd/C. The crude residue obtained on concentration of the filtrate to afford as sticky material. The crude material was taken next step without purification (0.2 g, 71.04%). LCMS (ESI positive ion) m/z: calculated: 383.44; observed: 384.3 (M+1).

Step 5: Synthesis of tert-butyl (3S,4S)-3-(4-(4-(2-(5-amino-8-(furan-2-yl)-2-oxothiazolo-[5,4-e][1,2,4]triazolo[1,5-c]pyrimidin-3(2H)-yl)ethyl)piperazin-1-yl)-3-fluorophenoxy)-4-fluoropyrrolidine-1-carboxylate (7B): To a stirred solution of tert-butyl (3S,4S)-3-(4-(4-(2-(5-amino-8-(furan-2-yl)-2-oxothiazolo-[5,4-e][1,2,4]triazolo[1,5-c]pyrimidin-3(2H)-yl)ethyl)piperazin-1-yl)-3-fluoro-phenoxy)-4-fluoropyrrolidine-1-carboxylate (5B, 70 mg, 0.187 mmol) in DCM (10 mL), 2-(5-amino-8-(furan-2-yl)-2-oxothiazolo[5,4-e][1,2,4]triazolo[1,5-c]pyrimidin-3 (2H)-yl)-acetaldehyde (57 mg, 0.187 mmol), and $Et_3N$ (52 mg, 0.548 mmol) were added. The resulting mixture was stirred at room temperature for 3 h. Then $NaBH(OAc)_3$ (77 mg, 0.365 mmol) was added and the resulting mixture was stirred at room temperature for 24 h. After completion, the reaction mixture was diluted with DCM. The organic part separated was washed successively with saturated bicarbonate solution, saturated brine solution. After drying over anhydrous $Na_2SO_4$, it was filtered and concentrated under reduced pressure. The crude obtained was purified by column chromatography (230-400 silica gel (5% MeOH/DCM as an eluent) to afford the product as off white solid (0.027 g, 19.9%). LCMS (ESI positive ion) m/z: calculated: 683.74; observed: 684.3 (M+1).

Step 6: Synthesis of 5-amino-3-(2-(4-(2-fluoro-4-(((3S,4S)-4-fluoropyrrolidin-3-yl)oxy)-phenyl)piperazin-1-yl) ethyl)-8-(furan-2-yl)thiazolo[5,4-e][1,2,4]triazolo[1,5-c]pyrimidin-2(3H)-one (Compound 102): To an ice cold stirred solution of tert-butyl (3S,4S)-3-(4-(4-(2-(5-amino-8-(furan-2-yl)-2-oxothiazolo[5,4-e][1,2,4]triazolo[1,5-c]pyrimidin-3 (2H)-yl)ethyl)piperazin-1-yl)-3-fluoro-phenoxy)-4-fluoro-pyrrolidine-1-carboxylate (7B, 25 mg, 0.037 mmol) in DCM (1 mL), HCl in ether (0.073 mL) was added. The resulting mixture was stirred at 0° C. for 1 h. After the completion of reaction, the reaction mixture was concentrated under reduced pressure. The crude product obtained was triturated with ether to afford product as off white solid (0.017 g, 69.7%). LCMS (ESI positive ion) m/z: calculated: 583.62; observed: 584.4 (M+1). HPLC purity (XB_0595TF): 93.18%. 1H-NMR (400 MHz, DMSO-d6): δ 10.27 (broad s, 1H), 9.69-9.82 (m, 2H), 8.41 (broad s, 2H), 7.97 (m, 1H), 7.26-7.27 (m, 1H), 7.05-7.10 (m, 2H), 6.87-6.90 (m, 1H), 6.75 (t, J=1.60 Hz, 1H), 5.49 (d, J=4.00 Hz, 1H), 5.07-5.13 (m, 1H), 4.32 (d, J=5.20 Hz, 2H), 3.73-3.93 (m, 2H), 3.49-3.66 (m, 2H), 3.40-3.44 (m, 3H), 3.30-3.39 (m, 2H), 3.25-3.30 (m, 3H), and 3.07-3.10 (n, 2H).

Example 111: 5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one

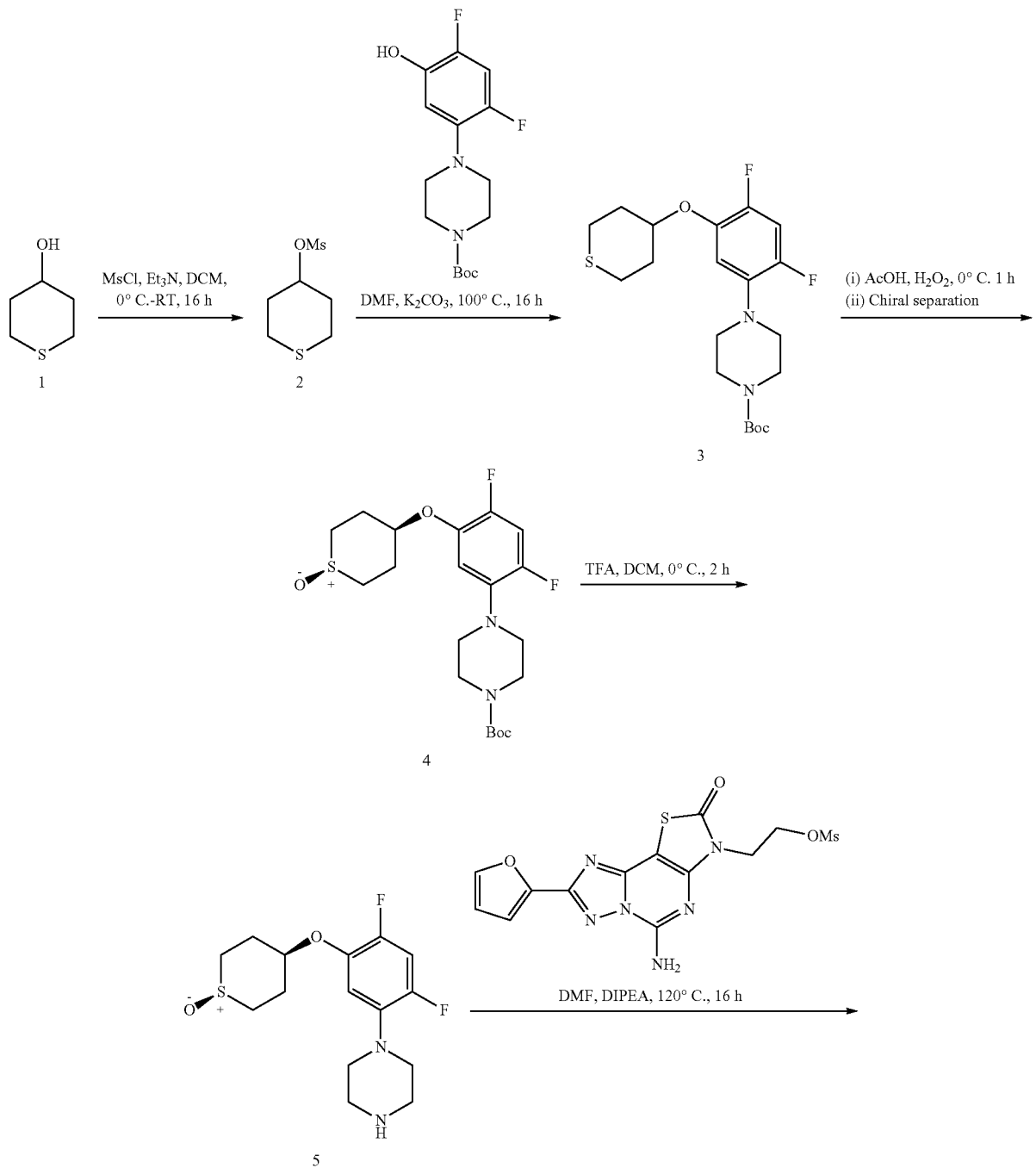

-continued

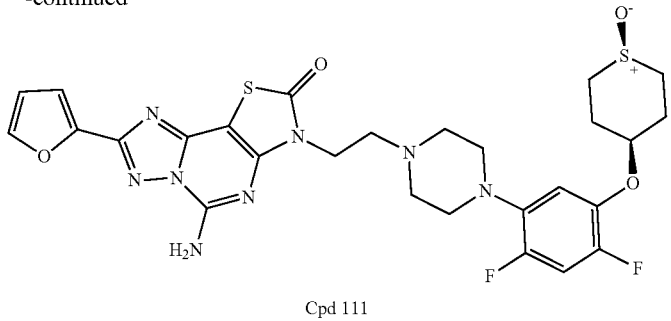

Cpd 111

Step 1: Synthesis of tetrahydro-2H-thiopyran-4-yl methane sulfonate (2): To an ice cold solution of tetrahydro-2H-thiopyran-4-ol (2.0 g, 16.94 mmol) and triethyl amine (4.26 g, 42.2 mmol) in dichloromethane (30 mL) was added wise, methane sulfonyl chloride (2.1 g, 18.62 mmol) and the reaction mixture was stirred at RT for 12 h. After the reaction completion the reaction mixture was diluted with water and the crude product was extracted with dichloromethane. The organic layer was dried, concentrated and purified by column chromatography (20% EtOAc/Hexane as eluent) to afford the title compound 2 as light brown liquid (3.1 g, 94%). The crude was directly taken for the next step as such.

Step 2: Synthesis of tert-butyl 4-(2,4-difluoro-5-((tetrahydro-2H-thiopyran-4-yl)oxy)phenyl)piperazine-1-carboxylate (3): To a solution of tetrahydro-2H-thiopyran-4-yl methanesulfonate (2, 2.25 g, 11.45 mmol) and tert-butyl 4-(2,4-difluoro-5-hydroxyphenyl)piperazine-1-carboxylate (3 g, 9.55 mmol) in N,N-dimethylformamide (10 mL), was added $K_2CO_3$ (2.69 g, 19.04 mmol) and the reaction mixture was heated at 100° C. for 16 h. After the reaction completion (TLC), the reaction mixture was diluted with water (30 mL) and extracted with ethyl acetate. Organic layer was washed with brine solution, water, dried over anhydrous $Na_2SO_4$, filtered and concentrated under reduced pressure to afford crude product, which was further purified by column chromatography (20% EtOAc/Hexane as eluent) to afford the title compound 3 as off white solid (1.7 g, 42.54%); LCMS (ESI positive ion) m/z: calculated: 414.51; observed: 415.1 (M+1).

Step 3: Synthesis of tert-butyl 4-(2,4-difluoro-5-((1-oxidotetrahydro-2H-thiopyran-4-yl)oxy)phenyl)piperazine-1-carboxylate (4): A solution of tert-butyl 4-(2,4-difluoro-5-(tetrahydro-2H-thiopyran-4-yl)oxy)phenyl) piperazine-1-carboxylate (3, 1.7 g, 4.101 mmol) in acetic acid (20 mL), was cooled to 0° C., $H_2O_2$(30%, 2 mL) was added and the reaction mixture was stirred at the same temperature for 1 h. After the reaction completion (TLC), reaction mixture was neutralized with cooled 10% NaOH solution and the crude product was extracted with dichloromethane. The organic layer was washed with brine, dried over anhydrous $Na_2SO_4$, filtered and concentrated under reduced pressure to afford racemic product as off white solid. Yield: (1.62 g, 91.8%). The isomers present in the racemic mixture were separated through SFC chiral method. The first peak eluted out (peak 1) was concentrated to afford the title compound 4 as off white solid (0.65 g, 80%); LCMS (ESI positive ion) m/z: calculated: 430.51; observed: 431.1 (M+1). 1H-NMR (400 MHz, DMSO-d6): 7.31 (t, J=12 Hz, 1H), 6.97-6.93 (s, J=8.8 Hz 1H), 4.43-4.40 (m, 1H), 3.46-3.16 (m, 4H), 2.96-2.90 (m, 6H), 2.75-2.67 (m, 2H), 2.50-2.30 (m, 2H), 1.86-1.83 (m, 2H), 1.42 (s, 9H).

Step 4: Synthesis of (1s, 4s)-4-(2,4-difluoro-5-(piperazin-1-yl)phenoxy)tetrahydro-2H-thiopyran 1-oxide (5): To an ice cold solution of tert-butyl 4-(2,4-difluoro-5-(((1s,4s)-1-oxidotetrahydro-2H-thiopyran-4-yl)oxy)phenyl)piperazine-1-carboxylate (4, 0.48 g, 1.11 mmol) in dichloromethane (10 mL), was added trifluoroacetic acid (1.3 mL) and the reaction mixture was stirred at RT for 5 h. After the reaction completion (TLC), excess TFA was removed by evaporation and the reaction mixture was neutralized by tosic acid resin treatment to afford the title compound 5 as off white solid (0.31 g, 84%); LCMS (ESI positive ion) m/z: calculated: 330.39; observed: 331.0 (M+1).

Step 5: Synthesis of 5-amino-3-(2-(4-(2,4-difluoro-5-(((1s, 4s)-1-oxidotetrahydro-2H-thiopyran-4-yl)oxy)phenyl)piperazin-1-yl)ethyl)-8-(furan-2-yl)thiazolo[5,4-e][1,2,4]-triazolo[1,5-c] pyrimidin-2(3H)-one (Compound 111): A mixture of 2-(5-amino-8-(furan-2-yl)-2-oxothiazolo[5,4-e][1,2,4]triazolo[1,5-c]pyrimidin-3(2H)-yl)ethyl methanesulfonate (0.35 g, 0.88 mmol), (1s,4s)-4-(2,4-difluoro-5-(piperazin-1-yl)phenoxy)tetrahydro-2H-thiopyran 1-oxide (5, 0.32 g, 0.97 mmol) and DIPEA (0.34 g, 2.64 mmol) in dry DMF (3 mL) was heated at 120° C. for 16 h in a sealed tube. After the completion (TLC), the reaction mixture was cooled to RT, diluted with water and the crude solid was filtered and purified by column chromatography (70% EtOAc/Hexane as eluent) to afford the title compound 111 as off white solid. LCMS (ESI positive ion) m/z: calculated: 630.39; observed: 631.1 (M+1); HPLC purity (XB_0595TF.M): 96.25%.

$^1$H-NMR (400 MHz, DMSO-d6): δ 8.29 (s, 2H), 7.94 (s, 1H), 7.23 (t, J=10.72 Hz, 2H), 6.80 (t, J=8.52 Hz, 1H), 6.72 (t, J=1.72 Hz, 1H), 4.36 (t, J=9.08 Hz, 1H), 4.05 (t, J=7.32 Hz, 2H), 2.90 (s, 6H), 2.79 (d, J=11.56 Hz, 2H), 2.73 (d, J=8.80 Hz, 2H), 2.69 (d, J=9.92 Hz, 4H), 2.14 (q, J=10.68 Hz, 2H), 1.97 (d, J=12.84 Hz, 2H).

Example 112: 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one

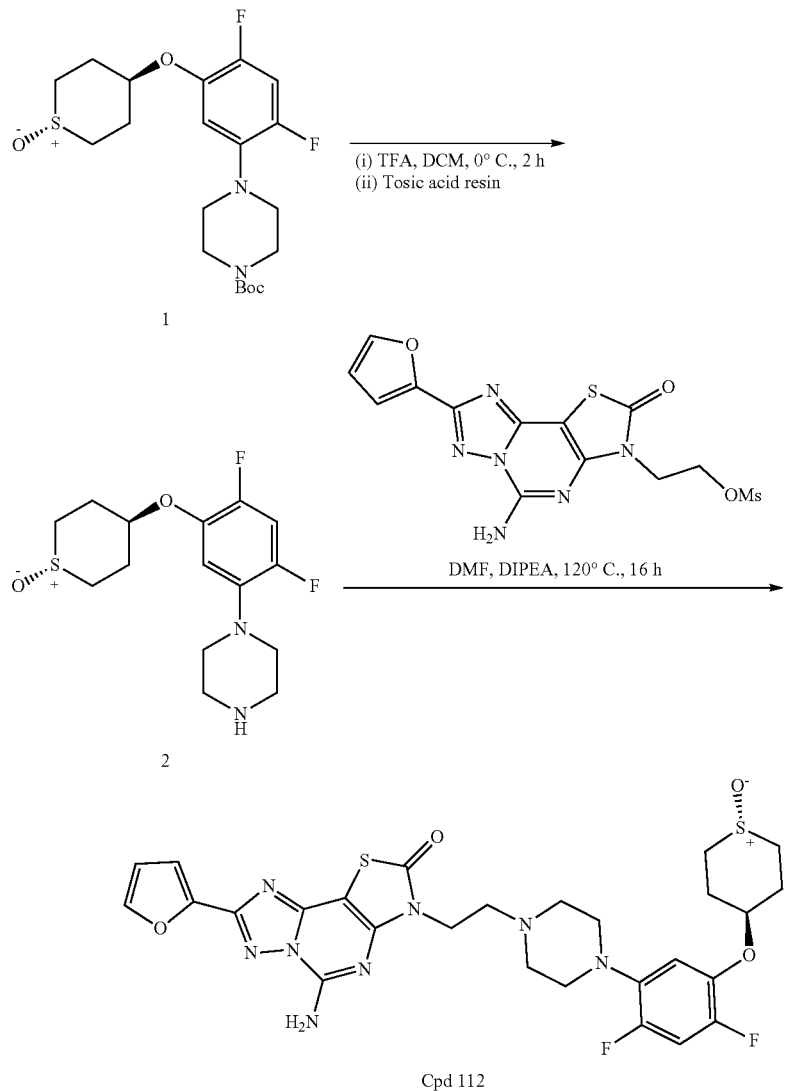

Step 1: Synthesis of (1r, 4r)-4-(2,4-difluoro-5-(piperazin-1-yl)phenoxy)tetrahydro-2H-thiopyran 1-oxide (2): To an ice cold solution of tert-butyl 4-(2,4-difluoro-5-(((1r,4r)-1-oxidotetrahydro-2H-thiopyran-4-yl)oxy)phenyl)piperazine-1-carboxylate (1, 0.3 g, 0.697 mmol) in dichloromethane (10 mL), was added trifluoroacetic acid (1.3 mL) and the reaction mixture was stirred at RT for 5 h. After the reaction completion (TLC), excess TFA was removed by evaporation and the reaction mixture was neutralized by tosic acid resin treatment to afford the title compound 2 as off white solid (0.20 g, 85%); LCMS (ESI positive ion) m/z: calculated: 330.39; observed: 331.0 (M+1).

Step 2: Synthesis of 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]-triazolo[1,5-c]pyrimidin-2(3H)-one (Compound 112): A mixture of 2-(5-amino-8-(furan-2-yl)-2-oxothiazolo[5,4-e][1,2,4]triazolo[1,5-c]pyrimidin-3(2H)-yl)ethyl methanesulfonate (0.23 g, 0.58 mmol), (1r,4r)-4-(2,4-difluoro-5-(piperazin-1-yl)phenoxy)tetrahydro-2H-thiopyran 1-oxide (2, 0.21 g, 0.63 mmol) and DIPEA (0.23 g, 1.74 mmol) in dry DMF (2.5 mL) was heated at 120° C. for 16 h in a sealed tube. After the completion (TLC), the reaction mixture was cooled to RT, diluted with water and the crude solid was filtered and purified by column chromatography (70% EtOAc/Hexane as eluent) to afford the title compound 3 as off white solid. LCMS (ESI positive ion) m/z: calculated: 630.39; observed: 631.1 (M+1); HPLC purity (XB_0595TF.M): 94.36%. $^1$H-NMR (400 MHz, DMSO-d6): δ 8.29 (s, 2H), 7.94 (s, 1H), 7.23 (t, J=11.8 Hz, 2H), 6.85 (t, J=8.64 Hz, 1H), 6.72 (t, J=1.72 Hz, 1H), 4.57 (s, 1H), 4.05 (t, J=7.32 Hz, 2H), 2.93 (brs, 6H), 2.72-2.67 (m, 4H), 2.62 (s, 6H), 2.34-2.32 (m, 2H), 1.85 (d, J=12.84 Hz, 2H).

Examples 119 and 120: (R)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one and (S)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one

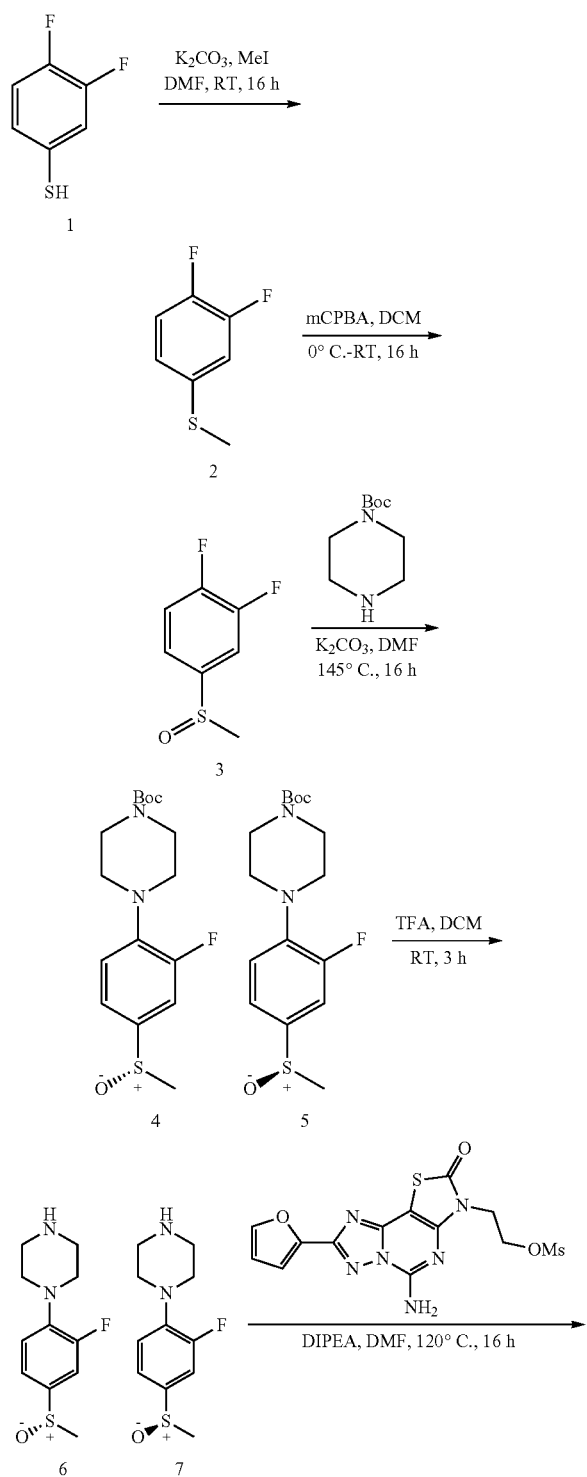

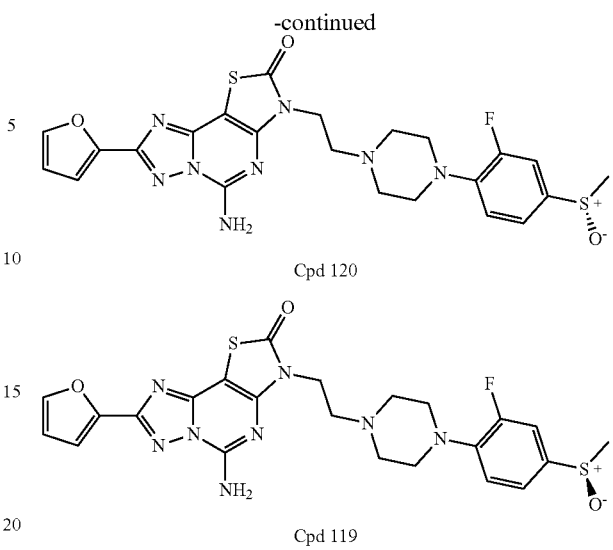

Step 1: Synthesis of (3,4-difluorophenyl)(methyl)sulfane (2): To a stirred solution of 3,4-difluorobenzenethiol (1, 8.0 g, 54.74 mmol) in DMF (25 mL) was added $K_2CO_3$ (9.08 g, 65.68 mmol) followed by MeI (8.5 g, 60.21 mmol) at 0° C. in sealed tube and stirred at RT for 16 h. After completion (TLC), the reaction mass was poured into ice cold water and extracted with diethyl ether. Organic layer was washed with saturated brine solution, dried over anhydrous $Na_2SO_4$, filtered and concentrated under reduced pressure to give the title compound. The crude product that was used for next step without purification (8.05 g, 88.1%).

Step 2: Synthesis of 1,2-difluoro-4-(methylsulfinyl)benzene (3): To a stirred solution of (3,4-difluorophenyl)(methyl)sulfane (2, 8.0 g, 49.94 mmol) in DCM (120 mL) was added mCPBA (8.6 g, 49.94 mmol) at 0° C. and stirred at RT for 16 h. After completion (TLC), the reaction mass was quenched with saturated sodium bicarbonate solution and extracted with DCM. Organic layer was washed with saturated brine solution, dried over anhydrous $Na_2SO_4$, filtered and concentrated under reduced pressure. The crude obtained was purified by column chromatography to give the title compound (5.0 g, 55.6%); LCMS (ESI positive ion) m/z: calculated: 176.01; observed: 177.0 (M+1).

Step 3: Synthesis of tert-butyl 4-(2-fluoro-4-(methylsulfinyl)phenyl)piperazine-1-carboxylate (4, 5): To a stirred solution of tert-butyl piperazine-1-carboxylate (5.3 g, 28.38 mmol) in DMF (50 mL) at 0° C. was added $K_2CO_3$ (7.8 g, 56.76 mmol) followed by 1,2-difluoro-4-(methylsulfinyl)benzene (3, 5.0 g, 28.38 mmol). The reaction mixture was stirred at 145° C. for 16 h. After completion (TLC), the reaction mass was quenched with water and extracted with ethyl acetate. Organic layer was washed with saturated brine solution, dried over anhydrous $Na_2SO_4$, filtered and concentrated under reduced pressure. The crude obtained was purified by column chromatography to give the title compound (2.2 g, 22.7%); LCMS (ESI positive ion) m/z: calculated: 342.14; Observed; 343.0 (M+1).

Racemic mixture (0.22 g) was subjected to chiral separation by SFC (0.22 g sample was dissolved in 3 mL of methanol), column—Lux A1 mobile phase: 70:30 (A:B), A=liquid $CO_2$, B=methanol, flow rate: 3.0 mL/min; wave length: 220 nm) to yield 810 mg of peak 1 (4) and 820 mg of peak 2 (5) respectively.

Note:
Peak 1 from SFC purification was arbitrarily considered as (S) isomer and peak 2 was considered as (R) isomer.

Step 4: Synthesis of (S)-1-(2-fluoro-4-(methylsulfinyl) phenyl)piperazine (6): To a stirred solution of tert-butyl (S)-4-(2-fluoro-4-(methylsulfinyl)phenyl)piperazine-1-carboxylate (4, 800 mg, 0.292 mmol) in DCM (18 mL) was added TFA (1.3 g, 11.68 mmol) at 0° C. The reaction mixture was stirred at RT for 3 h. After the reaction completion (TLC), the reaction mixture was concentrated under reduced pressure. The salt was dissolved in methanol and neutralized using Tosic acid scavenger resin to get the title compound as free base (510 mg, 88.2%); LCMS (ESI positive ion) m/z: calculated: 242.09; observed: 243.1 (M+1).

Step 5: Synthesis of (S)-5-amino-3-(2-(4-(2-fluoro-4-(methylsulfinyl)phenyl)piperazin-1-yl)ethyl)-8-(furan-2-yl) thiazolo[5,4-e][1,2,4]triazolo[1,5-c]pyrimidin-2(3H)-one (Compound 120): To a stirred solution of (S)-1-(2-fluoro-4-(methylsulfinyl)phenyl)piperazine (6, 200 mg, 0.825 mmol) in DMF (10 mL) was added DIPEA (426.7 mg, 3.302 mmol) followed by 2-(5-amino-8-(furan-2-yl)-2-oxothiazolo[5,4-e][1,2,4]triazolo[1,5-c]pyrimidin-3(2H)-yl)ethyl methane sulfonate (294 mg, 0.743 mmol) in sealed tube and stirred at 120° C. for 16 h. After completion (TLC & LCMS), the solvent was removed under reduced pressure. The reaction mass was quenched with water and extracted with ethyl acetate. Organic layer was washed with saturated brine solution, dried over anhydrous $Na_2SO_4$, filtered and concentrated under reduced pressure. The crude obtained was purified by column chromatography to get the title compound (180 mg, 37.7%); HPLC purity (XB0595TF): 94.08%; LCMS (ESI positive ion) m/z: calculated: 542.13; observed: 543.2 (M+1); $^1$H-NMR (400 MHz, DMSO-d6): δ 8.30 (brs, 2H), 7.95 (m, 1H), 7.48-7.39 (m, 2H), 7.24 (d, J=3.60 Hz, 1H), 7.15 (t, J=8.40 Hz, 1H), 6.74-6.73 (m, 1H), 4.09 (m, 2H), 3.04 (m, 4H), 2.72 (s, 3H), 2.67 (m, 4H).

Example 119: (S)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one Step 1: Synthesis of (R)-1-(2-fluoro-4-(methylsulfinyl) phenyl)piperazine (7):

To a stirred solution of tert-butyl (R)-4-(2-fluoro-4-(methylsulfinyl)phenyl)piperazine-1-carboxylate (5, 800 mg, 0.292 mmol) in DCM (18 mL) was added TFA (1.3 g, 11.68 mmol) at 0° C. The reaction mixture was stirred at RT for 3 h. After the reaction completion (TLC), the reaction mixture was concentrated under reduced pressure. The salt was dissolved in methanol and neutralized using Tosic acid scavenger resin to get the title compound as free base (510 mg, 88.8%); LCMS (ESI positive ion) m/z: calculated: 242.09; observed: 243.1 (M+1).

Step 2: Synthesis of (R)-5-amino-3-(2-(4-(2-fluoro-4-(methylsulfinyl)phenyl)piperazin-1-yl)ethyl)-8-(furan-2-yl) thiazolo[5,4-e][1,2,4]triazolo[1,5-c]pyrimidin-2(3H)-one (Compound 119): To a stirred solution of (R)-1-(2-fluoro-4-(methylsulfinyl)phenyl)piperazine (7, 200 mg, 0.825 mmol) in DMF (10 mL) was added DIPEA (426.7 mg, 3.302 mmol) followed by 2-(5-amino-8-(furan-2-yl)-2-oxothiazolo[5,4-e][1,2,4]triazolo[1,5-c]pyrimidin-3(2H)-yl)ethyl methane sulfonate (294 mg, 0.743 mmol) in sealed tube and stirred at 120° C. for 16 h. After completion (TLC & LCMS), the solvent was removed under reduced pressure. The reaction mass was treated with water and extracted with ethyl acetate. Organic layer was washed with saturated brine solution, dried over anhydrous $Na_2SO_4$, filtered and concentrated under reduced pressure. The crude obtained was purified by column chromatography to get the title compound (120 mg, 25.1%); HPLC purity (XB0595TF): 93.75%; LCMS (ESI positive ion) m/z: calculated: 542.13; observed: 541.0 (M−1); $^1$H-NMR (400 MHz, DMSO-d6): δ 8.32 (brs, 2H), 7.96 (s, 1H), 7.49-7.40 (m, 2H), 7.25 (d, J=3.16 Hz, 1H), 7.16 (t, J=8.52 Hz, 1H), 6.74-6.73 (m, 1H), 4.09 (m, 2H), 3.04 (m, 4H), 2.76-2.66 (m, 9H).

Examples 121 and 122: 5-amino-3-(2-(4-(2-fluoro-4-(((1s,4s)-1-oxidotetrahydro-2H-thiopyran-4-yl) oxy)phenyl)piperazin-1-yl)ethyl)-8-(furan-2-yl)thiazolo[5,4-e][1,2,4]triazolo[1,5-c]pyrimidin-2(3H)-one and 5-amino-3-(2-(4-(2-fluoro-4-(((1r,4r)-1-oxidotetrahydro-2H-thiopyran-4-yl)oxy)phenyl) piperazin-1-yl)ethyl)-8-(furan-2-yl)thiazolo[5,4-e][1, 2,4]triazolo[1,5-c]pyrimidin-2(3H)-one

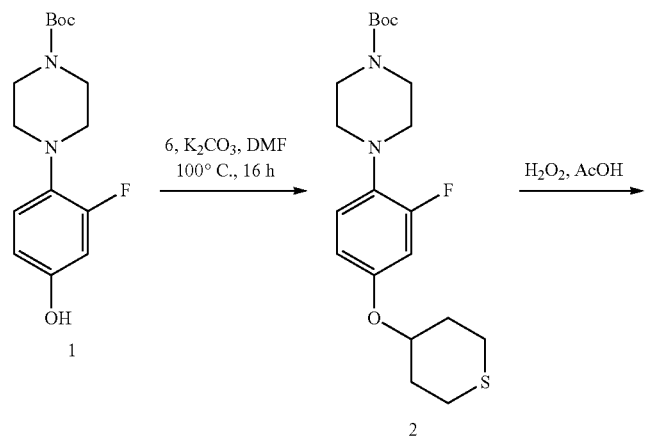

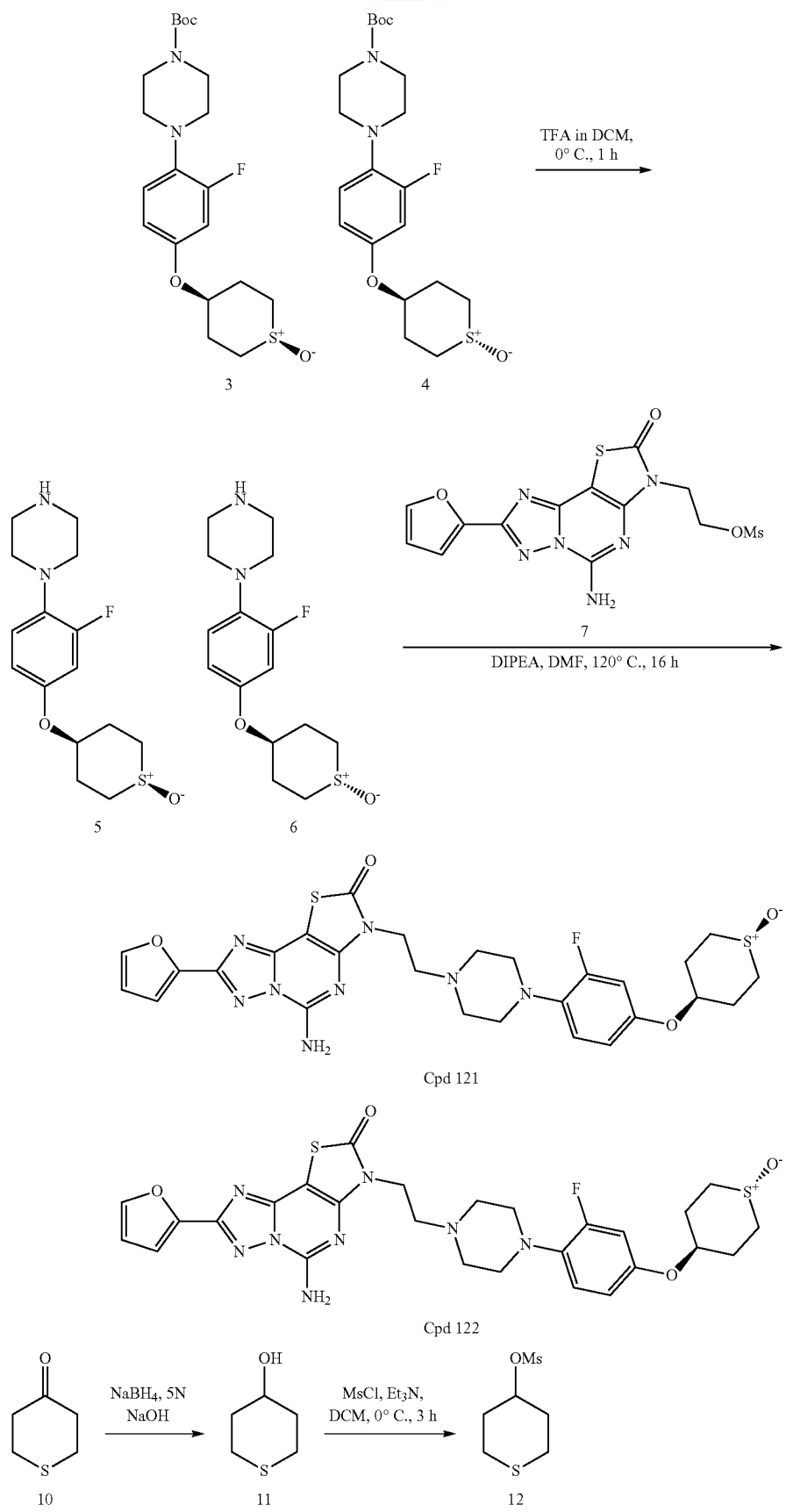

Step 1: Synthesis of tetrahydro-2H-thiopyran-4-ol (11): To an ice cold solution of tetrahydrothiopyran-4-one (10, 5 g, 0.043 mol) in methanol (40 mL), 5N sodium hydroxide solution (10 mL) solution was added slowly. Then sodium borohydride (0.488 g, 0.013 mol) was added portion wise. After addition, the reaction mixture was allowed to reach room temperature. After the reaction completion (~1 h), the reaction mixture was poured in to water and extracted with dichloromethane. Combined organic layer was washed with saturated brine solution, dried over anhydrous Na2SO4, and concentrated under reduced pressure. The crude product was purified by column chromatography using 5% methanol in DCM to afford the pure product (4 g, 51.90%). 1H-NMR (400 MHz, DMSO-d6): δ 4.69 (d, J=4.24 Hz, 1H), 3.41-3.47 (m, 1H), 2.65-2.70 (m, 2H), 2.50-2.54 (m, 1H), 2.47 (d, J=2.76 Hz, 1H), 2.00-2.02 (m, 2H), and 1.96-1.99 (m, 2H).

Step 2: Synthesis of tetrahydro-2H-thiopyran-4-yl methanesulfonate (12): To an ice cold solution of tetrahydrothiopyran-4-ol (11, 3.5 g, 0.030 mol) in dichloromethane (40 mL), triethyl amine (5.982 g, 0.059 mol) and methane sulfonyl chloride (0.727 g, 0.006 mol) were added. After 3 h, the reaction mixture poured into water and extracted with dichloromethane. Combined organic layer was washed with saturated brine solution, dried over anhydrous $Na_2SO_4$, and concentrated under reduced pressure. The crude residue was subjected to column chromatography using 2% methanol in DCM as eluent to afford the product (6 g, 98.07%).

Step 3: Synthesis of tert-butyl 4-(2-fluoro-4-((tetrahydro-2H-thiopyran-4-yl)oxy)phenyl)-piperazine-1-carboxylate (2): To a solution of tert-butyl 4-(2,4-difluoro-5-hydroxyphenyl)piperazine-1-carboxylate (1, 1.6 g, 5.399 mmol) and tetrahydrothiopyran-4-yl methane sulfonate (12, 1.272 g, 6.479 mmol) in DMF (20 mL), was added K2CO3 (1.490 g, 10.80 mmol). The resulting mixture was heated to 100° C. for 16 h. After the reaction completion (TLC), the reaction mixture was diluted with water and extracted with ethyl acetate. Combined organic layer was washed with saturated brine solution, dried over anhydrous $Na_2SO_4$, filtered and concentrated under reduced pressure. The crude obtained was purified by column chromatography (50% EtOAc/Hexane as eluent) to afford the product as off white solid (1.5 g, 69%). LCMS (ESI positive ion) m/z: calculated: 396.52; Observed; 397.1 (M+1).

Step 4: Synthesis of tert-butyl 4-(2-fluoro-4-((1-oxidotetrahydro-2H-thiopyran-4-yl)oxy)phenyl)piperazine-1-carboxylate (3, 4): To an ice cold mixture of tert-butyl4-(2-fluoro-4-tetrahydrothiopyran-4-yloxy-phenyl)-piperazine-1-carboxylate (1.650 g, 4.161 mmol, 1 eq) in acetic acid (25 mL), hydrogen peroxide (1 mL) was added drop wise and stirred at same temperature for 1 h. After the reaction completion (TLC), the reaction mixture poured in to 4N sodium hydroxide solution (20 mL) and extracted with ethyl acetate. Combined organic layer was washed with saturated brine solution, dried over anhydrous Na2SO4, filtered and concentrated under reduced pressure. The crude obtained was purified by column chromatography (80% EtOAc/Hexane as eluent) to afford the product as off white solid (1.4 g, 80.7%). LCMS (ESI positive ion) m/z: calculated: 412.52; Observed; 413.2 (M+1).

The racemic mixture (1.4 g) was subjected to chiral separation by SFC (1.4 g sample was dissolved in 10 mL of methanol), column—YMC Amylose-SA mobile phase: 70:30 (A:B), A=liquid CO2, B=0.5% DEA in Methanol flow rate: 3 mL/min; wave length: 210 nm. Yield 600 mg of peak 1 (3) and 500 mg of peak 2 (4).

Step 5: Synthesis of (1s,4s)-4-(3-fluoro-4-(piperazin-1-yl)phenoxy)tetrahydro-2H-thiopyran 1-oxide (5): To an ice cold solution of tert-butyl 4-(2-fluoro-4-(((1s,4s)-1-oxidotetrahydro-2H-thiopyran-4-yl)oxy)phenyl)-piperazine-1-carboxylate (3, 0.5 g, 1.212 mmol) in dichloromethane (10 mL), trifluoro acetic acid (0.207 g, 0.002 mol). After stirring at 0° C. for 1 h, the reaction mixture was concentrated under reduced pressure at ambient temperature. The residue obtained was triturated with diethyl ether. Then it was dissolved in methanol, passed through Si-Carbonate resin to afford the free base which was used directly for the next step (0.38 g, 99.35%). 1H-NMR (400 MHz, DMSO-d6): δ 7.02 (d, J=9.20 Hz, 1H), 6.90-6.98 (m, 1H), 6.76-6.79 (m, 1H), 4.40-4.43 (m, 1H), 3.18 (s, 1H), 3.05 (t, J=2.40 Hz, 4H), 2.93-2.99 (m, 4H), 2.85 (t, J=11.20 Hz, 1H), 2.79 (d, J=2.40 Hz, 2H), 2.12 (t, J=10.00 Hz, 2H), and 1.96 (d, J=12.40 Hz, 2H).

Step 6: Synthesis of 5-amino-3-(2-(4-(2-fluoro-4-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]-triazolo-[1,5-c]pyrimidin-2(3H)-one (Compound 121): To a mixture of 2-(5-amino-8-(furan-2-yl)-2-oxothiazolo[5,4-e][1,2,4]triazolo[1,5-c]pyrimidin-3(2H)-yl)ethyl methane sulfonate (7, 0.385 g, 0.971 mmol) and (1s,4s)-4-(3-fluoro-4-(piperazin-1-yl)phenoxy)tetrahydro-2H-thiopyran 1-oxide (0.334 g, 1.068 mmol) in DMF (4 mL), DIPEA (0.626 g, 4.856 mmol) was added. The reaction mixture was stirred at 90° C. for 16 h. After completion, the reaction mixture was diluted with water (10 mL) and extracted with ethyl acetate. Combined organic layer was washed with saturated brine solution, dried over anhydrous Na2SO4, filtered, concentrated. The crude product was purified by reverse phase preparative HPLC to afford the product as off white solid (0.045 g, 7.5%). LCMS (ESI positive ion) m/z: calculated: 612.70; Observed; 613 (M+1). HPLC purity (XB_0595TF): 99.21%. 1H-NMR (400 MHz, DMSO-d6): δ 8.31 (broad s, 2H), 7.95 (s, 1H), 7.24 (d, J=3.20 Hz, 1H), 6.88-6.93 (m, 2H), 6.73-6.77 (m, 2H), 4.59 (s, 1H), 4.08 (t, J=5.60 Hz, 2H), 3.50 (d, J=12.80 Hz, 2H), 2.86-2.95 (m, 6H), 2.63-2.71 (m, 6H), 2.27-2.33 (m, 2H) and 1.80-1.83 (m, 2H).

Example 122: 5-amino-3-(2-(4-(2-fluoro-4-(((1r,4r)-1-oxidotetrahydro-2H-thiopyran-4-yl)oxy)phenyl) piperazin-1-yl)ethyl)-8-(furan-2-yl)thiazolo[5,4-e][1, 2,4]triazolo[1,5-c]pyrimidin-2(3H)-one Step 5: Synthesis of (1r,4r)-4-(3-fluoro-4-(piperazin-1-yl) phenoxy)tetrahydro-2H-thiopyran 1-oxide (6): To an ice cold solution of tert-butyl 4-(2-fluoro-4-(((1r,4r)-1-oxidotetrahydro-2H-thiopyran-4-yl)oxy)phenyl)piperazine-1-carboxylate (4, 0.5 g, 1.212 mmol) in dichloromethane (10 mL), trifluoro acetic acid (0.207 g, 0.002 mol). After stirring at 0° C. for 1 h, the reaction mixture was concentrated under reduced pressure at ambient temperature. The residue obtained was triturated with diethyl ether. Then it was dissolved in methanol, passed through Si-Carbonate resin to afford the free base which was used directly for the next step (0.375 g, 98.05%). 1H-NMR (400 MHz, DMSO-d6): δ 7.02 (d, J=9.20 Hz, 1H), 6.90-6.98 (m, 1H), 6.76-6.79 (m, 1H), 4.40-4.43 (m, 1H), 3.18 (s, 1H), 3.05 (t, J=2.40 Hz, 4H), 2.93-2.99 (m, 4H), 2.85 (t, J=11.20 Hz, 1H), 2.79 (d, J=2.40 Hz, 2H), 2.12 (t, J=10.00 Hz, 2H), and 1.96 (d, J=12.40 Hz, 2H).

Step 6: Synthesis of 5-amino-3-(2-(4-(2-fluoro-4-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]-triazolo[1,5-c]pyrimidin-2(3H)-one (Compound 122): To a mixture of 2-(5-amino-8-(furan-2-yl)-2-oxothiazolo[5,4-e][1,2,4]triazolo[1,5-c]pyrimidin-3(2H)-yl)ethyl methane sulfonate (7, 0.235 g, 0.593 mmol) and (1s,4s)-4-(3-fluoro-4-(piperazin-1-yl)phenoxy)tetrahydro-2H-thiopyran 1-oxide (0.204 g, 0.652 mmol) in DMF (2 mL), DIPEA (0.382 g, 2.964 mmol) was added. The reaction mixture was stirred at 90° C. for 16 h. After completion, the reaction mixture was diluted with water (10 mL) and extracted with ethyl acetate. Combined organic layer was washed with saturated brine solution, dried over anhydrous $Na_2SO_4$, filtered, concentrated. The crude product was purified by reverse phase preparative HPLC to afford the product as off white solid (0.031 g, 8.4%). LCMS (ESI positive ion) m/z: calculated: 612.70; Observed; 613.1 (M+1). HPLC purity (XB_0595TF): 98.46%. 1H-NMR (400 MHz, DMSO-d6): δ 8.31 (broad s, 2H), 7.95 (s, 1H), 7.24 (d, J=3.20 Hz, 1H), 6.88-6.93 (m, 2H), 6.73-6.77 (m, 2H), 4.39 (t, J=9.20 Hz, 1H), 4.08 (t, J=6.00 Hz, 2H), 3.50 (d, J=12.40 Hz, 2H), 2.72-2.95 (m, 6H), 2.63-2.70 (m, 6H), 2.13-2.33 (m, 2H) and 1.85-1.99 (m, 2H).

Example 126: 5-amino-3-(2-(4-(2-fluoro-4-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one

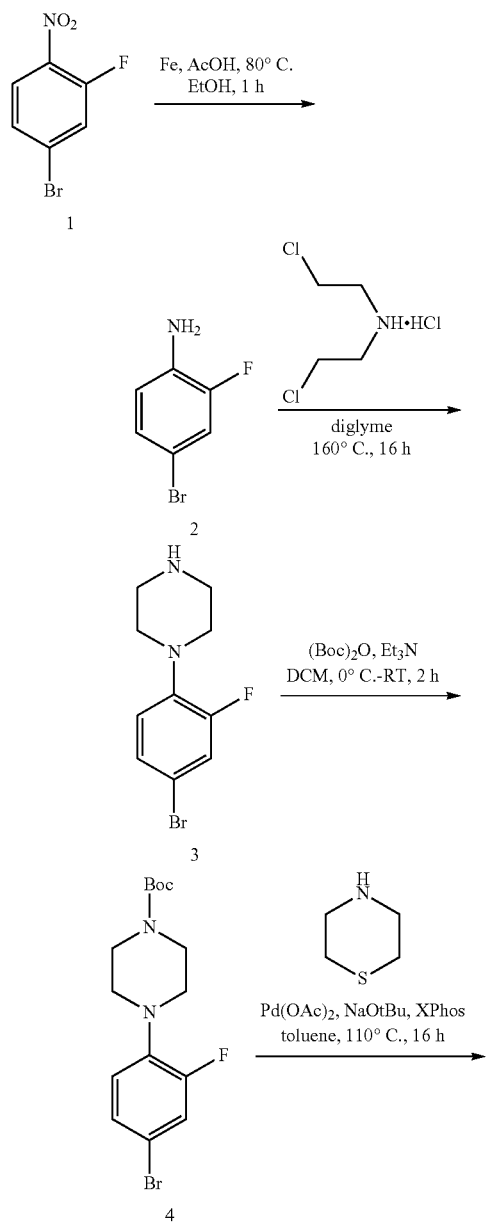
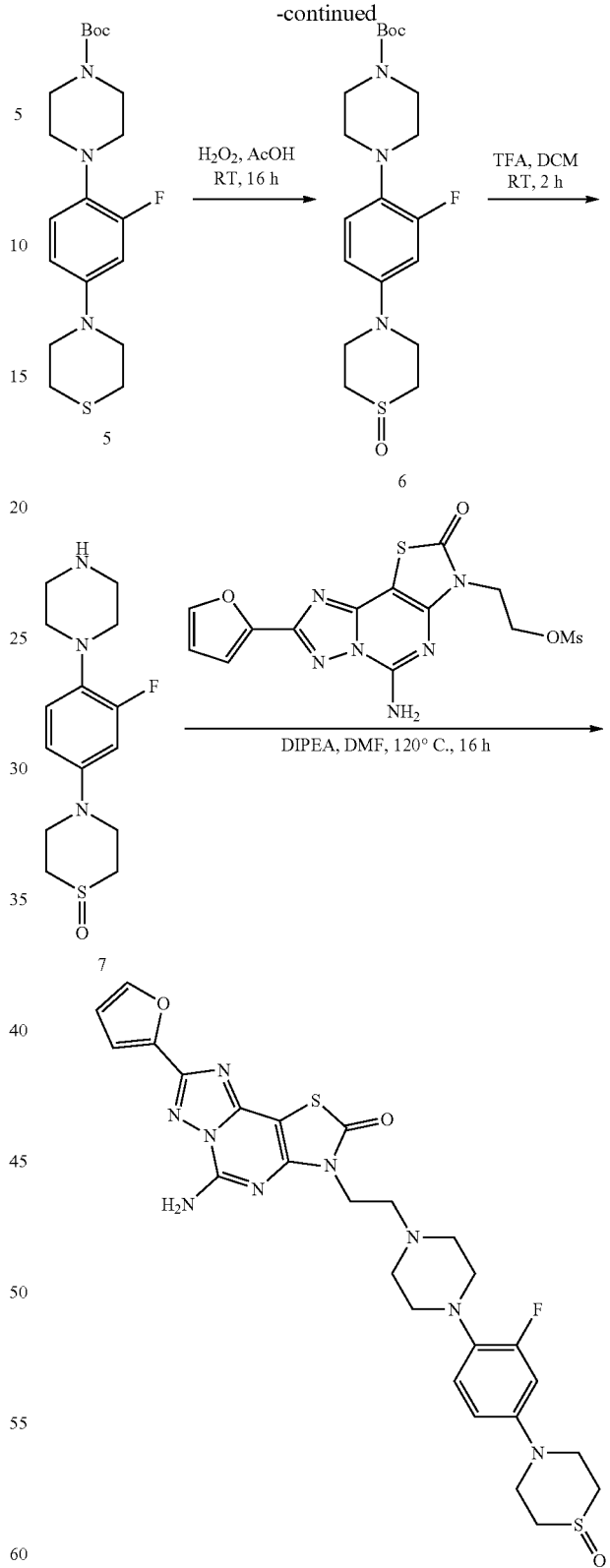

Cpd 126

Step 1: Synthesis of 4-bromo-2-fluoroaniline (2): To a stirred solution of 4-bromo-2-fluoro-1-nitrobenzene (1, 9.0 g, 13.64 mmol) and acetic acid (11.5 g, 0.57 mol) in ethanol (60 mL) was added iron powder (15.9 g, 0.285 mol). The reaction mixture was stirred at 80° C. for 1 h. After completion of the reaction, reaction mixture was diluted with EtOAc and filtered through celite bed. The filtrate was concentrated under reduced pressure to get the crude compound and it was used for the next step directly (6.0 g, 76.5%); LCMS (ESI positive ion) m/z: calculated: 188.96; observed: 192.0 (M+1).

Step 2: Synthesis of 1-(4-bromo-2-fluorophenyl)piperazine (3): To a stirred solution of 4-bromo-2-fluoroaniline (2, 6.0 g, 31.58 mmol) in diglyme (4.8 mL) was added bis(2-chloroethyl)amine hydrogen chloride (6.7 g, 37.89 mmol) and the reaction mixture was stirred at 160° C. for 16 h. After completion of the reaction (TLC), reaction mixture was cooled to RT and was treated with cold acetone. The precipitated solid was filtered and used for the next step directly (5.0 g, 61%); LCMS (ESI positive ion) m/z: calculated: 258.02; observed: 259.0 (M+1).

Step 3: Synthesis of tert-butyl 4-(4-bromo-2-fluorophenyl)piperazine-1-carboxylate (4): To a stirred solution of 1-(4-bromo-2-fluorophenyl)piperazine (3, 4.0 g, 15.4 mmol) and TEA (3.1 g, 30.9 mmol) in DCM (30 mL) at 0° C. was added di-tert-butyl dicarbonate (5.04 g, 23.1 mmol). The reaction mixture was stirred at RT for 2 h. After completion of the reaction (TLC), reaction mixture was treated with water and extracted with DCM. The separated organic layer was washed with NaHCO$_3$ solution, brine solution, dried over anhydrous Na$_2$SO$_4$ and concentrated under reduced pressure to afford crude product. The crude product was purified by column chromatography to get the title compound (4.0 g, 72.2%); LCMS (ESI positive ion) m/z: calculated: 358.07; observed: 259.0 (M−99+1).

Step 4: Synthesis of tert-butyl 4-(2-fluoro-4-thiomorpholinophenyl)piperazine-1-carboxylate (5): To a stirred solution of tert-butyl 4-(4-bromo-2-fluorophenyl)piperazine-1-carboxylate (4, 4.0 g, 11.1 mmol) and thiomorpholine (1.3 g, 12.3 mmol) in toluene (30 mL) was added XPhos (530 mg, 1.11 mmol) followed by NaO$^t$Bu (2.34 g, 24.4 mmol) in sealed tube. The reaction mixture was purged with N$_2$ gas and Pd(OAc)$_2$ (250 mg, 1.11 mmol) was added. The reaction mixture was heated at 110° C. for 16 h. After completion of the reaction (TLC), reaction mixture was treated with water and extracted with ethyl acetate. The separated organic layer was washed with NaHCO$_3$ solution, brine solution, dried over anhydrous Na$_2$SO$_4$ and concentrated under reduced pressure to afford crude product. The crude product was purified by column chromatography to get the title compound (1.53 g, 33.9%); LCMS (ESI positive ion) m/z: calculated: 381.19; observed: 382.1 (M+1).

Step 5: Synthesis of tert-butyl 4-(2-fluoro-4-thiomorpholinophenyl)piperazine-1-carboxylate (6): To a stirred solution of tert-butyl 4-(2-fluoro-4-thiomorpholinophenyl)piperazine-1-carboxylate (5, 1.8 g, 4.7 mmol) in acetic acid (20 mL) at 0° C. hydrogen peroxide (160.48 mg, 4.7 mmol) was added. The reaction mixture was stirred at RT for 16 h. After completion of the reaction (TLC), reaction mixture was treated with 10% NaOH solution (aq.) and extracted with DCM. The separated organic layer was washed with NaHCO$_3$ solution, brine solution, dried over anhydrous Na$_2$SO$_4$ and concentrated under reduced pressure to afford crude product. The crude product was purified by column chromatography to get the title compound (1.2 g, 62.6%); LCMS (ESI positive ion) m/z: calculated: 397.18; observed: 398.1 (M+1).

Step 6: Synthesis of 4-(3-fluoro-4-(piperazin-1-yl)phenyl)thiomorpholine 1-oxide (7): To a stirred solution of tert-butyl 4-(2-fluoro-4-(1-oxidothiomorpholino)phenyl)piperazine-1-carboxylate (6, 1.2 g, 3.0 mmol) in DCM (15 mL) at 0° C. TFA (330 mg, 9.0 mmol) was added. The reaction mixture was stirred at room temperature for 2 h. After completion of the reaction (TLC), reaction mixture was concentrated under reduced pressure. The residue was dissolved in methanol and neutralized using Tosic acid scavenger resin to get the free base (750 mg, 82.2%); LCMS (ESI positive ion) m/z: calculated: 297.13; observed: 298.1 (M+1).

Step 7: Synthesis of 5-amino-3-(2-(4-(2-fluoro-4-(1-oxidothiomorpholino)phenyl)-piperazin-1-yl)ethyl)-8-(furan-2-yl)thiazolo[5,4-e][1,2,4]triazolo[1,5-c]pyrimidin-2(3H)-one (Compound 126): To a stirred solution of 1-(3-fluoro-4-(piperazin-1-yl)phenyl)piperidin-4-one (350 mg, 1.26 mmol) in DMF (5 mL) was added 2-(5-amino-8-(furan-2-yl)-2-oxothiazolo[4,5-e][1,2,4]triazolo [1,5-c]pyrimidin-1 (2H)-yl)ethyl methanesulfonate (500 mg, 1.26 mmol) and DIPEA (815 mg, 6.31 mmol). The reaction mixture was stirred at 120° C. for 16 h. After completion the reaction mass was concentrated under reduced pressure and recrystallized with acetonitrile and diethyl ether to get the pure 5-amino-3-(2-(4-(2-fluoro-4-(1-oxidothiomorpholino)phenyl)piperazin-1-yl)ethyl)-8-(furan-2-yl)thiazolo[5,4-e][1,2,4]-triazolo[1,5-c]pyrimidin-2(3H)-one (Compound 126) (150 mg, 19%); HPLC purity (XB0595TF): 95.08%; LCMS (ESI positive ion) m/z: calculated: 597.17; observed: 598.2 (M+1); $^1$H-NMR (400 MHz, DMSO-d6): δ 8.31 (brs, 2H), 7.95 (s, 1H), 7.24 (d, J=3.2 Hz, 1H), 6.92-6.85 (m, 2H), 6.73-6.71 (m, 2H), 4.08-4.05 (m, 2H), 3.70-3.66 (m, 2H), 3.53-3.50 (m, 2H), 2.93-2.86 (m, 7H), 2.74-2.63 (m, 7H).

Example 127: (S)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one

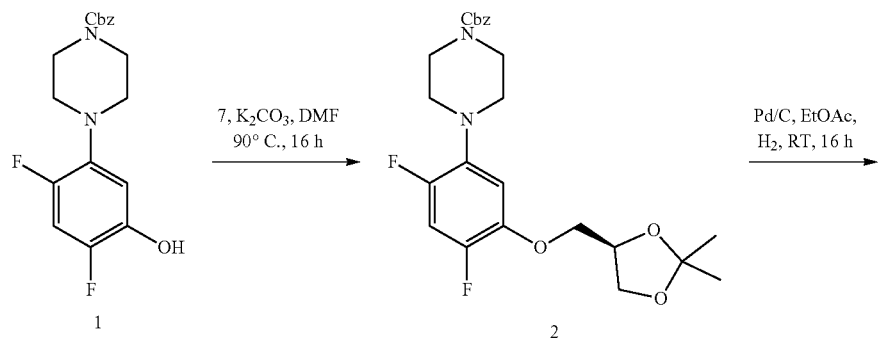

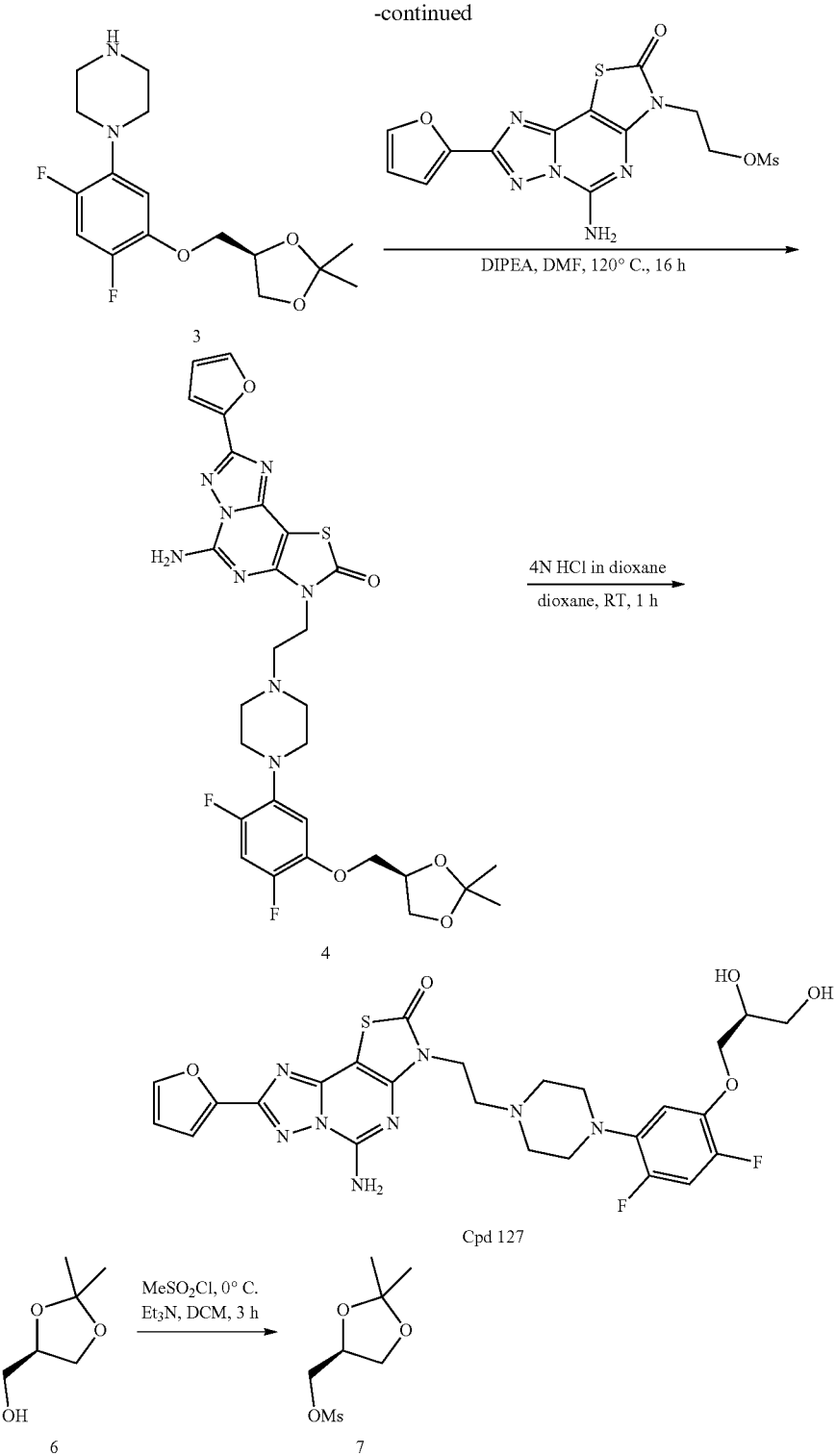

Step 1: Synthesis of (S)-(2,2-dimethyl-1,3-dioxolan-4-yl) methyl methanesulfonate (7): To a stirred solution of (R)-(2,2-dimethyl-1,3-dioxolan-4-yl)methanol (6, 2.5 g, 19 mmol) in DCM (30 mL) was added triethylamine (9.6 g, 95 mmol) and methane sulfonyl chloride (4.33 g, 38 mmol) at 0° C. The reaction mixture was allowed to stir for 3 h at 0° C. The reaction was monitored by TLC and after completion, the reaction mixture was diluted with water and extracted with DCM. The combined organic layer was washed with brine, dried over anhydrous $Na_2SO_4$, filtered then concentrated under reduced pressure to afford the title compound as yellow gummy liquid (3.0 g, 75.4%); $^1$H-NMR (400 MHz, $CDCl_3$): δ 4.39-4.43 (m, 1H), 4.25 (d, J=5.20 Hz, 2H), 4.11-4.15 (m, 1H), 3.84-3.87 (m, 1H), 3.09-3.15 (m, 3H), 1.45 (s, 3H), 1.43 (s, 3H).

Step 2: Synthesis of benzyl (R)-4-(5-((2,2-dimethyl-1,3-dioxolan-4-yl)methoxy)-2,4-difluorophenyl)piperazine-1-carboxylate (2): To a stirred solution of benzyl 4-(2,4-difluoro-5-hydroxyphenyl)piperazine-1-carboxylate (1, 1 g, 2.9 mmol) and (S)-(2,2-dimethyl-1,3-dioxolan-4-yl)methyl methanesulfonate (7, 1.15 g, 5.8 mmol) in DMF (20 mL) was added potassium carbonate (1.19 g, 8.7 mmol) and reaction mixture was heated to 90° C. for 16 h. The progress of the reaction was monitored by TLC. After completion, the reaction mass was diluted with water and extracted with EtOAc. The combined organic layer was washed with brine, dried over anhydrous $Na_2SO_4$, filtered and then concentrated under reduced pressure. The crude was purified by column chromatography (30% EtOAc/hexane) to afford benzyl (R)-4-(5-((2,2-dimethyl-1,3-dioxolan-4-yl)methoxy)-2,4-difluorophenyl) piperazine-1-carboxylate (2) as light brown solid (800 mg, 56.8%); LCMS (ESI positive ion) m/z: calculated: 462.20; observed: 463.0 (M+1).

Step 3: Synthesis of (R)-1-(5-((2,2-dimethyl-1,3-dioxolan-4-yl)methoxy)-2,4-difluoro-phenyl) piperazine (3): To a stirred solution of benzyl (R)-4-(5-((2,2-dimethyl-1,3-dioxolan-4-yl)methoxy)-2,4-difluorophenyl)piperazine-1-carboxylate (2, 0.8 g, 1.73 mmol) in EtOAc (20 mL), 10% Pd/C (0.2 g) was added under nitrogen atmosphere. The reaction mixture was stirred under $H_2$ atmosphere for 16 h. The progress of the reaction was monitored by TLC. After completion, the reaction mixture was filtered using celite to remove the Pd/C. The combined organic layer was dried over anhydrous $Na_2SO_4$ and concentrated under reduced pressure to get (R)-1-(5-((2,2-dimethyl-1,3-dioxolan-4-yl)methoxy)-2,4-difluorophenyl)piperazine (3) as a brown gummy material (0.45 g, 76.2%); LCMS (ESI positive ion) m/z: calculated: 328.16; observed: 329.1 (M+1).

Step 4: Synthesis of (R)-5-amino-3-(2-(4-(5-((2,2-dimethyl-1,3-dioxolan-4-yl)methoxy)-2,4-difluorophenyl)piperazin-1-yl)ethyl)-8-(furan-2-yl)thiazolo[5,4-e][1,2,4]triazolo[1,5-c]pyrimidin-2(3H)-one (4): To a stirred solution of (R)-1-(5-((2,2-dimethyl-1,3-dioxolan-4-yl)methoxy)-2,4-difluorophenyl) piperazine (3, 0.45 g, 1.4 mmol) and 2-(5-amino-8-(furan-2-yl)-2-oxothiazolo[5,4-e][1,2,4]triazolo[1,5-c]pyrimidin-3(2H)-yl)ethyl methane sulfonate (0.48 g, 1.2 mmol) in N,N-dimethylformamide (6 mL) was added DIPEA (0.71 g, 5.5 mmol) and the reaction mixture was stirred at 120° C. for 16 h. After completion of the reaction (TLC & LCMS), the solvent was removed under reduced pressure. The reaction mass was treated with water and extracted with ethyl acetate. Organic layer was washed with saturated brine solution, dried over anhydrous $Na_2SO_4$, filtered and concentrated under reduced pressure. The crude product was purified by column chromatography (14-16% MeOH/DCM) and it was further enriched by washing with 50% ACN/diethyl ether mixture to get the (R)-5-amino-3-(2-(4-(5-((2,2-dimethyl-1,3-dioxolan-4-yl)methoxy)-2,4-difluorophenyl)piperazin-1-yl)ethyl)-8-(furan-2-yl)thiazolo[5,4-e][1,2,4]triazolo[1,5-c]pyrimidin-2(3H)-one compound (4) as light yellow solid (100 g, 13.1%); LCMS (ESI positive ion) m/z: calculated: 628.20; Observed; 629.0 (M+1);

Step 5: Synthesis of (S)-5-amino-3-(2-(4-(5-(2,3-dihydroxypropoxy)-2,4-difluorophenyl)-piperazin-1-yl)ethyl)-8-(furan-2-yl)thiazolo[5,4-e][1,2,4]triazolo[1,5-c]pyrimidin-2(3H)-one (Compound 127): To a stirred solution of (R)-5-amino-3-(2-(4-(5-((2,2-dimethyl-1,3-dioxolan-4-yl)methoxy)-2,4-difluorophenyl)piperazin-1-yl)ethyl)-8-(furan-2-yl)thiazolo[5,4-e][1,2,4]triazolo[1,5-c]pyrimidin-2(3H)-one (4, 50 mg, 0.08 mmol) in 1,4-dioxane (4 mL) at 0° C., 4 N HCl in dioxane (20 mL) was added. Reaction mixture was allowed to stir for 1 h at room temperature. The progress of the reaction was monitored by TLC. After the completion of reaction, it was concentrated under reduced pressure to remove the solvent. The crude product was recrystallized using acetonitrile to afford (S)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one (Compound 127) as light brown solid (35 mg, 67.3%); HPLC purity (XB0595TF): 92.58%; LCMS (ESI positive ion) m/z: calculated: 588.17; observed: 589.2 (M+1); $^1$H-NMR (400 MHz, DMSO-d6): δ 9.67 (brs, 1H), 8.42 (brs, 2H), 7.97 (s, 1H), 7.35-7.26 (m, 2H), 6.86 (t, J=8.40 Hz, 1H), 6.75-6.74 (m, 1H), 4.31 (m, 2H), 4.09-4.05 (m, 1H), 3.97-3.92 (m, 3H), 3.77 (t, J=5.20 Hz, 1H), 3.43 (m, 2H), 3.29 (m, 2H), 3.06-2.99 (m, 2H).

Example 128: (R)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one

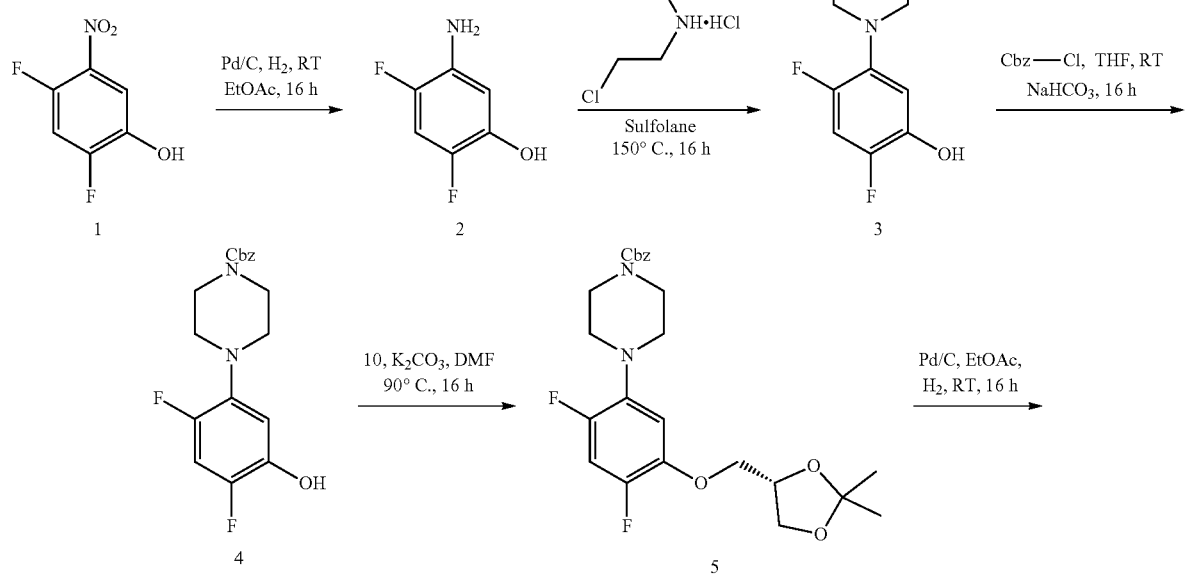

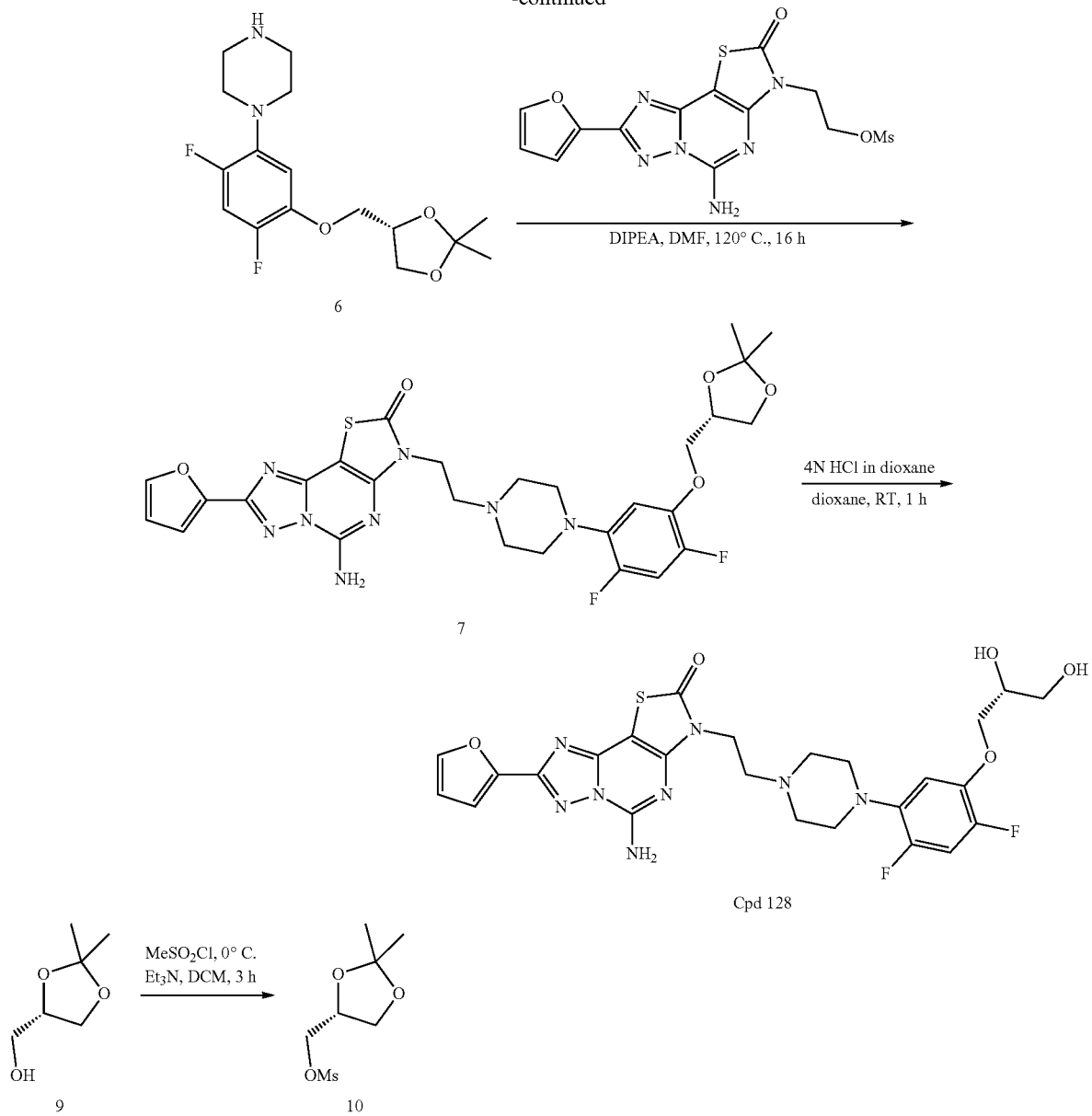

Step 1: Synthesis of 5-amino-2,4-difluorophenol (2): To a stirred solution of 2,4-difluoro-5-nitrophenol (1, 25 g, 0.143 mol) in EtOAc (200 mL), 10% Pd/C (4.55 g, 0.043 mol) was added. The reaction mixture was stirred at RT under $H_2$ for 16 h. After the reaction completion (TLC), the reaction mixture was filtered by using celite bed, washed with EtOAc (1000 mL) and concentrated under reduced pressure to afford 5-amino-2,4-difluorophenol (2) as off brown solid (20.10 g, 94.6%); LCMS (ESI positive ion) m/z: calculated: 145.03; observed: 146.2 (M+1).

Step 2: Synthesis of 2,4-difluoro-5-(piperazin-1-yl)phenol (3): To a stirred solution of 5-amino-2,4-difluorophenol (2, 20 g, 0.131 mol) in sulfolane (30 mL) bis(2-chloroethyl) amine hydrogen chloride (31 g, 0.170 mol) was added. The resulting mixture was stirred at 150° C. under nitrogen atmosphere for 16 h. It was cooled to RT and acetone was added to the crude reaction mixture and stirred at 0° C. for 1 h. After 1 h, the precipitated solid was filtered and washed with chilled acetone under nitrogen atmosphere. The solid material was dried under vacuum to afford 2,4-difluoro-5-(piperazin-1-yl)phenol (3) as off white solid (23 g, 80.3%); LCMS (ESI positive ion) m/z: calculated: 214.09; observed: 215.1 (M+1).

Step 3: Synthesis of benzyl 4-(2,4-difluoro-5-hydroxyphenyl)piperazine-1-carboxylate (4): To a stirred solution of 2,4-difluoro-5-(piperazin-1-yl)phenol hydrochloride (3, 25 g, 0.117 mol), in THF (250 mL) was added $NaHCO_3$ (14.7 g, 0.175 mol) and Cbz-Cl (16.66 mL, 0.117 mol) at 0° C. The reaction mixture was stirred at RT for 16 h. The progress of the reaction was monitored by TLC. The reaction mixture was extracted with ethyl acetate and the combined organic layers were washed with brine, dried over anhydrous $Na_2SO_4$ and then concentrated under reduced pressure. The crude obtained was purified by column chromatography (30% EtOAc/Hexane as eluent) to afford benzyl 4-(2,4-difluoro-5-hydroxyphenyl)piperazine-1-carboxylate as white solid (20 g, 45.8%); LCMS (ESI positive ion) m/z: calculated: 348.13; observed: 349.2 (M+1).

Step 4: Synthesis of (R)-(2,2-dimethyl-1,3-dioxolan-4-yl) methyl methanesulfonate (10): To a stirred solution of (S)-(2,2-dimethyl-1,3-dioxolan-4-yl)methanol (9, 12 g, 0.091 mol) in DCM (100 mL) was added triethylamine (37.76 mL, 0.272 mol) and methane sulfonyl chloride (8.4 mL, 0.109 mol) at 0° C. The reaction mixture was allowed to stir for 3 h at 0° C. The reaction was monitored by TLC and after completion, the reaction mixture was diluted with water and extracted with DCM. The combined organic layer was washed with brine, dried over anhydrous $Na_2SO_4$, filtered then concentrated under reduced pressure to afford the title compound as yellow gummy liquid (21.8 g, 77.8%); LCMS (ESI positive ion) m/z: calculated: 210.06; observed: 211.0 (M+1).

Step 5: Synthesis of benzyl (S)-4-(5-((2,2-dimethyl-1,3-dioxolan-4-yl)methoxy)-2,4-difluorophenyl)piperazine-1-carboxylate (5): To a stirred solution of benzyl 4-(2,4-difluoro-5-hydroxyphenyl)piperazine-1-carboxylate (4. 10 g, 0.029 mol) and (R)-(2,2-dimethyl-1,3-dioxolan-4-yl)methyl methanesulfonate (10, 7.2 g, 0.034 mol) in DMF (70 mL) was added potassium carbonate (11.9 g, 0.086 mol) and reaction mixture was heated to 90° C. for 16 h. The progress of the reaction was monitored by TLC. After completion, the reaction mass was diluted with water and extracted with EtOAc. The combined organic layer was washed with brine, dried over anhydrous $Na_2SO_4$, filtered and then concentrated under reduced pressure. The crude was purified by column chromatography (30% EtOAc/hexane) to afford benzyl (S)-4-(5-((2,2-dimethyl-1,3-dioxolan-4-yl)methoxy)-2,4-difluorophenyl) piperazine-1-carboxylate (5) as light brown solid (13 g, 70.50%); LCMS (ESI positive ion) m/z: calculated: 462.20; observed: 463.1 (M+1).

Step 6: Synthesis of (S)-1-(5-((2,2-dimethyl-1,3-dioxolan-4-yl)methoxy)-2,4-difluoro-phenyl) piperazine (6): To a stirred solution of benzyl (S)-4-(5-((2,2-dimethyl-1,3-dioxolan-4-yl)methoxy)-2,4-difluorophenyl)piperazine-1-carboxylate (5, 13 g, 0.028 mol) in EtOAc (100 mL), 10% Pd/C (4 g) was added under nitrogen atmosphere. The reaction mixture was stirred under $H_2$ atmosphere for 16 h. The progress of the reaction was monitored by TLC. After completion, the reaction mixture was filtered using celite to remove the Pd/C. The combined organic layer was dried over anhydrous $Na_2SO_4$ and concentrated under reduced pressure to get (S)-1-(5-((2,2-dimethyl-1,3-dioxolan-4-yl)methoxy)-2,4-difluorophenyl)piperazine (6) as a brown gummy material (8.55 g, 93.0%); LCMS (ESI positive ion) m/z: calculated: 328.16; observed: 329.2 (M+1).

Step 7: Synthesis of (S)-5-amino-3-(2-(4-(5-((2,2-dimethyl-1,3-dioxolan-4-yl)methoxy)-2,4-difluorophenyl)piperazin-1-yl)ethyl)-8-(furan-2-yl)thiazolo[5,4-e][1,2,4]triazolo[1,5-c]pyrimidin-2(3H)-one (7): To a stirred solution of (S)-1-(5-((2,2-dimethyl-1,3-dioxolan-4-yl)methoxy)-2,4-difluorophenyl)piperazine (6, 7 g, 0.021 mol) and 2-(5-amino-8-(furan-2-yl)-2-oxothiazolo-[5,4-e][1,2,4]triazolo[1,5-c]pyrimidin-3(2H)-yl)ethyl methane sulfonate (7.6 g, 0.019 mol) in N,N-dimethylformamide (50 mL) was added DIPEA (11.12 mL, 0.064 mol) and the reaction mixture was stirred at 120° C. for 16 h. After completion of the reaction (TLC & LCMS), the solvent was removed under reduced pressure. The reaction mass was treated with water and extracted with ethyl acetate. Organic layer was washed with saturated brine solution, dried over anhydrous $Na_2SO_4$, filtered and concentrated under reduced pressure. The crude product was purified by column chromatography (14-16% MeOH/DCM) and it was further enriched by washing with 50% ACN/diethyl ether mixture to get the (S)-5-amino-3-(2-(4-(5-((2,2-dimethyl-1,3-dioxolan-4-yl)methoxy)-2,4-difluorophenyl)piperazin-1-yl)ethyl)-8-(furan-2-yl)thiazolo[5,4-e][1,2,4]triazolo[1,5-c]pyrimidin-2(3H)-one compound (7) as light yellow solid (2.6 g, 17.8%); LCMS (ESI positive ion) m/z: calculated: 628.20; Observed; 629.2 (M+1).

Step 8: Synthesis of (R)-5-amino-3-(2-(4-(5-(2,3-dihydroxypropoxy)-2,4-difluorophenyl)-piperazin-1-yl)ethyl)-8-(furan-2-yl)thiazolo[5,4-e][1,2,4]triazolo[1,5-c]pyrimidin-2(3H)-one (Compound 128): To a stirred solution of (S)-5-amino-3-(2-(4-(5-((2,2-dimethyl-1,3-dioxolan-4-yl) methoxy)-2,4-difluorophenyl)piperazin-1-yl)ethyl)-8-(furan-2-yl)thiazolo[5,4-e][1,2,4]triazolo[1,5-c]pyrimidin-2 (3H)-one (7, 1.4 g, 2.23 mmol) in 1,4-dioxane (20 mL) at 0° C., 4 N HCl in dioxane (20 mL) was added. Reaction mixture was allowed to stir for 1 h at room temperature. The progress of the reaction was monitored by TLC. After the completion of reaction, it was concentrated under reduced pressure to remove the solvent. The crude product was recrystallized using acetonitrile to afford (R)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one (Compound 128) as white solid (1.2 g, 87%); HPLC purity (AM9010A3): 95.05%; LCMS (ESI positive ion) m/z: calculated: 588.17; observed: 589.2 (M+1); $^1$H-NMR (400 MHz, DMSO-d6): δ 10.34 (brs, 1H), 8.40 (brs, 2H), 7.95 (s, 1H), 7.33-7.24 (m, 2H), 6.87-6.82 (m, 1H), 6.73 (s, 1H), 4.31 (m, 2H), 4.08-4.05 (m, 1H), 3.96-3.91 (m, 3H), 3.76 (m, 1H), 3.59 (m, 2H), 3.51-3.48 (m, 2H), 3.42-3.38 (m, 2H), 3.29-3.27 (m, 2H), 3.14-3.08 (m, 2H).

The following examples were prepared according to similar procedures as those described for Examples above:

Example 9: 5-amino-8-(furan-2-yl)-3-(2-(4-(4-(2-hydroxyethoxy)phenyl)piperazin-1-yl)ethyl)thiazolo [5,4-e][1,2,4]triazolo[1,5-c]pyrimidin-2(3H)-one LCMS (ESI positive ion) m/z: calculated: 522.18; observed: 523.2 (M+1); HPLC purity (XB0595TF): 97.0%; $^1$H NMR (400 MHz, $CD_3OD$): δ 7.79 (s, 1H), 7.28 (d, J=3.2 Hz, 1H), 7.01 (d, J=8.1 Hz, 2H), 6.93 (d, J=9.2 Hz, 2H), 6.69 (dd, J=1.6 & 3.2 Hz, 1H), 4.49 (m, 2H), 4.01 (t, J=4.4 Hz, 2H), 3.86 (t, J=4.4 Hz, 2H), 3.67 (m, 4H).

Example 10: 2-(4-(4-(2-(5-amino-8-(furan-2-yl)-2-oxothiazolo[5,4-e][1,2,4]triazolo[1,5-c]pyrimidin-3 (2H)-yl)ethyl)piperazin-1-yl)phenoxy)acetic acid hydrochloride LCMS (ESI positive ion) m/z: calculated: 536.16; observed: 536.8 (M+1); HPLC purity (XB0595TF): 93.00%; $^1$H NMR (400 MHz, DMSO-d6): δ 12.92 (brs, 1H), 9.72 (brs, 1H), 8.44 (brs, 2H), 7.97 (t, J=0.8 Hz, 1H), 7.26 (dd, J=0.6 & 3.2 Hz, 1H), 6.96-6.94 (m, 2H), 6.88-6.84 (m, 2H), 6.75 (dd, J=1.6 & 3.2 Hz, 1H), 4.60 (s, 2H), 4.32 (m, 2H), 3.92-3.90 (m, 2H), 3.72-3.69 (m, 2H), 3.27-3.24 (m, 2H), 2.92 (m, 2H).

Example 11: 2-(4-(4-(2-(5-amino-8-(furan-2-yl)-2-oxothiazolo[5,4-e][1,2,4]triazolo[1,5-c]pyrimidin-3 (2H)-yl)ethyl)piperazin-1-yl)phenoxy)acetamide LCMS (ESI positive ion) m/z: calculated: 535.58; Observed 535.8 (M+); HPLC Purity (XB0595TF): 92.65%; $^1$H NMR (400 MHz, DMSO-d6): δ 8.31 (brs, 2H), 7.94 (m, 1H), 7.44 (m, 1H), 7.36 (m, 1H), 7.23 (d, J=3.20 Hz, 1H), 6.85 (t, J=4.40 Hz, 4H), 6.73 (s, 1H), 4.31 (s, 2H), 4.08 (m, 1H), 2.95 (m, 4H), 2.68 (d, J=6.00 Hz, 2H), 2.61 (m, 3H), and 2.30 (s, 2H).

Example 12: 5-amino-3-(2-(4-(4-(2,3-dihydroxypropoxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 552.19; observed: 552.8 (M+1); HPLC purity (XB0595TF): 91.20%; ¹H NMR (400 MHz, DMSO-d6): δ 9.7 (brs, 1H), 9.0 (brs, 1H), 8.41 (brs, 2H), 7.98 (dd, J=0.8 & 1.6 Hz, 1H), 7.27 (m, 1H), 6.87 (m, 2H), 6.76-7.68 (m, 3H), 4.39 (m, 3H), 3.28 (m, 3H), 2.85 (m, 4H).

Example 13: 5-amino-3-(2-(4-(4-(2-aminoethoxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 521.6; Observed; 522.2 (M+1); HPLC Purity (XB0595TF): 96.52%; ¹H NMR (400 MHz, DMSO-d6): δ 8.41 (brs, 2H), 8.23 (brs, 3H), 7.96 (dd, J=2 Hz, 1H), 7.25 (d, J=3.2 Hz, 1H), 6.99 (d, J=9.20 Hz, 2H), 6.93 (d, J=2.40 Hz, 2H), 6.74 (t, J=1.60 Hz, 1H), 4.33 (t, J=5.60 Hz, 2H), 4.12 (t, J=5.20 Hz, 2H), 3.88 (d, J=10.80 Hz, 2H), 3.69 (d, J=12.00 Hz, 2H), 3.58 (m, 2H), and 3.14-3.20 (m, 6H).

Example 14: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzamide LCMS (ESI positive ion) m/z: calculated: 505.56; Observed; 506.2 (M+1); HPLC purity (XB0595TF): 99.08%; ¹H NMR (400 MHz, DMSO-d6): δ 8.32 (brs, 2H), 7.95 (brs, 1H), 7.73 (brs, 3H), 7.24 (brs, 1H), 6.91-7.01 (m, 3H), 6.73 (brs, 1H), 4.09 (brs, 2H), 3.19 (brs, 4H), and 2.69 (brs, 6H).

Example 15: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-methylbenzamide LCMS (ESI positive ion) m/z: calculated: 519.58; Observed; 520.8 (M+1); HPLC purity (XB0595TF): 95.07%; ¹H NMR (400 MHz, DMSO-d6): δ 8.33 (brs, 2H), 8.13 (d, J=4.40 Hz, 1H), 7.95 (s, 1H), 7.70 (d, J=8.60 Hz, 2H), 7.24 (d, J=3.32 Hz, 1H), 6.91 (d, J=8.64 Hz, 2H), 6.73 (d, J=1.72 Hz, 1H), 4.09 (t, J=6.16 Hz, 2H), 3.18 (m, 4H), 2.72-2.74 (m, 5H), and 2.62-2.70 (m, 4H).

Example 16: 5-amino-8-(furan-2-yl)-3-(2-(4-(4-(2-morpholinoethoxy)phenyl)piperazin-1-yl)ethyl)thiazolo[5,4-e][1,2,4]triazolo[1,5-c]pyrimidin-2(3H)-one LCMS (ESI positive ion) m/z: calculated: 591.24; observed: 592.3 (M+1); HPLC purity (XB0595TF): 99.39%; ¹H NMR (400 MHz, DMSO-d6): δ 8.32 (brs, 2H), 7.95 (s, 1H), 7.24 (d, J=3.2 Hz, 1H), 6.85-6.79 (m, 4H), 6.73-6.72 (m, 1H), 4.08 (t, J=6.0 Hz, 2H), 3.99 (t, J=5.6 Hz, 2H), 3.57 (t, J=4.0 Hz, 4H), 2.94 (m, 4H), 2.71-2.62 (m, 8H), 2.46 (m, 4H).

Example 17: 5-amino-3-(2-(4-(4-(2-(dimethylamino)ethoxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 549.22; observed: 549.8 (M+1); HPLC purity (XB0595TF): 92.54%; ¹H NMR (400 MHz, DMSO-d6): δ 8.31 (brs, 2H), 7.95 (s, 1H), 7.24 (d, J=2.8 Hz, 1H), 6.85-6.79 (m, 4H), 6.73 (m, 1H), 4.08 (t, J=6.00 Hz, 2H), 3.95 (t, J=6.0 Hz, 2H), 2.94 (m, 4H), 2.69 (m, 2H), 2.61 (m, 4H), 2.56 (t, J=6.0 Hz, 2H), 2.19 (s, 6H).

Example 18: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzenesulfonamide LCMS (ESI positive ion) m/z: calculated: 541.13; observed: 542.2 (M+1); HPLC purity (XB0595TF): 90.64%; ¹H NMR (400 MHz, DMSO-d6): δ 8.31 (brs, 2H), 7.94 (d, J=0.40 Hz, 1H), 7.60 (d, J=8.4 Hz, 2H), 7.23 (d, J=3.6 Hz, 1H), 7.07-6.98 (m, 4H), 6.72 (m, 1H), 4.08 (m, 2H), 3.20 (m, 4H), 2.70-2.61 (m, 6H).

Example 19: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-methylbenzenesulfonamide LCMS (ESI positive ion) m/z: calculated: 555.15; observed: 556.3 (M+1); HPLC purity (XB0595TF): 93.45%; ¹H NMR (400 MHz, DMSO-d6): δ 8.33 (brs, 2H), 7.95 (s, 1H), 7.55 (d, J=8.8 Hz, 2H), 7.24 (d, J=3.2 Hz, 1H), 7.11 (q, J=4.80 Hz, 1H), 7.03 (d, J=8.8 Hz, 2H), 6.73 (m, 1H), 4.10 (t, J=5.6 Hz, 2H), 3.24 (m, 4H), 2.73-2.62 (m, 6H), 2.34 (d, J=5.20 Hz, 3H).

Example 20: 5-amino-8-(furan-2-yl)-3-(2-(4-(4-(methylsulfonyl)phenyl)piperazin-1-yl)ethyl)thiazolo[5,4-e][1,2,4]triazolo[1,5-c]pyrimidin-2(3H)-one LCMS: (ESI positive ion) m/z: calculated: 540.62; Observed; 541.3 (M+1); HPLC purity (XB0595TF): 98.58%; ¹H NMR (400 MHz, DMSO-d6): δ 8.31 (brs, 2H), 7.95 (s, 1H), 7.67 (d, J=8.80 Hz, 2H), 7.24 (d, J=3.20 Hz, 1H), 7.05 (d, J=8.80 Hz, 2H), 6.73 (q, J=2.00 Hz, 1H), 4.11-4.05 (m, 2H), 3.27 (m, 4H), 3.08 (m, 3H), 2.71 (t, J=6.00 Hz, 2H), and 2.51 (m, 4H).

Example 21: 5-amino-8-(furan-2-yl)-3-(2-(4-(4-(methylsulfinyl)phenyl)piperazin-1-yl)ethyl)thiazolo[5,4-e][1,2,4]triazolo[1,5-c]pyrimidin-2(3H)-one LCMS (ESI positive ion) m/z: calculated: 524.14; observed: 525.1; HPLC purity (XB0595TF): 98.99%; ¹H NMR: (400 MHz, DMSO-d6): δ 8.32 (brs, 2H), 7.95 (s, 1H), 7.49 (d, J=8.8 Hz, 2H), 7.24 (d, J=3.2 Hz, 1H), 7.06 (d, J=8.8 Hz, 2H), 6.73 (dd, J=1.6 & 3.2 Hz, 1H), 4.09 (t, J=6.0 Hz, 2H), 3.18 (m, 4H), 2.72-2.62 (m, 9H).

Example 22: 3-(4-(2-(5-amino-8-(furan-2-yl)-2-oxothiazolo[5,4-e][1,2,4]triazolo[1,5-c]pyrimidin-3(2H)-yl)ethyl)piperazin-1-yl)benzamide LCMS (ESI positive ion) m/z: calculated: 505.16; observed: 506.2 (M+1); HPLC purity (XB0595TF): 90.01%; ¹H NMR (400 MHz, DMSO-d6): δ 8.33 (brs, 2H), 7.95 (s, 1H), 7.89 (s, 1H), 7.38 (s, 1H), 7.26-7.23 (m, 4H), 7.05 (m, 1H), 6.73 (m, 1H), 4.10 (t, J=6.0 Hz, 2H), 3.12 (m, 4H), 2.73-2.63 (m, 6H).

Example 23: 5-amino-8-(furan-2-yl)-3-(2-(4-(3-(2-hydroxyethoxy)phenyl)piperazin-1-yl)ethyl)thiazolo[5,4-e][1,2,4]triazolo[1,5-c]pyrimidin-2(3H)-one LCMS (ESI positive ion) m/z: calculated: 522.18; observed: 522.8 (M+1); HPLC purity (XB0595TF): 92.67%; $^1$H NMR (400 MHz, DMSO-d6): δ 9.98 (brs, 1H), 8.43 (brs, 2H), 7.96 (t, J=0.8 Hz, 1H), 7.26 (d, J=0.8 Hz, 1H), 7.16 (t, J=8.0 Hz, 1H), 6.74 (dd, J=1.6 & 3.2 Hz, 1H), 6.57-6.52 (m, 2H), 6.46 (dd, J=2.0 & 8.0 Hz, 1H), 4.31 (t, J=5.6 Hz, 2H), 3.97-3.85 (m, 6H), 3.70 (t, J=5.2 Hz, 2H), 3.60 (m, 2H), 3.03 (m, 2H).

Example 24: 5-amino-3-(2-(4-(2-fluoro-4-(2-oxo-2-(piperazin-1-yl)ethoxy)phenyl)piperazin-1-yl)ethyl)-8-(furan-2-yl)thiazolo[5,4-e][1,2,4]triazolo[1,5-c]pyrimidin-2(3H)-one hydrochloride LCMS: (ESI positive ion); m/z: calculated: 622.68; Observed; 623.2 (M+1); HPLC purity (XB0595TF): 98.01%; $^1$H NMR (400 MHz, DMSO-d6): δ 8.90 (brs, 2H), 8.41 (brs, 2H), 7.97 (d, J=0.80 Hz, 1H), 7.26 (t, J=5.20 Hz, 1H), 7.00 (d, J=8.40 Hz, 1H), 6.90 (d, J=13.60 Hz, 1H), 6.75-6.74 (m, 2H), 4.86 (m, 2H), 4.30 (b s, 2H), 3.94 (b s, 2H), 3.64 (t, J=4.80 Hz, 4H), 3.49 (t, J=5.20 Hz, 2H), 3.22 (m, 4H), 3.18 (brs, 2H), 3.1 (brs, 2H), and 2.94 (brs, 2H).

Example 25: 5-amino-3-(2-(4-(2-fluoro-4-(piperidin-4-ylmethoxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 593.23; observed: 594.2 (M+1); HPLC purity (XB0595TF): 96.25%; $^1$H NMR (400 MHz, DMSO-d6): δ 10.25 (brs, 1H), 8.85 (brs, 1H), 8.55 (brs, 1H), 8.41 (brs, 2H), 7.96 (s, 1H), 7.26 (d, J=3.2 Hz, 1H), 7.03 (t, J=9.60 Hz, 1H), 6.88 (dd, J=2.4 & 14.0 Hz, 1H), 6.74 (m, 2H), 4.32 (m, 2H), 4.06 (m, 4H), 3.62 (m, 2H), 3.39 (m, 2H), 3.28 (m, 4H), 3.05 (t, J=12.4 Hz, 2H), 2.90 (m, 2H), 2.01 (m, 1H), 1.89 (m, 2H), 1.47 (m, 2H).

Example 26: 5-amino-3-(2-(4-(2-fluoro-4-(piperazine-1-carbonyl)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 592.21; observed: 592.9 (M+1); HPLC purity (XB0595TF): 95.39%; $^1$H NMR (400 MHz, DMSO-d6): δ 10.30 (brs, 1H), 9.22 (brs, 2H), 8.42 (brs, 2H), 7.96 (s, 1H), 7.34 (dd, J=1.6 & 12.8 Hz, 1H), 7.28 (m, 2H), 7.14 (t, J=8.8 Hz, 1H), 6.74 (dd, J=1.6 & 3.2 Hz, 1H), 4.33 (m, 2H), 3.96-3.88 (m, 2H), 3.17 (m, 6H), 2.32 (m, 6H).

Example 27: 5-amino-3-(2-(4-(2-fluoro-4-(2-(piperazin-1-yl)ethoxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 608.24; observed: 609.0 (M+1); HPLC purity (XB0595TF): 91.12%; $^1$H NMR (400 MHz, DMSO-d6): δ 10.52 (brs, 1H), 9.71 (brs, 2H), 8.42 (brs, 2H), 7.97 (s, 1H), 7.26 (d, J=3.6 Hz, 1H), 7.10-6.99 (m, 2H), 6.84-6.74 (m, 2H), 4.40 (t, J=4.4 Hz, 2H), 4.33 (t, J=4.8 Hz, 2H), 3.92 (m, 2H), 3.45-3.40 (m, 4H), 3.24 (m, 3H), 3.11 (m, 3H).

Example 28: 5-amino-3-(2-(4-(2-fluoro-4-(piperazin-1-ylsulfonyl)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 628.18; observed: 628.8 (M+1); HPLC purity (XB0595TF): 90.55%; $^1$H NMR (400 MHz, DMSO-d$_6$): δ 10.91 (brs, 1H), 9.26 (brs, 2H), 8.42 (brs, 2H), 7.96 (s, 1H), 7.64-7.54 (m, 2H), 7.3 (t, J=8.4 Hz, 1H), 7.25 (m, 1H), 6.74 (s, 1H), 4.33 (m, 2H), 4.07 (m, 8H), 3.95 (m, 2H), 3.76 (m, 2H), 3.60 (m, 2H), 3.33 (m, 4H).

Example 29: 5-amino-3-(2-(4-(2-fluoro-4-(methylsulfonyl)phenyl)piperazin-1-yl)ethyl)-8-(furan-2-yl)thiazolo[5,4-e][1,2,4]triazolo[1,5-c]pyrimidin-2(3H)-one LCMS: (ESI positive ion) m/z: calculated: 558.61; Observed; 559.8 (M+1); HPLC purity (XB0595TF): 97.88%; $^1$H NMR (400 MHz, DMSO-d6): δ 8.31 (brs, 2H), 7.95 (s, 1H), 7.62 (t, J=8.40 Hz, 2H), 7.24 (d, J=3.20 Hz, 1H), 7.16 (t, J=8.40 Hz, 1H), 6.73 (s, 1H), 4.11-4.04 (m, 2H), 3.18 (s, 3H), 3.12 (brs, 4H), and 2.73-2.65 (m, 6H).

Example 30: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-aminoethyl)-3-fluorobenzamide hydrochloride LCMS: (ESI positive ion) m/z: calculated: 566.62; Observed; 567.0 (M+1); HPLC purity (XB0595TF): 99.16%; $^1$H NMR (400 MHz, DMSO-d6): δ 10.92 (brs, 1H), 8.79 (t, J=5.60 Hz, 1H), 8.41 (brs, 2H), 8.10 (s, 3H), 7.97-7.96 (m, 1H), 7.79-7.75 (m, 2H), 7.26-7.25 (m, 1H), 7.16 (t, J=9.20 Hz, 1H), 6.74 (q, J=1.60 Hz, 1H), 4.33 (t, J=5.20 Hz, 2H), 3.94-3.92 (m, 2H), 3.69-3.66 (m, 2H), 3.59 (m, 2H), 3.53-3.49 (m, 2H), 3.26 (m, 4H), and 2.97 (m, 2H).

Example 31: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylamino)ethyl)benzamide hydrochloride LCMS: (ESI positive ion) m/z: calculated: 580.21; Observed; 581.2 (M+1); HPLC purity (XB0595TF): 98.97%; $^1$H NMR (400 MHz, DMSO-d6): δ 10.81 (b s, 1H), 8.94 (brs, 2H), 8.83 (t, J=4.80 Hz, 1H), 8.41 (br s, 2H), 7.97 (s, 1H), 7.80-7.76 (m, 2H), 7.26 (d, J=3.20 Hz, 1H), 7.16 (t, J=8.80 Hz, 1H), 6.74 (q, J=1.20 Hz, 1H), 4.33 (m, 2H), 3.93 (d, J=9.20 Hz, 2H), 3.68 (m, 6H), 3.26 (t, J=11.60 Hz, 4H), 3.09-3.08 (m, 2H), and 2.563 (t, J=4.8 Hz, 3H).

Example 32: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-3-fluorobenzamide LCMS (ESI positive ion) m/z: calculated: 594.23; observed: 595.0 (M+1); HPLC purity (XB0595TF.M): 96.47%; $^1$H NMR (400 MHz, DMSO-d6): δ 8.30 (m, 3H), 7.95 (d, J=1.20 Hz, 1H), 7.62-7.57 (m, 2H), 7.24 (d, J=3.20

Hz, 1H), 7.02 (t, J=8.80 Hz, 1H), 6.73 (dd, J=1.6 & 3.2 Hz, 1H), 4.09 (t, J=6.40 Hz, 2H), 3.04 (m, 4H), 2.72 (d, J=6.0 Hz, 2H), 2.66 (m, 4H), 2.42 (t, J=6.00 Hz, 2H), 2.19 (s, 6H).

Example 33: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-hydroxyethyl)benzamide LCMS (ESI positive ion) m/z: calculated: 567.18; observed: 567.8 (M+1); HPLC purity (XB0595TF): 98.37%; ¹H NMR (400 MHz, DMSO-d6): δ 8.34 (brs, 2H), 7.95 (s, 1H), 7.63 (s, 2H), 7.24 (m, 1H), 7.01-6.95 (m, 1H), 6.73 (m, 1H), 4.72 (m, 2H), 4.57 (m, 2H), 4.09 (m, 2H), 3.48 (m, 6H), 3.03 (m, 4H).

Example 34: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-3-fluorobenzamide LCMS (ESI positive ion) m/z: calculated: 597.19; observed: 597.8 (M+1); HPLC purity (XB0595TF): 95.11%; ¹H NMR (400 MHz, DMSO-d6): δ 8.36-8.31 (m, 4H), 7.95 (s, 1H), 7.64-7.60 (m, 2H), 7.24 (d, J=3.2 Hz, 1H), 7.02 (m, 1H), 6.73 (dd, J=1.6 & 3.2 Hz, 1H), 4.80 (m, 1H), 4.59 (m, 2H), 4.09 (t, J=6.0 Hz, 2H), 3.61 (m, 4H), 3.10 (m, 4H), 2.65 (m, 4H).

Example 35: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)acetic acid LCMS (ESI positive ion) m/z: calculated: 554.15; observed: 555.0 (M+1); HPLC purity (XB0595TF): 98.30%; ¹H NMR (400 MHz, DMSO-d6): δ 10.20 (brs, 1H), 8.42 (brs, 2H), 7.97 (t, J=0.8 Hz, 1H), 7.26 (d, J=3.6 Hz, 1H), 7.03 (t, J=9.2 Hz, 1H), 6.88 (dd, J=2.8, 14.0 Hz, 1H), 6.75-6.74 (m, 2H), 4.67 (s, 2H), 4.31 (m, 2H), 3.91 (m, 2H), 3.60 (m, 2H), 3.42 (m, 2H), 3.28 (q, J=10.0 Hz, 2H), 3.05 (t, J=12.00 Hz, 2H).

Example 36: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3,5-difluorophenoxy)acetic acid LCMS (ESI positive ion) m/z: calculated: 572.14; observed: 572.8 (M+1); HPLC purity (XB0595TF): 95.07%; ¹H NMR (400 MHz, DMSO-d6): δ 9.83 (brs, 1H), 8.41 (brs, 2H), 7.97 (dd, J=0.8 & 2.0 Hz, 1H), 7.26 (dd, J=0.80 & 3.2 Hz, 1H), 6.78-6.74 (m, 3H), 4.72 (s, 2H), 4.31 (m, 2H), 3.88 (m, 2H), 3.60 (m, 2H), 3.25 (m, 4H).

Example 37: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid LCMS (ESI positive ion) m/z: calculated: 568.17; observed: 568.8 (M+1); HPLC (XB0595TF): 95.55%; ¹H NMR (400 MHz, DMSO-d6): δ 10.15 (brs, 1H), 8.41 (brs, 2H), 7.96 (s, 1H), 7.26 (s, 1H), 7.03 (t, J=9.60 Hz, 1H), 6.82 (d, J=14.00 Hz, 1H), 6.74 (d, J=1.60 Hz, 1H), 6.67 (d, J=8.40 Hz, 1H), 4.83 (q, J=6.80 Hz, 1H), 4.32 (m, 2H), 3.91 (m, 2H), 3.59 (m, 2H), 3.40 (m, 2H), 3.28 (m, 2H), 3.04 (m, 2H), 1.48 (t, J=6.4 Hz, 3H);

Examples 38 and 53: (S)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid and (R)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid The racemic mixture of the products, prepared as described for the Examples above (135 mg) was subjected to chiral separation (0.08 g sample was dissolved in 10 mL of ethanol), Phenomenex Lux C4 mobile phase: 0.1% TFA in n-hexane:ethanol (30:70), flow rate: 1.0 mL/min; to yield 13 mg of peak 1 (S)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid and 13 mg of peak 2 ((R)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid) respectively. Note: Peak 1 was arbitrarily considered as (S) isomer and peak 2 was considered as (R) isomer.

(S)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid LCMS (ESI positive ion) m/z: calculated: 568.17; observed: 568.9 (M+1); HPLC purity (XB0595TF): 95.79%; Chiral HPLC purity: 100%; ¹H-NMR (400 MHz, DMSO-d6): δ 13.03 (brs, 1H), 9.21 (brs, 1H), 8.41 (brs, 2H), 7.96 (s, 1H), 7.26 (s, 1H), 7.04 (m, 1H), 6.82 (m, 1H), 6.75 (s, 1H), 6.67 (m, 1H), 4.82 (q, J=5.2 Hz, 1H), 4.31 (m, 2H), 3.97 (m, 2H), 3.63 (m, 2H), 2.93 (m, 2H), 1.48 (d, J=5.60 Hz, 3H).

(R)-2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)propanoic acid LCMS (ESI positive ion) m/z: calculated: 568.17; observed: 569.0 (M+1); HPLC purity (XB0595TF): 98.05%; Chiral HPLC purity: 95.46%; ¹H-NMR (400 MHz, DMSO-d6): δ 13.03 (brs, 1H), 9.25 (brs, 1H), 8.41 (brs, 2H), 7.97 (s, 1H), 7.26 (s, 1H), 7.03 (m, 1H), 6.82 (m, 1H), 6.75 (s, 1H), 6.67 (m, 1H), 4.82 (q, J=6.4 Hz, 1H), 4.30 (m, 2H), 3.96 (m, 2H), 3.62 (m, 2H), 3.30 (m, 2H), 2.93 (m, 2H), 1.48 (d, J=6.0 Hz, 3H).

Example 39: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-2-methylpropanoic acid hydrochloride LCMS (ESI positive ion) m/z: calculated: 582.61; Observed; 582.8 (M+); HPLC purity (XB0595TF): 90.46%; ¹H NMR (400 MHz, DMSO-d6): δ 10.9 (br s, 1H), 8.40 (brs, 2H), 7.96 (d, J=1.20 Hz, 1H), 7.25-7.26 (m, 1H), 7.01 (t, J=10.00 Hz, 1H), 6.75-6.73 (m, 2H), 6.65-6.63 (m, 1H), 4.32 (t, J=5.60 Hz, 2H), 3.88 (d, J=11.20 Hz, 2H), 3.57 (d, J=4.00

Hz, 2H), 3.41 (t, J=8.80 Hz, 2H), 3.25 (t, J=9.60 Hz, 2H), 3.13 (t, J=11.60 Hz, 2H), and 1.48 (s, 6H).

Example 40: 3-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenyl)propanoic acid LCMS (ESI positive ion) m/z: calculated: 553.18; observed: 552.9; HPLC purity (XB0595TF): 93.92%; $^1$H NMR (400 MHz, DMSO-d6): δ 9.62 (brs, 1H), 8.41 (brs, 2H), 7.96 (m, 1H), 7.25 (m, 1H), 7.10 (m, 1H), 6.99 (m, 2H), 6.74 (dd, J=2.0 & 3.6 Hz, 1H), 4.32 (m, 2H), 3.95 (m, 2H), 3.28 (m, 2H), 2.99 (m, 2H), 2.32 (m, 2H).

Example 41: 4-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)butanoic acid hydrochloride LCMS: (ESI positive ion); m/z: calculated: 582.61; Observed; 582.3 (M+1); HPLC purity (XB0595TF): 96.04%; $^1$H NMR (400 MHz, DMSO-d6): δ10.31 (br s, 1H) 8.41 (brs, 2H), 7.97 (d, J=0.80 Hz, 1H), 7.26 (d, J=3.20 Hz, 1H), 7.02 (t, J=9.60 Hz, 1H), 6.87 (q, J=2.40 Hz, 1H), 6.75-6.72 (m, 2H), 4.32 (m, 2H), 3.96-3.89 (m, 4H), 3.59 (m, 2H), 3.40 (d, J=11.60 Hz, 2H), 3.28 (d, J=10.00 Hz, 2H), 3.06-3.03 (m, 2H), 2.36 (t, J=7.20 Hz, 2H), and 1.91 (t, J=6.80 Hz, 2H).

Example 42: 2-(3-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,6-difluorophenoxy)acetic acid hydrochloride LCMS (ESI positive ion); m/z: calculated: 572.55; Observed; 573.0 (M+1); HPLC purity (XB0595TF): 93.35%; $^1$H NMR (400 MHz, DMSO-d6): δ 10.41 (brs, 1H), 8.42 (brs, 2H), 7.97 (t, J=0.96 Hz, 1H), 7.27 (d, J=4.04 Hz, 1H), 7.07 (t, J=9.40 Hz, 1H), 6.81-6.78 (m, 1H), 6.75-6.74 (m, 1H), 4.77 (m, 2H), 4.32 (d, J=5.20 Hz, 2H), 3.92 (d, J=8.84 Hz, 2H), 3.60 (m, 2H), 3.46 (d, J=12.04 Hz, 2H), 3.29 (d, J=9.16 Hz, 2H), and 3.10 (t, J=11.28 Hz, 2H).

Example 43: 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)acetic acid hydrochloride LC-MS: (ESI positive ion); m/z: calculated: 572.55; Observed; 573.0 (M+1); HPLC purity (XB0595TF): 96.60%; $^1$H NMR (400 MHz, DMSO-d6): δ 13.06 (brs, 1H), 10.23 (brs, 1H), 8.40 (brs, 2H), 7.96-7.96 (m, 1H), 7.33 (t, J=11.60 Hz, 1H), 7.25 (d, J=3.20 Hz, 1H), 6.82 (t, J=8.80 Hz, 1H), 6.73-6.75 (m, 1H), 4.79 (s, 2H), 4.32 (m, 2H), 3.89-3.92 (m, 2H), 3.60 (brs, 2H), 3.49-3.46 (m, 2H), 3.30-3.27 (m, 2H), ), and 3.07 (t, J=11.6 Hz, 2H).

Example 44: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorobenzoic acid LCMS (ESI positive ion); m/z: calculated: 524.14; observed: 525.0; HPLC purity (XB0595TF):89.07%; $^1$H NMR: (400 MHz, DMSO-d6): δ 12.80 (brs, 1H), 8.30 (brs, 2H), 7.95 (dd, J=0.8 & 1.6 Hz, 1H), 7.66 (dd, J=2.0 & 8.4 Hz, 1H), 7.54 (dd, J=2.0 & 14.0 Hz, 1H), 7.23 (dd, J=0.8 & 3.2 Hz, 1H), 7.04 (t, J=8.8 Hz, 1H), 6.73 (dd, J=1.6 & 3.2 Hz, 1H), 4.08 (t, J=6.0 Hz, 2H), 3.08 (m, 4H), 2.73-2.65 (m, 6H).

Example 45: 2-((2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)amino)acetamide hydrochloride LCMS: (ESI positive ion); m/z: calculated: 596.64; Observed; 597.0 (M+1); HPLC purity (XB0595TF): 94.28%; $^1$H NMR (400 MHz, DMSO-d6): δ 10.62 (brs, 1H), 9.12 (brs, 2H), 7.96 (t, J=0.80 Hz, 1H), 7.92 (s, 1H), 7.58 (brs, 1H), 7.26 (d, J=3.20 Hz, 1H), 7.07 (t, J=9.60 Hz, 1H), 6.96 (dd, J=2.80, 13.60 Hz, 1H), 6.81-6.78 (m, 2H), 4.33-4.32 (m, 2H), 4.24 (t, J=5.20 Hz, 2H), 3.76-3.77 (m, 2H), 3.59 (s, 2H), 3.42-3.35 (m, 8H), and 3.118 (m, 2H).

Example 46: 2-((2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)(methyl)amino)acetamide LCMS (ESI positive ion) m/z: calculated: 610.22; observed: 611.0 (M+1); HPLC purity (XB0595TF): 99.25%; $^1$H NMR (400 MHz, DMSO-d6): δ 8.30 (brs, 2H), 7.95 (d, J=0.8 Hz, 1H), 7.24 (m, 1H), 7.16 (brs, 1H), 7.11 (brs, 1H), 6.93 (d, J=9.6 Hz, 1H), 6.79 (dd, J=2.8 & 14.0 Hz, 1H), 6.73 (dd, J=1.6 & 3.2 Hz, 1H), 6.67 (m, 1H), 4.08-4.02 (m, 4H), 2.96 (s, 2H), 2.85 (m, 4H), 2.75-2.63 (m, 8H), 2.31 (s, 3H).

Example 47: 5-amino-3-(2-(4-(2-fluoro-4-(piperidin-4-yloxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 579.22; observed: 580.0 (M+1); HPLC purity (XB0595TF): 95.3%; $^1$H NMR (400 MHz, DMSO-d6): δ 10.29 (brs, 1H), 8.89 (brs, 2H), 8.42 (brs, 2H), 7.97 (s, 1H), 7.26 (d, J=3.2 Hz, 1H), 7.06-6.97 (m, 2H), 6.82-6.75 (m, 2H), 4.60 (m, 1H), 4.32 (m, 2H), 3.92 (m, 2H), 3.60 (m, 2H), 3.41 (m, 2H), 3.29-3.20 (m, 4H), 3.06 (m, 4H), 2.06 (m, 2H), 1.81 (m, 2H).

Example 48: 5-amino-3-(2-(4-(2-fluoro-4-(pyrrolidin-3-yloxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 565.20; observed: 566.0 (M+1); HPLC purity (XB0595TF): 97.96%; $^1$H NMR (400 MHz, DMSO-d6): δ 10.72 (brs, 1H), 9.72 (brs, 1H), 9.50 (brs, 1H), 8.42 (brs, 2H), 7.97 (s, 1H), 7.26 (d, J=3.6 Hz, 1H), 7.05 (t, J=9.2 Hz, 1H), 6.95 (dd, J=2.4 & 13.6 Hz, 1H), 6.80-6.74 (m, 2H), 5.10 (m, 1H), 4.33 (m, 2H), 3.90 (m, 2H), 3.59 (m, 2H), 3.42 (m, 3H), 3.28 (m, 5H), 3.13 (m, 2H), 2.14 (m, 2H).

Example 49: 3-(2-(4-(4-((1H-1,2,4-triazol-3-yl)methoxy)-2-fluorophenyl)piperazin-1-yl)ethyl)-5-amino-8-(furan-2-yl)thiazolo[5,4-e][1,2,4]triazolo[1,5-c]pyrimidin-2(3H)-one LCMS (ESI positive ion) m/z: calculated: 577.17; observed: 578.2 (M+1); HPLC purity (XB0595TF): 93.44%; $^1$H NMR (400 MHz, DMSO-d6): δ 14.09 (brs, 1H), 8.56 (brs, 1H), 8.31 (brs, 3H), 7.96 (s, 1H), 7.24 (d, J=3.20

Hz, 1H), 6.96-6.90 (m, 2H), 6.79-6.74 (m, 2H), 5.08 (s, 2H), 4.08 (t, J=6.0 Hz, 2H), 2.86 (m, 4H), 2.72-2.68 (m, 6H).

Example 50: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-(methylamino)ethyl)acetamide hydrochloride LCMS (ESI positive ion) m/z: calculated: 610.22; observed: 611.0 (M+1); HPLC purity (XB0595TF): 99.20%; $^1$H NMR (400 MHz, DMSO-d6): δ 10.36 (brs, 1H), 8.79 (brs, 2H), 8.42 (brs, 3H), 7.97 (t, J=0.8 Hz, 1H), 7.26 (t, J=3.2 Hz, 1H), 7.06 (t, J=9.6 Hz, 1H), 6.96 (dd, J=2.4 & 13.6 Hz, 1H), 6.80 (m, 1H), 6.74 (t, J=1.6 Hz, 1H), 4.50 (s, 2H), 4.33 (m, 2H), 3.59 (m, 2H), 3.46-3.40 (m, 4H), 3.28 (m, 2H), 3.10-2.99 (m, 4H), 2.55 (s, 3H).

Example 51: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-(dimethylamino)ethyl)acetamide LCMS (ESI positive ion) m/z: calculated: 624.24; observed: 625.0 (M+1); HPLC purity (XB0595TF): 97.22%; $^1$H NMR (400 MHz, DMSO-d6): δ 8.31 (brs, 2H), 7.95 (m, 2H), 7.24 (d, J=3.2 Hz, 1H), 6.94 (t, J=9.6 Hz, 1H), 6.83 (d, J=14.0 Hz, 1H), 6.74-6.69 (m, 2H), 4.42 (s, 2H), 4.08 (m, 2H), 3.20 (q, J=6.4 Hz, 2H), 2.86 (m, 4H), 2.70-2.63 (m, 6H), 2.29 (t, J=6.4 Hz, 2H), 2.13 (s, 6H).

Example 52: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-aminoethyl)acetamide hydrochloride LCMS (ESI positive ion) m/z: calculated: 596.21; observed: 597.0 (M+1); HPLC purity (XB0595TF): 93.18%; $^1$H NMR (400 MHz, DMSO-d6): δ 10.40 (brs, 1H), 8.39 (brs, 3H), 7.97 (m, 3H), 7.26 (dd, J=0.8 & 3.2 Hz, 1H), 7.06 (t, J=9.6 Hz, 1H), 6.95 (dd, J=2.4 & 13.6 Hz, 1H), 6.81-6.78 (m, 2H), 4.49 (s, 2H), 4.32 (t, J=5.2 Hz, 2H), 3.90 (m, 2H), 3.60 (m, 2H), 3.40 (m, 4H), 3.28 (a, J=10.00 Hz, 2H), 3.08 (m, 2H), 2.90 (m, 2H).

Example 54: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)acetamide LCMS (ESI positive ion) m/z: calculated: 553.16; observed: 554.0 (M+1); HPLC purity (XB0595TF): 95.07%; $^1$H NMR (400 MHz, DMSO-d6): δ 9.43 (brs, 1H), 8.41 (brs, 2H), 7.97 (s, 1H), 7.52 (brs, 1H), 7.40 (brs, 1H), 7.27 (m, 1H), 7.05 (t, J=9.20 Hz, 1H), 6.91-6.87 (m, 1H), 6.75 (m, 2H), 4.41 (s, 2H), 4.31 (m, 2H), 3.97 (m, 2H), 3.31 (m, 4H), 2.96 (m, 4H).

Example 55: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-methyl-N-(2-(methylamino)ethyl)benzamide hydrochloride LCMS (ESI positive ion) m/z: calculated: 594.23; observed: 595.2 (M+1); HPLC purity (XB0595TF): 93.61%; $^1$H NMR (400 MHz, DMSO-d6): δ 10.13 (brs, 1H), 8.63 (brs, 2H), 8.42 (brs, 2H), 7.97 (s, 1H), 7.40 (m, 1H), 7.32-7.26 (m, 2H), 7.14 (t, J=8.80 Hz, 1H), 6.75 (dd, J=0.8 & 3.2 Hz, 1H), 4.35 (m, 2H), 3.98 (m, 2H), 3.67 (m, 6H), 3.15 (m, 6H), 2.96 (s, 3H).

Example 56: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-3-fluoro-N-methylbenzamide LCMS (ESI positive ion) m/z: calculated: 608.70; Observed; 609.0 (M+1); HPLC Purity (XB0595TF): 99.46%; $^1$H NMR (400 MHz, DMSO-d6): δ 8.31 (s, 2H), 7.95 (s, 1H), 7.24 (d, J=3.36 Hz, 1H), 7.18-7.12 (m, 2H), 7.00 (t, J=8.48 Hz, 1H), 6.74-6.73 (m, 1H), 4.09 (t, J=12.60 Hz, 2H), 3.37-3.30 (m, 2H), 3.01-2.93 (m, 4H), 2.91 (s, 3H), 2.73-2.62 (m, 8H), 2.22 (m, 3H), and 2.02 (m, 3H).

Example 57: (R)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(1-(dimethylamino)propan-2-yl)-3-fluorobenzamide LCMS (ESI positive ion) m/z: calculated: 608.24; observed: 609.3 (M+1); HPLC purity (XB0595TF): 98.79%; $^1$H NMR (400 MHz, DMSO-d6): δ 8.32 (brs, 2H), 8.02 (m, 1H), 7.95 (s, 1H), 7.62-7.59 (m, 2H), 7.24 (d, J=3.2 Hz, 1H), 7.02 (t, J=8.8 Hz, 1H), 6.74 (m, 1H), 4.09 (m, 3H), 3.04 (m, 4H), 2.73-2.66 (m, 6H), 2.15 (m, 6H), 1.11 (d, J=6.4 Hz, 3H).

Example 58: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-methyl-N-(2-(methylamino)ethyl)acetamide hydrochloride LCMS (ESI positive ion) m/z: calculated: 624.24; observed: 625.0 (M+1); HPLC purity (XB0595TF): 92.37%; $^1$H NMR (400 MHz, DMSO-d6): δ 10.10 (brs, 1H), 8.63 (brs, 2H), 8.41 (brs, 1H), 7.96 (dd, J=0.8 & 1.6 Hz, 1H), 7.35 (d, J=2.4 Hz, 1H), 7.06-6.90 (m, 2H), 6.78-6.74 (m, 2H), 4.81 (s, 2H), 4.32 (m, 2H), 3.91 (d, J=10.80 Hz, 2H), 3.59 (m, 4H), 3.30 (m, 2H), 3.06 (m, 3H), 3.00 (s, 3H), 2.60-2.55 (m, 3H).

Example 59: 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-2-methylpropanoic acid hydrochloride LCMS: (ESI positive ion); m/z: calculated: 600.60; Observed; 601.0 (M+1); HPLC purity (XB0595TF): 97.84%; $^1$H NMR (400 MHz, DMSO-d6): δ 10.30 (brs, 1H), 8.40 (brs, 2H), 7.96 (brs, 1H), 7.34 (t, J=11.20 Hz, 1H), 7.26 (d, J=3.20 Hz, 1H), 6.80 (t, J=8.40 Hz, 1H), 6.79-6.73 (m, 1H), 4.32 (m, 2H), 3.93-3.90 (m, 2H), 3.60 (t, J=6.40 Hz, 2H), 3.46-3.43 (m, 2H), 3.30-3.28 (m, 2H), 3.03 (t, J=11.20 Hz, 2H), and 1.45 (s, and 6H).

Examples 60 and 61: (S)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)propanoic acid and (R)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)propanoic acid The racemic mixture of the products, prepared as described for the Examples above (0.08 g) was subjected to chiral separation (0.08 g sample was dissolved in 10 ml of ethanol), column-chiralpak AD-H, and mobile phase: 0.1% diethylamine in n-hexane: ethanol (70:30), flow rate: 1.0 mL/min; to yield 10 mg of peak 1 ((S)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)propanoic acid) and 13 mg of peak 2 ((R)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)propanoic acid) respectively. Note: Peak 1 was arbitrarily attributed as (S) isomer and peak 2 was considered as (R) isomer.

(S)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)propanoic acid LCMS (ESI positive ion) m/z: calculated: 586.16; observed: 587.2 (M+1); HPLC purity (XB0595TF): 99.69%; Chiral HPLC purity: 100%; $^1$H NMR (400 MHz, DMSO-d6): δ 13.03 (brs, 1H), 8.29 (brs, 2H), 7.94 (s, 1H), 7.24-7.18 (m, 2H), 6.72 (m, 1H), 6.67 (t, J=8.8 Hz, 1H), 4.90 (q, J=6.80 Hz, 1H), 4.07 (m, 2H), 2.86 (m, 4H), 2.70-2.62 (m, 6H), 1.47 (d, J=6.80 Hz, 3H).

(R)-2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)propanoic acid LCMS (ESI positive ion) m/z: calculated: 586.16; observed: 587.2 (M+1); HPLC purity (XB0595TF): 94.42%; Chiral HPLC purity: 98.71%; $^1$H NMR (400 MHz, DMSO-d6): δ 12.98 (brs, 1H), 8.30 (brs, 2H), 7.95 (s, 1H), 7.25-7.19 (m, 2H), 6.73-6.68 (m, 2H), 4.91 (q, J=6.40 Hz, 1H), 4.07 (m, 2H), 2.90 (m, 4H), 2.70-2.67 (m, 6H), 1.48 (d, J=6.40 Hz, 3H).

Example 62: 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-(methylamino)ethyl)acetamide hydrochloride LCMS (ESI positive ion) m/z: calculated: 628.21; observed: 629.2 (M+1); HPLC purity (XB0595TF): 95.15%; $^1$H NMR (400 MHz, DMSO-d6): δ 10.40 (brs, 1H), 8.66 (brs, 2H), 8.42 (brs, 2H), 8.33 (t, J=6.0 Hz, 1H), 7.97 (d, J=1.2 Hz, 1H), 7.38 (t, J=11.60 Hz, 1H), 7.26 (m, 1H), 6.90 (t, J=8.40 Hz, 1H), 6.75 (dd, J=2.00 & 3.6 Hz, 1H), 4.63 (s, 2H), 4.33 (m, 2H), 3.92 (m, 2H), 3.52-3.41 (m, 6H), 3.30 (m, 2H), 3.11 (m, 2H), 3.00 (t, J=6.0 Hz, 2H), 2.56 (s, 3H).

Example 63: 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-(dimethylamino)ethyl)acetamide LCMS (ESI positive ion) m/z: calculated: 642.23; observed: 643.3 (M+1); HPLC purity (XB0595TF): 96.98%; $^1$H NMR (400 MHz, DMSO-d6): δ 8.29 (brs, 2H), 7.95-7.91 (m, 2H), 7.24 (m, 2H), 6.67-6.74-6.67 (m, 2H), 4.53 (s, 2H), 4.07 (t, J=6.40 Hz, 2H), 3.19 (q, J=6.40 Hz, 2H), 2.88 (m, 4H), 2.71 (m, 2H), 2.63 (m, 4H), 2.27 (t, J=6.0 Hz, 2H), 2.07 (s, 6H).

Example 64: 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-2,4-difluoro-N-methylbenzamide LCMS (ESI positive ion) m/z: calculated: 626.69; Observed; 627.2 (M+1); HPLC Purity (XB0595TF): 92.93%; $^1$H NMR (400 MHz, DMSO-d6): δ 8.32 (m, 2H), 7.95 (s, 1H), 7.33-7.24 (m, 2H), 6.94-6.88 (m, 1H), 6.74-6.73 (m, 1H), 4.09-4.06 (m, 2H), 3.53-3.49 (m, 1H), 3.33 (m, 1H), 2.97-2.56 (m, 13H), 2.34-2.29 (m, 5H), and 1.90 (s, 3H).

Example 65: 4-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)butanoic acid LCMS (ESI positive ion) m/z: calculated: 600.17; observed: 601.0 (M+1); HPLC purity (XB0595TF): 90.64%; $^1$H NMR (400 MHz, DMSO-d6): δ 9.90 (brs, 1H), 8.42 (brs, 2H), 7.96 (s, 1H), 7.35-7.26 (m, 2H), 6.84 (t, J=9.60 Hz, 1H), 6.75 (dd, J=1.6 & 3.6 Hz, 1H), 4.32 (m, 2H), 4.06 (t, J=6.40 Hz, 2H), 3.91 (m, 2H), 3.51 (m, 2H), 3.29 (m, 2H), 3.07 (t, J=12.00 Hz, 2H), 2.39 (m, 2H), 1.93 (t, J=6.80 Hz, 2H).

Example 66: 3-(2-(4-(5-((1H-tetrazol-5-yl)methoxy)-2,4-difluorophenyl)piperazin-1-yl)ethyl)-5-amino-8-(furan-2-yl)thiazolo[5,4-e][1,2,4]triazolo[1,5-c]pyrimidin-2(3H)-one LCMS (ESI positive ion) m/z: calculated: 596.16; observed: 596.8 (M+1); HPLC purity (XB0595TF): 92.14%; $^1$H NMR (400 MHz, DMSO-d6): δ 8.32 (brs, 2H), 7.95 (s, 1H), 7.28-7.24 (m, 2H), 6.98 (t, J=8.0 Hz, 1H), 6.73 (d, J=1.20 Hz, 1H), 5.48 (s, 2H), 4.10 (m, 2H), 2.95 (m, 4H), 2.78-2.67 (m, 4H).

Example 67: 5-amino-3-(2-(4-(2-fluoro-4-((1-methyl-1H-1,2,4-triazol-3-yl)methoxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 591.63; Observed; 592.8 (M+1); HPLC Purity (XB0595TF): 98.87%; $^1$H NMR (400 MHz, DMSO-d6): δ 8.43 (s, 1H), 8.30 (m, 2H), 7.95 (m, 1H), 7.24 (m, 1H), 7.01-6.73 (m, 4H), 4.99 (s, 2H), 4.09-4.03 (m, 2H), 3.90 (s, 3H), 2.98-2.86 (m, 4H), and 2.72-2.67 (m, 6H).

Example 68: 5-amino-3-(2-(4-(2,4-difluoro-5-((1-methyl-1H-1,2,4-triazol-3-yl)methoxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 609.62; Observed; 610.2 (M+1); HPLC Purity (XB0595TF): 90.03%; $^1$H NMR (400 MHz, DMSO-d6): δ 8.70 (broad s, 1H), 8.49 (s, 1H), 7.94 (s, 1H), 7.32-7.07 (m, 3H), 6.72 (m, 1H), 5.15 (m, 2H), 4.35-4.31 (m, 2H), 3.91-3.86 (m, 5H), 3.69 (m, 4H), and 3.08 (m, 4H).

Example 69: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methyl(oxetan-3-yl)amino)ethyl)benzamide LCMS (ESI positive ion) m/z: calculated: 636.24; observed: 637.3 (M+1); HPLC purity (XB0595TF):

97.10%; ¹H NMR (400 MHz, DMSO-d6): δ 8.34 (brs, 2H), 7.96 (s, 1H), 7.60 (m, 2H), 7.24 (m, 1H), 7.03 (m, 1H), 6.73 (m, 1H), 4.51 (m, 2H), 4.37 (m, 2H), 4.09 (m, 2H), 3.55 (m, 1H), 3.05 (m, 4H), 2.68 (m, 6H), 2.11 (s, 3H).

Example 70: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-((2-hydroxyethyl)amino)ethyl)benzamide hydrochloride LCMS (ESI positive ion) m/z: calculated: 610.22; observed: 611.3 (M+1); HPLC purity (XB0595TF): 96.51%; ¹H NMR (400 MHz, DMSO-d6): δ 10.25 (brs, 1H), 8.72 (brs, 3H), 8.40 (brs, 2H), 7.95 (t, J=0.8 Hz, 1H), 7.72 (m, 2H), 7.25 (d, J=3.2 Hz, 1H), 7.16 (t, J=7.6 Hz, 1H), 6.73 (dd, J=1.6 & 3.2 Hz, 1H), 5.26 (brs, 1H), 4.32 (m, 2H), 3.94 (d, J=10.8 Hz, 2H), 3.68-3.56 (m, 8H), 3.16-3.03 (m, 6H).

Example 71: 2-amino-N-(2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)acetamide hydrochloride LCMS: (ESI positive ion); m/z: calculated: 596.64; Observed; 597.0 (M+1); HPLC purity (XB0595TF): 94.31%; ¹H NMR (400 MHz, DMSO-d6): δ 8.31 (brs, 1H), 8.22 (d, J=5.20 Hz, 1H), 7.95 (t, J=0.40 Hz, 1H), 7.24 (t, J=0.80 Hz, 1H), 6.95-6.91 (m, 1H), 6.81 (dd, J=2.80, 14.00 Hz, 1H), 6.73-6.74 (m, 1H), 6.69 (dd, J=2.00, 8.80 Hz, 1H), 5.00 (brs, 1H), 4.08 (t, J=6.40 Hz, 2H), 3.95 (t, J=5.60 Hz, 2H), 3.45 (q, J=5.60 Hz, 2H), 3.24 (brs, 2H), 2.85 (brs, 4H), 2.70-2.67 (m, 2H), and 2.63 (m, 4H).

Example 72: (S)-2-amino-N-(2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)-3-methylbutanamide hydrochloride LCMS: (ESI positive ion); m/z: calculated: 638.72; Observed; 639.1 (M+1); HPLC purity (AM9010A3): 98.36%; ¹H NMR (400 MHz, DMSO-d6): δ 8.44 (brs, 1H), 8.30 (brs, 2H), 7.94 (s, 1H), 7.23 (d, J=3.20 Hz, 1H), 6.92 (t, J=9.60 Hz, 1H), 6.80-6.73 (m, 3H), 4.05-4.08 (m, 4H), 3.56-3.53 (m, 1H), 3.41-3.40 (m, 1H), 2.84 (m, 4H), 2.71-2.671 (m, 3H), 2.62 (m, 3H), 2.33 (m, 1H), 1.94-1.99 (m, 1H), and 0.894-0.853 (m, 6H).

Example 73: ethyl 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)acetate LCMS (ESI positive ion) m/z: calculated: 600.17; observed: 601.2 (M+1); HPLC purity (XB0595TF): 96.15%; ¹H NMR (400 MHz, DMSO-d6): δ 8.31 (brs, 2H), 7.96 (s, 1H), 7.24 (m, 2H), 6.72 (m, 2H), 4.85 (s, 2H), 4.16 (q, J=6.80 Hz, 2H), 4.08 (m, 2H), 2.89 (m, 4H), 2.71-2.63 (m, 6H), 1.19 (t, J=6.80 Hz, 3H).

Example 74: 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)acetonitrile LCMS (ESI positive ion) m/z: calculated: 553.14; observed: 554.2 (M+1); HPLC purity (XB0595TF): 96.92%; ¹H NMR (400 MHz, DMSO-d6): δ 8.31 (brs, 2H), 7.95 (d, J=0.80 Hz, 1H), 7.33 (t, J=10.80 Hz, 1H), 7.24 (d, J=3.2 Hz, 1H), 6.94 (t, J=8.4 Hz, 1H), 6.73 (dd, J=1.6 & 3.2 Hz, 1H), 5.22 (s, 2H), 4.09 (t, J=5.6 Hz, 2H), 2.93 (m, 4H), 2.74-2.64 (m, 6H).

Example 75: 5-amino-8-(furan-2-yl)-3-(2-(4-(pyridin-4-yl)piperazin-1-yl)ethyl)thiazolo[5,4-e][1,2,4]triazolo[1,5-c]pyrimidin-2(3H)-one LCMS (ESI positive ion) m/z: calculated: 463.15; observed: 464.1 (M+1); HPLC purity (XB0595TF): 93.77%; ¹H NMR: (400 MHz, DMSO-d6): δ 8.30 (brs, 2H), 8.13 (d, J=6.40 Hz, 2H), 7.94 (d, J=0.80 Hz, 1H), 7.23 (d, J=3.60 Hz, 1H), 6.77 (d, J=6.40 Hz, 2H), 6.72 (dd, J=1.6 & 3.2 Hz, 1H), 4.08 (t, J=6.00 Hz, 2H), 3.23 (m, 4H), 2.71-2.67 (m, 2H), 2.58 (m, 4H).

Example 76: 5-amino-8-(furan-2-yl)-3-(2-(4-(pyrimidin-4-yl)piperazin-1-yl)ethyl)thiazolo[5,4-e][1,2,4]triazolo[1,5-c]pyrimidin-2(3H)-one LCMS (ESI positive ion) m/z: calculated: 464.15; observed: 465.1 (M+1); HPLC purity (XB0595TF): 95.02%; ¹H NMR: (400 MHz, DMSO-d6): δ 8.47 (s, 1H), 8.31 (brs, 2H), 8.16 (d, J=6.40 Hz, 1H), 7.95 (s, 1H), 7.23 (d, J=2.8 Hz, 1H), 6.79 (dd, J=0.8 & 6.0 Hz, 1H), 6.73 (dd, J=1.6 & 3.2 Hz, 1H), 4.08 (t, J=6.00 Hz, 2H), 3.53 (m, 4H), 2.69 (t, J=6.80 Hz, 2H), 2.55 (m, 4H).

Example 79: 5-amino-3-(2-(4-(6-fluoro-2-oxoindolin-5-yl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 535.16; observed: 536.0 (M+1); HPLC purity (XB0595TF): 82.71%; ¹H NMR (400 MHz, DMSO-d6): δ 10.26 (s, 1H), 8.30 (brs, 2H), 7.95 (s, 1H), 7.24 (d, J=3.60 Hz, 1H), 6.94 (d, J=8.40 Hz, 1H), 6.73-6.74 (m, 1H), 6.60 (d, J=12.00 Hz, 1H), 4.08 (t, J=5.60 Hz, 2H), 3.39 (s, 2H), 2.84 (m, 4H), 2.72-2.63 (m, 6H).

Example 82: 5-amino-3-(2-(4-(5-fluoro-2-methylpyridin-4-yl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 495.54; observed: 496.1 (M+1); HPLC purity (XB0595TF): 93.17%; H-NMR (400 MHz, DMSO-d6): δ 8.31 (broad s, 2H), 8.08 (d, J=5.60 Hz, 1H), 7.95 (s, 1H), 7.24 (t, J=2.40 Hz, 1H), 6.72-6.79 (m, 2H), 4.06-4.11 (m, 2H), 3.16 (t, J=6.00 Hz, 4H), 2.68-2.72 (m, 2H), 2.62 (s, 4H), and 2.33 (s, 3H).

Example 85: 5-amino-3-(2-(4-(2-fluoro-4-(2-hydroxy-2-methylpropoxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 568.20; observed: 569.3 (M+1); HPLC purity (XB0595TF): 92.42%; ¹H NMR (400 MHz, DMSO-d6): δ 8.31 (brs, 2H), 7.95 (s, 1H), 7.24 (s, 1H), 6.92 (t, J=9.60 Hz, 1H), 6.79-6.66 (m, 3H), 4.60 (s, 1H), 4.07 (m, 2H), 3.65 (s, 2H), 2.85 (m, 4H), 2.70-2.63 (m, 6H), 1.17 (s, 6H).

Example 86: 5-amino-3-(2-(4-(2-fluoro-4-(2-hydroxypropan-2-yl)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 538.60; observed: 539.2 (M+1); HPLC purity (XB0595TF): 94.02%; 1H-NMR (400 MHz, DMSO-d6): δ 8.31 (bs, 2H), 7.95 (s, 1H), 7.24 (s, 1H), 7.15 (m, 2H), 6.90 (m, 1H), 6.73 (m, 1H), 4.08 (t, J=6.00 Hz, 2H), 2.92 (broad s, 4H), 2.64-2.71 (m, 6H), and 1.38 (s, 6H).

Example 87: 5-amino-3-(2-(4-(2-fluoro-4-(3,3,3-trifluoro-2-hydroxypropoxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 608.16; observed: 609.0 (M+1); HPLC purity (XB0595TF): 95.69%; $^1$H NMR (400 MHz, DMSO-d6): δ 8.30 (brs, 2H), 7.95 (dd, J=0.8 Hz and 1.6 Hz, 1H), 7.24 (dd, J=0.8 Hz and 3.2 Hz, 1H), 6.94 (t, J=9.60 Hz, 1H), 6.85 (dd, J=2.80 Hz and 14.00 Hz, 1H), 6.74-6.71 (m, 2H), 6.63 (d, J=6.80 Hz, 1H), 4.35-4.33 (m, 1H), 4.10-3.99 (m, 4H), 2.86 (m, 4H), 2.70 (t, J=6.40 Hz, 2H), 2.63 (m, 4H).

Example 89: 5-amino-3-(2-(4-(2,4-difluoro-5-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 613.64; Observed 614.2 (M+1); HPLC Purity (XB_0595TF): 96.82%; 1H-NMR (400 MHz, DMSO-d6): δ 10.95 (brs, 1H), 9.71 (m, 1H), 9.51-9.49 (m, 1H), 8.40 (brs, 2H), 7.96 (s, 1H), 7.36 (t, J=11.6 Hz, 1H), 7.25-7.24 (m, 1H), 6.89 (t, J=8.4 Hz, 1H), 6.74-6.73 (m, 1H), 4.33-4.31 (m, 2H), 4.18-4.11 (m, 3H), 4.01-3.79 (m, 2H), 3.58-3.48 (m, 2H), 3.29-3.31 (m, 4H), 3.15-2.96 (m, 6H), 2.95-2.93 (m, 2H).

Example 92: 5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 601.61; observed: 602.2 (M+1); HPLC purity (XB_0595TF): 96.09% 1H-NMR (400 MHz, DMSO-d6): δ 10.50 (s, 1H), 9.92 (s, 2H), 8.40 (s, 2H), 7.96 (d, J=0.8 Hz, 1H), 7.46 (t, J=11.6 Hz, 1H), 7.26-7.25 (m, 1H), 7.13-7.08 (m, 1H), 6.75-6.74 (m, 1H), 5.42 (s, 1H), 5.26-5.24 (m, 1H), 4.33 (m, 2H), 3.93-3.90 (m, 2H), 3.70-3.54 (m, 8H), 3.41-3.36 (m, 2H), 3.30-3.16 (m, 2H).

Example 93: 5-amino-3-(2-(4-(2,4-difluoro-5-(((3R,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 601.61; Observed; 602.1 (M+1); HPLC Purity (XB_0595TF): 95.74%; $^1$H NMR (400 MHz, DMSO-d6): δ 10.60 (s, 1H), 9.83-9.75 (m, 2H), 8.41 (s, 2H), 7.97 (s, 1H), 7.41 (t, J=11.60 Hz, 1H), 7.26 (d, J=3.20 Hz, 1H), 7.02 (t, J=8.40 Hz, 1H), 6.74 (q, J=1.60 Hz, 1H), 5.45 (m, 1H), 5.21-5.15 (m, 1H), 4.42 (s, 2H), 3.91 (d, J=10.80 Hz, 2H), 3.69-3.64 (m, 2H), 3.61 (s, 4H), 3.38 (s, 4H), 3.16 (d, J=8.80 Hz, 2H).

Example 94: 5-amino-3-(2-(4-(2,4-difluoro-5-(((3S,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 601.61; Observed; 602.2 (M+1); HPLC purity (PG_AM9010.M): 91.76%; $^1$H NMR (400 MHz, DMSO-d6): δ 8.31 (s, 2H), 7.95 (s, 1H), 7.26-7.23 (m, 2H), 6.83 (d, J=8 Hz, 1H), 6.74 (d, J=5.6 Hz, 1H), 5.24-5.15 (m, 1H), 4.73-4.71 (m, 1H), 4.09 (t, J=6 Hz, 2H), 2.91 (m, 5H), 2.73-2.63 (m, 8H), 1.92 (s, 4H),

Example 97: 2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-morpholinoethyl)acetamide LCMS (ESI positive ion) m/z: calculated: 684.24; observed: 685.0 (M+1); HPLC purity (XB0595TF): 90.92%; $^1$H NMR (400 MHz, DMSO-d6): δ 8.30 (brs, 2H), 7.95 (d, J=0.80 Hz, 1H), 7.90 (d, J=5.60 Hz, 1H), 7.29-7.18 (m, 2H), 6.76-6.70 (m, 2H), 4.55 (s, 2H), 4.08 (t, J=6.40 Hz, 2H), 3.53 (m, 4H), 3.23 (t, J=6.00 Hz, 2H), 2.90 (m, 4H), 2.72 (m, 2H), 2.67 (m, 4H), 2.35 (m, 6H).

Example 98: 5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(morpholin-3-ylmethyl)benzamide hydrochloride LCMS (ESI positive ion) m/z: calculated: 640.67; Observed; 641.1 (M+1); HPLC purity (XB_0595TF): 95.86%; $^1$H NMR (400 MHz, DMSO-d6): δ 10.57 (s, 1H), 9.50 (d, J=7.60 Hz, 1H), 9.29 (d, J=8.00 Hz, 1H), 8.64 (s, 1H), 8.41 (s, 2H), 7.97 (s, 1H), 7.44 (m, 2H), 7.26 (d, J=3.20 Hz, 1H), 6.75 (q, J=1.60 Hz, 1H), 4.33 (m, 2H), 3.90 (m, 4H), 3.49-3.57 (m, 8H), 3.11-3.33 (m, 7H).

Example 103: 5-amino-3-(2-(4-(2-fluoro-4-(((3R,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 583.62; observed: 584.2 (M+1); HPLC purity (XB0595TF): 90.29%; 1H-NMR (400 MHz, DMSO-d6): δ 10.27 (broad s, 1H), 9.69-9.82 (m, 2H), 8.41 (broad s, 2H), 7.97 (m, 1H), 7.26-7.27 (m, 1H), 7.05-7.10 (m, 2H), 6.87-6.90 (m, 1H), 6.75 (t, J=1.60 Hz, 1H), 5.49 (m, 1H), 5.07-5.13 (m, 1H), 4.32 (d, J=5.20 Hz, 2H), 3.73-3.93 (m, 2H), 3.49-3.66 (m, 2H), 3.40-3.44 (m, 3H), 3.30-3.39 (m, 3H), 3.25-3.30 (m, 3H), 3.07-3.10 (m, 2H).

Example 104: 5-amino-3-(2-(4-(2-fluoro-4-(((3S,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 583.62; observed: 584.2 (M+1); HPLC purity (XB0595TF): 96.80%; 1H-NMR (400 MHz, DMSO-d6): δ 10.40 (broad s, 1H), δ 9.94 (m, 2H), 8.42 (broad s, 2H), 7.97 (s, 1H), 7.26 (d, J=3.60 Hz, 1H), 7.06-7.10 (m, 2H), 6.87 (d, J=8.40 Hz, 1H), 6.74-6.76 (m, 1H), 5.49 (d, J=4.00 Hz, 1H), 5.07-5.13 (m, 1H), 4.32 (s, 2H), 3.90 (m, 2H), 3.62 (d, J=5.20 Hz, 2H), 3.39 (m, 6H), and 3.02-3.33 (brs, 4H).

Example 105: 2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-N-(2-morpholinoethyl)acetamide LCMS (ESI positive ion) m/z: calculated: 666.25; observed: 667.0 (M+1); HPLC purity (XB0595TF): 92.35%; $^1$H NMR (400 MHz, DMSO-d6): δ 8.30 (brs, 2H), 7.95-7.90 (m, 2H), 7.24 (dd, J=0.8 Hz and 3.2 Hz, 1H), 6.94 (t, J=10.00 Hz, 1H), 6.85-6.80 (m, 1H), 6.74-6.69 (m, 2H), 4.43 (s, 2H), 4.08 (t, J=6.00 Hz, 2H), 3.53 (m, 4H), 3.22 (m, 2H), 2.90 (m, 4H), 2.72-2.63 (m, 6H), 2.37-2.34 (m, 6H).

Example 106: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-morpholinoethyl)benzamide LCMS (ESI positive ion) m/z: calculated: 636.71; observed: 637.0 (M+1); HPLC purity (XB0595TF): 92.87%; 1H-NMR (400 MHz, DMSO-d6): δ 8.29-8.32 (broad s, 2H), 7.95 (s, 1H), 7.59 (m, 2H), 7.24 (s, 1H), 7.02 (m, 1H), 6.73 (m, 1H), 4.07-4.10 (m, 2H), 3.55-3.57 (m, 4H), 3.33 (m, 2H), 3.04 (m, 4H), 2.72 (m, 2H), 2.67-2.68 (m, 4H), and 2.51 (m, 6H).

Example 107: 4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(morpholin-3-ylmethyl)benzamide LCMS (ESI positive ion) m/z: calculated: 622.68; observed: 623.3 (M+1); HPLC purity (XB0595TF): 95.43%; 1H-NMR (400 MHz, DMSO-d6): 10.58 (broad s, 1H), 9.52 (d, J=8.80 Hz, 1H), 9.33 (d, J=8.40 Hz, 1H), 8.81 (d, J=5.20 Hz, 1H), 8.42 (broad s, 2H), 7.97 (s, 1H), 7.75-7.79 (m, 2H), 7.26 (d, J=3.20 Hz, 1H), 7.17 (t, J=8.80 Hz, 1H), 6.74-6.75 (m, 1H), 4.33 (broad s, 2H), 3.86-3.96 (m, 3H), 3.71 (s, 1H), 3.58 (t, J=11.60 Hz, 2H), 3.46-3.51 (m, 4H), 3.44 (d, J=5.60 Hz, 1H), 3.41 (d, J=9.60 Hz, 1H), 3.18-3.32 (m, 6H), and 3.05-3.08 (m, 1H).

Example 108: 5-amino-3-(2-(4-(4-(azetidin-3-yloxy)phenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 533.20; observed: 534.1 (M+1); HPLC purity (XB0595TF): 88.50%; $^1$H NMR (400 MHz, DMSO-d6): δ 10.17 (brs, 1H), 9.22 (brs, 1H), 9.09 (brs, 1H), 8.41 (brs, 2H), 7.96 (s, 1H), 7.25 (d, J=3.56 Hz, 1H), 6.95 (d, J=8.80 Hz, 2H), 6.80 (d, J=8.92 Hz, 2H), 6.73 (t, J=1.64 Hz, 1H), 4.98 (m, 1H), 4.41-4.32 (m, 4H), 3.94-3.90 (m, 4H), 3.72 (m, 2H), 3.24-3.21 (m, 2H), 2.97 (m, 2H).

Example 109: (S)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 560.12; observed: 561.1 (M+1); HPLC purity (XB0595TF): 99.33%; $^1$H NMR (400 MHz, DMSO-d6): δ 8.32 (brs, 2H), 7.95 (s, 1H), 7.45 (dd, J=9.2 Hz and 12.0 Hz, 1H), 7.29-7.24 (m, 2H), 6.73 (dd, J=1.6 Hz and 3.2 Hz, 1H), 4.08 (t, J=8.0 Hz, 2H), 2.99 (m, 4H), 2.80 (s, 3H), 2.73-2.67 (m, 6H).

Example 110: (R)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 560.12; observed: 561.0 (M+1); HPLC purity (XB0595TF): 98.18%; $^1$H NMR (400 MHz, DMSO-d6): δ 8.32 (brs, 2H), 7.95 (s, 1H), 7.47-7.42 (dd, J=9.2 Hz and 12.0 Hz, 1H), 7.29-7.23 (m, 2H), 6.74-6.73 (dd, J=1.6 Hz and 3.2 Hz, 1H), 4.08 (t, J=8.0 Hz, 2H), 2.99-2.98 (m, 4H), 2.8 (s, 3H), 2.73-2.67 (m, 6H).

Example 113: (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide LCMS (ESI positive ion) m/z: calculated: 631.68; observed: 632.2 (M+1); HPLC purity (XB0595TF): 95.04%; $^1$H-NMR (400 MHz, DMSO-d6) 8.52 (d, J=2.00 Hz, 1H), 8.32 (broad s, 2H), 7.95 (s, 1H), 7.28-7.34 (m, 1H), 7.20-7.25 (m, 2H), 6.73-6.74 (m, 1H), 4.07 (d, J=6.40 Hz, 2H), 3.58-3.64 (m, 2H), 2.99-3.06 (m, 4H), 2.84-2.93 (m, 2H), 2.69-2.72 (m, 2H), 2.65-2.69 (m, 4H), and 2.60 (s, 3H).

Example 114: (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide LCMS (ESI positive ion) m/z: calculated: 631.68; observed: 632.2 (M+1); HPLC purity (XB0595TF): 96.65%; $^1$H-NMR (400 MHz, DMSO-d6) δ 8.52 (d, J=2.00 Hz, 1H), 8.32 (broad s, 2H), 7.95 (s, 1H), 7.28-7.34 (m, 1H), 7.20-7.25 (m, 2H), 6.73-6.74 (m, 1H), 4.07 (d, J=6.40 Hz, 2H), 3.58-3.64 (m, 3H), 3.30 (m, 2H), 2.99-3.06 (m, 4H), 2.84-2.93 (m, 2H), 2.69-2.72 (m, 2H), 2.65-2.69 (m, 4H), 2.60 (s, 3H).

Example 115: (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-methyl-N-(2-(methylsulfinyl)ethyl)benzamide LCMS (ESI positive ion) m/z: calculated: 645.70; observed: 646.2 (M+1); HPLC purity (XB0595TF): 99.10%; $^1$H-NMR (400 MHz, DMSO-d6): δ 8.13 (br s, 1H), 7.85 (br s, 1H), 7.37 (t, J=9.28 Hz, 1H), 7.01-7.10 (m, 3H), 6.64-6.66 (m, 1H), 4.17 (t, J=9.08 Hz, 2H), 3.87 (m, 1H), 3.72-3.78 (m, 2H), 3.39-3.66 (m, 2H), 3.08-3.17 (m, 10H), 2.89-3.01 (m, 2H), and 2.60-2.67 (m, 3H).

Example 116: (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-methyl-N-(2-(methylsulfinyl)ethyl)benzamide LCMS (ESI positive ion) m/z: calculated: 645.7; observed: 646.1 (M+1); HPLC purity (XB0595TF): 93.418%; $^1$H-NMR (400 MHz, DMSO-d6): δ 8.29 (br s, 2H), 7.94 (s, 1H), 7.22-7.32 (m, 2H), 6.95 (t, J=7.72 Hz, 1H), 6.72 (d, J=1.28 Hz, 1H), 4.06 (t, J=5.92 Hz, 2H), 3.50-3.54 (m, 1H), 3.06-3.11 (m, 1H), 2.96-3.02 (m, 2H), 2.86-3.00 (m, 4H), 2.78-2.86 (m, 2H), 2.68-2.71 (m, 2H), 2.62 (s, 6H), and 2.47-2.50 (m, 2H).

Example 117: 5-amino-3-(2-(4-(2,4-difluoro-5-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 643.69; observed: 644.1 (M+1); HPLC purity (XB0595TF): 92.78%; $^1$H-NMR (400 MHz, DMSO-d6): δ 7.85-7.88 (m, 2H), 7.38-7.44 (m, 1H), 7.18-7.22 (m, 1H), 7.04-6.98 (m, 1H), 6.81 (s, 1H), 6.65-6.71 (m, 1H), 4.35 (broad s, 1H), 4.16 (t, J=9.20 Hz, 2H), 3.79-4.01 (m, 1H), 3.51-3.77 (m, 3H), 3.41-3.49 (m, 4H), 3.17-3.39 (m, 2H), 2.95-3.07 (m, 4H), and 2.75-2.90 (m, 3H).

Example 118: 5-amino-3-(2-(4-(2,4-difluoro-5-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 615.68; observed: 616.2 (M+1); HPLC purity (XB0595NHC): 93.08%; $^1$H-NMR (400 MHz, DMSO-d6): δ 8.32 (broad s, 2H), 7.95 (s, 1H), 7.24 (s, 1H), 7.16 (m, 1H), 6.72 (m, 2H), 4.06-4.10 (m, 2H), 3.49-3.54 (m, 2H), 3.14-3.18 (m, 2H), 2.93-3.00 (m, 6H), 2.82-2.85 (m, 2H), 2.67-2.72 (m, 2H), and 2.50-2.63 (m, 4H).

Example 123: (S)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide LCMS (ESI positive ion) m/z: calculated: 613.17; observed: 612.0 (M−1); HPLC purity (XB0595NHC): 99.46%; $^1$H NMR (400 MHz, DMSO-d6): δ 8.32 (brs, 2H), 8.09 (m, 1H), 7.95 (s, 1H), 7.58 (t, J=8.8 Hz, 1H), 7.24 (d, J=3.6 Hz, 1H), 6.79-6.71 (m, 3H). 4.09 (t, J=6.0 Hz, 2H), 3.61 (q, J=6.0 Hz, 2H), 3.22 (m, 4H), 3.07-3.00 (m, 1H), 2.90-2.85 (m, 1H), 2.72-2.69 (m, 2H), 2.60 (m, 7H).

Example 124: (R)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide LCMS (ESI positive ion) m/z: calculated: 613.17; observed: 614.1 (M+1); HPLC purity (XB0595NHC): 98.08%; $^1$H NMR (400 MHz, DMSO-d6): δ 8.32 (brs, 2H), 8.09 (m, 1H), 7.95 (s, 1H), 7.58 (t, J=8.8 Hz, 1H), 7.24 (m, 1H), 6.79-6.70 (m, 3H). 4.09 (t, J=6.0 Hz, 2H), 3.61 (q, J=6.0 Hz, 2H), 3.22 (m, 4H), 3.05-3.00 (m, 1H), 2.90-2.85 (m, 1H), 2.72-2.68 (m, 2H), 2.60 (n, 7H).

Example 125: 5-amino-3-(2-(4-(2-fluoro-4-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 625.17; observed: 626.0 (M+1); HPLC purity (XB0595TF): 95.09%; $^1$H NMR (400 MHz, DMSO-d6): δ 8.30 (brs, 2H), 7.94 (s, 1H), 7.24 (m, 2H), 6.79-6.72 (m, 3H), 4.36-4.35 (m, 1H), 4.08 (t, J=6.04 Hz, 2H), 3.78-3.62 (m, 2H), 3.55-3.46 (m, 1H), 3.17 (m, 4H), 2.83 (m, 3H), 2.71-2.66 (m, 3H), 2.59 (m, 4H).

Example 129: (S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-2,4-difluorobenzamide LCMS (ESI positive ion) m/z: calculated: 615.62; observed: 616.1 (M+1); HPLC purity (XB0595NHC): 97.60%; $^1$H-NMR (400 MHz, DMSO-d6): broad peaks were observed in 1H NMR.

Example 130: (R)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2,3-dihydroxypropyl)-2,4-difluorobenzamide LCMS (ESI positive ion) m/z: calculated: 615.62; observed: 616.2 (M+1); HPLC purity (XB0595NHC): 95.00%; $^1$H-NMR (400 MHz, DMSO-d6): δ 8.32 (broad m, 2H), 8.09 (s, 1H), 7.95 (s, 1H), 7.24-7.42 (m, 3H), 6.73 (s, 1H), 4.84 (s, 1H), 4.60 (s, 1H), 4.32 (s, 1H), 3.96-4.08 (m, 2H), 3.56 (t, J=2.80 Hz, 2H), 3.17 (t, J=6.04 Hz, 2H), 2.94 (s, 4H), 2.65-2.71 (m, 6H).

Example 131: 5-amino-3-(2-(4-(4-(azetidin-3-yloxy)-2-fluorophenyl)piperazin-1-yl)ethyl)-8-(furan-2-yl)thiazolo[5,4-e][1,2,4]triazolo[1,5-c]pyrimidin-2(3H)-one hydrochloride LCMS (ESI positive ion) m/z: calculated: 551.19; observed: 552.2 (M+1); HPLC purity (XB0595NHC): 90.50%; $^1$H NMR (400 MHz, DMSO-d6): δ 10.33 (brs, 1H), 9.33 (brs, 1H), 9.21 (brs, 1H), 8.42 (brs, 2H), 7.97 (s, 1H), 7.26 (d, J=3.2 Hz, 1H), 7.05 (t, J=9.6 Hz, 1H), 6.87 (d, J=13.6 Hz, 1H), 6.74-6.73 (m, 1H), 6.67 (d, J=8.4 Hz, 1H), 5.03 (s, 1H), 4.44-4.32 (m, 4H), 3.93 (m, 4H), 3.60 (m, 2H), 3.43-3.06 (m, 6H).

Example 132: 5-amino-3-(2-(4-(5-(azetidin-3-yloxy)-2,4-difluorophenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 569.18; observed: 570.0 (M−1); HPLC purity (XB0595TF): 94.68%; $^1$H NMR (400 MHz, DMSO-d6): δ 8.32 (brs, 2H), 7.95 (s, 1H), 7.27-7.21 (m, 2H), 6.74 (s, 1H), 6.43 (t, J=8.40 Hz, 1H), 5.01 (m, 1H), 4.07 (t, J=5.60 Hz, 2H), 3.71 (t, J=7.20 Hz, 2H), 3.53-3.47 (m, 2H), 2.90 (m, 4H), 2.72-2.63 (m, 6H).

Example 133: (S)-5-amino-3-(2-(4-(2,4-difluoro-5-(3-(methylsulfinyl)propoxy)phenyl)piperazin-1-yl)ethyl)-8-(furan-2-yl)thiazolo[5,4-e][1,2,4]triazolo[1,5-c]pyrimidin-2(3H)-one LCMS (ESI positive ion) m/z: calculated: 618.16; observed: 617.2 (M−1); HPLC purity (XB0595NHC): 97.91%; $^1$H NMR (400 MHz, DMSO-d6): δ 8.30 (brs, 2H), 7.94 (s, 1H), 7.23-7.18 (m, 2H), 6.77-6.73 (m, 2H), 4.14-4.07 (m, 4H), 2.89 (m, 5H), 2.77-2.55 (m, 10H), 2.05 (m, 2H).

II. BIOLOGY EXAMPLES

II.1. Assays for A2A Functional Activities

The two following assays aim at showing that the compounds of the invention effectively inhibit A2A receptor by showing that they inhibit its functional activities.

II.1.A. Inhibition of cAMP Production in HEK Cells

Purpose.

When the A2A receptor is activated, is induces the production of cAMP. The present assay thus aims at showing that cAMP production is inhibited in HEK cells in response to their exposure to the compounds of the invention.

Method.

HEK-293 cells with a stable transfection of A2A receptor were bought from PerkinElmer® (# ES-011-C). Cells were cultured in EMEM medium (Lonza, # BE12-611F) supplemented with 10% FBS (Lonza, # DE14-801F) and 200 µg/mL of G418 (Tocris, #4131) at 37° C. and 5% $CO_2$. Fresh media without the selection marker was added on the day immediately before the experiment to stop selection pressure.

cAMP inhibition and antagonist $IC_{50}$ determination were accessed using the LANCE® Ultra cAMP Kit from PerkinElmer® (# TRF0262) on white half area 96 well plates (PerkinElmer®, #6005560). The assays were conducted in two different stimulation buffers:
- a) normal with 1×HBSS (Gibco®, #141750-95), 5 mM HEPES (Lonza, # BE17-737E), 0.1% BSA and 25 µM Rolipram and
- b) HSA with 1×HBSS (Gibco®, #141750-95), 5 mM HEPES (Lonza, # BE17-737E), 2% Human Serum Albumin (Sigma-Aldrich®-A1653), 30 µM of EHNA (Tocris—#1261) and 100 µM Rolipram. Stimulation buffer b) mimics the human situation by increasing the amount of albumin present in the assay.

Compounds of the present invention were diluted 100× in either of the buffers depending on the assay performed. A total of 1000 cells per well were pre-incubated for 10 minutes with the compounds of the present invention before adding the corresponded EC80 of A2A agonist (3 nM of NECA in normal buffer and 5 nM of NECA in HSA buffer) or 5 µM of Adenosine for a total reaction time of 30 minutes. The total volume of the reaction was 20 µl (10 µl of cells, 5 µl of antagonist and 5 µl of agonist). The reaction was finalized by adding 10 µl of 4× EU-cAMP tracer working solution and 10 µl of 4× ULight-anti-cAMP working solution. The TR-FRET signal was measured after 1 hour using a Spectramax Paradigm (Molecular Devices).

Results.

As evidenced in Table 2 below, the compounds of the present invention inhibit the production of cAMP in response to the stimulation of A2A-overexpressing HEK cells with an A2A agonist or with Adenosine, in different conditions.

TABLE 2

| Compound | $IC_{50}$ (nM) (3 nM NECA as agonist, 0.1% BSA) | $IC_{50}$ (nM) (5 nM NECA as agonist, 2% HSA) | $IC_{50}$ (nM) (5 µM Adenosine as agonist, 2.0% HSA) |
|---|---|---|---|
| 1 | 0.6 | 9 | 511 |
| 2 | 0.3 | 17 | 708 |
| 4 | 0.5 | 2 | 49 |
| 5 | 0.4 | 8 | 241 |
| 6 | 0.5 | 8 | 179 |
| 7 | 0.8 | 2 | 35 |
| 8a | 0.6 | 2 | 25 |
| 8b | 0.6 | 3 | 28 |
| 9 | 3.4 | — | — |
| 10 | 2.3 | 14 | 607 |
| 11 | 2.0 | — | — |
| 12 | 14.2 | — | — |
| 13 | 0.6 | 2 | 63 |
| 14 | 0.7 | 11 | 567 |
| 15 | 2.6 | — | — |
| 16 | 3.2 | 14 | 0 |
| 17 | 1.0 | — | — |
| 18 | 1.7 | 85 | 2170 |
| 19 | 2.6 | — | — |
| 20 | 1.9 | 352 | — |
| 21 | 1.6 | 52 | 1306 |
| 22 | 1.4 | 6 | 352 |
| 23 | 0.6 | — | — |
| 24 | 0.8 | 2 | 137 |
| 25 | 1.2 | 6 | 300 |
| 27 | 0.3 | 2 | 112 |
| 28 | 0.2 | 4 | 115 |
| 29 | 0.4 | 11 | 350 |
| 30 | 0.4 | 1 | 42 |
| 31 | 0.4 | 1 | 42 |
| 32 | 4.3 | 7 | 356 |
| 34 | 0.3 | 6 | 207 |
| 35 | 0.7 | 13 | 378 |
| 36 | 0.7 | 8 | 260 |
| 37 | 0.8 | 9 | 398 |
| 38 | 0.3 | 9 | 552 |
| 39 | 0.8 | 15 | 719 |
| 40 | 0.7 | 7 | 261 |
| 41 | 0.8 | 14 | 423 |
| 42 | 0.4 | 19 | 332 |
| 43 | 0.2 | 1 | 36 |
| 44 | 0.5 | 11 | 127 |
| 45 | 0.8 | 3 | 100 |
| 47 | 1.8 | 1 | 43 |
| 48 | 0.1 | 0 | 9 |
| 49 | 0.5 | 16 | 465 |
| 50 | 0.3 | 0 | 13 |
| 51 | 0.3 | 0 | 16 |
| 52 | 0.3 | 1 | 26 |
| 53 | — | 4 | 127 |
| 54 | 0.8 | 3 | 138 |
| 55 | 1.0 | 2 | 141 |
| 56 | 0.2 | 1 | 25 |
| 57 | 0.2 | 2 | 56 |
| 58 | 0.3 | 1 | 41 |
| 59 | 0.9 | 21 | 1066 |
| 60 | 0.8 | 4 | 240 |
| 61 | 0.9 | 15 | 810 |
| 62 | 0.5 | 1 | 21 |
| 63 | 0.3 | 1 | 12 |
| 64 | 0.6 | 1 | 36 |
| 65 | 0.6 | 27 | 494 |
| 66 | 0.8 | 13 | 543 |
| 67 | 0.6 | 9 | 378 |
| 68 | 14.0 | 123 | 2697 |
| 69 | 0.5 | 5 | 211 |
| 70 | 0.6 | 3 | 124 |
| 71 | 0.4 | 3 | 79 |
| 72 | 1.0 | 3 | 86 |
| 73 | 3.4 | 8 | 304 |
| 74 | 1.2 | 20 | 495 |
| 75 | 24 | 100 | — |
| 76 | 5 | 151 | — |
| 77 | 0.5 | 3 | 158 |
| 78 | 0.6 | — | 130 |
| 79 | 0.3 | — | 77 |
| 80 | 0.4 | — | 146 |
| 81 | 117 | — | — |
| 82 | 0.2 | — | 15 |
| 83 | 0.4 | — | 212 |

TABLE 2-continued

| Compound | IC$_{50}$ (nM)<br>(3 nM NECA<br>as agonist,<br>0.1% BSA) | IC$_{50}$ (nM)<br>(5 nM NECA<br>as agonist,<br>2% HSA) | IC$_{50}$ (nM)<br>(5 μM Adenosine<br>as agonist,<br>2.0% HSA) |
|---|---|---|---|
| 84 | 0.1 | — | 71 |
| 85 | 0.4 | — | 220 |
| 86 | 0.6 | — | 747 |
| 87 | 1.1 | — | 432 |
| 88 | 0.2 | — | 22 |
| 89 | 0.6 | — | 9 |
| 90 | 5.7 | — | 24 |
| 91 | 0.8 | — | 168 |
| 92 | 0.7 | — | 388 |
| 93 | 0.4 | — | 33 |
| 95 | 0.7 | — | 37 |
| 96 | 0.4 | — | 19 |
| 97 | 1.1 | — | 30 |
| 98 | 0.1 | — | 7 |
| 99 | 0.5 | — | 64 |
| 100 | 0.1 | — | 10 |
| 101 | 0.7 | — | 124 |
| 102 | 0.7 | — | 185 |
| 103 | 1.1 | — | — |
| 104 | 0.5 | — | 45 |
| 105 | 0.7 | — | 95 |
| 106 | 0.3 | — | 205 |
| 107 | 0.1 | — | 35 |
| 108 | 0.7 | — | 172 |
| 111 | 0.6 | — | 91 |
| 112 | 0.8 | — | 53 |
| 113 | 0.4 | — | 37 |
| 114 | 0.3 | — | 80 |
| 116 | 1.2 | — | 245 |
| 117 | 329 | — | 3162 |
| 119 | 0.4 | — | 183 |
| 120 | 0.4 | — | 123 |
| 121 | 0.8 | — | 232 |
| 122 | 0.8 | — | 187 |
| 123 | 1.5 | — | 1443 |
| 124 | 2.3 | — | 2045 |
| 125 | 2.6 | — | 3620 |
| 126 | 0.6 | — | 78 |
| 127 | 0.5 | — | 35 |
| 128 | 0.4 | — | 46 |

II.1.B. Restoration of the Production of Pro-Inflammatory Cytokines by Human T-Cells Purpose.

When T-cells are activated, they produce pro-inflammatory cytokines. When the A2A receptor is activated in T cells, the amount of cytokines produced in response to stimulation of T-cells is reduced. The present assay thus aims at showing that the production of pro-inflammatory cytokines by T-cells may be restored by exposure to the compounds of the invention.

PBMC and CD3+ T Cell Isolation.

Venous blood from healthy volunteers, all of whom signed an informed consent approved by the Ethics Committee (FOR-UIC-BV-050-01-01 ICF_HBS_HD Version 5.0), was obtained via ImmuneHealth (Centre Hospitalier Universitaire Tivoli, La Louviere, Belgium). Mononuclear cells were collected by density gradient centrifugation, using SepMate-50 tubes (StemCell Technologies, Grenoble, France) and Lymphoprep (Axis-shield, Oslo, Norway) according to the manufacturer's instructions. CD3+ T cells were isolated by immunomagnetic negative selection, using the EasySep Human T Cell Isolation Kit (StemCell Technologies) as per manufacturer's instructions. CD3+ T cells were stored in heat inactivated foetal bovine serum (hiFBS; Gibco, ThermoFisher Scientific, Merelbeke, Belgium) containing 10% DMSO in liquid nitrogen.

Human IL-2 T Cell Assay.

Human purified CD3+ T cells were thawed and washed twice with RPMI1640 medium (with UltraGlutamine; Lonza, Verviers, Belgium) supplemented with 1× non-essential amino acids (Lonza), 2% Pen/Strep (Lonza) and 1 mM Sodium Pyruvate (Gibco) (complete media), containing 10% hiFBS. The cells were suspended either in complete media containing 20% hiFBS or in 100% heat inactivated human serum (hiHS; Sigma-Aldrich, Diegem, Belgium). Cells were activated by adding anti-CD3 and anti-CD28 coated microbeads (Dynabeads human T-activator CD3/CD28; Life Technologies, Paisley, UK), suspended either in complete media containing 20% hiFBS or in 100% hiHS. Selective A2A R agonist CGS-21680 (Sigma-Aldrich; stock solution of 10 mM in DMSO) was added at a final assay concentration of 0.5 or 5 μM. Serial dilutions of the compounds of the present invention were prepared and added to the wells. The cells were placed in a 37° C. humidified tissue culture incubator with 5% CO$_2$ for 72 hours. After 72 hours, supernatants were sampled and IL-2 was quantified using the IL-2 (human) AlphaLISA Biotin-Free Detection Kit (AL333F; Perkin-Elmer, Zaventem, Belgium), according to the manufacturer's instructions.

Results.

Addition of the A2A selective agonist CGS-21680 to CD3+ T cells decreases the amount of cytokines produced in response to stimulation with anti-CD3 and anti-CD28 coated microbeads. The compounds of the present invention dose-dependently restore the production of pro-inflammatory cytokines IL2 in CGS-21680-treated human T cells, with potencies indicated in Table 3 below.

TABLE 3

| Compound | IC$_{50}$ (nM)<br>(500 nM<br>CGS-21680<br>as agonist,<br>10% FBS) | IC$_{50}$ (nM)<br>(500 nM<br>CGS-21680<br>as agonist,<br>50% HSA) | IC$_{50}$ (nM)<br>(5000 nM<br>CGS-21680<br>as agonist,<br>10% FBS) | IC$_{50}$ (nM)<br>(5000 nM<br>CGS-21680<br>as agonist,<br>50% HSA) |
|---|---|---|---|---|
| 31 | 2.1 | 5.4 | 8.3 | 14 |
| 35 | 0.6 | 0.5 | 3.9 | 84 |
| 39 | 1.0 | 12 | 5.3 | 150 |
| 50 | 1.0 | 2.2 | 4.3 | 28 |
| 32 | — | — | — | 28 |
| 43 | — | — | — | 51 |
| 1 | — | — | — | 120 |
| 44 | — | — | — | 33 |
| 49 | — | — | — | 61 |
| 4 | 0.3 | — | — | 63 |
| 2 | 0.9 | — | — | 18 |

II.1.C. Restoration of the Production of Pro-Inflammatory Cytokines in Human Whole Blood Preparation of Test Tubes.

Tubes containing selected stimulants (SEB, LPS, zymosan, anti-CD3/CD28) and TruCulture medium were purchased from Myriad RBM (catalogue numbers respectively 782-001124, 782-001087, 782-001259 and 782-001125) and A2a agonists (CGS-21680 and NECA) and were added and the tubes directly frozen at −20° C. until use in the cell culture experiments.

Compound 7 was dissolved in DMSO at 10 mM and then dilutions were made with TC medium. Solutions were microscopically inspected to rule out the presence of particles. Freshly-prepared Compound 7-containing solutions were added to thawed TC tubes containing stimulants and 1 M CGS-21680, where appropriate.

Cell Culture.

Blood was drawn from healthy donors from the pre-tested donor pool of HOT Screen GmbH (age: 20-65 years, both sexes). Heparinized fresh peripheral whole blood (1 mL) from 3 healthy donors was added to thawed TC tubes and incubated in a heating block at 37° C. for 24 hours (LPS and zymosan stimulations), or 48 hours (SEB and anti-CD3/CD28 stimulation). At the end of the culture period, seraplas filters were inserted for harvesting of the supernatants. Supernatants were carefully collected, mixed, aliquoted and frozen at −20° C.

Mediators Quantification.

Cytokines and chemokines released in TC supernatants were measured using Human Cytokine MAP A panel for Luminex assays. The following mediators were analysed: GM-CSF, IFNg, IL-2, IL-3, IL-4, IL-5, IL-6, IL-7, IL-8, IL-10, IL-18, MCP-1, MIP-1a, MIP-1b, TNF-a, TNF-b.

Data Analysis.

To assess the biological activity of CGS-21680 and NECA, alterations of cytokine and chemokine secretion in TC supernatants induced by increasing doses of A2A agonists were analyzed. The percentage change of the concentrations of soluble mediators (SM) was calculated for each stimulation condition as follows:

% change=100×[$SMTC$+$A2A$ agonist]/[$SMTC$−$A2A$ agonist].

To assess the biological activity of Compound 7, the Compound 7-induced restoration of cytokine and chemokine secretion in CGS-21680-supplemented TC to baseline levels (i.e. TC stimulation without supplementation of CGS-21680) was analyzed.

The rescue of cytokine secretion was estimated by calculating the percentage control for each stimulation condition of whole blood TC as follows:

% control=100×[$SMTC$+$CGS$+Compound 7]/[$SMTC$−$CGS$−Compound 7].

Results.

LPS, zymosan, SEB and anti-CD3/CD28 induce the secretion of several cytokines and chemokines in whole blood cell cultures. The biological activity of two A2A agonists (CGS-21680 and NECA) on whole blood cell cultures stimulated with LPS, zymosan, SEB or anti-CD3/CD28 was assessed. Both agonists dose-dependently altered the secretion of several cytokines and chemokines. The effect was reproducible across the three tested donors, although the extent of alterations differed between individuals.

When 1 μM CGS-21680 or NECA were added to LPS- or zymosan-stimulated whole blood cultures, the effect on the release of both pro- and anti-inflammatory cytokines reached a plateau. In particular, levels of pro-inflammatory cytokines IFNg and TNFa were reduced by more than 50%, while levels of anti-inflammatory cytokines IL-8 and IL-10 were doubled.

Figure 1B:
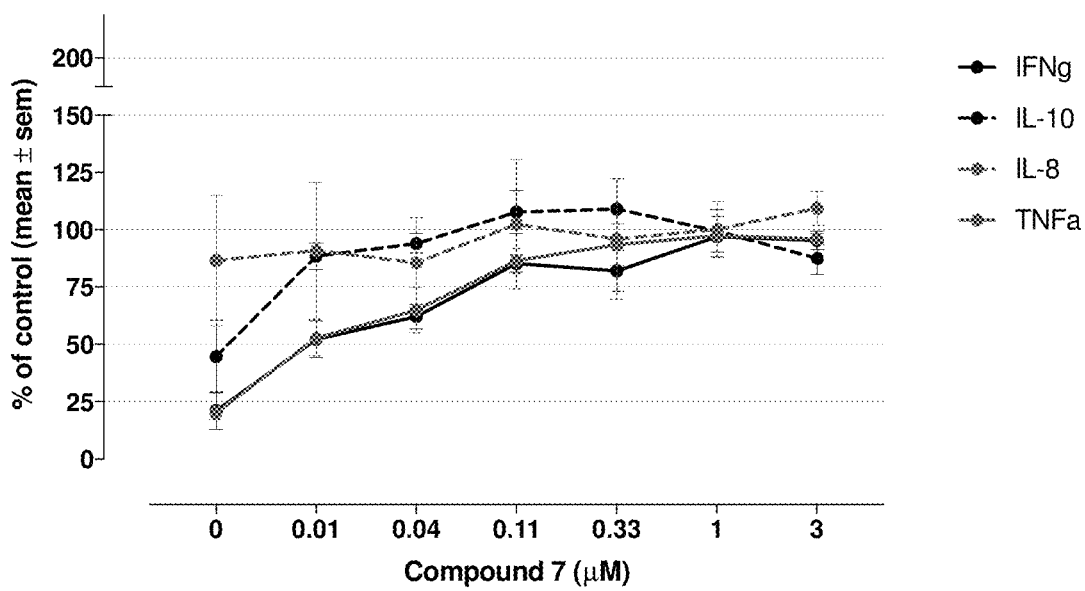

The ability of Compound 7 to revert alterations of cytokine and chemokine secretion induced by CGS-21680 on whole blood cell cultures stimulated with LPS, zymosan, or anti-CD3/CD28 was assessed. As shown in FIGS. 1A and 1B, Compound 7 dose-dependently restored the alterations of cytokine and chemokine secretion induced by CGS-21680, with a full rescue achieved with concentrations of 100-1000 nM of compound, depending on the conditions tested. The effect was reproducible across the three tested donors, although the extent of alterations differed between individuals.

Secretion of IFNg, TNFa, IL-8 and IL-10 in LPS- and zymosan-stimulated whole blood TC was mostly affected by CGS-21680 treatment, and was fully rescued by 40-100 nM Compound 7.

II.2. Modulation of pCREB

II.2.A. Modulation of pCREB in Human Immune Cells

Purpose.

The A2A receptor is known to mediate CREB phosphorylation. The present assay aims at showing that the compounds of the invention effectively inhibit A2A receptor by showing that CREB phosphorylation may be inhibited by exposing human immune cells to compounds of the invention.

Method.

Venous blood from healthy volunteers, all of whom signed an informed consent approved by the Ethics Committee (FOR-UIC-BV-050-01-01 ICF_HBS_HD Version 5.0), was obtained via ImmuneHealth (Centre Hospitalier Universitaire Tivoli, La Louviere, Belgium). Peripheral blood cells were treated with A2AR agonists CGS-21680 or NECA (Sigma-Aldrich, Diegem, Belgium), and a serial dilution of compounds of the present invention (all used stock solutions at 10 mM in DMSO). All dilutions were prepared in RPMI1640 medium (with UltraGlutamine; Lonza, Verviers, Belgium), and cells were incubated with compounds in a 37° C. humidified tissue culture incubator with 5% $CO_2$. After stimulation, cells were fixed and permeabilized, followed by intracellular staining using mouse anti-human pCREB antibodies (Clone J151-21; BD Biosciences) at room temperature. Data were acquired using an LSRFortessa flow cytometer (BD Biosciences) and analyzed using FlowJo software (FlowJo, LLC, Ashland, Oreg.).

Results.

Figure 2:
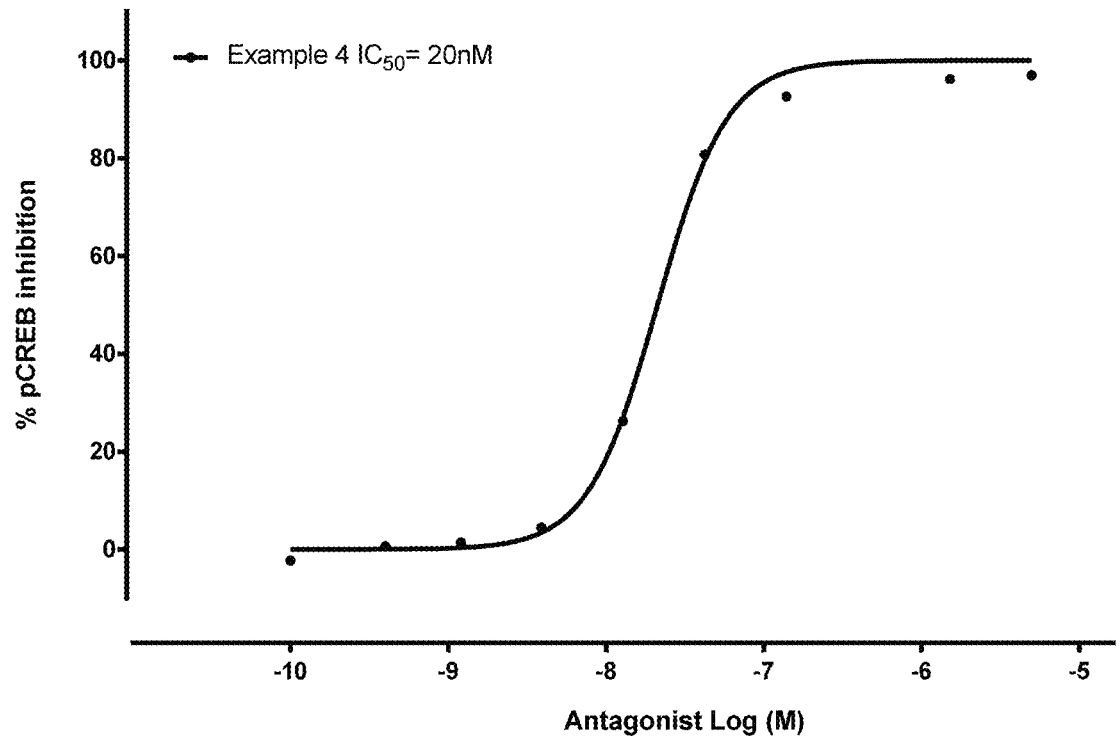
FIG. 2 is a graph showing the percentage pCREB inhibition in peripheral blood lymphocytes over the concentration of compound 4 of the present invention.

The compounds of the present invention were found to inhibit A2A-mediated CREB phosphorylation. For example, compound 4 exhibits an $IC_{50}$ of 20 nM in peripheral blood lymphocytes activated by NECA, as shown in FIG. 2.

II.2.B. Modulation of pCREB Ex Vivo in Mice

Purpose.

The A2A receptor is known to mediate CREB phosphorylation. The present assay aims at showing that the compounds of the invention effectively inhibit A2A receptor by showing that CREB phosphorylation may be inhibited in mice by dosing compounds of the invention to mice.

Method.

Compound 7 was formulated in 10% DMSO, 10% solutol, 80% water, pH 3 to obtain a homogeneous solution. Volume was calculated in order to administer the final dose in 100 μl per oral (PO). BALB/cAnNCrl female mice were purchased from Charles River Laboratories. Mice were orally treated with a single dose of A2A receptor antagonist. At the specific time point, animals were anesthetized with IP injection of 200 μl of ketamine 10%/xylazine 0.1% in PBS and blood was collected via retro-orbital bleeding in EDTA tubes. 45 μl of blood/well was dispensed in a master block. A2A receptor agonist NECA (Tocris) was prepared at concentration of 3 μM in RPMI 1640 (Lonza) supplemented with medium 2% Penicillin/Streptomycin (Lonza) and 50

μM 2-Mercaptoethanol (Sigma), and 50 μl was added to the wells and incubated for 45 minutes in a 37° C. humidified cell culture incubator with 5% CO2. The final concentration of DMSO in the assay was 0.125%. Cells were fixed by adding 1 ml of pre-warmed Lyse/Fix buffer (BD Biosciences) in each well, carefully mixed and incubated for 10 minutes in a 37DC humidified cell culture incubator with 5% CO2. Cells were pelleted by centrifugation at 600×g for 5 minutes. After a wash with 1 ml of DPBS with Ca2+Mg2+ (Lonza), cells were permeabilized with 200 μl of ice-cold Perm Buffer II (BD Biosciences) and incubated for 30 minutes on ice. During permeabilization, cells were transferred to a 96-well U-bottom plate. Cells were pelleted and washed twice with FACS buffer composed by PBS (Lonza), 0.1% BSA (VWR), 2 mM EDTA (Ambion). The FACS staining was performed resuspending the cells in FACS buffer containing Fc block (CD16/CD32 Monoclonal Antibody (93), eBioscience); after 5 min incubation at room temperature the antibody mix was added and cells incubated for 1 hour at room temperature. Cells were washed with FACS buffer and resuspended in the same for acquisition at BD Fortessa (BD Biosciences).

Data obtained with flow cytometry were analyzed with FlowJo 10.4 software. MFI (median fluorescence intensity) of our marker of interest, pCREB, was evaluated, normalized by the respective DMSO control (ratio) and reported in graph. Dose-response data were analyzed with GraphPad Prism 7.0 software using nonlinear regression applied to a sigmoidal dose-response model. Data were acquired using an LSRFortessa flow cytometer (BD Biosciences) and analyzed using FlowJo software (FlowJo, LLC, Ashland, Oreg.).

Results.

Compound 8a demonstrates full inhibition of A2A signaling pathway at CD4+ T cells 30 minutes after p.o. at a dose of 0.1 mg/Kg (Table 4). More than 70% of inhibition of A2A signaling pathway is still observed at the dose of 1 mg/Kg 12 hours after dosing. Similar data are obtained for the CD8+ T cells (Table 5).

TABLE 4

Activity of Compound 8a 30 minutes after oral administration. CREB phosphorylation assessed in CD4+ T cells

| | Treatment | Mean % inhibition | P value vs Group-1 |
|---|---|---|---|
| Group-1 | Vehicle | 0.0 | — |
| Group-2 | Compound 8a (0.01 mg/kg) | 28.3 | 0.0005 |
| Group-3 | Compound 8a (0.03 mg/kg) | 84.0 | <0.0001 |
| Group-4 | Compound 8a (0.1 mg/kg) | 100.7 | <0.0001 |
| Group-5 | Compound 8a (0.3 mg/kg) | 102.1 | <0.0001 |
| Group-6 | Compound 8a (1 mg/kg) | 101.0 | <0.0001 |

TABLE 5

Activity of Compound 8a 12 hours after oral administration. CREB phosphorylation assessed in CD4+ T cells

| | Treatment | Mean % inhibition | P value vs Group-1 |
|---|---|---|---|
| Group-1 | Vehicle | 0.0 | — |
| Group-2 | Compound 8a (0.1 mg/kg) | 40.0 | 0.0003 |
| Group-3 | Compound 8a (0.3 mg/kg) | 43.2 | 0.0001 |
| Group-4 | Compound 8a (1 mg/kg) | 72.9 | <0.0001 |
| Group-5 | Compound 8a (3 mg/kg) | 75.2 | <0.0001 |

II.3. Cytotoxicity Assay

Purpose.

The activation of the A2A receptor provides an immunosuppressive signal that inhibit cytotoxicity. The present assay aims at showing that the compounds of the invention effectively inhibit A2A receptor by showing that cytotoxicity may be increased by exposure to compounds of the invention.

Method.

A cytotoxicity assay was conducted to assess the antigen-specific cytotoxic activity of OT-I CD8 cells towards OVA-pulsed target cells and the effect of the compounds of the present invention to alleviate A2AR mediated inhibition of Cytotoxicity: OT1 cells were isolated from the spleens of C57BL/6-Tg(TcraTcrb)1100Mjb/Crl mice (Charles River). OT1 cells were primed with 1 ug/ml OVA peptide (Ovalbumin (257-264) chicken (S7951-1MG), Sigma Aldrich), in the presence of 5 μM CGS-21680 (Sigma-Aldrich) and increasing concentrations of compounds of the present invention, for 3 days in a 37° C. humidified tissue culture incubator with 5% $CO_2$. On day 3 all the cells were pooled and counted. For the cytotoxicity assay on day 3, Panc02 (target cells) were pulsed with 1 μg/ml OVA. Target cells and non-pulsed Panc02 cells (non-target bystander) were labelled with CFSE (C1157 (ThermoFisher)) and Cell-Trace™ Far Red Cell Proliferation Kit (C34564, ThermoFisher) respectively, according to manufacturer instructions. The stimulated OT-1 cells were added as effector cells in a 10:1 effector to target ratio. The co-culture reaction was incubated at 37° C. humidified tissue culture incubator with 5% $CO_2$. After 24 hrs cells were washed and stained with Live/dead fixable violet dead cell staining kit (Molecular Probes, L34955). Cytotoxic-killing of target cells was then measured by monitoring the change in the ratio of living target cells to non-target cells by flow-cytometry (MACSQuant® Analyzer 10—Miltenyi Biotec).

The % cytotoxicity is calculated as follows: % Cytotoxicity=$(1-R1/R2)*100$ wherein R1=(% of Target cells)/(% non-target cells)*100 in presence of effector cells and R2=(% of Target cells)/(% non-target cells)*100 in absence of effector cells.

Results.

Figure 3:
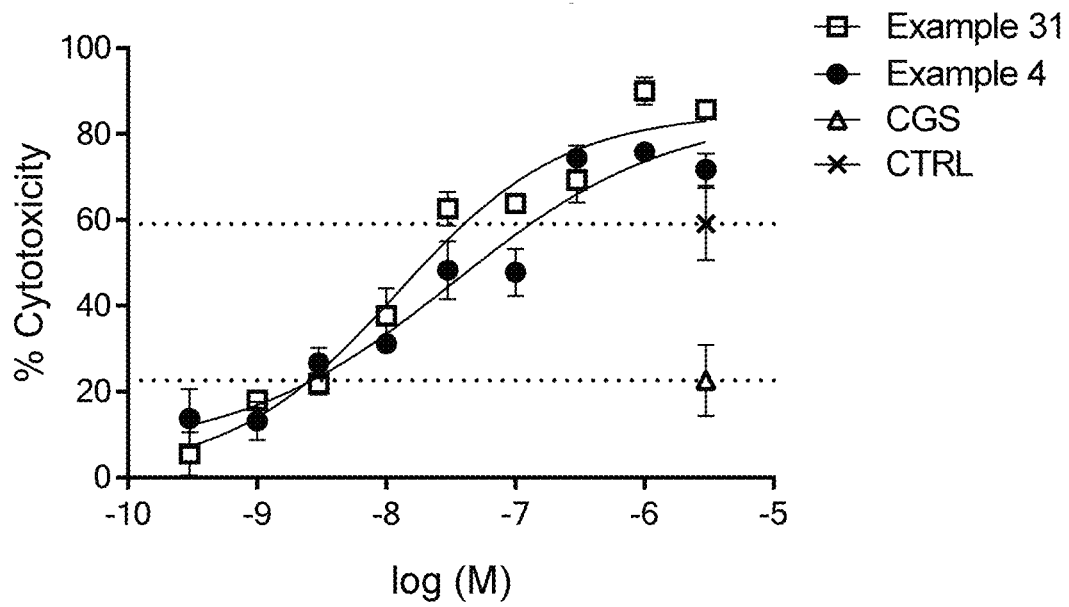
FIG. 3 is a graph showing the percentage of cytotoxicity over the over the concentration of compounds 4 and 31 of the present invention.

Addition to the media of A2A agonist CGS-21680 leads to a decrease of the cytotoxicity, which can be reduced dose-dependently by compounds of the present invention (Table 6). This is for example illustrated in FIG. 3 for compounds 4 and 31 of the invention.

TABLE 6

| Compound | IC$_{50}$ (nM) |
| --- | --- |
| Compound 31 | 12.6 |
| Compound 4 | 25.7 |
| Compound 7 | 108.5 |
| Compound 8a | 107.4 |
| Compound 77 | 663.9 |

III. PHARMACOKINETIC EXAMPLES

III.1. Determination of Permeability and Efflux in Caco-2 Cells

Purpose.

As mentioned in the introduction, the compounds of the invention have to exhibit a limited, if any, CNS penetrance, in order to avoid deleterious side effects that can occur if these compounds penetrate significantly into the brain.

The present assay aims at showing that the compounds of the invention do not have any significant CNS penetrance by showing that they are substrates of transporters that efflux them from brain.

Indeed, it is well known in the art that xenobiotics that are substrates of transporters such as P-Glycoprotein are not efficient in penetrating the Blood-Brain Barrier, and are thus less effective in the Central Nervous System (Alfred H. Schinkel, "P-Glycoprotein, a gatekeeper in the blood-brain barrier", Advanced Drug Delivery Reviews 36 (1999) 179-194).

The present assay thus aims at showing that the compounds of the present invention are substrates to such transporters present in the Caco-2 cell line and thus do not cross the Blood-Brain Barrier.

Material.

The transport buffer (TB, pH 7.4) used in the study is Hank's Buffered Saline Solution (HBSS, Gibco, Cat #14025-076) with 10 mM HEPES at pH 7.4. Fetal bovine serum (FBS) (Corning, Cat # Corning-35-076-CV, or other vendors), Minimum Essential Media (MEM) (Gibco, Cat #41500-034) as well as its supplements are purchased from Invitrogen (Carlsbad, Calif., USA). Caco-2 cell line (Cat # HTB-37) is purchased from the ATCC (Rockville, Md., USA). The organic solvents used in the study are purchased from Sigma Aldrich (St. Louis, Mo., USA).

Preparation of Working Solutions.

For reference compounds (fenoterol, propranolol and digoxin) and test compounds, 0.4 mM intermediate solutions are prepared by diluting 10 mM or other appropriate concentrations of DMSO stock solutions with DMSO. 2 µM dosing solutions for reference compounds and test compounds are prepared by spiking the appropriate volume of intermediate solution to TB with and without 1 µM Zosuquidar. The final concentration of DMSO is no more than 1% (v/v).

Caco-2 Cell Culture.

Caco-2 cells are grown in MEM supplemented with 2 mM L-glutamine, 10% FBS, 100 U/mL penicillin-G and 100 µg/mL streptomycin. The cells are incubated at 37° C., 5% $CO_2$ and relatively saturated humidity. After reaching 80-90% confluency, the cells are gently detached with 0.05% trypsin-EDTA solution. Cells at passage 30-50 are seeded on the 96-well BD insert system (Cat #359274) at the density of 1×105 cells/cm2 and cultured for 21-28 days with medium changed every 4-5 days.

Transport Procedures.

TB and dosing solutions were pre-warmed to 37° C. before transport assay. The cell monolayer was washed twice with HBSS containing 10 mM HEPES. For A-B (apical to basolateral) directional transport assay, 75 µL dosing solution is added to the apical well. Fill each basolateral well with 250 µL TB. For B-A (basolateral to apical) directional transport assay, 250 µL of dosing solution is added to the basolateral well after filling each apical well with 75 µL TB. Test compound(s) and digoxin are tested at 2 µM in the presence or absence of 1 µM zosuquidar bidirectionally in duplicate. Atenolol and propranolol are tested at 2 µM in the absence of zosuquidar in A to B direction in duplicate. The plates are incubated for 120 minutes at 37° C. with 5% $CO_2$ and saturated humidity. The time zero samples are generated by mixing 50 µL initial dosing solution of test compound or reference compound with 100 µL TB and 250 µL quench solution (acetonitrile (ACN) or other appropriate solvent with internal standard(s), based on the bioanalytical method development). At 120 minutes, 150 µL of solution is collected from each A-B receiver well followed by addition of 250 µL quench solution to get A-B receiver sample. And for other samples (A-B donor, B-A donor and receiver), 50 µL of solution is collected from each corresponding well followed by addition of 250 µL quench solution and 100 µL TB. All samples are vortex-mixed and centrifuged at 3220 g for 20 minutes. Subsequently, supernatant is diluted with ultra pure water for LC-MS/MS analysis. The concentrations of test compound in all samples are determined by LC-MS/MS and expressed as peak area ratio of analyte to internal standard.

The concentration of samples is expressed using the peak area ratio of Analyte to Internal Standard (Analyte/IS).

The apparent permeability coefficient (Papp) is calculated using the following equation:

$$P_{app} = V_R/(\text{Area}*\text{Time})*(C_R/C_0)$$

wherein $V_R$ is the solution volume in the receiver chamber (0.075 mL on the apical side, 0.25 mL on the basolateral side); Area is the surface area for the transport, i.e. 0.0804 cm2 for the area of the monolayer; Time is incubation time, expressed in seconds, 2 h=2×3600 s; $C_0$ is the initial concentration in the donor chamber; $C_R$ is the final concentrations in receiver chamber.

The efflux ratio is calculated using the following equation:

$$\text{Efflux ratio} = P_{app}(A-B)/P_{app}(B-A)$$

where Papp (A–B) and Papp (B–A) are the Papp values of compound in Apical to Basolateral and Basolateral to Apical directional transport, respectively.

Results.

Compounds are generally considered to be P-Glycoprotein substrates when the value of efflux ratio is >3. Compounds of the present invention typically have efflux ratios >3, as evidenced in Table 7 below.

TABLE 7

| Compounds | Efflux ratio |
| --- | --- |
| 1 | 48 |
| 2 | 28 |
| 3 | 4 |
| 4 | 123 |
| 5 | 67 |
| 6 | 59 |
| 7 | 1871 |
| 8a | 207 |

TABLE 7-continued

| Compounds | Efflux ratio |
|---|---|
| 8b | 300 |
| 9 | 8 |
| 10 | 24 |
| 24 | 117 |
| 25 | 472 |
| 27 | 187 |
| 30 | 3 |
| 31 | 28 |
| 32 | 329 |
| 34 | 192 |
| 35 | 26 |
| 39 | 110 |
| 40 | 25 |
| 43 | 164 |
| 44 | 69 |
| 45 | 41 |
| 46 | 30 |
| 47 | 329 |
| 48 | 166 |
| 49 | 97 |
| 50 | 38 |
| 51 | 469 |
| 52 | 34 |
| 54 | 24 |
| 55 | 205 |
| 56 | 1751 |
| 57 | 2196 |
| 62 | 23 |
| 63 | 264 |
| 64 | 60 |
| 66 | 1012 |
| 67 | 15 |
| 68 | 108 |
| 69 | 201 |
| 70 | 53 |
| 71 | 28 |
| 72 | 21 |
| 74 | 4 |
| 77 | 43 |
| 78 | 45 |
| 79 | 47 |
| 80 | 149 |
| 82 | 3 |
| 83 | 29 |
| 84 | 24 |
| 85 | 5 |
| 86 | 5 |
| 87 | 7 |
| 88 | 19 |
| 89 | 456 |
| 90 | 86 |
| 91 | 195 |
| 92 | 101 |
| 94 | 173 |
| 95 | 137 |
| 96 | 118 |
| 98 | 53 |
| 99 | 13 |
| 100 | 66 |
| 101 | 81 |
| 102 | 91 |
| 103 | 20 |
| 104 | 20 |
| 107 | 680 |
| 108 | 191 |
| 111 | 583 |
| 112 | 605 |
| 113 | 374 |
| 114 | 403 |
| 116 | 421 |
| 117 | 12 |
| 119 | 31 |
| 120 | 33 |
| 121 | 90 |
| 122 | 349 |
| 123 | 120 |
| 124 | 54 |
| 125 | 127 |
| 126 | 83 |
| 128 | 419 |

III.2. Determination of the Concentration A2A Antagonists in Brain and Cerebrospinal Fluid Compared to Plasma Purpose.

The present assay aims at showing that the compounds of the invention do not have any significant CNS penetrance by determining the concentration of these compounds in brain and cerebrospinal fluid (CSF) compared to plasma.

Method.

7-9 weeks old female Balb-c mice (obtained from SLAC Laboratory Animal Co. Ltd., Shanghai, China or SIPPR-B&K Laboratory Animal Co. Ltd., Shanghai, China) were dosed orally at a dose of 10 mg/kg, as a 1.00 mg/mL suspension in 10% DMSO+10% solutol+80% water, adjusted to pH 3-4 (homogenous opaque suspension).

Animals were fasted at least 12 hours prior to the administration. All animals had access to Certified Rodent Diet (Catalog # M01-F, SLAC Laboratory Animal Cl. Ltd., Shanghai, China) ad libitum 4 hours post dosing. Serial bleeding (about 30 μL blood per time point) were performed from submadibular or saphenous vein. Those samples were transferred into prechilled microcentrifuge tubes containing 2 μL of K2EDTA (0.5M) as anti-coagulant and placed on wet ice for further treatment. Immediately after blood collection, the whole brain was harvested immediately at the designed time points. At selected timepoints post-dose, CSF was collected from cisterna magna.

Blood samples were processed for plasma by centrifugation at approximately 4° C., 3000 g 15 min within half an hour of collection. Plasma samples were stored in polypropylene tubes, quick frozen over dry ice and kept at −70° C. until LC/MS/MS analysis. Brain samples were weighed, rinsed in cold distilled water to remove blood, and homogenized using pre-cooled water at the ratio of 1:4 (1 g brain used 4 mL water). And the brain homogenization was kept at −70° C. until LC/MSMS analysis. CSF was quick frozen over dry ice and kept at −70° C. until LC/MS/MS analysis.

Results.

For example, for compound 4 of the invention, no measurable quantity could be found in brain or CSF of mice in these conditions.

Individual and Mean Concentration of Example 4 after PO Administration (10 mg/kg) are provided in Table 8 below.

TABLE 8

| Time (h) | Mouse 1 | Mouse 2 | Mouse 3 | Mean |
|---|---|---|---|---|
| Plasma Concentration (ng/mL) | | | | |
| 0.500 | 576 | 995 | 765 | 779 |
| Brain Concentration (ng/g) | | | | |
| 0.500 | <15 | 16.9 | <15 | <16 |

TABLE 8-continued

| Time (h) | Mouse 1 | Mouse 2 | Mouse 3 | Mean |
|---|---|---|---|---|
| CSF Concentration (ng/mL) | | | | |
| 0.500 | <3 | <3 | <3 | <3 |
| Brain/Plasma Ratio | | | | |
| 0.500 | <0.026 | 0.0169 | <0.020 | <0.021 |
| CSF/Plasma Ratio | | | | |
| 0.500 | <0.005 | <0.003 | <0.004 | <0.004 |

III.3. Determination of the CNS Activity by a Locomotion Assay

Purpose.

In addition to adenosines immune-suppressive effects, it has also been established that adenosine modulates neuronal functions via its interaction with A2AR in the central nervous system. This interaction mediates part of the dopamine pathway which is involved in movement. Prevention of this signalling in the brain, by highly brain penetrant A2AR antagonist compounds such as Preladenant (originally synthesised for prevention of Parkinson's disease), have been shown to induce hyper locomotion in animals. This could potentially pose a problem with compounds that were purposed for Parksons's therapy (like Prelandenant) that are being repurposed for cancer immunotherapy.

The present assay aims at showing that the compounds of the invention do not have any significant CNS activity by using a method published by Hodgson et al. (J. Pharma. And Exp. Thera. 2009). The principle of this assay is that CGS21680, a brain penetrant A2AR specific adenosine analogue, induces immobility (hypolocomotion) within minutes after subcutaneous (s.c.) injection in mice. Therefore a mouse treated with a brain penetrant A2AR antagonist prior to treatment with CGS21680 will prevent hypolocomotion.

Preladenant, a reference brain penetrant compound, was compared to the compounds of the present invention at various concentrations per os (PO) for their effect on CGS21680 induced immobility.

Methods.

Compounds were administered 30 min prior to CGS21680 and locomotion was monitored over a 30 min period. Mice were scored (Table 9) for immobility, using a range of scores described in Table 10.

Results.

CGS21680, after 30 min, induced complete immobility when administered alone at 1 mg/kg (s.c.). Preladenant inhibited CGS21680 induced immobility when administered P.O. at 10 mg/kg, while the compounds of the present invention failed to completely prevent immobility when administered at equivalent doses. These data support the PK data from brain and spinal fluid, confirming that compounds of the present invention have decreased brain penetrance and CNS activity compared to Preladenant.

TABLE 9

Compounds of the present invention have decreased brain penetrant activity

| Compound | Dose (PO) | Score* |
|---|---|---|
| Vehicle | n/a | ++++ |
| Compound 4 | 10 mg/kg | +++ |
| Compound 7 | 10 mg/kg | +++ |

TABLE 9-continued

Compounds of the present invention have decreased brain penetrant activity

| Compound | Dose (PO) | Score* |
|---|---|---|
| Preladenant | 1 mg/kg | + |
| Preladenant | 10 mg/kg | 0 |

*Score observed in at least 60-100% of mice for 30 minutes, n = 3-5 mice per group

TABLE 10

Locomotion scoring

| Score | Description |
|---|---|
| 0 | Fully active - alert, running cage perimeter, rearing up, stretch, climbing, digging, gnawing, feeding |
| + | Active - alert, localized running, digging, rear up, stretching, gnawing |
| ++ | Activity limited - intermittent localized walking, gnawing, lethargic, some hunching |
| +++ | Activity severely abrogated/sleep - intermittent rearing up and gnawing, no walking, lethargic, eyes partly closed, hunched |
| ++++ | No activity/deep sleep - no movement, eyes closed, shivering |

The invention claimed is:
1. A compound of Formula (I)

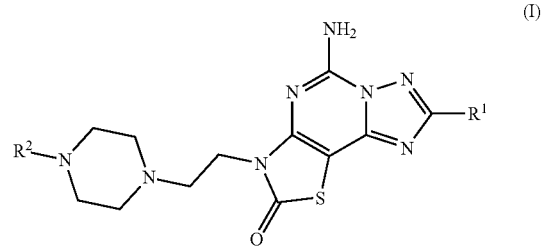

or a pharmaceutically acceptable salt thereof, wherein:
$R^1$ represents 5- or 6-membered heteroaryl or 5- or 6-membered aryl, wherein heteroaryl or aryl groups are optionally substituted by one or more substituent selected from C1-C6 alkyl and halo;
$R^2$ represents 6-membered aryl or 6-membered heteroaryl, wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkyl sulfonyl, aminosulfonyl, heterocyclylsulfonyl, alkylsulfonimidoyl, carbonylamino, sulfonylamino and alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl alkylsulfonyl and alkylsulfonealkyl; or the heteroaryl or aryl groups are optionally substituted with two substituents that form together with the atoms to which they are attached a 5- or 6-membered aryl ring, a 5- or 6-membered heretoaryl ring, a 5- or 6-membered cycloalkyl ring or a 5- or 6-membered heretocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkyl sulfoxidealkyl, alkylsulfonyl and alkylsulfonealkyl.

2. The compound according to claim 1, of Formula (Ia)

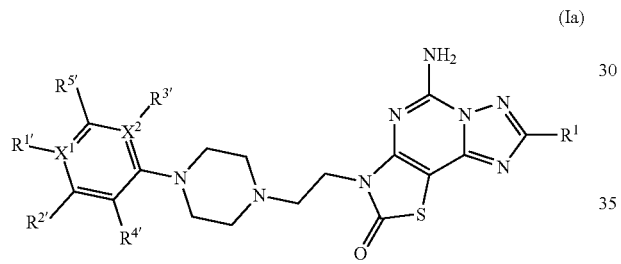

(Ia)

or a pharmaceutically acceptable salt thereof, wherein:
$R^1$ represents 5- or 6-membered heteroaryl or 5- or 6-membered aryl, wherein heteroaryl or aryl groups are optionally substituted by one or more substituent selected from $C_1$-$C_6$ alkyl and halo;
$X^1$ and $X^2$ represent each independently C or N;
$R^{1'}$ is absent when $X^1$ is N; or when $X^1$ is C, $R^{1'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkyl sulfonyl, aminosulfonyl, heterocyclylsulfonyl, alkylsulfonimidoyl, carbonylamino, sulfonylamino or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{2'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkyl sulfonyl, aminosulfonyl, heterocyclylsulfonyl, alkylsulfonimidoyl, carbonylamino, sulfonylamino, or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkyl sulfoxidealkyl, alkylsulfonyl and alkylsulfonealkyl;
$R^{1'}$ and $R^{2'}$ form together with the atoms to which they are attached a 5- or 6-membered aryl ring, a 5- or 6-membered heretoaryl ring, a 5- or 6-membered cycloalkyl ring or a 5- or 6-membered heretocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;
$R^{3'}$ is absent when $X^2$ is N; or when $X^2$ is C, $R^{3'}$ represents H or halo, preferably H or F;
$R^{4'}$ represents H or halo, preferably H or F; and
$R^{5'}$ represents H or halo, preferably H or F.

3. The compound according to claim 2, of Formula (Ia-1)

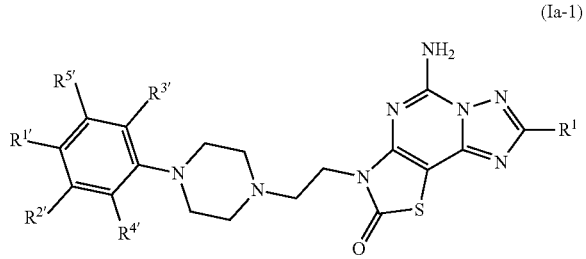

(Ia-1)

or a pharmaceutically acceptable salt thereof, wherein:
$R^1$ represents 5- or 6-membered heteroaryl or 5- or 6-membered aryl, wherein heteroaryl or aryl groups are optionally substituted by one or more substituent selected from $C_{1-6}$ alkyl and halo;

R[1'] is absent when X[1] is N; or when X[1] is C, R[1'] represents H, halo, alkyl, hetercyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, diakylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

R[2'] represents H, halo, alkyl, hetercyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl; said substituents being optionally substituted by one or more substituent selected from oxo, halo, hycroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, diakylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

or R[1'] and R[2'] form together with the atoms to which they are attached a 5- or 6- membered aryl ring, a 5- or 6-membered heretoaryl ring, a 5- or 6-membered cycloalkyl ring or a 5- or 6-membered heretycyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, diakylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarobnyl, hetercyclylcarbonyl, alkenylcarbonyl, alkynylcarbonyl, alkylsulfoxide, alkylsulfoxidealkyl, alkylsulfonyl and alkylsulfonealkyl;

R[3'] is absent when X[2] is N; or when X[2] is C, R[3'] represents H or halo, preferably H or F;

R[4'] represents H or halo, preferably H or F; and

R[5'] represents H or Halo, prefereably H or F.

4. The compound according to claim 2, of Formula (Ia-1a)

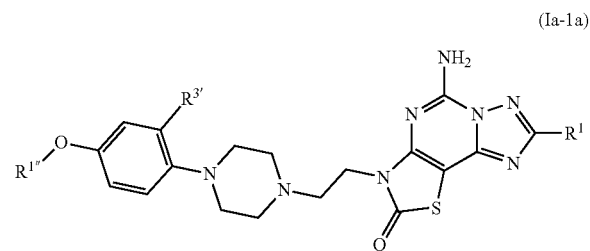

(Ia-1a)

or a pharmaceutically acceptable salt thereof, wherein:

R[1] represents 5- or 6-membered heteraryl or 5- or 6-membered aryl, wherein heteroaryl or aryl groups are optionally substituted by one or more substituent selected from $C_{1-6}$ alkyl and halo;

R[3'] is absent when X[2] is N; or when X[2] is C, R[3'] represents H or halo, preferably H or F; and R[1"] represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, hetercyclylcarbonyl, alkenylcarbonyl, alkynylcarbonyl, alkylsulfoxide, alkylsulfoxidealkyl, alkylsulfonyl and alkylsulfonealkyl.

5. The compound according to claim 2, of Formula (Ia-1b)

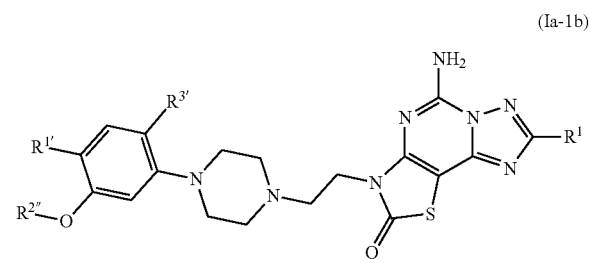

(Ia-1b)

or a pharmaceutically acceptable salt thereof, wherein:

R[1] represents 5- or 6-membered heteraryl or 5- or 6-membered aryl, wherein heteroaryl or aryl groups are optionally substituted by one or more substituent selected from $C_1$-$C_6$ alkyl and halo;

213

R3' is absent when X2 is N; or when X2 is C, R3' represents H or halo, preferably H or F;
R1' represents H or halo, preferably H or F; and
R2'' represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

6. The compound according to claim 2, of Formula (Ia-1c) or (Ia-1d)

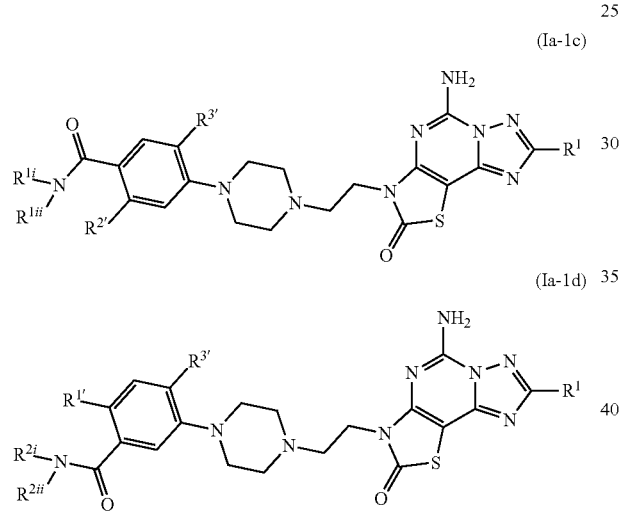

(Ia-1c)

(Ia-1d)

or a pharmaceutically acceptable salt thereof, wherein:
R1 represents 5- or 6-membered heteraryl or 5- or 6-membered aryl, wherein heteroaryl or aryl groups are optionally substituted by one or more substituent selected from C1-C6 alkyl and halo;
R3' is absent when X2 is N; or when X2 is C, R3' represents H or halo, preferably H or F;
R1' represents H or halo, preferably H or F;
R2' represents H or halo, preferably H or F;
R1i and R1ii represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl,

214 dialkylaminoalkylcarbonyl, heterocyclylcarbonyl, alkenylcarbonyl, alkynylcarbonyl, alkylsulfoxidealkyl or alkylsulfonealkyl; and
R2i and R2ii represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

7. The compound according to claim 2, of Formulae (Ia-2) or (Ia-3)

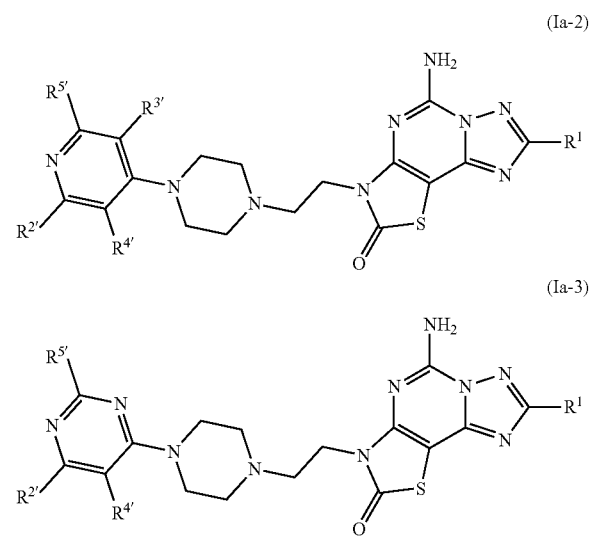

(Ia-2)

(Ia-3)

or a pharmaceutically acceptable salt thereof, wherein:
R1 represents 5- or 6-membered heteroaryl or 5- or 6-membered aryl, wherein heteroaryl or aryl groups are optionally substituted by one or more substituent selected from C1-C6 alkyl and halo
R2' represents H, halo, alkyl, hetercyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl; said substituents being optionally substituted by one or more substitutent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{3'}$ is absent when $X^2$ is N; or when $X^2$ is C, $R^{3'}$ represents H or halo, preferably H or F;

$R^{4'}$ represents H or halo, preferably H or F; and $R^{5'}$ represents H or halo, preferably H or F.

8. The compound of claim 1, selected from the group consisting of:
- 3-(2-(4-(4-((1H-1,2,3-triazolo-1-yl)methoxy-2fluorophenyl)piperazine-1-yl)ethyl)-5-amino-(8-(furan-2-yl)thiazolo[5,4-e][1,2,4]triazolo[1,5-c]pyrimidine-2(3H)-one;
- 5-((4-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-3-fluorophenoxy)methyl)-1,3,4-oxadiazol-2 (3H)-one;
- 5-amino-3-(2-(4-(3-fluoropyridin-4-yl)piperazin-1-yl) ethyl)-8-(furan-2-yl)thiazolo[5,4-e][1,2,4]triazolo[1,5-c]pyrimidin-2(3H)-one;
- 2-(5-(4-(2-(5-amino-8-(furan-2-yl)-2-oxothiazolo[5,4-e] [1,2,4]triazolo [1,5-c] pyrimidin-3(2H)-yl)ethyl)piperazin-1-yl)-2,4-difluorophenoxy)acetamide;
- (S)-5-amino-3-(2-(4-(2-fluoro-4-(2-(methylsulfinyl) ethoxy)phenyl)piperazin-1-yl)ethyl)-8-(furan-2-yl)thiazolo[5,4-e][1,2,4]triazolo[1,5-c]pyrimidin-2(3H)-one;
- (R)-5-amino-3-(2-(4-(2-fluoro-4-(2-(methylsulfinyl) ethoxy)phenyl)-piperazin-1-yl)ethyl)-8-(furan-2-yl) thiazolo[5,4-e][1,2,4]triazolo[1,5-c]pyrimidin-2(3H)-one;
- (R,S)-5-amino-3-(2-(4-(2,4-difluoro-5-(2-(methylsulfinyl)ethoxy)phenyl)piperazin-1-yl)ethyl)-8-(furan-2-yl) thiazolo[5,4-e] [1,2,4]triazolo[1,5-c]pyrimidin-2(3H)-one;
- (R)-5-amino-3-(2-(4-(2,4-difluoro-5-(2-(methylsulfinyl) ethoxy)phenyl)piperazin-1-yl)ethyl)-8-(furan-2-yl)thiazolo[5,4-e][1,2,4]triazolo[1,5-c]pyrimidin-2(3H)-one;
- (S)-5-amino-3-(2-(4-(2,4-difluoro-5-(2-(methylsulfinyl) ethoxy)phenyl)piperazin-1-yl)ethyl)-8-(furan-2-yl)thiazolo[5,4-e] [1,2,4]triazolo[1,5-c]pyrimidin-2(3H)-one;
- 5-amino-8-(furan-2-yl)-3-(2-(4-(4-(2-hydroxyethoxy) phenyl)piperazin-1-yl)ethyl)thiazolo[5,4-e][1,2,4]triazolo[1,5-c]pyrimidin-2(3H)-one;
- 2-(4-(4-(2-(5-amino-8-(furan-2-yl)-2-oxothiazolo [5,4-e] [1,2,4]triazolo[1,5-c]pyrimidin-3(2H)-yl)ethyl)piperazin-1-yl)phenoxy)acetic acid; 2-(4-(4-(2-(5-amino-8-(furan-2-yl)-2-oxothiazolo [5,4-e][1,2,4]triazolo[1,5-c] pyrimidin-3(2H)-yl)ethyl)piperazin-1-yl)phenoxy) acetamide;
- 5-amino-3-(2-(4-(4-(2,3-dihydroxypropoxy)phenyl)piperazin-1-yl)ethyl)-8-(furan-2-yl)thiazolo [5,4-e] [1,2,4] triazolo [1,5-c]pyrimidin-2(3H)-one; 5-amino-3-(2-(4-(4-(2-aminoethoxy)phenyl)piperazin-1-yl)ethyl)-8-(furan-2-yl)thiazolo[5,4-e] [1,2,4]triazolo[1,5-c] pyrimidin-2(3H)-one;
- 4-(4-(2-(5-amino-8-(furan-2-yl)-2-oxothiazolo[5,4-e] [1,2,4]triazolo[1,5-c]pyrimidin-3(2H)-yl) ethyl)piperazin-1-yl)benzamide;
- 4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-N-methylbenzamide;
- 5-amino-8-(furan-2-yl)-3-(2-(4-(4-(2-morpholinoethoxy) phenyl)piperazin-1-yl)ethyl)thiazolo[5,4-e][1,2,4]triazolo[1,5-c]pyrimidin-2(3H)-one;
- 5-amino-3-(2-(4-(4-(2-(dimethylamino)ethoxy)phenyl) piperazin-1-yl)ethyl)-8-(furan-2-yl)thiazolo [5,4-e] [1,2,4]triazolo [1,5-c]pyrimidin-2(3H)-one;
- 4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)benzenesulfonamide;
- 4-(4-(2-(5-amino-8-(furan-2-yl)-2-oxothiazolo[5,4-e][1, 2,4]triazolo[1,5-c] pyrimidin-3(2H)-yl)ethyl) piperazin-1-yl)-N-methylbenzenesulfonamide;
- 5-amino-8-(furan-2-yl)-3-(2-(4-(4-(methylsulfonyl) phenyl)piperazin-1-yl)ethyl)thiazolo[5,4-e][1,2,4]triazolo [1,5-c]pyrimidin-2(3H)-one;
- 5-amino-8-(furan-2-yl)-3-(2-(4-(4-(methylsulfinyl) phenyl)piperazin-1-yl)ethyl)thiazolo[5,4-e][1,2,4]triazolo [1,5-c]pyrimidin-2(3H)-one;
- 3-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)benzamide;
- 5-amino-8-(furan-2-yl)-3-(2-(4-(3-(2-hydroxyethoxy) phenyl)piperazin-1-yl)ethyl)thiazolo[5,4-e][1,2,4]triazolo[1,5-c]pyrimidin-2(3H)-one;
- 5-amino-3-(2-(4-(2-fluoro-4-(2-oxo-2-(piperazin-1-yl) ethoxy)phenyl)piperazin-1-yl)ethyl)-8-(furan-2-yl)thiazolo[5,4-e][1,2,4]triazolo[1,5-c]pyrimidin-2(3H)-one;
- 5-amino-3-(2-(4-(2-fluoro-4-(piperidin-4-ylmethoxy) phenyl)piperazin-1-yl)ethyl)-8-(furan-2-yl)thiazolo[5, 4-e][1,2,4]triazolo[1,5-c]pyrimidin-2(3H)-one;
- 5-amino-3-(2-(4-(2-fluoro-4-(piperazine-1-carbonyl) phenyl)piperazin-1-yl)ethyl)-8-(furan-2-yl)thiazolo[5, 4-e][1,2,4]triazolo[1,5-c]pyrimidin-2(3H)-one;
- 5-amino-3-(2-(4-(2-fluoro-4-(2-(piperazin-1-yl)ethoxy) phenyl)piperazin-1-yl)ethyl)-8-(furan-2-yl)thiazolo[5, 4-e][1,2,4]triazolo[1,5-c]pyrimidin-2(3H)-one;
- 5-amino-3-(2-(4-(2-fluoro-4-(piperazin-1-yl sulfonyl) phenyl)piperazin-1-yl)ethyl)-8-(furan-2-yl)thiazolo[5, 4-e][1,2,4]triazolo[1,5-c]pyrimidin-2(3H)-one;
- 5-amino-3-(2-(4-(2-fluoro-4-(methylsulfonyl)phenyl) piperazin-1-yl)ethyl)-8-(furan-2-yl)thiazolo [5,4-e] [1,2,4]triazolo [1,5-c]pyrimidin-2(3H)-one;
- 4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-N-(2-aminoethyl)-3-fluorobenzamide;
- 4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-3-fluoro-N-(2-(methylamino)ethyl) benzamide;
- 4-(4-(2-(5-amino-8-(furan-2-yl)-2-oxothiazolo[5,4-e][1, 2,4]triazolo[1,5-c]pyrimidin-3 (2H)-yl)ethyl)piperazin-1-yl)-N-(2-(dimethylamino)ethyl)-3-fluorobenzamide;
- 4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-3-fluoro-N-(2-hydroxyethyl)benzamide;
- 4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-N-(2,3-dihydroxypropyl)-3-fluorobenzamide;
- 2-(4-(4-(2 5-amino-8-(furan-2-yl)-2-oxothiazolo[5,4-e] [1,2,4]triazolo[1,5-c]pyrimidin-3(2H)-yl)ethyl)piperazin-1-yl)-3-fluorophenoxy)acetic acid;
- 2-(4-(4-(2-(5-amino-8-(furan-2-yl)-2-oxothiazolo [5,4-e] [1,2,4]triazolo[1,5-c]pyrimidin-3(2H)-yl)ethyl) piperazin-1-yl)-3,5-difluorophenoxy) acetic acid;
- 2-(4-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-3-fluorophenoxy)propanoic acid;

(S)-2-(4-(4-(2-(5-amino-8-(furan-2-yl)-2-oxothiazolo [5,4-e][1,2,4]triazolo[1,5-c]pyrimidin-3(2H)-yl)ethyl) piperazin-1-yl)-3-fluorophenoxy)propanoic acid;

2-(4-(4-(2 5-amino-8-(furan-2-yl)-2-oxothiazolo[5,4-e] [1,2,4]triazolo[1,5-c]pyrimidin-3(2H)-yl)ethyl)piperazin-1-yl)-3-fluorophenoxy)-2-methylpropanoic acid;

3-(4-(4-(2 5-amino-8-(furan-2-yl)-2-oxothiazolo[5,4-e] [1,2,4]triazolo[1,5-c]pyrimidin-3(2H)-yl)ethyl)piperazin-1-yl)-3-fluorophenyl)propanoic acid;

4-(4-(4-(2-(5-amino-8-(furan-2-yl)-2-oxothiazolo [5,4-e] [1,2,4]triazolo[1,5-c]pyrimidin-3(2H)-yl)ethyl)piperazin-1-yl)-3-fluorophenoxy)butanoic acid;

2-(3-(4-(2-(5-amino-8-(furan-2-yl)-2-oxothiazolo[5,4-e] [1,2,4]triazolo[1,5-c]pyrimidin-3(2H)-yl)ethyl)piperazin- 1-yl)-2,6-difluorophenoxy) acetic acid;

2-(5-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-2,4-difluorophenoxy) acetic acid;

4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-3-fluorobenzoic acid;

2-((2-(4-(4-(2-(5-amino-8-(furan-2-yl)-2-oxothiazolo [5,4-e][1,2,4]triazolo[1,5-c]pyrimidin-3 (2H)-yl)ethyl) piperazin-1-yl)-3-fluorophenoxy)ethyl) amino)acetamide;

2-((2-(4-(4-(2-(5-amino-8-(furan-2-yl)-2-oxothiazolo [5,4-e][1,2,4]triazolo[1,5-c]pyrimidin-3(2H)-yl)ethyl) piperazin-1-yl)-3-fluorophenoxy)ethyl)(methyl)amino) acetamide;

5-amino-3-(2-(4-(2-fluoro-4-(piperidin-4-yloxy) phenyl) piperazin-1-yl) ethyl)-8-(furan-2-yl) thiazolo[5,4-e][1, 2,4] triazolo[1,5-c]pyrimidin-2(3H)-one;

5-amino-3-(2-(4-(2-fluoro-4-(pyrrolidin-3-yloxy)phenyl) piperazin-1-yl)ethyl)-8-(furan-2-yl)thiazolo[5,4-e][1,2, 4]triazolo[1,5-c]pyrimidin-2(3H)-one;

3-(2-(4-(4-((1H-1,2,4-triazol-3-yl)methoxy)-2-fluorophenyl)piperazin-1-yl)ethyl)-5-amino-8-(iuran-2-yl)thiazolo[5,4-e][1,2,4]triazolo[1,5-c]pyrimidin-2(3H)-one;

2-(4-(4-(2-(5-amino-8-(furan-2-yl)-2-oxothiazolo [5,4-e] [1,2,4]triazolo[1,5-c]pyrimidin-3 (2H)-yl)ethyl)piperazin-1-yl)-3-fluorophenoxy)-N-(2-(methylamino) ethyl) acetamide;

2-(4-(4-(2-(5-amino-8-(furan-2-yl)-2-oxothiazolo [5,4-e] [1,2,4]triazolo[1,5-c]pyrimidin-3(2H)-yl) ethyl)piperazin-1-yl)-3-fluorophenoxy)-N-(2-(dimethylamino) ethyl) acetamide;

2-(4-(4-(2-(5-amino-8-(furan-2-yl)-2-oxothiazolo [5,4-e] [1,2,4]triazolo[1,5-c]pyrimidin-3 (2H)-yl)ethyl)piperazin-1-yl)-3-fluorophenoxy)-N-(2-aminoethyl)acetamide;

(R)-2-(4-(4-(2-(5-amino-8-(furan-2-yl)-2-oxothiazolo [5,4-e][1,2,4]triazolo[1,5-c]pyrimidin-3(2H)-yl)ethyl) piperazin-1-yl)-3-fluorophenoxy)propanoic acid;

2-(4-(4-(2-(5-amino-8-(furan-2-yl)-2-oxothiazolo [5,4-e] [1,2,4]triazolo[1,5-c]pyrimidin-3(2H)-yl) ethyl)piperazin-1-yl)-3-fluorophenoxy)acetamide;

4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-3-fluoro-N-methyl-N-(2-(methylamino)ethyl) benzamide;

4-(4-(2-(5-amino-8-(furan-2-yl)-2-oxothiazolo[5,4-e][1, 2,4]triazolo[1,5-c]pyrimidin-3 (2H)-yl)ethyl)piperazin-1-yl)-N-(2-(dimethylamino)ethyl)-3-fluoro-N-methylbenzamide;

(R)-4-(4-(2-(5-amino-8-(furan-2-yl)-2-oxothiazolo [5,4-e][1,2,4]triazolo[1,5-c]pyrimidin-3 (2H)-yl) ethyl)piperazin-1-yl)-N-(1-(dimethylamino) propan-2-yl)-3-fluorobenzamide;

2-(4-(4-(2-(5-amino-8-(furan-2-yl)-2-oxothiazolo [5,4-e] [1,2,4]triazolo[1,5-c]pyrimidin-3(2H)-yl) ethyl)piperazin-1-yl)-3-fluorophenoxy)-N-methyl-N-(2-(methylamino)ethyl) acetamide;

2-(5-(4-(2-(5-amino-8-(furan-2-yl)-2-oxothiazolo [5,4-e] [1,2,4]triazolo[1,5-c]pyrimidin-3(2H)-yl)ethyl)piperazin-1-yl)-2,4-difluorophenoxy)-2-methylpropanoic acid;

(S)-2-(5-(4-(2-(5-amino-8-(furan-2-yl)-2-oxothiazolo [5,4-e][1,2,4]triazolo[1,5-c]pyrimidin-3(2H)-yl)ethyl) piperazin-1-yl)-2,4-difluorophenoxy) propanoic acid;

(R)-2-(5-(4-(2-(5-amino-8-(furan-2-yl)-2-oxothiazolo [5,4-e][1,2,4]triazolo[1,5-c]pyrimidin-3(2H)-yl)ethyl) piperazin-1-yl)-2,4-difluorophenoxy) propanoic acid;

2-(5-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-2,4-difluorophenoxy)-N-(2-(methylamino) ethyl) acetamide;

2-(5-(4-(2-(5-amino-8-(furan-2-yl)-2-oxothiazolo [5,4-e] [1,2,4]triazolo[1,5-c]pyrimidin-3(2H)-yl)ethyl)piperazin-1-yl)-2,4-difluorophenoxy)-N-(2-(dimethylamino)ethyl) acetamide;

5-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-N-(2-(dimethylamino)ethyl)-2,4-difluoro-N-methylbenzamide;

4-(5-(4-(2-(5-amino-8-(furan-2-yl)-2-oxothiazolo [5,4-e] [1,2,4]triazolo[1,5-c]pyrimidin-3(2H)-yl)ethyl)piperazin-1-yl)-2,4-difluorophenoxy) butanoic acid;

3-(2-(4-(5-(1H-tetrazol-5-yl)methoxy)-2,4-difluorophenyl)piperazin-1-yl)ethyl)-5-amino-8-(furan-2-yl)thiazolo[5,4-e][1,2,4]triazolo[1,5-c]pyrimidin-2(3H)-one;

5-amino-3-(2-(4-(2-fluoro-4-((1-methyl-1H-1,2,4-triazol-3-yl)methoxy) phenyl)piperazin-1-yl)ethyl)-8-(furan-2-yl)thiazolo[5,4-e] [1,2,4]triazolo [1,5-c]pyrimidin-2 (3H)-one;

5-amino-3-(2-(4-(2,4-difluoro-5-((1-methyl-1H-1,2,4-triazol-3-yl) methoxy)phenyl)piperazin-1-yl)ethyl)-8-(furan-2-yl)thiazolo[5,4-e] [1,2,4]triazolo[1,5-c]pyrimidin-2(3H)-one;

4-(4-(2-(5-amino-8-(furan-2-yl)-2-oxothiazolo[5,4-e][1, 2,4]triazolo[1,5-c]pyrimidin-3(2H)-yl) ethyl)piperazin-1-yl)-3-fluoro-N-(2-(methyl (oxetan-3-yl)amino) ethyl) benzamide;

4-(4-(2-(5-amino-8-(furan-2-yl)-2-oxothiazolo[5,4-e][1, 2,4]triazolo[1,5-c]pyrimidin-3(2H)-yl)ethyl)piperazin-1-yl)-3-fluoro-N-(2-(2-hydroxyethyl)amino)ethyl) benzamide;

2-amino-N-(2-(4-(4-(2-(5-amino-8-(furan-2-yl)-2-oxothiazolo[5,4-e] [1,2,4]triazolo[1,5-c] pyrimidin-3(2H)-yl) ethyl)piperazin-1-yl)-3-fluorophenoxy)ethyl) acetamide;

(S)-2-amino-N-(2-(4-(4-(2-(5-amino-8-(furan-2-yl)-2-oxothiazolo[5,4-e] [1,2,4]triazolo[1,5-c]pyrimidin-3 (2H)-yl)ethyl)piperazin-1-yl)-3-fluorophenoxy)ethyl)-3-methylbutanamide;

ethyl 2-(5-(4-(2-(5-amino-8-(furan-2-yl)-2-oxothiazolo [5,4-e] [1,2,4]triazolo[1,5-c] pyrimidin-3(2H)-yl) ethyl)piperazin-1-yl)-2,4-difluorophenoxy) acetate;

2-(5-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-2,4-difluorophenoxy) acetonitrile;

5-amino-8-(furan-2-yl)-3-(2-(4-(pyridin-4-yl) piperazin-1-yl)ethyl)thiazolo[5,4-e] [1,2,4]triazolo[1,5-c]pyrimidin-2(3H)-one;
5-amino-8-(furan-2-yl)-3-(2-(4-(pyrimidin-4-yl)piperazin-1-yl)ethyl)thiazolo[5,4-e][1,2,4]triazolo[1,5-c]pyrimidin-2(3H)-one;
5-amino-3-(2-(4-(2,4-difluoro-5-(2-(methylsulfonyl)ethoxy)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2-fluoro-4-(2-(methylsulfonyl)ethoxy)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(6-fluoro-2-oxoindolin-5-yl)piperazin-1-yl)ethyl)-8-(furan-2-yl)thiazolo[5,4-e][1,2,4]triazolo[1,5-c]pyrimidin-2(3H)-one;
5-amino-3-(2-(4-(2-fluoro-4-(S-methylsulfonimidoyl)phenyl)piperazin-1-yl)ethyl)-8-(furan-2-yl)thiazolo[5,4-e][1,2,4]triazolo[1,5-c]pyrimidin-2(3H)-one;
5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-N-(2-(dimethylamino)ethyl)-2,4-difluorobenzamide;
5-amino-3-(2-(4-(5-fluoro-2-methylpyridin-4-yl)piperazin-1-yl)ethyl)-8-(furan-2-yl)thiazolo[5,4-e][1,2,4]triazolo[1,5-c]pyrimidin-2(3H)-one;
5-amino-3-(2-(4-(2-fluoro-4-(((3R,4R)-4-hydroxytetrahydrofuran-3-yl)oxy)phenyl)piperazin-1-yl)ethyl)-8-(furan-2-yl)thiazolo [5,4-e] [1,2,4]triazolo[1,5-c]pyrimidin-2(3H)-one;
5-amino-3-(2-(4-(2-fluoro-4-(((3S,4S)-4-hydroxytetrahydrofuran-3-yl)oxy)phenyl)piperazin-1-yl)ethyl)-8-(furan-2-yl)thiazolo [5,4-e] [1,2,4]triazolo[1,5-c]pyrimidin-2(3H)-one;
5-amino-3-(2-(4-(2-fluoro-4-(2-hydroxy-2-methylpropoxy)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2-fluoro-4-(2-hydroxypropan-2-yl)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2-fluoro-4-(3,3,3-trifluoro-2-hydroxypropoxy)phenyl)piperazin-1-yl)ethyl)-8-(furan-2-yl)thiazolo[5,4-e] [1,2,4]triazolo[1,5-c]pyrimidin-2(3H)-one;
5-amino-3-(2-(4-(2-fluoro-5-(2-hydroxyethoxy)phenyl)piperazin-1-yl)ethyl)-8-(furan-2-yl)thiazolo [5,4-e] [1,2,4]triazolo [1,5-c]pyrimidin-2(3H)-one;
5-amino-3-(2-(4-(2,4-difluoro-5-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2,4-difluoro-5-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo [5,4-e] [1,2,4]triazolo[1,5-c]pyrimidin-2(3H)-one;
5-amino-3-(2-(4-(2,4-difluoro-5-(((3S,4S)-4-fluoropyrrolidin-3-yl)oxy)phenyl)piperazin-1-yl)ethyl)-8-(furan-2-yl)thiazolo [5,4-e] [1,2,4]triazolo[1,5-c]pyrimidin-2(3H)-one;
5-amino-3-(2-(4-(2,4-difluoro-5-(((3R,4S)-4-fluoropyrrolidin-3-yl)oxy)phenyl)piperazin-1-yl)ethyl)-8-(furan-2-yl)thiazolo [5,4-e] [1,2,4]triazolo[1,5-c]pyrimidin-2(3H)-one;
5-amino-3-(2-(4-(2,4-difluoro-5-(((3S,4R)-4-fluoropyrrolidin-3-yl)oxy)phenyl)piperazin-1-yl)ethyl)-8-(furan-2-yl)thiazolo [5,4-e] [1,2,4]triazolo[1,5-c]pyrimidin-2(3H)-one;
(S)-5-amino-3-(2-(4-(2,4-difluoro-5-((2-oxopyrrolidin-3-yl)oxy)phenyl)piperazin-1-yl)ethyl)-8-(furan-2-yl)thiazolo [5,4-e] [1,2,4]triazolo[1,5-c]pyrimidin-2(3H)-one;
(R)-5-amino-3-(2-(4-(2,4-difluoro-5-((2-oxopyrrolidin-3-yl)oxy)phenyl)piperazin-1-yl)ethyl)-8-(furan-2-yl)thiazolo [5,4-e] [1,2,4]triazolo[1,5-c]pyrimidin-2(3H)-one;
2-(5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluorophenoxy)-N-(2-morpholinoethyl)acetamide;
5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(morpholin-3-ylmethyl)benzamide;
5-amino-3-(2-(4-(2-fluoro-4-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2-fluoro-4-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2-fluoro-4-(((3R,4R)-4-fluoropyrrolidin-3-yl)oxy)phenyl)piperazin-1-yl)ethyl)-8-(furan-2-yl)thiazolo [5,4-e] [1,2,4]triazolo [1,5-c]pyrimidin-2(3H)-one;
5-amino-3-(2-(4-(2-fluoro-4-(((3S,4S)-4-fluoropyrrolidin-3-yl)oxy)phenyl)piperazin-1-yl)ethyl)-8-(furan-2-yl)thiazolo [5,4-e] [1,2,4]triazolo [1,5-c]pyrimidin-2(3H)-one;
5-amino-3-(2-(4-(2-fluoro-4-(((3R,4S)-4-fluoropyrrolidin-3-yl)oxy)phenyl)piperazin-1-yl)ethyl)-8-(furan-2-yl)thiazolo [5,4-e] [1,2,4]triazolo [1,5-c]pyrimidin-2(3H)-one;
5-amino-3-(2-(4-(2-fluoro-4-(((3S,4R)-4-fluoropyrrolidin-3-yl)oxy)phenyl)piperazin-1-yl)ethyl)-8-(furan-2-yl)thiazolo [5,4-e] [1,2,4]triazolo [1,5-c]pyrimidin-2(3H)-one;
2-(4-(4-(2-(5-amino-8-(furan-2-yl)-2-oxothiazolo[5,4-e][1,2,4]triazolo[1,5-c]pyrimidin-3 (2H)-yl)ethyl)piperazin-1-yl)-3-fluorophenoxy)-N-(2-morpholinoethyl) acetamide;
4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-morpholinoethyl)benzamide;
4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(morpholin-3-ylmethyl)benzamide;
5-amino-3-(2-(4-(4-(azetidin-3-yloxy)phenyl)piperazin-1-yl)ethyl)-8-(furan-2-yl)thiazolo[5,4-e][1,2,4]triazolo[1,5-c]pyrimidin-2(3H)-one;
(S)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one;
(R)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one;
5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)thiazolo [5,4-e] [1,2,4]triazolo[1,5-c]pyrimidin-2(3H)-one;

5-amino-3-(2-(4-(2,4-difluoro-5-(((1r,4r)-1-oxidotetra-hydro-2H-thiopyran-4-yl)oxy)phenyl)piperazin-1-yl)ethyl)-8-(furan-2-yl)thiazolo [5,4-e] [1,2,4]triazolo[1,5-c]pyrimidin-2(3H)-one;

(S)-5-(4 2-(5-amino-8-(furan-2-yl)-2-oxothiazolo[5,4-e] [1,2,4]triazolo[1,5-c]pyrimidin-3(2H)-yl)ethyl)piperazin-1-yl)-2,4-difluoro-N-(2-(methylsulfinyl)ethyl)benzamide;

(R)-5-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-2,4-difluoro-N-(2-(methylsulfinyl)ethyl)benzamide;

(S)-5-(4 2-(5-amino-8-(furan-2-yl)-2-oxothiazolo[5,4-e] [1,2,4]triazolo[1,5-c]pyrimidin-3(2H)-yl)ethyl)piperazin-1-yl)-2,4-difluoro-N-methyl-N-(2-(methylsulfinyl)ethyl)benzamide;

(R)-5-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-2,4-difluoro-N-methyl-N-(2-(methylsulfinyl)ethyl)benzamide;

5-amino-3-(2-(4-(2,4-difluoro-5-(1-oxidothiomorpholine-4-carbonyl)phenyl)piperazin-1-yl)ethyl)-8-(furan-2-yl)thiazolo [5,4-e] [1,2,4]triazolo[1,5-c]pyrimidin-2(3H)-one;

5-amino-3-(2-(4-(2,4-difluoro-5-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one;

(R)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one;

(S)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one;

5-amino-3-(2-(4-(2-fluoro-4-(((1S,4S)-1-oxidotetra-hydro-2H-thiopyran-4-yl)oxy)phenyl)piperazin-1-yl)ethyl)-8-(furan-2-yl)thiazolo [5,4-e] [1,2,4]triazolo[1,5-c]pyrimidin-2(3H)-one;

5-amino-3-(2-(4-(2-fluoro-4-(((1R,4R)-1-oxidotetra-hydro-2H-thiopyran-4-yl)oxy)phenyl)piperazin-1-yl)ethyl)-8-(furan-2-yl)thiazolo [5,4-e] [1,2,4]triazolo[1,5-c]pyrimidin-2(3H)-one;

(S)-4-(4 2-(5-amino-8-(furan-2-yl)-2-oxothiazolo[5,4-e] [1,2,4]triazolo[1,5-c]pyrimidin-3(2H)-yl)ethyl)piperazin-1-yl)-3-fluoro-N-(2-(methylsulfinyl)ethyl)benzamide;

(R)-4-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-3-fluoro-N-(2-(methylsulfinyl)ethyl)benzamide;

5-amino-3-(2-(4-(2-fluoro-4-(1-oxidothiomorpholine-4-carbonyl)phenyl)piperazin-1-yl)ethyl)-8-(furan-2-yl)thiazolo[5,4-e] [1,2,4]triazolo[1,5-c]pyrimidin-2(3H)-one;

5-amino-3-(2-(4-(2-fluoro-4-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one;

(S)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one;

(R)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one;

(S)-5-(4 2-(5-amino-8-(furan-2-yl)-2-oxothiazolo[5,4-e] [1,2,4]triazolo[1,5-c]pyrimidin-3(2H)-yl)ethyl)piperazin-1-yl)-N-(2,3-dihydroxypropyl)-2,4-difluorobenzamide;

(R)-5-(4-(2-(5-amino-8-(furan-2-yl)-2-oxothiazolo[5,4-e] [1,2,4]triazolo[1,5-c]pyrimidin-3(2H)-yl)ethyl)piperazin-1-yl)-N-(2,3-dihydroxypropyl)-2,4-difluorobenzamide;

5-amino-3-(2-(4-(4-(azetidin-3-yloxy)-2-fluorophenyl)piperazin-1-yl)ethyl)-8-(furan-2-yl)thiazolo [5,4-e] [1,2,4]triazolo [1,5-c]pyrimidin-2(3H)-one;

5-amino-3-(2-(4-(5-(azetidin-3-yloxy)-2,4-difluorophenyl)piperazin-1-yl)ethyl)-8-(furan-2-yl)thiazolo[5,4-e] [1,2,4]triazolo[1,5-c]pyrimidin-2(3H)-one;

(S)-5-amino-3-(2-(4-(2,4-difluoro-5-(3-(methylsulfinyl)propoxy)phenyl)piperazin-1-yl)ethyl)-8-(furan-2-yl)thiazolo[5,4-e][1,2,4]triazolo[1,5-c]pyrimidin-2(3H)-one;

and pharmaceutically acceptable salts thereof.

9. A pharmaceutical composition comprising a compound of claim 1, or a pharmaceutically acceptable salt thereof, and at least one pharmaceutically acceptable carrier.

10. Medicament comprising a compound according to claim 1, or a pharmaceutically acceptable salt thereof.

11. Process for manufacturing a compound of Formula (Ia) according to claim 2, or a pharmaceutically acceptable salt thereof, characterized in that it comprises the coupling between amine intermediate of Formula (A) and intermedia of Formula (B)

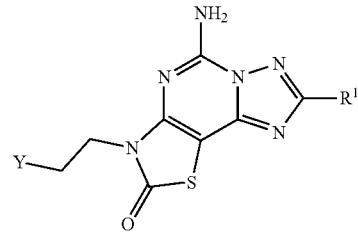

wherein
$X^1$ and $X^2$ represent each independently C or N;
$R^{1'}$ is absent when $X^1$ is N; or when $X^1$ is C, $R^{1'}$ represents H, halo alkyl, heterocyclyl, alkoxy, cycloalkyloxy, heterocycloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, diakylaminoalkyl, (heterocyclyl)(alkyl)aminoalkyl, heterocyclyl, heteroaryl, alkylheteroaryl, alkyne, alkoxy, amino, diakylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, diakylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;
$R^{2'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl; said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxide, alkylsulfoxidealkyl, alkylsulfonyl and alkylsulfonealkyl;

or $R^{1'}$ and $R^{2'}$ form together with the atoms to which they are attached a 1- or 6- membered aryl ring, a 5- or 6-membered heretoaryl ring, a 5- or 6-membered cycloalkyl ring or a 5- or 6-membered heretocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{3'}$ is absent when $X^2$ is N; or when $X^2$ is C, $R^{3'}$ represents H or halo, preferably H or F;

$R^{4'}$ represents H or halo, preferably H or F;

$R^{5'}$ represents H or halo, preferably H or F;

$R^1$ represents 5- or 6-membered heteroaryl or 5- or 6-membered aryl, wherein heteroaryl or aryl groups are optionally substituted by one or more substituent selected from $C_1$-$C_6$ alkyl and halo; and Y represents halo, alkylsulfonyloxy having 1 to 6 carbon atoms or arylsulfonyloxy having 6 to 10 carbon atoms.

12. The compound according to claim 1, wherein $R^1$ represents 5-membered heteroaryl.

13. The compound according to claim 1, wherein $R^1$ represents furyl.

14. The compound according to claim 1, wherein the compound is (+)-5-amino-3-(2-)4-(2,4-difluoro-5-(2-(methylsulfinyl)ethoxy)phenyl)piperazin-1-yl)ethyl-8-(furan-2-yl)thiazolo[5,4-e][1,2,4]triazolo[1,5-c]pyrimidin-2(3H)-one or a pharmaceutically acceptable salt or solvate thereof.

15. The compound according to claim 1, wherein the compound is (+)-5-amino-3-(2-(4-(2,4-difluoro-5-(2-(methylsulfinyl)ethoxy)phenyl)piperazin-1-yl)ethyl-8-(furan-2-yl)thiazolo[5,4-e][1,2,4]triazolo[1,5-c]pyrimidin-2(3H)-one or a pharmaceutically acceptable salt thereof.

16. The compound according to claim 1, wherein the compound is (+)-5-amino-3-(2-(4- (2,4-difluoro-5-(2-(methylsulfinyl(ethoxy)phenyl)piperazin-1-yl)ethyl)-8-(furan-2-yl)thiazolo[5,4-e][1,2,4]triazolo[1,5-c]pyrimidin-2(3H)-one.

17. The compound according to claim 1, wherein the compound is (S)-5-amino-3-(2-(4-(2,4-difluoro-5-(2-(methylsulfinyl)ethoxy)phenyl)piperazin-1-yl)ethyl-8-(furan-2-yl)thiazolo[5,4-e][1,2,4]triazolo[1,5-c[1,5-c]pyrimidin-2(3H)-one or a pharmaceutically acceptable salt or solvate thereof.

18. The compound according to claim 1, wherein the compound is (S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one or a pharmaceutically acceptable salt thereof.

19. The compound according to claim 1, wherein the compound is (S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one.

20. The compound according to claim 1, wherein the compound is (R)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin2(3H)-one or a pharmaceutically acceptable salt thereof.

21. The compound according to claim 1, wherein the compound (R,S)-5-amino-3-(2-(4-(2,4-difluoro-5(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one or a pharmaceutically acceptable salt thereof.

22. The pharmaceutical composition according to claim 9, wherein the compound is (S)-5amino-3-(2-(4-(2,4-difluoro-5-(2-(methylsulfinyl)ethoxy)phenyl)piperazin-1-yl)ethyl)-8-(furan-2yl)thiazolo[5,4-e][1,2,4]triazolo[1,5-c]pyrimidin-2(3H)-one or a pharmaceutically acceptable salt thereof.

* * * * *

UNITED STATES PATENT AND TRADEMARK OFFICE
CERTIFICATE OF CORRECTION

PATENT NO. : 10,995,101 B2
APPLICATION NO. : 16/354022
DATED : May 4, 2021
INVENTOR(S) : Stefano Crosignani, Bruno Gomes and Erica Houthuys It is certified that error appears in the above-identified patent and that said Letters Patent is hereby corrected as shown below:

In the Claims

In Claim 1, Column 208, Line 51:
"alkyl sulfonyl" should read --alkylsulfonyl--

In Claim 1, Column 208, Lines 61-62:
"aminocarbonylalkyl)" should read --(aminocarbonylalkyl)--

In Claim 1, Column 209, Line 2:
"alkylsulfoxidealkyl alkylsulfonyl" should read --alkylsulfoxidealkyl, alkylsulfonyl--

In Claim 1, Column 209, Line 6:
"heretoaryl" should read --heteroaryl--

In Claim 1, Column 209, Line 8:
"heretocyclyl" should read --heterocyclyl--

In Claim 1, Column 209, Line 23:
"alkyl sulfoxidealkyl" should read --alkylsulfoxidealkyl--

In Claim 2, Column 209, Line 48:
"alkyl sulfonyl" should read --alkylsulfonyl--

In Claim 2, Column 210, Line 4:
"alkyl sulfonyl" should read --alkylsulfonyl--

In Claim 2, Column 210, Line 23:
"alkyl sulfoxidealkyl" should read --alkylsulfoxidealkyl--

Signed and Sealed this
Twenty-sixth Day of March, 2024

Katherine Kelly Vidal
*Director of the United States Patent and Trademark Office*

In Claim 2, Column 210, Line 25:
"$R^{1'}$ and $R^{2'}$ form together" should read --or $R^{1'}$ and $R^{2'}$ form together--

In Claim 2, Column 210, Line 27:
"heretoaryl" should ready --heteroaryl--

In Claim 2, Column 210, Line 28:
"heretocyclyl" should read --heterocyclyl--

In Claim 2, Column 210, Lines 46-47:
"$R^{3'}$ represents H or halo, preferably H or F;" should read --$R^{3'}$ represents H or halo;--

In Claim 2, Column 210, Line 48:
"$R^{4'}$ represents H or halo, preferably H or F; and" should read --$R^{4'}$ represents H or halo; and--

In Claim 2, Column 210, Line 49:
"$R^{5'}$ represents H or halo, preferably H or F." should read --$R^{5'}$ represents H or halo.--

In Claim 3, Column 211, Lines 1-2:
"$R^{1'}$ is absent when $X^1$ is N; or when $X^1$ is C, $R^{1'}$ represents H," should read --$R^{1'}$ represents H,--

In Claim 3, Column 211, Line 2:
"hetercyclyl" should read --heterocyclyl--

In Claim 3, Column 211, Line 26:
"hetercyclyl" should read --heterocyclyl--

In Claim 3, Column 211, Line 33:
"hycroxy" should read --hydroxy--

In Claim 3, Column 211, Line 52:
"heretoaryl" should read --heteroaryl--

In Claim 3, Column 211, Line 53:
"heretycyclyl" should read --heterocyclyl--

In Claim 3, Column 212, Line 1:
"hetercyclylcarbonyl" should read --heterocyclylcarbonyl--

In Claim 3, Column 212, Lines 5-6:
"$R^{3'}$ is absent when $X^2$ is N; or when $X^2$ is C, $R^{3'}$ represents H or halo, preferably H or F;" should read --$R^{3'}$ represents H or halo;--

In Claim 3, Column 212, Line 7:
"$R^{4'}$ represents H or halo, preferably H or F; and" should read --$R^{4'}$ represents H or halo; and--

In Claim 3, Column 212, Line 8:
"$R^{5'}$ represents H or Halo, preferably H or F." should read --$R^{5'}$ represents H or halo.--

In Claim 4, Column 212, Line 24:
"heteraryl" should read --heteroaryl--

In Claim 4, Column 212, Lines 25-26:
"$R^{3'}$ is absent when $X^2$ is N; or when $X^2$ is C, $R^{3'}$ represents H or halo, preferably H or F; and" should read --$R^{3'}$ represents H or halo; and--

In Claim 4, Column 212, Line 46:
"hetercyclylcarbonyl" should read --heterocyclylcarbonyl--

In Claim 5, Column 212, Line 64:
"heteraryl" should read --heteroaryl--

In Claim 5, Column 213, Lines 1-2:
"$R^{3'}$ is absent when $X^2$ is N; or when $X^2$ is C, $R^{3'}$ represents H or halo, preferably H or F;" should read --$R^{3'}$ represents H or halo;--

In Claim 5, Column 213, Line 3:
"$R^{1'}$ represents H or halo, preferably H or F; and" should read --$R^{1'}$ represents H or halo; and--

In Claim 6, Column 213, Line 23:
"(1a-Id)" should read --Ia-1d--

In Claim 6, Column 213, Line 47:
"heteraryl" should read --heteroaryl--

In Claim 6, Column 213, Lines 51-52:
"$R^{3'}$ is absent when $X^2$ is N; or when $X^2$ is C, $R^{3'}$ represents H or halo, preferably H or F;" should read --$R^{3'}$ represents H or halo;--

In Claim 6, Column 213, Line 53:
"$R^{1'}$ represents H or halo, preferably H or F;" should read --$R^{1'}$ represents H or halo;--

In Claim 6, Column 213, Line 54:
"$R^{2'}$ represents H or halo, preferably H or F;" should read --$R^{2'}$ represents H or halo;--

In Claim 7, Column 214, Line 50:
"halo" should read --halo;--

In Claim 7, Column 214, Line 51:
"hetercyclyl" should read --heterocyclyl--

CERTIFICATE OF CORRECTION (continued)
U.S. Pat. No. 10,995,101 B2

In Claim 7, Column 215, Lines 8-9:
"$R^{3'}$ is absent when $X^2$ is N; or when $X^2$ is C, $R^{3'}$ represents H or halo, preferably H or F;" should read --$R^{3'}$ represents H or halo;--

In Claim 7, Column 215, Line 10:
"$R^{4'}$ represents H or halo, preferably H or F; and" should read --$R^{4'}$ represents H or halo; and--

In Claim 7, Column 215, Line 11:
"$R^{5'}$ represents H or halo, preferably H or F." should read --$R^{5'}$ represents H or halo.--

In Claim 8, Column 215, Lines 14 to 17:
"3-(2-(4-(4-((lH-l,2,3-triazolo-1-yl)methoxy-2fluorophenyl)piperazine-l-yl)ethyl)-5-amino-(8-(furan-2-yl)thiazolo[5,4-e][l,2,4]triazolo[l,5-c]pyrimidine-2(3H)-one;" should read
--3-(2-(4-(4-((1H-1,2,3-triazolo-4-yl)methoxy-2-fluorophenyl)piperazin-l-yl)ethyl)-5-amino-(8-(furan-2-yl)thiazolo[5,4-e][1,2,4]triazolo[1,5-c]pyrimidine-2(3H)-one;--

In Claim 8, Column 216, Lines 37 to 39:
"5-amino-3-(2-(4-(2-fluoro-4-(piperazin-1-yl sulfonyl)phenyl)piperazin-1-yl)ethyl)-8-(furan-2-yl)thiazolo[5,4-e][l,2,4]triazolo[l,5-c]pyrimidin-2(3H)-one;" should read
--5-amino-3-(2-(4-(2-fluoro-4-(piperazin-1-ylsulfonyl)phenyl)piperazin-1-yl)ethyl)-8-(furan-2-yl)thiazolo[5,4-e][1,2,4]triazolo[1,5-c]pyrimidin-2(3H)-one;--

In Claim 8, Column 216, Lines 59 to 61:
"2-(4-(4-(2 5-amino-8-(furan-2-yl)-2-oxothiazolo[5,4-e][l,2,4]triazolo[l,5-c]pyrimidin-3(2H)-yl)ethyl)piperazin-1-yl)-3-fluorophenoxy)acetic acid;" should read
--2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)acetic acid;--

In Claim 8, Column 216, Lines 62 to 64:
"2-(4-(4-(2-(5-amino-8-(furan-2-yl)-2-oxothiazolo [5,4-e][l,2,4]triazolo[l,5-c]pyrimidin-3(2H)-yl)ethyl) piperazin-1-y l)-3,5-difluorophenoxy) acetic acid" should read
--2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3,5-difluorophenoxy)acetic acid--

In Claim 8, Column 217, Lines 4 to 6:
"2-(4-(4-(2 5-amino-8-(furan-2-yl)-2-oxothiazolo[5,4-e][l,2,4]triazolo[l,5-c]pyrimidin-3(2H)-yl)ethyl)piperazin-1-yl)-3-fluorophenoxy)2- methylpropanoic acid;" should read
--2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)-2-methylpropanoic acid;--

In Claim 8, Column 217, Lines 7 to 9:
"3-(4-(4-(2 5-amino-8-(furan-2-yl)-2-oxothiazolo[5,4-e][l,2,4]triazolo[l,5-c]pyrimidin-3(2H)-yl)ethyl)piperazin-1-yl)-3-fluorophenyl)propanoic acid;" should read
--3-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenyl)propanoic acid;--

CERTIFICATE OF CORRECTION (continued)

In Claim 8, Column 217, Lines 37 to 38:
"3-(2-(4-(4-((1H-1,2,4-triazol-3-yl)methoxy)-2-fluorophenyl)piperazin-1-yl)ethyl)-5-amino-8-(iuran-2-yl)thiazolo[5,4-e][1,2,4]triazolo[1,5-c]pyrimidin-2(3H)-one" should read
--3-(2-(4-(4-((1H-1,2,4-triazol-3-yl)methoxy)-2-fluorophenyl)piperazin-1-yl)ethyl)-5-amino-8-(furan-2-yl)thiazolo[5,4-e][1,2,4]triazolo[1,5-c]pyrimidin-2(3H)-one--

In Claim 8, Column 218, Lines 50 to 53:
"4-(4-(2-(5-amino-8-(furan-2-yl)-2-oxothiazolo[5,4-e][l,2,4]triazolo[l,5-c]pyrimidin-3(2H)-yl)ethyl)piperazin-1-yl)-3-fluoro-N-(2-(2-hydroxyethyl)amino)ethyl) benzamide;" should read
--4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-((2-hydroxyethyl)amino)ethyl)benzamide;--

In Claim 8, Column 220, Lines 9 to 12:
"(R)-5-amino-3-(2-(4-(2,4-difluoro-5-(2-oxopyrrolidin-3-yl)oxy)phenyl)piperazin-1-yl)ethyl)-8-(furan-2-yl)thiazolo [5,4-e][1,2,4]triazolo[1,5-c]pyrimidin-2(3H)-one;" should read
--(R)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one;--

In Claim 8, Column 221, Lines 5 to 8:
"(S)-5-(4 2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide;" should read
--(S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-(2-(methylsulfinyl)ethyl)benzamide;--

In Claim 8, Column 221, Lines 13 to 16:
"(S)-5-(4 2-(5-amino-8-(furan-2-yl)-2-oxothiazolo[5,4-e][l,2,4]triazolo[l,5-c]pyrimidin-3(2H)-yl)ethyl)piperazin-1-yl)-2,4-difluoro-N-methyl-N-(2-(methylsulfinyl)ethyl)benzamide;" should read
--(S)-5-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-2,4-difluoro-N-methyl-N-(2-(methylsulfinyl)ethyl)benzamide;--

In Claim 8, Column 221, Lines 43 to 46:
"(S)-4-(4 2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide;" should read
--(S)-4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluoro-N-(2-(methylsulfinyl)ethyl)benzamide;--

In Claim 8, Column 221, Lines 64 to 67:
"(S)-5-(4 2-(5-amino-8-(furan-2-yl)-2-oxothiazolo[5,4-e][l,2,4]triazolo[l,5-c]pyrimidin-3(2H)-yl)ethyl)piperazin-l-yl)-N-(2,3-dihydroxypropyl)-2,4-difluorobenzamide;" should read
--(S)-5-(4-(2-(5-amino-8-(furan-2-yl)-2-oxothiazolo[5,4-e][l,2,4]triazolo[l,5-c]pyrimidin-3(2H)-yl)ethyl)piperazin-l-yl)-N-(2,3-dihydroxypropyl)-2,4-difluorobenzamide;--

In Claim 11, Column 222, Line 25:
"intermedia" should read --intermediate--

In Claim 11, Column 222, Lines 27 to 38:

" 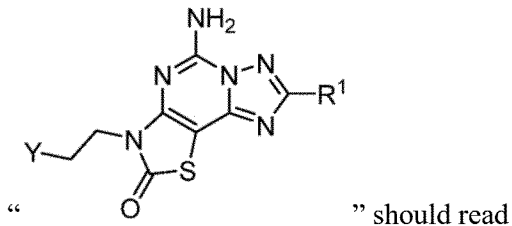 " should read

-- 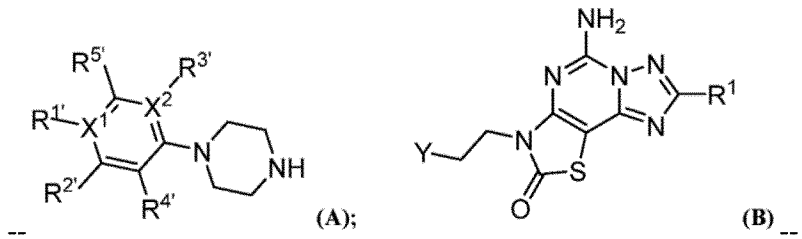 --

In Claim 11, Column 222, Line 42:
"halo alkyl" should read --haloalkyl--

In Claim 11, Column 223, Line 10:
"heterocyclyl)(alkyl)aminoalkyl," should read --(heterocyclyl)(alkyl)aminoalkyl,--

In Claim 11, Column 223, Lines 21-23:
"alkynylcarbonyl, alkylsulfoxide, alkylsulfoxide, alkylsulfoxidealkyl" should read --alkynylcarbonyl, alkylsulfoxide, alkylsulfoxidealkyl--

In Claim 11, Column 223, Line 24:
"1- or 6-membered" should read --5- or 6-membered--

In Claim 11, Column 223, Line 25:
"heretoaryl" should read --heteroaryl--

In Claim 11, Column 223, Line 26:
"heretocyclyl" should read --heterocyclyl--

In Claim 11, Column 223, Lines 45-46:
"$R^{3'}$ represents H or halo, preferably H or F;" should read --$R^{3'}$ represents H or halo;--

In Claim 11, Column 223, Line 47:
"$R^{4'}$ represents H or halo, preferably H or F;" should read --$R^{4'}$ represents H or halo;--

In Claim 11, Column 223, Line 48:
"$R^{5'}$ represents H or halo, preferably H or F;" should read --$R^{5'}$ represents H or halo;--

In Claim 14, Column 224, Lines 8-10:
"(+)-5-amino-3-(2-)4-(2,4-difluoro-5-(2-(methylsulfinyl)ethoxy)phenyl)piperazin-1-yl)ethyl-8-(furan-2-yl)thiazolo[5,4-e][1,2,4]triazolo[1,5-c]pyrimidin-2(3H)-one" should read --(+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one--

In Claim 15, Column 224, Lines 14-16:
"(+)-5-amino-3-(2-(4-(2,4-difluoro-5-(2-(methylsulfinyl)ethoxy)phenyl)piperazin-1-yl)ethyl-8-(furan-2-yl)thiazolo[5,4-e][1,2,4]triazolo[1,5-c]pyrimidin-2(3H)-one" should read
--(+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one--

In Claim 16, Column 224, Lines 17 to 21:
"The compound according to claim 1, wherein the compound is (+)-5-amino-3-(2-(4- (2,4-difluoro-5-(2-(methylsulfinyl(ethoxy)phenyl)piperazin-1-yl)ethyl)-8-(furan-2-yl)thiazolo[5,4-e][1,2,4]triazolo[1,5-c]pyrimidin-2(3H)-one." should read
--The compound according to claim 1, wherein the compound is (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one.--

In Claim 17, Column 224, Lines 22 to 27:
"The compound according to claim 1, wherein the compound is (S)-5-amino-3-(2-(4-(2,4-difluoro-5-(2-(methylsulfinyl)ethoxy)phenyl)piperazin-1-yl)ethyl-8-(furan-2-yl)thiazolo[5,4-e][1,2,4]triazolo[1,5-c[1,5-c]pyrimidin-2(3H)-one or a pharmaceutically acceptable salt or solvate thereof." should read
--The compound according to claim 1, wherein the compound is (S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one or a pharmaceutically acceptable salt or solvate thereof.--

In Claim 20, Column 224, Lines 38 to 42:
"The compound according to claim 1, wherein the compound is (R)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin2(3H)-one or a pharmaceutically acceptable salt thereof." should read
--The compound according to claim 1, wherein the compound is (R)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one or a pharmaceutically acceptable salt thereof.--

In Claim 21, Column 224, Lines 43 to 47:
"The compound according to claim 1, wherein the compound (R,S)-5-amino-3-(2-(4-(2,4-difluoro-5(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one or a pharmaceutically acceptable salt thereof." should read
--The compound according to claim 1, wherein the compound is (R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one or a pharmaceutically acceptable salt thereof.--

In Claim 22, Column 224, Lines 48 to 52:
"The pharmaceutical composition according to claim 9, wherein the compound is (S)-5amino-3-(2-(4-(2,4-difluoro-5-(2-(methylsulfinyl)ethoxy)phenyl)piperazin-1-yl)ethyl)-8-(furan-2yl)thiazolo[5,4-e][1,2,4]triazolo[1,5-c]pyrimidin-2(3H)-one or a pharmaceutically acceptable salt thereof." should read --The pharmaceutical composition according to claim 9, wherein the compound is (S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one or a pharmaceutically acceptable salt thereof.--